US007759314B2

(12) United States Patent
Fallon et al.

(10) Patent No.: US 7,759,314 B2
(45) Date of Patent: Jul. 20, 2010

(54) TREATMENT OF MUSCULAR DYSTROPHIES AND RELATED DISORDERS

(75) Inventors: Justin R. Fallon, Harvard, MA (US); Michael Rafii, Baltimore, MD (US); Alison Amenta, Pawtucket, RI (US); Mark Bowe, Damasus, MD (US); Beth McKechnie, Franklin, MA (US); Mary Lynn Mercado, Robbinsville, NJ (US); Hiroki Hagiwara, Bunkyo-Ku (JP)

(73) Assignee: Brown University, Providence, RI (US)

( * ) Notice: Subject to any disclaimer, the term of this patent is extended or adjusted under 35 U.S.C. 154(b) by 14 days.

(21) Appl. No.: 10/486,678

(22) PCT Filed: Aug. 15, 2002

(86) PCT No.: PCT/US02/26201

§ 371 (c)(1),
(2), (4) Date: Sep. 1, 2004

(87) PCT Pub. No.: WO03/015615

PCT Pub. Date: Feb. 27, 2003

(65) Prior Publication Data

US 2005/0043221 A1    Feb. 24, 2005

Related U.S. Application Data

(60) Provisional application No. 60/312,551, filed on Aug. 15, 2001.

(51) Int. Cl.
*A01N 37/18* (2006.01)
*A61K 38/00* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)

(52) U.S. Cl. ........................................ 514/20; 530/300
(58) Field of Classification Search ........................ None
See application file for complete search history.

(56) References Cited

U.S. PATENT DOCUMENTS

| 5,340,934 | A | | 8/1994 | Termine et al. |
| 5,654,270 | A | * | 8/1997 | Ruoslahti et al. ............... 514/8 |
| 5,705,609 | A | | 1/1998 | Ruoslahti et al. |
| 6,864,236 | B1 | * | 3/2005 | Fallon et al. .................. 514/12 |
| 2004/0063627 | A1 | | 4/2004 | Fallon et al. |
| 2005/0059580 | A1 | | 3/2005 | Fallon et al. |

FOREIGN PATENT DOCUMENTS

| EP | 0 686 397 A2 | 4/1995 |
| WO | WO-93/10808 A1 | 6/1993 |
| WO | WO-95/13298 A1 | 5/1995 |
| WO | WO 01/36475 | 5/2001 |
| WO | WO-03/015615 A2 | 2/2003 |
| WO | WO-03/070195 A2 | 8/2003 |

OTHER PUBLICATIONS

Gregorevic P, Chamberlain JS.Gene therapy for muscular dystrophy—a review of promising progress.Expert Opin Biol Ther. Aug. 2003;3(5):803-14.*
Athanasopoulos T, Graham IR, Foster H, Dickson G.Recombinant adeno-associated viral (rAAV) vectors as therapeutic tools for Duchenne muscular dystrophy (DMD). Gene Ther. Oct. 2004;11 Suppl 1:S109-21.*
Lamandé SR, Bateman JF, Hutchison W, McKinlay Gardner RJ, Bower SP, Byrne E, Dahl HH. Reduced collagen VI causes Bethlem myopathy: a heterozygous COL6A1 nonsense mutation results in mRNA decay and functional haploinsufficiency. Hum. Mol Genet. Jun. 1998;7(6):981-9.*
Langton et al., 1998, The Journal of Biological Chemistry, 273: 16778-16781.*
Xu et al., 1998, Nature Genetics, 20: 78-82.*
Farooqi et al., 1999, New England Journal of Medicine, 341: 879-884.*
Hocking et al., 1996, The Journal of Biological Chemistry, 271: 19571-19577.*
Brown ("Hybridization Analysis of DNA Blots" in Current Protocols in Molecular Biology John Wiley & Sons, Inc., 2003).*
Raffi et al., "Interactions of the Proteoglycan Biglycan with the Dystrophin Associated Protein Complex and its Roles in Muscular Dystrophy and Synaptogenesis," *Molecular Biology of the Cell* vol. 11 pp. 146a (2000).
Chan, Y., et al., "Molecular Organization of Sarcoglycan Complex in Mouse Myotubes in Culture," *J. Cell Bio.*, 143(7):2033-2044 (1998).
Crosbie, R., et al., "Membrane Targeting and Stabilization of Sarcospan is Mediated by the Sarcoglycan Subcomplex," *J. Cell Bio.*, 145(1):153-165 (1999).
Ervasti, J.M. and Campbell, K.P., "A Role for the Dystrophin-Glycoprotein Complex as a Transmembrane Linker between Laminin and Actin," *J. Cell Bio.*, 122(4):809-823 (1993).
Ferri, R.T., et al., "A role for biglycan in agrin-induced postsynaptic differentiation," *Society for Neuroscience Abstracts*, 26 (2000) (Abstract only).
Gee, S.H., et al., "Dystroglycan-α, a Dystrophin-Associated Glycoprotein, Is a Functional Agrin Receptor," *Cell*, 77:675-686 (1994).

(Continued)

*Primary Examiner*—Joanne Hama
(74) *Attorney, Agent, or Firm*—Ropes & Gray LLP

(57) ABSTRACT

The invention provides, among other aspects, compositions and methods for treating, preventing, and diagnosing diseases or conditions associated with an abnormal level or activity of biglycan; diseases or conditions associated with an abnormal level or activity of collagen VI; disorders associated with an unstable cytoplasmic membrane, due, e.g., to an unstable dystrophin associated protein complex (DAPC); and disorders associated with abnormal synapses or neuromuscular junctions, including those resulting from an abnormal MuSK activation or acetylcholine receptor (AChR) aggregation.

12 Claims, 24 Drawing Sheets

OTHER PUBLICATIONS

Hoch, W., "Formation of the neuromuscular junction: Agrin and its unusual receptors," *Eur. J. Biochem.*, 265:1-10 (1999).

Holt, K.H., et al., "Functional Rescue of the Sarcoglycan Complex in the BIO 14.6 Hamster Using δ-Sarcoglycan Gene Transfer," *Molecular Cell*, 1:841-848 (1998).

Jarvelainen, H.T., et al., "Differential Expression of Small Chondroitin/Dermatan Sulfate Proteoglycans, PG-I/Biglycan and PG-II/Decorin, by Vascular Smooth Muscle and Endothelial Cells in Culture," *J. Biol. Chem.*, 266:23274-23281 (1991).

Junghans, U., et al., "Purification of a Meningeal Cell-derived Chondroitin Sulphate Proteoglycan with Neurotrophic Activity for Brain Neurons and its Identification as Biglycan," *Eur. J. Neuroscience*, 7:2341-2350 (1995).

Khurana, T.S., et al., "Interaction of Aria, A Neuregulin, with the Dystroglycan / Sarcoglycan Complex in Skeletal Muscle."

Sakamoto, A., et al., "Both hypertrophic and dilated cardiomyopathies are caused by mutation of the same gene, δ-sarcoglycan, in hamster: An animal model of disrupted dystrophin-associated glycoprotein complex," *Proc. Natl. Acad. Sci. USA*, 94:13873-13878 (1997).

Tomoyasu, H., et al., "Identification of haemopoietic biglycan in hyperplastic thymus associated with myasthenia gravis," *J Neuroimmunology*, 89:59-63 (1998).

Winder, S.J., "The complexities of dystroglycan," *Trends in Biochem. Sci.*, 26:118-124 (2001).

Ibraghimov-Beskrovnaya, O., et al., "Human dystroglycan: skeletal muscle cDNA, genomic structure, origin of tissue specific isoforms and chromosomal localization," *Hum. Mol. Genet.*, 2(10):1651-1657 (1993).

Coral-Vazquez, R., et al., "Disruption of the Sarcoglycan-Sarcospan Complex in Vascular Smooth Muscle: A Novel Mechanism for Cardomyopathy and Muscular Dystrophy," *Cell*, 98:465-474 (1999).

Bianco, P., et al., "Expression and Localization of the Two Small Proteoglycans Biglycan and Decorin in Developing Human Skeletal and Non-skeletal Tissues," *J. Histochem. Cytochem.*, 38(11):1549-1563 (1990).

Fisher, L.W., et al., "Deduced Protein Sequence of Bone Small Proteoglycan I (Biglycan) Shows Homology with Proteoglycan II (Decorin) and Several Nonconnective Tissue Proteins in a Variety of Species," *J. Bio. Chem.*, 264(8):4571-4576 (1989).

Bowe, M.A., et al., "The Small Leucine-rich Repeat Proteoglycan Biglycan Binds to Dystroglycan and Is Upregulated in Dystrophic Muscle," *J. Cell Biol.*, 148(4):801-810 (2000).

Hocking, A.M., et al., "Eukaryotic Expression of Recombinant Biglycan," *Am. Soc. for Biochem. and Molecular Biol.*, 271(32):19571-19577 (1996).

Krishnan, P., et al., "Distinct Secondary Structures of the Leucine-rich Repeat Proteoglycans Decorin and Biglycan," *J. Biol. Chem.*, 274(16):10945-10950 (1999).

Iozzo, R.V., "Matrix Proteoglycans: From Molecular Design to Cellular Function," *Annu. Rev. Biochem.*, 67:609-52 (1998).

Wibert et al., "Biglycan and Decorin Bind Close to the N-terminal Region of the Collagen VI Triple Helix," J. of Biological Chemistry, 276(22):18947-18952(2001).

Guglieri, et al., "Molecular Etiopathogenesis of Limb Girdle Muscular and Congenital Muscular Dystrophies: Boundaries and Contiguities," Clinica Chimica Acta 361 (2005) 54-79.

Lampe et al., "Collagen VI Related Muscle Disorders," J. Med. Genet. 2005;42;673-685.

Vanegas et al., "Ullrich scleroatonic muscular dystrophy is caused by recessive mutations in collagen type VI," PNAS vol. 98, No. 13, 2001.

Spence et al., "Muscular dystrophies, the cytoskeleton and cell adhesion," BioEssays 24:542-552, 2002.

Wiberg et al., "Biglycan and Decorin Bind Close to the N-terminal Region of the Collagen VI Triple Helix," J. Biol. Chem., 276;22, 18947-18952, 2001.

Speer et al., "Evidence for locus heterogeneity in the Bethlem myopathy and linkage to 2q37," Hum. Mol. Genet. Jul. 1996;5(7):1043-6.

Von der Mark et al., "Immunochemistry, genuine size and tissue localization of collagen VI," Eur. J. Biochem. 142(3):493-502, 1984.

Hasenehrl et al., "Facilitation of learning following injection of the chondroitin sulfate proteoglycan biglycan into the vicinity of the nucleus basalis magnocellularis," Behav. Brain Research 70(1995) 59-67.

* cited by examiner

| TORPEDO | IQAIEFEDL | LGLGFNEIR |
|---------|-----------|-----------|
|         | \|\|\|\|\| \|\|\| | \|\|\|\| \| \|\| |
| HUMAN   | IQAIELEDL | LGLGHNQIR |
|         | 241     249 | 258   266 |

| TORPEDO | TSYHGISLFNNPVNYWDVL |
|---------|---------------------|
|         | \| \|\|\|\|\|\|\|\|\| \|\| \| |
| HUMAN   | AYYNGISLFNNPVPYWEVQ |
|         | 330               348 |

SEQUENCE LISTING

```
<160> NUMBER OF SEQ ID NOS: 19

<210> SEQ ID NO 1
<211> LENGTH: 9
<212> TYPE: PRT
<213> ORGANISM: Torpedo sp.

<400> SEQUENCE: 1

Ile Gln Ala Ile Glu Phe Glu Asp Leu
 1               5

<210> SEQ ID NO 2
<211> LENGTH: 9
<212> TYPE: PRT
<213> ORGANISM: Torpedo sp.
```

-continued

<400> SEQUENCE: 2

Leu Gly Leu Gly Phe Asn Glu Ile Arg
1               5

<210> SEQ ID NO 3
<211> LENGTH: 19
<212> TYPE: PRT
<213> ORGANISM: Torpedo sp.

<400> SEQUENCE: 3

Thr Ser Tyr His Gly Ile Ser Leu Phe Asn Asn Pro Val Asn Tyr Trp
1               5                   10                  15

Asp Val Leu

<210> SEQ ID NO 4
<211> LENGTH: 9
<212> TYPE: PRT
<213> ORGANISM: Homo sapiens

<400> SEQUENCE: 4

Ile Gln Ala Ile Glu Leu Glu Asp Leu
1               5

<210> SEQ ID NO 5
<211> LENGTH: 9
<212> TYPE: PRT
<213> ORGANISM: Homo sapiens

<400> SEQUENCE: 5

Leu Gly Leu Gly His Asn Gln Ile Arg
1               5

<210> SEQ ID NO 6
<211> LENGTH: 19
<212> TYPE: PRT
<213> ORGANISM: Homo sapiens

<400> SEQUENCE: 6

Ala Tyr Tyr Asn Gly Ile Ser Leu Phe Asn Asn Pro Val Pro Tyr Trp
1               5                   10                  15

Glu Val Gln

<210> SEQ ID NO 7
<211> LENGTH: 1685
<212> TYPE: DNA
<213> ORGANISM: Homo sapiens

<400> SEQUENCE: 7
gagtagctgc tttcggtccg ccggacacac cggacagata gacgtgcgga cggcccacca      60
ccccagcccg ccaactagtc agcctgcgcc tggcgcctcc cctctccagg tccatccgcc     120
atgtggcccc tgtggcgcct cgtgtctctg ctggccctga gccaggccct gccctttgag     180
cagagaggct tctgggactt caccctggac gatgggccat tcatgatgaa cgatgaggaa     240
gcttcgggcg ctgacaccct caggcgtcct gacccggact ctgtcacacc cacctacagc     300
gccatgtgtc ctttcggctg ccactgccac ctgcgggtgg ttcagtgctc cgacctgggt     360
ctgaagtctg tgcccaaaga gatctcccct gacaccacgc tgctggacct gcagaacaac     420
gacatctccg agctccgcaa ggatgacttc aagggtctcc agcacctcta cgccctcgtc     480
ctggtgaaca caagatctc caagatccat gagaaggcct tcagcccact gcggaagctg     540

```
cagaagctct acatctccaa gaaccacctg gtggagatcc cgcccaacct acccagctcc    600
ctggtggagc tccgcatcca cgacaaccgc atccgcaagg tgcccaaggg agtgttcagc    660
gggctccgga acatgaactg catcgagatg ggcgggaacc cactgagaaa cagtggcttt    720
gaacctggag ccttcgatgg cctgaagctc aactacctgc gcatctcaga ggccaagctg    780
actggcatcc ccaaagacct ccctgagacc ctgaatgaac tccacctaga ccacaacaaa    840
atccaggcca tcgaactgga ggacctgctt cgctactcca agctgtacag gctgggccta    900
ggccacaacc agatcaggat gatcgagaac gggagcctga gcttcctgcc cacccctccgg   960 gagctccact tggacaacaa caagttggcc agggtgccct cagggctccc agacctcaag   1020
ctcctccagg tggtctatct gcactccaac aacatcacca agtgggtgt caacgacttc    1080 tgtcccatgg gcttcggggt gaagcgggcc tactacaacg gcatcagcct cttcaacaac   1140
cccgtgccct actgggaggt gcagccggcc actttccgct gcgtcactga ccgcctggcc   1200
atccagtttg gcaactacaa aaagtagagg cagctgcagc caccgcgggg cctcagtggg   1260
ggtctctggg gaacacagcc agacatcctg atggggaggc agagccagga agctaagcca   1320
gggcccagct gcgtccaacc cagccccca cctcaggtcc ctgaccccag ctcgatgccc    1380
catcaccgcc tctccctggc tcccaagggt gcaggtgggc gcaaggcccg gcccccatca   1440
catgttccct tggcctcaga gctgccctg ctctcccacc acagccaccc agaggcaccc    1500
catgaagctt ttttctcgtt cactcccaaa cccaagtgtc caaagctcca gtcctaggag   1560
aacagtccct gggtcagcag ccaggaggcg gtccataaga atggggacag tgggctctgc   1620
cagggctgcc gcacctgtcc agaacaacat gttctgttcc tcctcctcat gcatttccag   1680
ccttg                                                             1685

<210> SEQ ID NO 8
<211> LENGTH: 1104
<212> TYPE: DNA
<213> ORGANISM: Homo sapiens

<400> SEQUENCE: 8
atgtggcccc tgtggcgcct cgtgtctctg caggccctga gccaggccct gccctttgag     60
cagagaggct tctgggactt caccctggac gatgggccat tcatgatgaa cgatgaggaa    120
gcttcgggcg ctgacacctc aggcgtcctg gacccggact ctgtcacacc cacctacagc    180
gccatgtgtc ctttcggctg ccactgccac ctgcgggtgg ttcagtgctc cgacctgggt    240
ctgaagtctg tgcccaaaga gatctccct gacaccacgc tgctggacct gcagaacaac    300
gacatctccg agctccgcaa ggatgacttc aagggtctcc agcacctcta cgccctcgtc    360
ctggtgaaca caagatctc caagatccat gagaaggcct tcagcccact gcggaagctg    420
cagaagctct acatctccaa gaaccacctg gtggagatcc cgcccaacct acccagctcc    480
ctggtggagc tccgcatcca cgacaaccgc atccgcaagg tgcccaaggg agtgttcagc    540
gggctccgga acatgaactg catcgagatg ggcgggaacc cactgagaaa cagtggcttt    600
gaacctggag ccttcgatgg cctgaagctc aactacctgc gcatctcaga ggccaagctg    660
actggcatcc ccaaagacct ccctgagacc ctgaatgaac tccacctaga ccacaacaaa    720
atccaggcca tcgaactgga ggacctgctt cgctactcca agctgtacag gctgggccta    780
ggccacaacc agatcaggat gatcgagaac gggagcctga gcttcctgcc cacccctccgg   840 gagctccact tggacaacaa caagttggcc agggtgccct cagggctccc agacctcaag    900
```

```
ctcctccagg tggtctatct gcactccaac aacatcacca aagtgggtgt caacgacttc      960
tgtcccatgg gcttcggggt gaagcgggcc tactacaacg catcagcct cttcaacaac     1020 cccgtgccct actgggaggt gcagccggcc actttccgct gcgtcactga ccgcctggcc    1080
atccagtttg gcaactacaa aaag                                            1104
```

<210> SEQ ID NO 9
<211> LENGTH: 373
<212> TYPE: PRT
<213> ORGANISM: Homo sapiens

<400> SEQUENCE: 9

```
Met Trp Pro Leu Trp Arg Leu Val Ser Leu Ala Leu Ser Gln Ala
 1               5                  10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
 50                  55                  60

Phe Gly Tyr Cys His Cys His Leu Arg Val Val Gln Cys Ser Asp Leu
65                  70                  75                  80

Gly Leu Lys Ser Val Pro Lys Gly Ile Ser Pro Asp Thr Thr Leu Leu
                85                  90                  95

Asp Leu Gln Asn Asn Asp Ile Ser Glu Leu Arg Lys Asp Asp Phe Lys
            100                 105                 110

Gly Leu Gly Asn His Leu Tyr Ala Leu Val Leu Val Asn Asn Lys Ile
        115                 120                 125

Ser Lys Ile His Glu Lys Ala Phe Ser Pro Leu Arg Lys Leu Gln Lys
    130                 135                 140

Leu Tyr Ile Ser Lys Asn His Leu Val Glu Ile Pro Pro Asn Leu Pro
145                 150                 155                 160

Ser Ser Leu Val Glu Leu Arg Ile His Asp Asn Arg Ile Arg Lys Val
                165                 170                 175

Pro Lys Gly Val Phe Ser Gly Leu Arg Asn Met Asn Cys Ile Glu Met
            180                 185                 190

Gly Gly Asn Pro Leu Glu Asn Ser Gly Phe Glu Pro Gly Ala Phe Asp
        195                 200                 205

Gly Leu Lys Leu Asn Tyr Leu Arg Ile Ser Glu Ala Lys Leu Thr Gly
    210                 215                 220

Ile Pro Lys Asp Leu Pro Glu Thr Leu Asn Glu Leu His Leu Asp His
225                 230                 235                 240

Asn Lys Ile Gln Ala Ile Glu Leu Glu Asp Leu Leu Arg Tyr Ser Lys
                245                 250                 255

Leu Tyr Arg Leu Gly Leu Gly His Asn Gln Ile Glu Arg Met Ile Glu
            260                 265                 270

Asn Gly Ser Leu Ser Phe Leu Pro Thr Leu Arg Glu Leu His Leu Asp
        275                 280                 285

Asn Asn Lys Leu Ala Arg Val Pro Ser Gly Leu Pro Asp Leu Lys Leu
    290                 295                 300

Leu Gln Val Val Tyr Leu His Ser Asn Asn Ile Thr Lys Val Gly Val
305                 310                 315                 320

Asn Asp Phe Cys Pro Met Gly Phe Gly Val Lys Arg Ala Tyr Tyr Asn
                325                 330                 335
```

-continued

```
Gly Ile Ser Leu Phe Asn Asn Pro Val Pro Tyr Trp Glu Val Gln Pro
            340                 345                 350

Ala Thr Phe Arg Cys Val Thr Asp Arg Leu Ala Leu Leu Glu Gln Phe
        355                 360                 365

Gly Asn Tyr Lys Lys
    370

<210> SEQ ID NO 10
<211> LENGTH: 12
<212> TYPE: PRT
<213> ORGANISM: Artificial Sequence
<220> FEATURE:
<223> OTHER INFORMATION: Plasmid pQE-biglycan

<400> SEQUENCE: 10

Met Arg Gly Ser His His His His His His Gly Ser
1               5                   10

<210> SEQ ID NO 11
<211> LENGTH: 1028
<212> TYPE: PRT
<213> ORGANISM: Homo sapiens

<400> SEQUENCE: 11

Met Arg Ala Ala Arg Ala Leu Leu Pro Leu Leu Leu Gln Ala Cys Trp
1               5                   10                  15

Thr Ala Ala Gln Asp Glu Pro Glu Thr Pro Arg Ala Val Ala Phe Gln
            20                  25                  30

Asp Cys Pro Val Asp Leu Phe Phe Val Leu Asp Thr Ser Glu Ser Val
        35                  40                  45

Ala Leu Arg Leu Lys Pro Tyr Gly Ala Leu Val Asp Lys Val Lys Ser
    50                  55                  60

Phe Thr Lys Arg Phe Ile Asp Asn Leu Arg Asp Arg Tyr Tyr Arg Cys
65                  70                  75                  80

Asp Arg Asn Leu Val Trp Asn Ala Gly Ala Leu His Tyr Ser Asp Glu
                85                  90                  95

Val Glu Ile Ile Gln Gly Leu Thr Arg Met Pro Gly Gly Arg Asp Ala
            100                 105                 110

Leu Lys Ser Ser Val Asp Ala Val Lys Tyr Phe Gly Lys Gly Thr Tyr
        115                 120                 125

Thr Asp Cys Ala Ile Lys Lys Gly Leu Glu Gln Leu Leu Val Gly Gly
    130                 135                 140

Ser His Leu Lys Glu Asn Lys Tyr Leu Ile Val Val Thr Asp Gly His
145                 150                 155                 160

Pro Leu Glu Gly Tyr Lys Glu Pro Cys Gly Gly Leu Glu Asp Ala Val
                165                 170                 175

Asn Glu Ala Lys His Leu Gly Val Lys Val Phe Ser Val Ala Ile Thr
            180                 185                 190

Pro Asp His Leu Glu Pro Arg Leu Ser Ile Ile Ala Thr Asp His Thr
        195                 200                 205

Tyr Arg Arg Asn Phe Thr Ala Ala Asp Trp Gly Gln Ser Arg Asp Ala
    210                 215                 220

Glu Glu Ala Ile Ser Gln Thr Ile Asp Thr Ile Val Asp Met Ile Lys
225                 230                 235                 240

Asn Asn Val Glu Gln Val Cys Cys Ser Phe Glu Cys Gln Pro Ala Arg
                245                 250                 255

Gly Pro Pro Gly Leu Arg Gly Asp Pro Gly Phe Glu Gly Glu Arg Gly
```

```
            260                 265                 270
Lys Pro Gly Leu Pro Gly Glu Lys Gly Glu Ala Gly Asp Pro Gly Arg
            275                 280                 285
Pro Gly Asp Leu Gly Pro Val Gly Tyr Gln Gly Met Lys Gly Glu Lys
        290                 295                 300
Gly Ser Arg Gly Glu Lys Gly Ser Arg Gly Pro Lys Gly Tyr Lys Gly
305                 310                 315                 320
Glu Lys Gly Lys Arg Gly Ile Asp Gly Val Asp Gly Val Lys Gly Glu
                325                 330                 335
Met Gly Tyr Pro Gly Leu Pro Gly Cys Lys Gly Ser Pro Gly Phe Asp
            340                 345                 350
Gly Ile Gln Gly Pro Pro Gly Pro Lys Gly Asp Pro Gly Ala Phe Gly
        355                 360                 365
Leu Lys Gly Glu Lys Gly Glu Pro Gly Ala Asp Gly Glu Ala Gly Arg
    370                 375                 380
Pro Gly Ala Arg Gly Pro Ser Gly Asp Glu Gly Pro Ala Gly Glu Pro
385                 390                 395                 400
Gly Pro Pro Gly Glu Lys Gly Glu Ala Gly Asp Glu Gly Asn Pro Gly
                405                 410                 415
Pro Asp Gly Ala Pro Gly Glu Arg Gly Gly Pro Gly Glu Arg Gly Pro
            420                 425                 430
Arg Gly Thr Pro Gly Pro Arg Gly Pro Arg Gly Asp Pro Gly Glu Ala
        435                 440                 445
Gly Pro Gln Gly Asp Gln Gly Arg Glu Gly Pro Val Gly Val Pro Gly
    450                 455                 460
Asp Pro Gly Glu Ala Gly Pro Ile Gly Pro Lys Gly Tyr Arg Gly Asp
465                 470                 475                 480
Glu Gly Pro Pro Gly Ser Gly Ala Arg Gly Ala Pro Gly Pro Pro Ala
                485                 490                 495
Gly Pro Pro Gly Asp Pro Gly Leu Met Gly Glu Arg Gly Glu Asp Gly
            500                 505                 510
Pro Ala Gly Asn Gly Thr Glu Gly Phe Pro Gly Phe Pro Gly Tyr Pro
        515                 520                 525
Gly Asn Arg Gly Ala Pro Gly Ile Asn Gly Thr Lys Gly Tyr Pro Gly
    530                 535                 540
Leu Lys Gly Asp Glu Gly Glu Ala Gly Asp Pro Gly Asp Asp Asn Asn
545                 550                 555                 560
Asp Ile Ala Pro Arg Gly Val Lys Gly Ala Lys Gly Tyr Arg Gly Pro
                565                 570                 575
Glu Gly Pro Gln Gly Pro Pro Gly His Gln Gly Pro Pro Gly Pro Asp
            580                 585                 590
Glu Cys Glu Ile Leu Asp Ile Ile Met Lys Met Cys Ser Cys Cys Glu
        595                 600                 605
Cys Lys Cys Gly Pro Ile Asp Leu Leu Phe Val Leu Asp Ser Ser Glu
    610                 615                 620
Ser Ile Gly Leu Gln Asn Phe Glu Ile Ala Lys Asp Phe Val Val Lys
625                 630                 635                 640
Val Ile Asp Arg Leu Ser Arg Asp Glu Leu Val Lys Phe Glu Pro Gly
                645                 650                 655
Gln Ser Tyr Ala Gly Val Val Gln Tyr Ser His Ser Gln Met Gln Glu
            660                 665                 670
His Val Ser Leu Arg Ser Pro Ser Ile Arg Asn Val Gln Glu Leu Lys
        675                 680                 685
```

```
Glu Ala Ile Lys Ser Leu Gln Trp Met Ala Gly Gly Thr Phe Thr Gly
    690             695                 700
Glu Ala Leu Gln Tyr Thr Arg Asp Gln Leu Leu Pro Pro Ser Pro Asn
705                 710                 715                 720
Asn Arg Ile Ala Leu Val Ile Thr Asp Gly Arg Ser Asp Thr Gln Arg
        725                 730                 735
Asp Thr Thr Pro Leu Asn Val Leu Cys Ser Pro Gly Ile Gln Val Val
            740                 745                 750
Ser Val Gly Ile Lys Asp Val Phe Asp Phe Ile Pro Gly Ser Asp Gln
        755                 760                 765
Leu Asn Val Ile Ser Cys Gln Gly Leu Ala Pro Ser Gln Gly Arg Pro
    770                 775                 780
Gly Leu Ser Leu Val Lys Glu Asn Tyr Ala Glu Leu Leu Glu Asp Ala
785                 790                 795                 800
Phe Leu Lys Asn Val Thr Ala Gln Ile Cys Ile Asp Lys Lys Cys Pro
                805                 810                 815
Asp Tyr Thr Cys Pro Ile Thr Phe Ser Ser Pro Ala Asp Ile Thr Ile
            820                 825                 830
Leu Leu Asp Gly Ser Ala Ser Val Gly Ser His Asn Phe Asp Thr Thr
        835                 840                 845
Lys Arg Phe Ala Lys Arg Leu Ala Glu Arg Phe Leu Thr Ala Gly Arg
    850                 855                 860
Thr Asp Pro Ala His Asp Val Arg Val Ala Val Val Gln Tyr Ser Gly
865                 870                 875                 880
Thr Gly Gln Gln Arg Pro Glu Arg Ala Ser Leu Gln Phe Leu Gln Asn
                885                 890                 895
Tyr Thr Ala Leu Ala Ser Ala Val Asp Ala Met Asp Phe Ile Asn Asp
            900                 905                 910
Ala Thr Asp Val Asn Asp Ala Leu Gly Tyr Val Thr Arg Phe Tyr Arg
        915                 920                 925
Glu Ala Ser Ser Gly Ala Ala Lys Lys Arg Leu Leu Leu Phe Ser Asp
    930                 935                 940
Gly Asn Ser Gln Gly Ala Thr Pro Ala Ala Ile Glu Lys Ala Val Gln
945                 950                 955                 960
Glu Ala Gln Arg Ala Gly Ile Glu Ile Phe Val Val Val Gly Arg
                965                 970                 975
Gln Val Asn Glu Pro His Ile Arg Val Leu Val Thr Gly Lys Thr Ala
                980                 985                 990
Glu Tyr Asp Val Pro Tyr Gly Glu Ser His Leu Phe Arg Val Pro Ser
        995                 1000                1005
Tyr Gln Ala Leu Leu Arg Gly Val Phe His Gln Thr Val Ser Arg Lys
    1010                1015                1020
Val Ala Leu Gly
1025

<210> SEQ ID NO 12
<211> LENGTH: 1009
<212> TYPE: PRT
<213> ORGANISM: Homo sapiens

<400> SEQUENCE: 12

Gln Asp Glu Pro Glu Thr Pro Arg Ala Val Ala Phe Gln Asp Cys Pro
1               5                   10                  15
Val Asp Leu Phe Phe Val Leu Asp Thr Ser Glu Ser Val Ala Leu Arg
```

-continued

```
                20                  25                  30
Leu Lys Pro Tyr Gly Ala Leu Val Asp Lys Val Lys Ser Phe Thr Lys
            35                  40                  45
Arg Phe Ile Asp Asn Leu Arg Asp Arg Tyr Tyr Arg Cys Asp Arg Asn
 50                  55                  60
Leu Val Trp Asn Ala Gly Leu His Tyr Ser Asp Glu Val Glu Ile
 65                  70                  75                  80
Ile Gln Gly Leu Thr Arg Met Pro Gly Gly Arg Asp Ala Leu Lys Ser
                85                  90                  95
Ser Val Asp Ala Val Lys Tyr Phe Gly Lys Gly Thr Tyr Thr Asp Cys
            100                 105                 110
Ala Ile Lys Lys Gly Leu Glu Gln Leu Leu Val Gly Ser His Leu
            115                 120                 125
Lys Glu Asn Lys Tyr Leu Ile Val Val Thr Asp Gly His Pro Leu Glu
            130                 135                 140
Gly Tyr Lys Glu Pro Cys Gly Gly Leu Glu Asp Ala Val Asn Glu Ala
145                 150                 155                 160
Lys His Leu Gly Val Lys Val Phe Ser Val Ala Ile Thr Pro Asp His
                165                 170                 175
Leu Glu Pro Arg Leu Ser Ile Ile Ala Thr Asp His Thr Tyr Arg Arg
            180                 185                 190
Asn Phe Thr Ala Ala Asp Trp Gly Gln Ser Arg Asp Ala Glu Glu Ala
            195                 200                 205
Ile Ser Gln Thr Ile Asp Thr Ile Val Asp Met Ile Lys Asn Asn Val
            210                 215                 220
Glu Gln Val Cys Cys Ser Phe Glu Cys Gln Pro Ala Arg Gly Pro Pro
225                 230                 235                 240
Gly Leu Arg Gly Asp Pro Gly Phe Glu Gly Arg Gly Lys Pro Gly
                245                 250                 255
Leu Pro Gly Glu Lys Gly Glu Ala Gly Asp Pro Gly Arg Pro Gly Asp
                260                 265                 270
Leu Gly Pro Val Gly Tyr Gln Gly Met Lys Gly Glu Lys Gly Ser Arg
            275                 280                 285
Gly Glu Lys Gly Ser Arg Gly Pro Lys Gly Tyr Lys Gly Glu Lys Gly
            290                 295                 300
Lys Arg Gly Ile Asp Gly Val Asp Gly Val Lys Gly Glu Met Gly Tyr
305                 310                 315                 320
Pro Gly Leu Pro Gly Cys Lys Gly Ser Pro Gly Phe Asp Gly Ile Gln
                325                 330                 335
Gly Pro Pro Gly Pro Lys Gly Asp Pro Gly Ala Phe Gly Leu Lys Gly
                340                 345                 350
Glu Lys Gly Glu Pro Gly Ala Asp Gly Glu Ala Gly Arg Pro Gly Ala
            355                 360                 365
Arg Gly Pro Ser Gly Asp Glu Gly Pro Ala Gly Pro Gly Pro Pro
            370                 375                 380
Gly Glu Lys Gly Glu Ala Gly Asp Glu Gly Asn Pro Gly Pro Asp Gly
385                 390                 395                 400
Ala Pro Gly Glu Arg Gly Gly Pro Gly Glu Arg Gly Pro Arg Gly Thr
                405                 410                 415
Pro Gly Pro Arg Gly Pro Arg Gly Asp Pro Gly Glu Ala Gly Pro Gln
            420                 425                 430
Gly Asp Gln Gly Arg Glu Gly Pro Val Gly Val Pro Gly Asp Pro Gly
            435                 440                 445
```

-continued

```
Glu Ala Gly Pro Ile Gly Pro Lys Gly Tyr Arg Gly Asp Glu Gly Pro
    450                 455                 460
Pro Gly Ser Glu Gly Ala Arg Gly Ala Pro Gly Pro Ala Gly Pro Pro
465                 470                 475                 480
Gly Asp Pro Gly Leu Met Gly Glu Arg Gly Glu Asp Gly Pro Ala Gly
                485                 490                 495
Asn Gly Thr Glu Gly Phe Pro Gly Phe Pro Gly Tyr Pro Gly Asn Arg
            500                 505                 510
Gly Ala Pro Gly Ile Asn Gly Thr Lys Gly Tyr Pro Gly Leu Lys Gly
        515                 520                 525
Asp Glu Gly Glu Ala Gly Asp Pro Gly Asp Asp Asn Asp Ile Ala
    530                 535                 540
Pro Arg Gly Val Lys Gly Ala Lys Gly Tyr Arg Gly Pro Glu Gly Pro
545                 550                 555                 560
Gln Gly Pro Pro Gly His Gln Gly Pro Pro Gly Pro Asp Glu Cys Glu
                565                 570                 575
Ile Leu Asp Ile Ile Met Lys Met Cys Ser Cys Cys Glu Cys Lys Cys
            580                 585                 590
Gly Pro Ile Asp Leu Leu Phe Val Leu Asp Ser Ser Glu Ser Ile Gly
        595                 600                 605
Leu Gln Asn Phe Glu Ile Ala Lys Asp Phe Val Val Lys Val Ile Asp
    610                 615                 620
Arg Leu Ser Arg Asp Glu Leu Val Lys Phe Glu Pro Gly Gln Ser Tyr
625                 630                 635                 640
Ala Gly Val Val Gln Tyr Ser His Ser Gln Met Gln Glu His Val Ser
                645                 650                 655
Leu Arg Ser Pro Ser Ile Arg Asn Val Gln Glu Leu Lys Glu Ala Ile
            660                 665                 670
Lys Ser Leu Gln Trp Met Ala Gly Gly Thr Phe Thr Gly Glu Ala Leu
        675                 680                 685
Gln Tyr Thr Arg Asp Gln Leu Leu Pro Pro Ser Pro Asn Asn Arg Ile
    690                 695                 700
Ala Leu Val Ile Thr Asp Gly Arg Ser Asp Thr Gln Arg Asp Thr Thr
705                 710                 715                 720
Pro Leu Asn Val Leu Cys Ser Pro Gly Ile Gln Val Val Ser Val Gly
                725                 730                 735
Ile Lys Asp Val Phe Asp Phe Ile Pro Gly Ser Asp Gln Leu Asn Val
            740                 745                 750
Ile Ser Cys Gln Gly Leu Ala Pro Ser Gln Gly Arg Pro Gly Leu Ser
        755                 760                 765
Leu Val Lys Glu Asn Tyr Ala Glu Leu Leu Glu Asp Ala Phe Leu Lys
    770                 775                 780
Asn Val Thr Ala Gln Ile Cys Ile Asp Lys Lys Cys Pro Asp Tyr Thr
785                 790                 795                 800
Cys Pro Ile Thr Phe Ser Ser Pro Ala Asp Ile Thr Ile Leu Leu Asp
                805                 810                 815
Gly Ser Ala Ser Val Gly Ser His Asn Phe Asp Thr Thr Lys Arg Phe
            820                 825                 830
Ala Lys Arg Leu Ala Glu Arg Phe Leu Thr Ala Gly Arg Thr Asp Pro
        835                 840                 845
Ala His Asp Val Arg Val Ala Val Val Gln Tyr Ser Gly Thr Gly Gln
    850                 855                 860
```

-continued

```
Gln Arg Pro Glu Arg Ala Ser Leu Gln Phe Leu Gln Asn Tyr Thr Ala
865                 870                 875                 880

Leu Ala Ser Ala Val Asp Ala Met Asp Phe Ile Asn Asp Ala Thr Asp
            885                 890                 895

Val Asn Asp Ala Leu Gly Tyr Val Thr Arg Phe Tyr Arg Glu Ala Ser
        900                 905                 910

Ser Gly Ala Ala Lys Arg Leu Leu Leu Phe Ser Asp Gly Asn Ser
        915                 920                 925

Gln Gly Ala Thr Pro Ala Ala Ile Glu Lys Ala Val Gln Glu Ala Gln
    930                 935                 940

Arg Ala Gly Ile Glu Ile Phe Val Val Val Gly Arg Gln Val Asn
945                 950                 955                 960

Glu Pro His Ile Arg Val Leu Val Thr Gly Lys Thr Ala Glu Tyr Asp
                965                 970                 975

Val Pro Tyr Gly Glu Ser His Leu Phe Arg Val Pro Ser Tyr Gln Ala
            980                 985                 990

Leu Leu Arg Gly Val Phe His Gln Thr Val Ser Arg Lys Val Ala Leu
        995                1000                1005

Gly
```

<210> SEQ ID NO 13
<211> LENGTH: 1019
<212> TYPE: PRT
<213> ORGANISM: Homo sapiens

<400> SEQUENCE: 13

```
Met Leu Gln Gly Thr Cys Ser Val Leu Leu Leu Trp Gly Ile Leu Gly
1               5                   10                  15

Ala Ile Gln Ala Gln Gln Gln Glu Val Ile Ser Pro Asp Thr Thr Glu
                20                  25                  30

Arg Asn Asn Asn Cys Pro Glu Lys Thr Asp Cys Pro Ile His Val Tyr
            35                  40                  45

Phe Val Leu Asp Thr Ser Glu Ser Val Thr Met Gln Ser Pro Thr Asp
        50                  55                  60

Ile Leu Leu Phe His Met Lys Gln Phe Val Pro Gln Phe Ile Ser Gln
65                  70                  75                  80

Leu Gln Asn Glu Phe Tyr Leu Asp Gln Val Ala Leu Ser Trp Arg Tyr
                85                  90                  95

Gly Gly Leu His Phe Ser Asp Gln Val Glu Val Phe Ser Pro Pro Gly
            100                 105                 110

Ser Asp Arg Ala Ser Phe Ile Lys Asn Leu Gln Gly Ile Ser Ser Phe
        115                 120                 125

Arg Arg Gly Thr Phe Thr Asp Cys Ala Leu Ala Asn Met Thr Glu Gln
    130                 135                 140

Ile Arg Gln Asp Arg Ser Lys Gly Thr Val His Phe Ala Val Val Ile
145                 150                 155                 160

Thr Asp Gly His Val Thr Gly Ser Pro Cys Gly Gly Ile Lys Leu Gln
                165                 170                 175

Ala Glu Arg Ala Arg Glu Glu Gly Ile Arg Leu Phe Ala Val Ala Pro
            180                 185                 190

Asn Gln Asn Leu Lys Glu Gln Gly Leu Arg Asp Ile Ala Ser Thr Pro
        195                 200                 205

His Glu Leu Tyr Arg Asn Asp Tyr Ala Thr Met Leu Pro Asp Ser Thr
    210                 215                 220
```

-continued

```
Glu Ile Asn Gln Asp Thr Ile Asn Arg Ile Ile Lys Val Met Lys His
225                 230                 235                 240

Glu Ala Tyr Gly Glu Cys Tyr Lys Val Ser Cys Leu Glu Ile Pro Gly
            245                 250                 255

Pro Ser Gly Pro Lys Gly Tyr Arg Gly Gln Lys Gly Ala Lys Gly Asn
        260                 265                 270

Met Gly Glu Pro Gly Glu Pro Gly Gln Lys Gly Arg Gln Gly Asp Pro
    275                 280                 285

Gly Ile Glu Gly Pro Ile Gly Phe Pro Gly Pro Lys Gly Val Pro Gly
290                 295                 300

Phe Lys Gly Glu Lys Gly Glu Phe Gly Ala Asp Gly Arg Lys Gly Ala
305                 310                 315                 320

Pro Gly Leu Ala Gly Lys Asn Gly Thr Asp Gly Gln Lys Gly Lys Leu
            325                 330                 335

Gly Arg Ile Gly Pro Pro Gly Cys Lys Gly Asp Pro Gly Asn Arg Gly
        340                 345                 350

Pro Asp Gly Tyr Pro Gly Glu Ala Gly Ser Pro Gly Glu Arg Gly Asp
    355                 360                 365

Gln Gly Gly Lys Gly Asp Pro Gly Arg Pro Gly Arg Arg Gly Pro Pro
370                 375                 380

Gly Glu Ile Gly Ala Lys Gly Ser Lys Gly Tyr Gln Gly Asn Asn Gly
385                 390                 395                 400

Ala Pro Gly Ser Pro Gly Val Lys Gly Ala Lys Gly Pro Gly Pro
            405                 410                 415

Arg Gly Pro Lys Gly Glu Pro Gly Arg Arg Gly Asp Pro Gly Thr Lys
        420                 425                 430

Gly Ser Pro Gly Ser Asp Gly Pro Lys Gly Glu Lys Gly Asp Pro Gly
    435                 440                 445

Pro Glu Gly Pro Arg Gly Leu Ala Gly Glu Val Gly Asn Lys Gly Ala
450                 455                 460

Lys Gly Asp Arg Gly Leu Pro Gly Pro Arg Gly Pro Gln Gly Ala Leu
465                 470                 475                 480

Gly Glu Pro Gly Lys Gln Gly Ser Arg Gly Asp Pro Gly Asp Ala Gly
            485                 490                 495

Pro Arg Gly Asp Ser Gly Gln Pro Gly Pro Lys Gly Asp Pro Gly Arg
        500                 505                 510

Pro Gly Phe Ser Tyr Pro Gly Pro Arg Gly Ala Pro Gly Glu Lys Gly
    515                 520                 525

Glu Pro Gly Pro Arg Gly Pro Glu Gly Gly Arg Gly Asp Phe Gly Leu
530                 535                 540

Lys Gly Glu Pro Gly Arg Lys Gly Glu Lys Gly Glu Pro Ala Asp Pro
545                 550                 555                 560

Gly Pro Pro Gly Glu Pro Gly Pro Arg Gly Pro Arg Gly Val Pro Gly
            565                 570                 575

Pro Glu Gly Glu Pro Gly Pro Pro Gly Asp Pro Gly Leu Thr Glu Cys
        580                 585                 590

Asp Val Met Thr Tyr Val Arg Glu Thr Cys Gly Cys Cys Asp Cys Glu
    595                 600                 605

Lys Arg Cys Gly Ala Leu Asp Val Val Phe Val Ile Asp Ser Ser Glu
610                 615                 620

Ser Ile Gly Tyr Thr Asn Phe Thr Leu Glu Lys Asn Phe Val Ile Asn
625                 630                 635                 640

Val Val Asn Arg Leu Gly Ala Ile Ala Lys Asp Pro Lys Ser Glu Thr
```

645                 650                 655
Gly Thr Arg Val Gly Val Val Gln Tyr Ser His Glu Gly Thr Phe Glu
                660                 665                 670

Ala Ile Gln Leu Asp Asp Glu His Ile Asp Ser Leu Ser Ser Phe Lys
            675                 680                 685

Glu Ala Val Lys Asn Leu Glu Trp Ile Ala Gly Thr Trp Thr Pro
        690                 695                 700

Ser Ala Leu Lys Phe Ala Tyr Asp Arg Leu Ile Lys Glu Ser Arg Arg
705                 710                 715                 720

Gln Lys Thr Arg Val Phe Ala Val Val Ile Thr Asp Gly Arg His Asp
                725                 730                 735

Pro Arg Asp Asp Asp Leu Asn Leu Arg Ala Leu Cys Asp Arg Asp Val
                740                 745                 750

Thr Val Thr Ala Ile Gly Ile Gly Asp Met Phe His Glu Lys His Glu
            755                 760                 765

Ser Glu Asn Leu Tyr Ser Ile Ala Cys Asp Lys Pro Gln Gln Val Arg
        770                 775                 780

Asn Met Thr Leu Phe Ser Asp Leu Val Ala Glu Lys Phe Ile Asp Asp
785                 790                 795                 800

Met Glu Asp Val Leu Cys Pro Asp Pro Gln Ile Val Cys Pro Asp Leu
                805                 810                 815

Pro Cys Gln Thr Glu Leu Ser Val Ala Gln Cys Thr Gln Arg Pro Val
                820                 825                 830

Asp Ile Val Phe Leu Leu Asp Gly Ser Glu Arg Leu Gly Glu Gln Asn
            835                 840                 845

Phe His Lys Ala Arg Arg Phe Val Glu Gln Val Ala Arg Arg Leu Thr
        850                 855                 860

Leu Ala Arg Arg Asp Asp Asp Pro Leu Asn Ala Arg Val Ala Leu Leu
865                 870                 875                 880

Gln Phe Gly Gly Pro Gly Glu Gln Gln Val Ala Phe Pro Leu Ser His
                885                 890                 895

Asn Leu Thr Ala Ile His Glu Ala Leu Glu Thr Thr Gln Tyr Leu Asn
            900                 905                 910

Ser Phe Ser His Val Gly Ala Gly Val Val His Ala Ile Asn Ala Ile
        915                 920                 925

Val Arg Ser Pro Arg Gly Gly Ala Arg Arg His Ala Glu Leu Ser Phe
930                 935                 940

Val Phe Leu Thr Asp Gly Val Thr Gly Asn Asp Ser Leu His Glu Ser
945                 950                 955                 960

Ala His Ser Met Arg Asn Glu Asn Val Val Pro Thr Val Leu Ala Leu
                965                 970                 975

Gly Ser Asp Val Asp Met Asp Val Leu Thr Thr Leu Ser Leu Gly Asp
            980                 985                 990

Arg Ala Ala Val Phe His Glu Lys Asp Tyr Asp Ser Leu Ala Gln Pro
        995                 1000                1005

Gly Phe Phe Asp Arg Phe Ile Arg Trp Ile Cys
    1010                1015

<210> SEQ ID NO 14
<211> LENGTH: 999
<212> TYPE: PRT
<213> ORGANISM: Homo sapiens

<400> SEQUENCE: 14

-continued

```
Gln Gln Gln Glu Val Ile Ser Pro Asp Thr Thr Glu Arg Asn Asn Asn
 1               5                  10                  15

Cys Pro Glu Lys Thr Asp Cys Pro Ile His Val Tyr Phe Val Leu Asp
             20                  25                  30

Thr Ser Glu Ser Val Thr Met Gln Ser Pro Thr Asp Ile Leu Leu Phe
         35                  40                  45

His Met Lys Gln Phe Val Pro Gln Phe Ile Ser Gln Leu Gln Asn Glu
 50                  55                  60

Phe Tyr Leu Asp Gln Val Ala Leu Ser Trp Arg Tyr Gly Gly Leu His
 65                  70                  75                  80

Phe Ser Asp Gln Val Glu Val Phe Ser Pro Gly Ser Asp Arg Ala
                 85                  90                  95

Ser Phe Ile Lys Asn Leu Gln Gly Ile Ser Ser Phe Arg Arg Gly Thr
                100                 105                 110

Phe Thr Asp Cys Ala Leu Ala Asn Met Thr Glu Gln Ile Arg Gln Asp
             115                 120                 125

Arg Ser Lys Gly Thr Val His Phe Ala Val Val Ile Thr Asp Gly His
         130                 135                 140

Val Thr Gly Ser Pro Cys Gly Gly Ile Lys Leu Gln Ala Glu Arg Ala
145                 150                 155                 160

Arg Glu Glu Gly Ile Arg Leu Phe Ala Val Ala Pro Asn Gln Asn Leu
                 165                 170                 175

Lys Glu Gln Gly Leu Arg Asp Ile Ala Ser Thr Pro His Glu Leu Tyr
             180                 185                 190

Arg Asn Asp Tyr Ala Thr Met Leu Pro Asp Ser Thr Glu Ile Asn Gln
         195                 200                 205

Asp Thr Ile Asn Arg Ile Ile Lys Val Met Lys His Glu Ala Tyr Gly
210                 215                 220

Glu Cys Tyr Lys Val Ser Cys Leu Glu Ile Pro Gly Pro Ser Gly Pro
225                 230                 235                 240

Lys Gly Tyr Arg Gly Gln Lys Gly Ala Lys Gly Asn Met Gly Glu Pro
                 245                 250                 255

Gly Glu Pro Gly Gln Lys Gly Arg Gln Gly Asp Pro Gly Ile Glu Gly
             260                 265                 270

Pro Ile Gly Phe Pro Gly Pro Lys Gly Val Pro Gly Phe Lys Gly Glu
         275                 280                 285

Lys Gly Glu Phe Gly Ala Asp Gly Arg Lys Gly Ala Pro Gly Leu Ala
         290                 295                 300

Gly Lys Asn Gly Thr Asp Gly Gln Lys Gly Lys Leu Gly Arg Ile Gly
305                 310                 315                 320

Pro Pro Gly Cys Lys Gly Asp Pro Gly Asn Arg Gly Pro Asp Gly Tyr
             325                 330                 335

Pro Gly Glu Ala Gly Ser Pro Gly Glu Arg Gly Asp Gln Gly Gly Lys
         340                 345                 350

Gly Asp Pro Gly Arg Pro Gly Arg Arg Gly Pro Pro Gly Glu Ile Gly
         355                 360                 365

Ala Lys Gly Ser Lys Gly Tyr Gln Gly Asn Asn Gly Ala Pro Gly Ser
         370                 375                 380

Pro Gly Val Lys Gly Ala Lys Gly Gly Pro Gly Pro Arg Gly Pro Lys
385                 390                 395                 400

Gly Glu Pro Gly Arg Arg Gly Asp Pro Gly Thr Lys Gly Ser Pro Gly
                 405                 410                 415

Ser Asp Gly Pro Lys Gly Glu Lys Gly Asp Pro Gly Pro Glu Gly Pro
```

-continued

```
                420                 425                 430
Arg Gly Leu Ala Gly Glu Val Gly Asn Lys Ala Lys Gly Asp Arg
            435                 440                 445
Gly Leu Pro Gly Pro Arg Gly Pro Gln Gly Ala Leu Gly Glu Pro Gly
450                 455                 460
Lys Gln Gly Ser Arg Gly Asp Pro Gly Asp Ala Gly Pro Arg Gly Asp
465                 470                 475                 480
Ser Gly Gln Pro Gly Pro Lys Gly Asp Pro Gly Arg Pro Gly Phe Ser
                        485                 490                 495
Tyr Pro Gly Pro Arg Gly Ala Pro Gly Glu Lys Gly Glu Pro Gly Pro
                500                 505                 510
Arg Gly Pro Glu Gly Gly Arg Gly Asp Phe Gly Leu Lys Gly Glu Pro
                515                 520                 525
Gly Arg Lys Gly Glu Lys Gly Glu Pro Ala Asp Pro Gly Pro Pro Gly
            530                 535                 540
Glu Pro Gly Pro Arg Gly Pro Arg Gly Val Pro Gly Pro Glu Gly Glu
545                 550                 555                 560
Pro Gly Pro Pro Gly Asp Pro Gly Leu Thr Glu Cys Asp Val Met Thr
                        565                 570                 575
Tyr Val Arg Glu Thr Cys Gly Cys Cys Asp Cys Glu Lys Arg Cys Gly
                580                 585                 590
Ala Leu Asp Val Val Phe Val Ile Asp Ser Ser Glu Ser Ile Gly Tyr
            595                 600                 605
Thr Asn Phe Thr Leu Glu Lys Asn Phe Val Asn Val Val Asn Arg
610                 615                 620
Leu Gly Ala Ile Ala Lys Asp Pro Lys Ser Glu Thr Gly Thr Arg Val
625                 630                 635                 640
Gly Val Val Gln Tyr Ser His Glu Gly Thr Phe Glu Ala Ile Gln Leu
                        645                 650                 655
Asp Asp Glu His Ile Asp Ser Leu Ser Ser Phe Lys Glu Ala Val Lys
                660                 665                 670
Asn Leu Glu Trp Ile Ala Gly Gly Thr Trp Thr Pro Ser Ala Leu Lys
                675                 680                 685
Phe Ala Tyr Asp Arg Leu Ile Lys Glu Ser Arg Arg Gln Lys Thr Arg
            690                 695                 700
Val Phe Ala Val Val Ile Thr Asp Gly Arg His Asp Pro Arg Asp Asp
705                 710                 715                 720
Asp Leu Asn Leu Arg Ala Leu Cys Asp Arg Asp Val Thr Val Thr Ala
                        725                 730                 735
Ile Gly Ile Gly Asp Met Phe His Glu Lys His Glu Ser Glu Asn Leu
                740                 745                 750
Tyr Ser Ile Ala Cys Asp Lys Pro Gln Gln Val Arg Asn Met Thr Leu
                755                 760                 765
Phe Ser Asp Leu Val Ala Glu Lys Phe Ile Asp Asp Met Glu Asp Val
            770                 775                 780
Leu Cys Pro Asp Pro Gln Ile Val Cys Pro Asp Leu Pro Cys Gln Thr
785                 790                 795                 800
Glu Leu Ser Val Ala Gln Cys Thr Gln Arg Pro Val Asp Ile Val Phe
                        805                 810                 815
Leu Leu Asp Gly Ser Glu Arg Leu Gly Glu Gln Asn Phe His Lys Ala
                820                 825                 830
Arg Arg Phe Val Glu Gln Val Ala Arg Arg Leu Thr Leu Ala Arg Arg
            835                 840                 845
```

```
Asp Asp Asp Pro Leu Asn Ala Arg Val Ala Leu Leu Gln Phe Gly Gly
        850                 855                 860

Pro Gly Glu Gln Gln Val Ala Phe Pro Leu Ser His Asn Leu Thr Ala
865                 870                 875                 880

Ile His Glu Ala Leu Glu Thr Thr Gln Tyr Leu Asn Ser Phe Ser His
                885                 890                 895

Val Gly Ala Gly Val Val His Ala Ile Asn Ala Ile Val Arg Ser Pro
                900                 905                 910

Arg Gly Gly Ala Arg Arg His Ala Glu Leu Ser Phe Val Phe Leu Thr
            915                 920                 925

Asp Gly Val Thr Gly Asn Asp Ser Leu His Glu Ser Ala His Ser Met
        930                 935                 940

Arg Asn Glu Asn Val Val Pro Thr Val Leu Ala Leu Gly Ser Asp Val
945                 950                 955                 960

Asp Met Asp Val Leu Thr Thr Leu Ser Leu Gly Asp Arg Ala Ala Val
                965                 970                 975

Phe His Glu Lys Asp Tyr Asp Ser Leu Ala Gln Pro Gly Phe Phe Asp
                980                 985                 990

Arg Phe Ile Arg Trp Ile Cys
            995

<210> SEQ ID NO 15
<211> LENGTH: 3176
<212> TYPE: PRT
<213> ORGANISM: Homo sapiens

<400> SEQUENCE: 15

Met Arg Lys His Arg His Leu Pro Leu Val Ala Val Phe Cys Leu Phe
1               5                   10                  15

Leu Ser Gly Phe Pro Thr Thr His Ala Gln Gln Gln Gln Ala Asp Val
                20                  25                  30

Lys Asn Gly Ala Ala Ala Asp Ile Ile Phe Leu Val Asp Ser Ser Trp
            35                  40                  45

Thr Ile Gly Glu Glu His Phe Gln Leu Val Arg Glu Phe Leu Tyr Asp
        50                  55                  60

Val Val Lys Ser Leu Ala Val Gly Glu Asn Asp Phe His Phe Ala Leu
65                  70                  75                  80

Val Gln Phe Asn Gly Asn Pro His Thr Glu Phe Leu Leu Asn Thr Tyr
                85                  90                  95

Arg Thr Lys Gln Glu Val Leu Ser His Ile Ser Asn Met Ser Tyr Ile
                100                 105                 110

Gly Gly Thr Asn Gln Thr Gly Lys Gly Leu Glu Tyr Ile Met Gln Ser
            115                 120                 125

His Leu Thr Lys Ala Ala Gly Ser Arg Ala Gly Asp Gly Val Pro Gln
        130                 135                 140

Val Ile Val Val Leu Thr Asp Gly His Ser Lys Asp Gly Leu Ala Leu
145                 150                 155                 160

Pro Ser Ala Glu Leu Lys Ser Ala Asp Val Asn Val Phe Ala Ile Gly
                165                 170                 175

Val Glu Asp Ala Asp Glu Gly Ala Leu Lys Glu Ile Ala Ser Glu Pro
                180                 185                 190

Leu Asn Met His Met Phe Asn Leu Glu Asn Phe Thr Ser Leu His Asp
            195                 200                 205

Ile Val Gly Asn Leu Val Ser Cys Val His Ser Ser Val Ser Pro Glu
```

-continued

```
            210                 215                 220
Arg Ala Gly Asp Thr Glu Thr Leu Lys Asp Ile Thr Ala Gln Asp Ser
225                 230                 235                 240

Ala Asp Ile Ile Phe Leu Ile Asp Gly Ser Asn Asn Thr Gly Ser Val
                245                 250                 255

Asn Phe Ala Val Ile Leu Asp Phe Leu Val Asn Leu Leu Glu Lys Leu
                260                 265                 270

Pro Ile Gly Thr Gln Gln Ile Arg Val Gly Val Val Gln Phe Ser Asp
                275                 280                 285

Glu Pro Arg Thr Met Phe Ser Leu Asp Thr Tyr Ser Thr Lys Ala Gln
290                 295                 300

Val Leu Gly Ala Val Lys Ala Leu Gly Phe Ala Gly Gly Glu Leu Ala
305                 310                 315                 320

Asn Ile Gly Leu Ala Leu Asp Phe Val Glu Asn His Phe Thr Arg
                325                 330                 335

Ala Gly Gly Ser Arg Val Glu Glu Gly Val Pro Gln Val Leu Val Leu
                340                 345                 350

Ile Ser Ala Gly Pro Ser Ser Asp Glu Ile Arg Tyr Gly Val Val Ala
                355                 360                 365

Leu Lys Gln Ala Ser Val Phe Ser Phe Gly Leu Gly Ala Gln Ala Ala
                370                 375                 380

Ser Arg Ala Glu Leu Gln His Ile Ala Thr Asp Asp Asn Leu Val Phe
385                 390                 395                 400

Thr Val Pro Glu Phe Arg Ser Phe Gly Asp Leu Gln Glu Lys Leu Leu
                405                 410                 415

Pro Tyr Ile Val Gly Val Ala Gln Arg His Ile Val Leu Lys Pro Pro
                420                 425                 430

Thr Ile Val Thr Gln Val Ile Glu Val Asn Lys Arg Asp Ile Val Phe
                435                 440                 445

Leu Val Asp Gly Ser Ser Ala Leu Gly Leu Ala Asn Phe Asn Ala Ile
                450                 455                 460

Arg Asp Phe Ile Ala Lys Val Ile Gln Arg Leu Glu Ile Gly Gln Asp
465                 470                 475                 480

Leu Ile Gln Val Ala Val Ala Gln Tyr Ala Asp Thr Val Arg Pro Glu
                485                 490                 495

Phe Tyr Phe Asn Thr His Pro Thr Lys Arg Glu Val Ile Thr Ala Val
                500                 505                 510

Arg Lys Met Lys Pro Leu Asp Gly Ser Ala Leu Tyr Thr Gly Ser Ala
                515                 520                 525

Leu Asp Phe Val Arg Asn Asn Leu Phe Thr Ser Ser Ala Gly Tyr Arg
530                 535                 540

Ala Ala Glu Gly Ile Pro Lys Leu Leu Val Leu Ile Thr Gly Gly Lys
545                 550                 555                 560

Ser Leu Asp Glu Ile Ser Gln Pro Ala Gln Glu Leu Lys Arg Ser Ser
                565                 570                 575

Ile Met Ala Phe Ala Ile Gly Asn Lys Gly Ala Asp Gln Ala Glu Leu
                580                 585                 590

Glu Glu Ile Ala Phe Asp Ser Ser Leu Val Phe Ile Pro Ala Glu Phe
                595                 600                 605

Arg Ala Ala Pro Leu Gln Gly Met Leu Pro Gly Leu Leu Ala Pro Leu
610                 615                 620

Arg Thr Leu Ser Gly Thr Pro Glu Val His Ser Asn Lys Arg Asp Ile
625                 630                 635                 640
```

```
Ile Phe Leu Leu Asp Gly Ser Ala Asn Val Gly Lys Thr Asn Phe Pro
            645                 650                 655

Tyr Val Arg Asp Phe Val Met Asn Leu Val Asn Ser Leu Asp Ile Gly
            660                 665                 670

Asn Asp Asn Ile Arg Val Gly Leu Val Gln Phe Ser Asp Thr Pro Val
            675                 680                 685

Thr Glu Phe Ser Leu Asn Thr Tyr Gln Thr Lys Ser Asp Ile Leu Gly
            690                 695                 700

His Leu Arg Gln Leu Gln Leu Gln Gly Gly Ser Gly Leu Asn Thr Gly
705                 710                 715                 720

Ser Ala Leu Ser Tyr Val Tyr Ala Asn His Phe Thr Glu Ala Gly Gly
                725                 730                 735

Ser Arg Ile Arg Glu His Val Pro Gln Leu Leu Leu Leu Leu Thr Ala
                740                 745                 750

Gly Gln Ser Glu Asp Ser Tyr Leu Gln Ala Ala Asn Ala Leu Thr Arg
                755                 760                 765

Ala Gly Ile Leu Thr Phe Cys Val Gly Ala Ser Gln Ala Asn Lys Ala
                770                 775                 780

Glu Leu Glu Gln Ile Ala Phe Asn Pro Ser Leu Val Tyr Leu Met Asp
785                 790                 795                 800

Asp Phe Ser Ser Leu Pro Ala Leu Pro Gln Gln Leu Ile Gln Pro Leu
                805                 810                 815

Thr Thr Tyr Val Ser Gly Gly Val Glu Glu Val Pro Leu Ala Gln Pro
                820                 825                 830

Glu Ser Lys Arg Asp Ile Leu Phe Leu Phe Asp Gly Ser Ala Asn Leu
                835                 840                 845

Val Gly Gln Phe Pro Val Val Arg Asp Phe Leu Tyr Lys Ile Ile Asp
                850                 855                 860

Glu Leu Asn Val Lys Pro Glu Gly Thr Arg Ile Ala Val Ala Gln Tyr
865                 870                 875                 880

Ser Asp Asp Val Lys Val Glu Ser Arg Phe Asp Glu His Gln Ser Lys
                885                 890                 895

Pro Glu Ile Leu Asn Leu Val Lys Arg Met Lys Ile Lys Thr Gly Lys
                900                 905                 910

Ala Leu Asn Leu Gly Tyr Ala Leu Asp Tyr Ala Gln Arg Tyr Ile Phe
                915                 920                 925

Val Lys Ser Ala Gly Ser Arg Ile Glu Asp Gly Val Leu Gln Phe Leu
                930                 935                 940

Val Leu Leu Val Ala Gly Arg Ser Ser Asp Arg Val Asp Gly Pro Ala
945                 950                 955                 960

Ser Asn Leu Lys Gln Ser Gly Val Val Pro Phe Ile Phe Gln Ala Lys
                965                 970                 975

Asn Ala Asp Pro Ala Glu Leu Glu Gln Ile Val Leu Ser Pro Ala Phe
                980                 985                 990

Ile Leu Ala Ala Glu Ser Leu Pro Lys Ile Gly Asp Leu His Pro Gln
                995                 1000                1005

Ile Val Asn Leu Leu Lys Ser Val His Asn Gly Ala Pro Ala Pro Val
                1010                1015                1020

Ser Gly Glu Lys Asp Val Val Phe Leu Leu Asp Gly Ser Glu Gly Val
1025                1030                1035                1040

Arg Ser Gly Phe Pro Leu Leu Lys Glu Phe Val Gln Arg Val Val Glu
                1045                1050                1055
```

```
Ser Leu Asp Val Gly Gln Asp Arg Val Arg Val Ala Val Val Gln Tyr
            1060                1065                1070

Ser Asp Arg Thr Arg Pro Glu Phe Tyr Leu Asn Ser Tyr Met Asn Lys
            1075                1080                1085

Gln Asp Val Val Asn Ala Val Arg Gln Leu Thr Leu Leu Gly Gly Pro
            1090                1095                1100

Thr Pro Asn Thr Gly Ala Ala Leu Glu Phe Val Leu Arg Asn Ile Leu
1105                1110                1115                1120

Val Ser Ser Ala Gly Ser Arg Ile Thr Glu Gly Val Pro Gln Leu Leu
            1125                1130                1135

Ile Val Leu Thr Ala Asp Arg Ser Gly Asp Asp Val Arg Asn Pro Ser
            1140                1145                1150

Val Val Val Lys Arg Gly Gly Ala Val Pro Ile Gly Ile Gly Ile Gly
            1155                1160                1165

Asn Ala Asp Ile Thr Glu Met Gln Thr Ile Ser Phe Ile Pro Asp Phe
            1170                1175                1180

Ala Val Ala Ile Pro Thr Phe Arg Gln Leu Gly Thr Val Gln Gln Val
1185                1190                1195                1200

Ile Ser Glu Arg Val Thr Gln Leu Thr Arg Glu Glu Leu Ser Arg Leu
            1205                1210                1215

Gln Pro Val Leu Gln Pro Leu Pro Ser Pro Gly Val Gly Gly Lys Arg
            1220                1225                1230

Asp Val Val Phe Leu Ile Asp Gly Ser Gln Ser Ala Gly Pro Glu Phe
            1235                1240                1245

Gln Tyr Val Arg Thr Leu Ile Glu Arg Leu Val Asp Tyr Leu Asp Val
            1250                1255                1260

Gly Phe Asp Thr Thr Arg Val Ala Val Ile Gln Phe Ser Asp Asp Pro
1265                1270                1275                1280

Lys Ala Glu Phe Leu Leu Asn Ala His Ser Ser Lys Asp Glu Val Gln
            1285                1290                1295

Asn Ala Val Gln Arg Leu Arg Pro Lys Gly Gly Arg Gln Ile Asn Val
            1300                1305                1310

Gly Asn Ala Leu Glu Tyr Val Ser Arg Asn Ile Phe Lys Arg Pro Leu
            1315                1320                1325

Gly Ser Arg Ile Glu Glu Gly Val Pro Gln Phe Leu Val Leu Ile Ser
            1330                1335                1340

Ser Gly Lys Ser Asp Asp Glu Val Val Pro Ala Val Glu Leu Lys
1345                1350                1355                1360

Gln Phe Gly Val Ala Pro Phe Thr Ile Ala Arg Asn Ala Asp Gln Glu
            1365                1370                1375

Glu Leu Val Lys Ile Ser Leu Ser Pro Glu Tyr Val Phe Ser Val Ser
            1380                1385                1390

Thr Phe Arg Glu Leu Pro Ser Leu Glu Gln Lys Leu Leu Thr Pro Ile
            1395                1400                1405

Thr Thr Leu Thr Ser Glu Gln Ile Gln Lys Leu Leu Ala Ser Thr Arg
            1410                1415                1420

Tyr Pro Pro Pro Ala Val Glu Ser Asp Ala Ala Asp Ile Val Phe Leu
1425                1430                1435                1440

Ile Asp Ser Ser Glu Gly Val Arg Pro Asp Gly Phe Ala His Ile Arg
            1445                1450                1455

Asp Phe Val Ser Arg Ile Val Arg Arg Leu Asn Ile Gly Pro Ser Lys
            1460                1465                1470

Val Arg Val Gly Val Val Gln Phe Ser Asn Asp Val Phe Pro Glu Phe
```

-continued

```
                1475                1480                1485
Tyr Leu Lys Thr Tyr Arg Ser Gln Ala Pro Val Leu Asp Ala Ile Arg
        1490                1495                1500
Arg Leu Arg Leu Arg Gly Gly Ser Pro Leu Asn Thr Gly Lys Ala Leu
1505                1510                1515                1520
Glu Phe Val Ala Arg Asn Leu Phe Val Lys Ser Ala Gly Ser Arg Ile
                1525                1530                1535
Glu Asp Gly Val Pro Gln His Leu Val Leu Val Leu Gly Gly Lys Ser
        1540                1545                1550
Gln Asp Asp Val Ser Arg Phe Ala Gln Val Ile Arg Ser Ser Gly Ile
        1555                1560                1565
Val Ser Leu Gly Val Gly Asp Arg Asn Ile Asp Arg Thr Glu Leu Gln
        1570                1575                1580
Thr Ile Thr Asn Asp Pro Arg Leu Val Phe Thr Val Arg Glu Phe Arg
1585                1590                1595                1600
Glu Leu Pro Asn Ile Glu Glu Arg Ile Met Asn Ser Phe Gly Pro Ser
                1605                1610                1615
Ala Ala Thr Pro Ala Pro Pro Gly Val Asp Thr Pro Pro Ser Arg
        1620                1625                1630
Pro Glu Lys Lys Lys Ala Asp Ile Val Phe Leu Leu Asp Gly Ser Ile
        1635                1640                1645
Asn Phe Arg Arg Asp Ser Phe Gln Glu Val Leu Arg Phe Val Ser Glu
        1650                1655                1660
Ile Val Asp Thr Val Tyr Glu Asp Gly Asp Ser Ile Gln Val Gly Leu
1665                1670                1675                1680
Val Gln Tyr Asn Ser Asp Pro Thr Asp Glu Phe Phe Leu Lys Asp Phe
                1685                1690                1695
Ser Thr Lys Arg Gln Ile Ile Asp Ala Ile Asn Lys Val Val Tyr Lys
                1700                1705                1710
Gly Gly Arg His Ala Asn Thr Lys Val Gly Leu Glu His Leu Arg Val
        1715                1720                1725
Asn His Phe Val Pro Glu Ala Gly Ser Arg Leu Asp Gln Arg Val Pro
        1730                1735                1740
Gln Ile Ala Phe Val Ile Thr Gly Gly Lys Ser Val Glu Asp Ala Gln
1745                1750                1755                1760
Asp Val Ser Leu Ala Leu Thr Gln Arg Gly Val Lys Val Phe Ala Val
                1765                1770                1775
Gly Val Arg Asn Ile Asp Ser Glu Glu Val Gly Lys Ile Ala Ser Asn
                1780                1785                1790
Ser Ala Thr Ala Phe Arg Val Gly Asn Val Gln Glu Leu Ser Glu Leu
        1795                1800                1805
Ser Glu Gln Val Leu Glu Thr Leu His Asp Ala Met His Glu Thr Leu
        1810                1815                1820
Cys Pro Gly Val Thr Asp Ala Ala Lys Ala Cys Asn Leu Asp Val Ile
1825                1830                1835                1840
Leu Gly Phe Asp Gly Ser Arg Asp Gln Asn Val Phe Val Ala Gln Lys
                1845                1850                1855
Gly Phe Glu Ser Lys Val Asp Ala Ile Leu Asn Arg Ile Ser Gln Met
                1860                1865                1870
His Arg Val Ser Cys Ser Gly Gly Arg Ser Pro Thr Val Arg Val Ser
        1875                1880                1885
Val Val Ala Asn Thr Pro Ser Gly Pro Val Glu Ala Phe Asp Phe Asp
        1890                1895                1900
```

-continued

```
Glu Tyr Gln Pro Glu Met Leu Glu Lys Phe Arg Asn Met Arg Ser Gln
1905                1910                1915                1920

His Pro Tyr Val Leu Thr Glu Asp Thr Leu Lys Val Tyr Leu Asn Lys
            1925                1930                1935

Phe Arg Gln Ser Ser Pro Asp Ser Val Lys Val Val Ile His Phe Thr
        1940                1945                1950

Asp Gly Ala Asp Gly Asp Leu Ala Asp Leu His Arg Ala Ser Glu Asn
    1955                1960                1965

Leu Arg Gln Glu Gly Val Arg Ala Leu Ile Leu Val Gly Leu Glu Arg
1970                1975                1980

Val Val Asn Leu Glu Arg Leu Met His Leu Glu Phe Gly Arg Gly Phe
1985                1990                1995                2000

Met Tyr Asp Arg Pro Leu Arg Leu Asn Leu Leu Asp Leu Asp Tyr Glu
                2005                2010                2015

Leu Ala Glu Gln Leu Asp Asn Ile Ala Glu Lys Ala Cys Cys Gly Val
            2020                2025                2030

Pro Cys Lys Cys Ser Gly Gln Arg Gly Asp Arg Gly Pro Ile Gly Ser
        2035                2040                2045

Ile Gly Pro Lys Gly Ile Pro Gly Glu Asp Gly Tyr Arg Gly Tyr Pro
    2050                2055                2060

Gly Asp Glu Gly Pro Gly Glu Arg Gly Pro Pro Gly Val Asn Gly
2065                2070                2075                2080

Thr Gln Gly Phe Gln Gly Cys Pro Gly Gln Arg Gly Val Lys Gly Ser
                2085                2090                2095

Arg Gly Phe Pro Gly Glu Lys Gly Glu Val Gly Glu Ile Gly Leu Asp
            2100                2105                2110

Gly Leu Asp Gly Glu Asp Gly Asp Lys Gly Leu Pro Gly Ser Ser Gly
        2115                2120                2125

Glu Lys Gly Asn Pro Gly Arg Arg Gly Asp Lys Gly Pro Arg Gly Glu
    2130                2135                2140

Lys Gly Glu Arg Gly Asp Val Gly Ile Arg Gly Asp Pro Gly Asn Pro
2145                2150                2155                2160

Gly Gln Asp Ser Gln Glu Arg Gly Pro Lys Gly Glu Thr Gly Asp Leu
                2165                2170                2175

Gly Pro Met Gly Val Pro Gly Arg Asp Gly Val Pro Gly Gly Pro Gly
            2180                2185                2190

Glu Thr Gly Lys Asn Gly Gly Phe Gly Arg Arg Gly Pro Pro Gly Ala
        2195                2200                2205

Lys Gly Asn Lys Gly Gly Pro Gly Gln Pro Gly Phe Glu Gly Glu Gln
    2210                2215                2220

Gly Thr Arg Gly Ala Gln Gly Pro Ala Gly Pro Ala Gly Pro Pro Gly
2225                2230                2235                2240

Leu Ile Gly Glu Gln Gly Ile Ser Gly Pro Arg Gly Ser Gly Gly Ala
                2245                2250                2255

Arg Gly Ala Pro Gly Glu Arg Gly Arg Thr Gly Pro Leu Gly Arg Lys
            2260                2265                2270

Gly Glu Pro Gly Glu Pro Gly Pro Lys Gly Gly Ile Gly Asn Pro Gly
        2275                2280                2285

Pro Arg Gly Glu Thr Gly Asp Asp Gly Arg Asp Gly Val Gly Ser Glu
    2290                2295                2300

Gly Arg Arg Gly Lys Lys Gly Glu Arg Gly Phe Pro Gly Tyr Pro Gly
2305                2310                2315                2320
```

-continued

```
Pro Lys Gly Asn Pro Gly Glu Pro Gly Leu Asn Gly Thr Thr Gly Pro
            2325                2330                2335
Lys Gly Ile Arg Gly Arg Arg Gly Asn Ser Gly Pro Pro Gly Ile Val
            2340                2345                2350
Gly Gln Lys Gly Arg Pro Gly Tyr Pro Gly Pro Ala Gly Pro Arg Gly
            2355                2360                2365
Asn Arg Gly Asp Ser Ile Asp Gln Cys Ala Leu Ile Gln Ser Ile Lys
            2370                2375                2380
Asp Lys Cys Pro Cys Cys Tyr Gly Pro Leu Glu Cys Pro Val Phe Pro
2385                2390                2395                2400
Thr Glu Leu Ala Phe Ala Leu Asp Thr Ser Glu Gly Val Asn Gln Asp
            2405                2410                2415
Thr Phe Gly Arg Met Arg Asp Val Val Leu Ser Ile Val Asn Val Leu
            2420                2425                2430
Thr Ile Ala Glu Ser Asn Cys Pro Thr Gly Ala Arg Val Ala Val Val
            2435                2440                2445
Thr Tyr Asn Asn Glu Val Thr Thr Glu Ile Arg Phe Ala Asp Ser Lys
            2450                2455                2460
Arg Lys Ser Val Leu Leu Asp Lys Ile Lys Asn Leu Gln Val Ala Leu
2465                2470                2475                2480
Thr Ser Lys Gln Gln Ser Leu Glu Thr Ala Met Ser Phe Val Ala Arg
            2485                2490                2495
Asn Thr Phe Lys Arg Val Arg Asn Gly Phe Leu Met Arg Lys Val Ala
            2500                2505                2510
Val Phe Phe Ser Asn Thr Pro Thr Arg Ala Ser Pro Gln Leu Arg Glu
            2515                2520                2525
Ala Val Leu Lys Leu Ser Asp Ala Gly Ile Thr Pro Leu Phe Leu Thr
            2530                2535                2540
Arg Gln Glu Asp Arg Gln Leu Ile Asn Ala Leu Gln Ile Asn Asn Thr
2545                2550                2555                2560
Ala Val Gly His Ala Leu Val Leu Pro Ala Gly Arg Asp Leu Thr Asp
            2565                2570                2575
Phe Leu Glu Asn Val Leu Thr Cys His Val Cys Leu Asp Ile Cys Asn
            2580                2585                2590
Ile Asp Pro Ser Cys Gly Phe Gly Ser Trp Arg Pro Ser Phe Arg Asp
            2595                2600                2605
Arg Arg Ala Ala Gly Ser Asp Val Asp Ile Asp Met Ala Phe Ile Leu
            2610                2615                2620
Asp Ser Ala Glu Thr Thr Thr Leu Phe Gln Phe Asn Glu Met Lys Lys
2625                2630                2635                2640
Tyr Ile Ala Tyr Leu Val Arg Gln Leu Asp Met Ser Asp Pro Lys
            2645                2650                2655
Ala Ser Gln His Phe Ala Arg Val Ala Val Val Gln His Ala Pro Ser
            2660                2665                2670
Glu Ser Val Asp Asn Ala Ser Met Pro Pro Val Lys Val Glu Phe Ser
            2675                2680                2685
Leu Thr Asp Tyr Gly Ser Lys Glu Lys Leu Val Asp Phe Leu Ser Arg
            2690                2695                2700
Gly Met Thr Gln Leu Gln Gly Thr Arg Ala Leu Gly Ser Ala Ile Glu
2705                2710                2715                2720
Tyr Thr Ile Glu Asn Val Phe Glu Ser Ala Pro Asn Pro Arg Asp Leu
            2725                2730                2735
Lys Ile Val Val Leu Met Leu Thr Gly Glu Val Pro Glu Gln Gln Leu
```

-continued

```
                2740                2745                2750
Glu Glu Ala Gln Arg Val Ile Leu Gln Ala Lys Cys Lys Gly Tyr Phe
        2755                2760                2765
Phe Val Val Leu Gly Ile Gly Arg Lys Val Asn Ile Lys Glu Val Tyr
    2770                2775                2780
Thr Phe Ala Ser Glu Pro Asn Asp Val Phe Lys Leu Val Asp Lys
2785                2790                2795                2800
Ser Thr Glu Leu Asn Glu Pro Leu Met Arg Phe Gly Arg Leu Leu
        2805                2810                2815
Pro Ser Phe Val Ser Ser Glu Asn Ala Phe Tyr Leu Ser Pro Asp Ile
        2820                2825                2830
Arg Lys Gln Cys Asp Trp Phe Gln Gly Asp Gln Pro Thr Lys Asn Leu
        2835                2840                2845
Val Lys Phe Gly His Lys Gln Val Asn Val Pro Asn Asn Val Thr Ser
        2850                2855                2860
Ser Pro Thr Ser Asn Pro Val Thr Thr Lys Pro Val Thr Thr Thr
2865                2870                2875                2880
Lys Pro Val Thr Thr Thr Lys Pro Val Thr Thr Thr Lys Pro
            2885                2890                2895
Val Thr Ile Ile Asn Gln Pro Ser Val Lys Pro Ala Ala Lys Pro
            2900                2905                2910
Ala Pro Ala Lys Pro Val Ala Ala Lys Pro Val Ala Thr Lys Thr Ala
        2915                2920                2925
Thr Val Arg Pro Pro Val Ala Val Lys Pro Ala Thr Ala Ala Lys Pro
        2930                2935                2940
Val Ala Ala Lys Pro Ala Ala Val Arg Pro Pro Ala Ala Ala Lys
2945                2950                2955                2960
Pro Val Ala Thr Lys Pro Glu Val Pro Arg Pro Gln Ala Ala Lys Pro
            2965                2970                2975
Ala Ala Thr Lys Pro Ala Thr Thr Lys Pro Val Val Lys Met Leu Arg
        2980                2985                2990
Glu Val Gln Val Phe Glu Ile Thr Glu Asn Ser Ala Lys Leu His Trp
        2995                3000                3005
Glu Arg Pro Glu Pro Pro Gly Pro Tyr Phe Tyr Asp Leu Thr Val Thr
    3010                3015                3020
Ser Ala His Asp Gln Ser Leu Val Leu Lys Gln Asn Leu Thr Val Thr
3025                3030                3035                3040
Asp Arg Val Ile Gly Gly Leu Leu Ala Gly Gln Thr Tyr His Val Ala
            3045                3050                3055
Val Val Cys Tyr Leu Arg Ser Gln Val Arg Ala Thr Tyr His Gly Ser
        3060                3065                3070
Phe Ser Thr Lys Lys Ser Gln Pro Pro Pro Gln Pro Ala Arg Ser
    3075                3080                3085
Ala Ser Ser Ser Thr Ile Asn Leu Met Val Ser Thr Glu Pro Leu Ala
        3090                3095                3100
Leu Thr Glu Thr Asp Ile Cys Lys Leu Pro Lys Asp Glu Gly Thr Cys
3105                3110                3115                3120
Arg Asp Phe Ile Leu Lys Trp Tyr Tyr Asp Pro Asn Thr Lys Ser Cys
            3125                3130                3135
Ala Arg Phe Trp Tyr Gly Gly Cys Gly Gly Asn Glu Asn Lys Phe Gly
            3140                3145                3150
Ser Gln Lys Glu Cys Glu Lys Val Cys Ala Pro Val Leu Ala Lys Pro
        3155                3160                3165
```

```
Gly Val Ile Ser Val Met Gly Thr
    3170            3175

<210> SEQ ID NO 16
<211> LENGTH: 3151
<212> TYPE: PRT
<213> ORGANISM: Homo sapiens

<400> SEQUENCE: 16

Gln Gln Gln Gln Ala Asp Val Lys Asn Gly Ala Ala Asp Ile Ile
  1               5                  10                  15

Phe Leu Val Asp Ser Ser Trp Thr Ile Gly Glu Glu His Phe Gln Leu
                 20                  25                  30

Val Arg Glu Phe Leu Tyr Asp Val Val Lys Ser Leu Ala Val Gly Glu
             35                  40                  45

Asn Asp Phe His Phe Ala Leu Val Gln Phe Asn Gly Asn Pro His Thr
 50                  55                  60

Glu Phe Leu Leu Asn Thr Tyr Arg Thr Lys Gln Glu Val Leu Ser His
 65                  70                  75                  80

Ile Ser Asn Met Ser Tyr Ile Gly Gly Thr Asn Gln Thr Gly Lys Gly
                 85                  90                  95

Leu Glu Tyr Ile Met Gln Ser His Leu Thr Lys Ala Ala Gly Ser Arg
            100                 105                 110

Ala Gly Asp Gly Val Pro Gln Val Ile Val Leu Thr Asp Gly His
            115                 120                 125

Ser Lys Asp Gly Leu Ala Leu Pro Ser Ala Glu Leu Lys Ser Ala Asp
        130                 135                 140

Val Asn Val Phe Ala Ile Gly Val Glu Asp Ala Asp Glu Gly Ala Leu
145                 150                 155                 160

Lys Glu Ile Ala Ser Glu Pro Leu Asn Met His Met Phe Asn Leu Glu
                165                 170                 175

Asn Phe Thr Ser Leu His Asp Ile Val Gly Asn Leu Val Ser Cys Val
            180                 185                 190

His Ser Ser Val Ser Pro Glu Arg Ala Gly Asp Thr Glu Thr Leu Lys
        195                 200                 205

Asp Ile Thr Ala Gln Asp Ser Ala Asp Ile Ile Phe Leu Ile Asp Gly
    210                 215                 220

Ser Asn Asn Thr Gly Ser Val Asn Phe Ala Val Ile Leu Asp Phe Leu
225                 230                 235                 240

Val Asn Leu Leu Glu Lys Leu Pro Ile Gly Thr Gln Gln Ile Arg Val
                245                 250                 255

Gly Val Val Gln Phe Ser Asp Glu Pro Arg Thr Met Phe Ser Leu Asp
            260                 265                 270

Thr Tyr Ser Thr Lys Ala Gln Val Leu Gly Ala Val Lys Ala Leu Gly
        275                 280                 285

Phe Ala Gly Gly Glu Leu Ala Asn Ile Gly Leu Ala Leu Asp Phe Val
    290                 295                 300

Val Glu Asn His Phe Thr Arg Ala Gly Gly Ser Arg Val Glu Glu Gly
305                 310                 315                 320

Val Pro Gln Val Leu Val Leu Ile Ser Ala Gly Pro Ser Ser Asp Glu
                325                 330                 335

Ile Arg Tyr Gly Val Val Ala Leu Lys Gln Ala Ser Val Phe Ser Phe
            340                 345                 350

Gly Leu Gly Ala Gln Ala Ala Ser Arg Ala Glu Leu Gln His Ile Ala
```

```
                355                 360                 365
Thr Asp Asp Asn Leu Val Phe Thr Val Pro Glu Phe Arg Ser Phe Gly
    370                 375                 380

Asp Leu Gln Glu Lys Leu Leu Pro Tyr Ile Val Gly Val Ala Gln Arg
385                 390                 395                 400

His Ile Val Leu Lys Pro Pro Thr Ile Val Thr Gln Val Ile Glu Val
                405                 410                 415

Asn Lys Arg Asp Ile Val Phe Leu Val Asp Gly Ser Ser Ala Leu Gly
            420                 425                 430

Leu Ala Asn Phe Asn Ala Ile Arg Asp Phe Ile Ala Lys Val Ile Gln
        435                 440                 445

Arg Leu Glu Ile Gly Gln Asp Leu Ile Gln Val Ala Val Ala Gln Tyr
    450                 455                 460

Ala Asp Thr Val Arg Pro Glu Phe Tyr Phe Asn Thr His Pro Thr Lys
465                 470                 475                 480

Arg Glu Val Ile Thr Ala Val Arg Lys Met Lys Pro Leu Asp Gly Ser
                485                 490                 495

Ala Leu Tyr Thr Gly Ser Ala Leu Asp Phe Val Arg Asn Asn Leu Phe
            500                 505                 510

Thr Ser Ser Ala Gly Tyr Arg Ala Ala Glu Gly Ile Pro Lys Leu Leu
        515                 520                 525

Val Leu Ile Thr Gly Gly Lys Ser Leu Asp Glu Ile Ser Gln Pro Ala
    530                 535                 540

Gln Glu Leu Lys Arg Ser Ser Ile Met Ala Phe Ala Ile Gly Asn Lys
545                 550                 555                 560

Gly Ala Asp Gln Ala Glu Leu Glu Glu Ile Ala Phe Asp Ser Ser Leu
                565                 570                 575

Val Phe Ile Pro Ala Glu Phe Arg Ala Ala Pro Leu Gln Gly Met Leu
            580                 585                 590

Pro Gly Leu Leu Ala Pro Leu Arg Thr Leu Ser Gly Thr Pro Glu Val
        595                 600                 605

His Ser Asn Lys Arg Asp Ile Ile Phe Leu Leu Asp Gly Ser Ala Asn
    610                 615                 620

Val Gly Lys Thr Asn Phe Pro Tyr Val Arg Asp Phe Val Met Asn Leu
625                 630                 635                 640

Val Asn Ser Leu Asp Ile Gly Asn Asp Asn Ile Arg Val Gly Leu Val
                645                 650                 655

Gln Phe Ser Asp Thr Pro Val Thr Glu Phe Ser Leu Asn Thr Tyr Gln
            660                 665                 670

Thr Lys Ser Asp Ile Leu Gly His Leu Arg Gln Leu Gln Leu Gln Gly
        675                 680                 685

Gly Ser Gly Leu Asn Thr Gly Ser Ala Leu Ser Tyr Val Tyr Ala Asn
    690                 695                 700

His Phe Thr Glu Ala Gly Gly Ser Arg Ile Arg Glu His Val Pro Gln
705                 710                 715                 720

Leu Leu Leu Leu Leu Thr Ala Gly Gln Ser Glu Asp Ser Tyr Leu Gln
                725                 730                 735

Ala Ala Asn Ala Leu Thr Arg Ala Gly Ile Leu Thr Phe Cys Val Gly
            740                 745                 750

Ala Ser Gln Ala Asn Lys Ala Glu Leu Glu Gln Ile Ala Phe Asn Pro
        755                 760                 765

Ser Leu Val Tyr Leu Met Asp Asp Phe Ser Ser Leu Pro Ala Leu Pro
    770                 775                 780
```

-continued

```
Gln Gln Leu Ile Gln Pro Leu Thr Thr Tyr Val Ser Gly Gly Val Glu
785                 790                 795                 800

Glu Val Pro Leu Ala Gln Pro Glu Ser Lys Arg Asp Ile Leu Phe Leu
                805                 810                 815

Phe Asp Gly Ser Ala Asn Leu Val Gly Gln Phe Pro Val Val Arg Asp
                820                 825                 830

Phe Leu Tyr Lys Ile Ile Asp Glu Leu Asn Val Lys Pro Glu Gly Thr
                835                 840                 845

Arg Ile Ala Val Ala Gln Tyr Ser Asp Asp Val Lys Val Glu Ser Arg
850                 855                 860

Phe Asp Glu His Gln Ser Lys Pro Glu Ile Leu Asn Leu Val Lys Arg
865                 870                 875                 880

Met Lys Ile Lys Thr Gly Lys Ala Leu Asn Leu Gly Tyr Ala Leu Asp
                885                 890                 895

Tyr Ala Gln Arg Tyr Ile Phe Val Lys Ser Ala Gly Ser Arg Ile Glu
                900                 905                 910

Asp Gly Val Leu Gln Phe Leu Val Leu Leu Val Ala Gly Arg Ser Ser
                915                 920                 925

Asp Arg Val Asp Gly Pro Ala Ser Asn Leu Lys Gln Ser Gly Val Val
930                 935                 940

Pro Phe Ile Phe Gln Ala Lys Asn Ala Asp Pro Ala Glu Leu Glu Gln
945                 950                 955                 960

Ile Val Leu Ser Pro Ala Phe Ile Leu Ala Ala Glu Ser Leu Pro Lys
                965                 970                 975

Ile Gly Asp Leu His Pro Gln Ile Val Asn Leu Leu Lys Ser Val His
                980                 985                 990

Asn Gly Ala Pro Ala Pro Val Ser Gly Glu Lys Asp Val Val Phe Leu
                995                 1000                1005

Leu Asp Gly Ser Glu Gly Val Arg Ser Gly Phe Pro Leu Leu Lys Glu
        1010                1015                1020

Phe Val Gln Arg Val Val Glu Ser Leu Asp Val Gly Gln Asp Arg Val
1025                1030                1035                1040

Arg Val Ala Val Val Gln Tyr Ser Asp Arg Thr Arg Pro Glu Phe Tyr
                1045                1050                1055

Leu Asn Ser Tyr Met Asn Lys Gln Asp Val Val Asn Ala Val Arg Gln
                1060                1065                1070

Leu Thr Leu Leu Gly Gly Pro Thr Pro Asn Thr Gly Ala Ala Leu Glu
        1075                1080                1085

Phe Val Leu Arg Asn Ile Leu Val Ser Ser Ala Gly Ser Arg Ile Thr
        1090                1095                1100

Glu Gly Val Pro Gln Leu Leu Ile Val Leu Thr Ala Asp Arg Ser Gly
1105                1110                1115                1120

Asp Asp Val Arg Asn Pro Ser Val Val Lys Arg Gly Gly Ala Val
                1125                1130                1135

Pro Ile Gly Ile Gly Ile Gly Asn Ala Asp Ile Thr Glu Met Gln Thr
                1140                1145                1150

Ile Ser Phe Ile Pro Asp Phe Ala Val Ala Ile Pro Thr Phe Arg Gln
        1155                1160                1165

Leu Gly Thr Val Gln Gln Val Ile Ser Glu Arg Val Thr Gln Leu Thr
        1170                1175                1180

Arg Glu Glu Leu Ser Arg Leu Gln Pro Val Leu Gln Pro Leu Pro Ser
1185                1190                1195                1200
```

-continued

```
Pro Gly Val Gly Gly Lys Arg Asp Val Val Phe Leu Ile Asp Gly Ser
            1205                1210                1215
Gln Ser Ala Gly Pro Glu Phe Gln Tyr Val Arg Thr Leu Ile Glu Arg
            1220                1225                1230
Leu Val Asp Tyr Leu Asp Val Gly Phe Asp Thr Thr Arg Val Ala Val
            1235                1240                1245
Ile Gln Phe Ser Asp Asp Pro Lys Ala Glu Phe Leu Leu Asn Ala His
            1250                1255                1260
Ser Ser Lys Asp Glu Val Gln Asn Ala Val Gln Arg Leu Arg Pro Lys
1265                1270                1275                1280
Gly Gly Arg Gln Ile Asn Val Gly Asn Ala Leu Glu Tyr Val Ser Arg
            1285                1290                1295
Asn Ile Phe Lys Arg Pro Leu Gly Ser Arg Ile Glu Glu Gly Val Pro
            1300                1305                1310
Gln Phe Leu Val Leu Ile Ser Ser Gly Lys Ser Asp Asp Glu Val Val
            1315                1320                1325
Val Pro Ala Val Glu Leu Lys Gln Phe Gly Val Ala Pro Phe Thr Ile
            1330                1335                1340
Ala Arg Asn Ala Asp Gln Glu Glu Leu Val Lys Ile Ser Leu Ser Pro
1345                1350                1355                1360
Glu Tyr Val Phe Ser Val Ser Thr Phe Arg Glu Leu Pro Ser Leu Glu
            1365                1370                1375
Gln Lys Leu Leu Thr Pro Ile Thr Thr Leu Thr Ser Glu Gln Ile Gln
            1380                1385                1390
Lys Leu Leu Ala Ser Thr Arg Tyr Pro Pro Ala Val Glu Ser Asp
            1395                1400                1405
Ala Ala Asp Ile Val Phe Leu Ile Asp Ser Ser Glu Gly Val Arg Pro
            1410                1415                1420
Asp Gly Phe Ala His Ile Arg Asp Phe Val Ser Arg Ile Val Arg Arg
1425                1430                1435                1440
Leu Asn Ile Gly Pro Ser Lys Val Arg Val Gly Val Val Gln Phe Ser
            1445                1450                1455
Asn Asp Val Phe Pro Glu Phe Tyr Leu Lys Thr Tyr Arg Ser Gln Ala
            1460                1465                1470
Pro Val Leu Asp Ala Ile Arg Arg Leu Arg Leu Arg Gly Gly Ser Pro
            1475                1480                1485
Leu Asn Thr Gly Lys Ala Leu Glu Phe Val Ala Arg Asn Leu Phe Val
            1490                1495                1500
Lys Ser Ala Gly Ser Arg Ile Glu Asp Gly Val Pro Gln His Leu Val
1505                1510                1515                1520
Leu Val Leu Gly Gly Lys Ser Gln Asp Val Ser Arg Phe Ala Gln
            1525                1530                1535
Val Ile Arg Ser Ser Gly Ile Val Ser Leu Gly Val Gly Asp Arg Asn
            1540                1545                1550
Ile Asp Arg Thr Glu Leu Gln Thr Ile Thr Asn Asp Pro Arg Leu Val
            1555                1560                1565
Phe Thr Val Arg Glu Phe Arg Glu Leu Pro Asn Ile Glu Glu Arg Ile
            1570                1575                1580
Met Asn Ser Phe Gly Pro Ser Ala Ala Thr Pro Ala Pro Pro Gly Val
1585                1590                1595                1600
Asp Thr Pro Pro Pro Ser Arg Pro Glu Lys Lys Lys Ala Asp Ile Val
            1605                1610                1615
Phe Leu Leu Asp Gly Ser Ile Asn Phe Arg Arg Asp Ser Phe Gln Glu
```

-continued

```
            1620                1625                1630
Val Leu Arg Phe Val Ser Glu Ile Val Asp Thr Val Tyr Glu Asp Gly
        1635                1640                1645
Asp Ser Ile Gln Val Gly Leu Val Gln Tyr Asn Ser Asp Pro Thr Asp
        1650                1655                1660
Glu Phe Phe Leu Lys Asp Phe Ser Thr Lys Arg Gln Ile Ile Asp Ala
1665                1670                1675                1680
Ile Asn Lys Val Val Tyr Lys Gly Gly Arg His Ala Asn Thr Lys Val
                1685                1690                1695
Gly Leu Glu His Leu Arg Val Asn His Phe Val Pro Glu Ala Gly Ser
        1700                1705                1710
Arg Leu Asp Gln Arg Val Pro Gln Ile Ala Phe Val Ile Thr Gly Gly
        1715                1720                1725
Lys Ser Val Glu Asp Ala Gln Asp Val Ser Leu Ala Leu Thr Gln Arg
        1730                1735                1740
Gly Val Lys Val Phe Ala Val Gly Val Arg Asn Ile Asp Ser Glu Glu
1745                1750                1755                1760
Val Gly Lys Ile Ala Ser Asn Ser Ala Thr Ala Phe Arg Val Gly Asn
                1765                1770                1775
Val Gln Glu Leu Ser Glu Leu Ser Glu Gln Val Leu Glu Thr Leu His
        1780                1785                1790
Asp Ala Met His Glu Thr Leu Cys Pro Gly Val Thr Asp Ala Ala Lys
        1795                1800                1805
Ala Cys Asn Leu Asp Val Ile Leu Gly Phe Asp Gly Ser Arg Asp Gln
        1810                1815                1820
Asn Val Phe Val Ala Gln Lys Gly Phe Glu Ser Lys Val Asp Ala Ile
1825                1830                1835                1840
Leu Asn Arg Ile Ser Gln Met His Arg Val Ser Cys Ser Gly Gly Arg
                1845                1850                1855
Ser Pro Thr Val Arg Val Ser Val Val Ala Asn Thr Pro Ser Gly Pro
        1860                1865                1870
Val Glu Ala Phe Asp Phe Asp Glu Tyr Gln Pro Glu Met Leu Glu Lys
        1875                1880                1885
Phe Arg Asn Met Arg Ser Gln His Pro Tyr Val Leu Thr Glu Asp Thr
        1890                1895                1900
Leu Lys Val Tyr Leu Asn Lys Phe Arg Gln Ser Ser Pro Asp Ser Val
1905                1910                1915                1920
Lys Val Val Ile His Phe Thr Asp Gly Ala Asp Gly Asp Leu Ala Asp
                1925                1930                1935
Leu His Arg Ala Ser Glu Asn Leu Arg Gln Glu Gly Val Arg Ala Leu
        1940                1945                1950
Ile Leu Val Gly Leu Glu Arg Val Val Asn Leu Glu Arg Leu Met His
        1955                1960                1965
Leu Glu Phe Gly Arg Gly Phe Met Tyr Asp Arg Pro Leu Arg Leu Asn
        1970                1975                1980
Leu Leu Asp Leu Asp Tyr Glu Leu Ala Glu Gln Leu Asp Asn Ile Ala
1985                1990                1995                2000
Glu Lys Ala Cys Cys Gly Val Pro Cys Lys Cys Ser Gly Gln Arg Gly
                2005                2010                2015
Asp Arg Gly Pro Ile Gly Ser Ile Gly Pro Lys Gly Ile Pro Gly Glu
                2020                2025                2030
Asp Gly Tyr Arg Gly Tyr Pro Gly Asp Glu Gly Pro Gly Glu Arg
                2035                2040                2045
```

-continued

```
Gly Pro Pro Gly Val Asn Gly Thr Gln Gly Phe Gln Gly Cys Pro Gly
    2050                2055                2060

Gln Arg Gly Val Lys Gly Ser Arg Gly Phe Pro Gly Glu Lys Gly Glu
2065                2070                2075                2080

Val Gly Glu Ile Gly Leu Asp Gly Leu Asp Gly Glu Asp Gly Asp Lys
            2085                2090                2095

Gly Leu Pro Gly Ser Ser Gly Glu Lys Gly Asn Pro Gly Arg Arg Gly
        2100                2105                2110

Asp Lys Gly Pro Arg Gly Glu Lys Gly Glu Arg Gly Asp Val Gly Ile
        2115                2120                2125

Arg Gly Asp Pro Gly Asn Pro Gly Gln Asp Ser Gln Glu Arg Gly Pro
    2130                2135                2140

Lys Gly Glu Thr Gly Asp Leu Gly Pro Met Gly Val Pro Gly Arg Asp
2145                2150                2155                2160

Gly Val Pro Gly Gly Pro Gly Glu Thr Gly Lys Asn Gly Gly Phe Gly
            2165                2170                2175

Arg Arg Gly Pro Pro Gly Ala Lys Gly Asn Lys Gly Pro Gly Gln
        2180                2185                2190

Pro Gly Phe Glu Gly Glu Gln Gly Thr Arg Gly Ala Gln Gly Pro Ala
        2195                2200                2205

Gly Pro Ala Gly Pro Pro Gly Leu Ile Gly Glu Gln Gly Ile Ser Gly
    2210                2215                2220

Pro Arg Gly Ser Gly Gly Ala Arg Gly Ala Pro Gly Glu Arg Gly Arg
2225                2230                2235                2240

Thr Gly Pro Leu Gly Arg Lys Gly Glu Pro Gly Glu Pro Gly Pro Lys
            2245                2250                2255

Gly Gly Ile Gly Asn Pro Gly Pro Arg Gly Glu Thr Gly Asp Asp Gly
        2260                2265                2270

Arg Asp Gly Val Gly Ser Glu Gly Arg Arg Gly Lys Lys Gly Glu Arg
        2275                2280                2285

Gly Phe Pro Gly Tyr Pro Gly Pro Lys Gly Asn Pro Gly Glu Pro Gly
    2290                2295                2300

Leu Asn Gly Thr Thr Gly Pro Lys Gly Ile Arg Gly Arg Arg Gly Asn
2305                2310                2315                2320

Ser Gly Pro Pro Gly Ile Val Gly Gln Lys Gly Arg Pro Gly Tyr Pro
            2325                2330                2335

Gly Pro Ala Gly Pro Arg Gly Asn Arg Gly Asp Ser Ile Asp Gln Cys
        2340                2345                2350

Ala Leu Ile Gln Ser Ile Lys Asp Lys Cys Pro Cys Cys Tyr Gly Pro
        2355                2360                2365

Leu Glu Cys Pro Val Phe Pro Thr Glu Leu Ala Phe Ala Leu Asp Thr
    2370                2375                2380

Ser Glu Gly Val Asn Gln Asp Thr Phe Gly Arg Met Arg Asp Val Val
2385                2390                2395                2400

Leu Ser Ile Val Asn Val Leu Thr Ile Ala Glu Ser Asn Cys Pro Thr
            2405                2410                2415

Gly Ala Arg Val Ala Val Val Thr Tyr Asn Asn Glu Val Thr Thr Glu
        2420                2425                2430

Ile Arg Phe Ala Asp Ser Lys Arg Lys Ser Val Leu Leu Asp Lys Ile
        2435                2440                2445

Lys Asn Leu Gln Val Ala Leu Thr Ser Lys Gln Gln Ser Leu Glu Thr
    2450                2455                2460
```

-continued

```
Ala Met Ser Phe Val Ala Arg Asn Thr Phe Lys Arg Val Arg Asn Gly
2465                2470                2475                2480

Phe Leu Met Arg Lys Val Ala Val Phe Phe Ser Asn Thr Pro Thr Arg
                2485                2490                2495

Ala Ser Pro Gln Leu Arg Glu Ala Val Leu Lys Leu Ser Asp Ala Gly
                2500                2505                2510

Ile Thr Pro Leu Phe Leu Thr Arg Gln Glu Asp Arg Gln Leu Ile Asn
                2515                2520                2525

Ala Leu Gln Ile Asn Asn Thr Ala Val Gly His Ala Leu Val Leu Pro
2530                2535                2540

Ala Gly Arg Asp Leu Thr Asp Phe Leu Glu Asn Val Leu Thr Cys His
2545                2550                2555                2560

Val Cys Leu Asp Ile Cys Asn Ile Asp Pro Ser Cys Gly Phe Gly Ser
                2565                2570                2575

Trp Arg Pro Ser Phe Arg Asp Arg Arg Ala Ala Gly Ser Asp Val Asp
                2580                2585                2590

Ile Asp Met Ala Phe Ile Leu Asp Ser Ala Glu Thr Thr Thr Leu Phe
                2595                2600                2605

Gln Phe Asn Glu Met Lys Lys Tyr Ile Ala Tyr Leu Val Arg Gln Leu
2610                2615                2620

Asp Met Ser Pro Asp Pro Lys Ala Ser Gln His Phe Ala Arg Val Ala
2625                2630                2635                2640

Val Val Gln His Ala Pro Ser Glu Ser Val Asp Asn Ala Ser Met Pro
                2645                2650                2655

Pro Val Lys Val Glu Phe Ser Leu Thr Asp Tyr Gly Ser Lys Glu Lys
                2660                2665                2670

Leu Val Asp Phe Leu Ser Arg Gly Met Thr Gln Leu Gln Gly Thr Arg
                2675                2680                2685

Ala Leu Gly Ser Ala Ile Glu Tyr Thr Ile Glu Asn Val Phe Glu Ser
2690                2695                2700

Ala Pro Asn Pro Arg Asp Leu Lys Ile Val Val Leu Met Leu Thr Gly
2705                2710                2715                2720

Glu Val Pro Glu Gln Gln Leu Glu Glu Ala Gln Arg Val Ile Leu Gln
                2725                2730                2735

Ala Lys Cys Lys Gly Tyr Phe Phe Val Val Leu Gly Ile Gly Arg Lys
                2740                2745                2750

Val Asn Ile Lys Glu Val Tyr Thr Phe Ala Ser Glu Pro Asn Asp Val
                2755                2760                2765

Phe Phe Lys Leu Val Asp Lys Ser Thr Glu Leu Asn Glu Glu Pro Leu
                2770                2775                2780

Met Arg Phe Gly Arg Leu Leu Pro Ser Phe Val Ser Ser Glu Asn Ala
2785                2790                2795                2800

Phe Tyr Leu Ser Pro Asp Ile Arg Lys Gln Cys Asp Trp Phe Gln Gly
                2805                2810                2815

Asp Gln Pro Thr Lys Asn Leu Val Lys Phe Gly His Lys Gln Val Asn
                2820                2825                2830

Val Pro Asn Asn Val Thr Ser Ser Pro Thr Ser Asn Pro Val Thr Thr
                2835                2840                2845

Thr Lys Pro Val Thr Thr Thr Lys Pro Val Thr Thr Thr Thr Lys Pro
                2850                2855                2860

Val Thr Thr Thr Thr Lys Pro Val Thr Ile Ile Asn Gln Pro Ser Val
2865                2870                2875                2880

Lys Pro Ala Ala Ala Lys Pro Ala Pro Ala Lys Pro Val Ala Ala Lys
```

```
                    2885              2890              2895
Pro Val Ala Thr Lys Thr Ala Thr Val Arg Pro Val Ala Val Lys
                2900              2905              2910
Pro Ala Thr Ala Ala Lys Pro Val Ala Lys Pro Ala Ala Val Arg
                2915              2920              2925
Pro Pro Ala Ala Ala Ala Lys Pro Val Ala Thr Lys Pro Glu Val Pro
                2930              2935              2940
Arg Pro Gln Ala Ala Lys Pro Ala Ala Thr Lys Pro Ala Thr Thr Lys
2945              2950              2955              2960
Pro Val Val Lys Met Leu Arg Glu Val Gln Val Phe Glu Ile Thr Glu
                2965              2970              2975
Asn Ser Ala Lys Leu His Trp Glu Arg Pro Glu Pro Gly Pro Tyr
                2980              2985              2990
Phe Tyr Asp Leu Thr Val Thr Ser Ala His Asp Gln Ser Leu Val Leu
                2995              3000              3005
Lys Gln Asn Leu Thr Val Thr Asp Arg Val Ile Gly Gly Leu Leu Ala
                3010              3015              3020
Gly Gln Thr Tyr His Val Ala Val Val Cys Tyr Leu Arg Ser Gln Val
3025              3030              3035              3040
Arg Ala Thr Tyr His Gly Ser Phe Ser Thr Lys Lys Ser Gln Pro Pro
                3045              3050              3055
Pro Pro Gln Pro Ala Arg Ser Ala Ser Ser Ser Thr Ile Asn Leu Met
                3060              3065              3070
Val Ser Thr Glu Pro Leu Ala Leu Thr Glu Thr Asp Ile Cys Lys Leu
                3075              3080              3085
Pro Lys Asp Glu Gly Thr Cys Arg Asp Phe Ile Leu Lys Trp Tyr Tyr
                3090              3095              3100
Asp Pro Asn Thr Lys Ser Cys Ala Arg Phe Trp Tyr Gly Gly Cys Gly
3105              3110              3115              3120
Gly Asn Glu Asn Lys Phe Gly Ser Gln Lys Glu Cys Glu Lys Val Cys
                3125              3130              3135
Ala Pro Val Leu Ala Lys Pro Gly Val Ile Ser Val Met Gly Thr
                3140              3145              3150

<210> SEQ ID NO 17
<211> LENGTH: 4164
<212> TYPE: DNA
<213> ORGANISM: Homo sapiens

<400> SEQUENCE: 17
cactctggct gggagcagaa ggcagcctcg gtctctgggc ggcggcggcg gccctctctg       60
ccctggccgc gctgtgtggt gaccgcaggc ccgagacatg agggcggccc gtgctctgct      120 gccccctgctg ctgcaggcct gctggacagc cgcgcaggat gagccggaga ccccgagggc      180
cgtggccttc caggactgcc ccgtggacct gttctttgtg ctggacacct ctgagagcgt      240
ggccctgagg ctgaagccct acggggccct cgtggacaaa gtcaagtcct tcaccaagcg      300
cttcatcgac aacctgaggg acaggtacta ccgctgtgac cgaaacctgg tgtggaacgc      360
aggcgcgctg cactacagtg acgaggtgga gatcatccaa ggcctcacgc gcatgcctgg      420
cggccgcgac gcactcaaaa gcagcgtgga cgcggtcaag tactttggga agggcaccta      480
caccgactgc gctatcaaga aggggctgga gcagctcctc gtgggggggct cccacctgaa      540 ggagaataag tacctgattg tggtgaccga cggcacccc ctggagggct acaaggaacc      600
ctgtgggggg ctggaggatg ctgtgaacga ggccaagcac ctgggcgtca agtcttctc      660
```

```
ggtggccatc acacccgacc acctggagcc gcgtctgagc atcatcgcca cggaccacac    720
gtaccggcgc aacttcacgg cggctgactg gggccagagc cgcgacgcag aggaggccat    780
cagccagacc atcgacacca tcgtggacat gatcaaaaat aacgttgagc aagtgtgctg    840
ctccttcgaa tgccagcctg caagaggacc tccgggcctc cggggcgacc ccggctttga    900
gggagaacga ggcaagccgg ggctcccagg agagaaggga gaagccggag atcctggaag    960
acccggggac ctcggacctg ttgggtacca gggaatgaag ggagaaaaag ggagccgtgg   1020
ggagaagggc tccaggggac caaagggcta caagggagaa agggcaagc gtggcatcga   1080
cggggtggac ggcgtgaagg gggagatggg gtacccaggc ctgccaggct gcaagggctc   1140
gccgggtttt gacggcattc aaggaccccc tggccccaag ggagacccg cgcctttgg     1200
actgaaagga gaaaagggcg agcctggagc tgacggggag gccgggagac caggagctcg   1260
gggaccatct ggagacgagg ggccagccgg agagcctggg cccccggag agaaggaga     1320
ggcgggcgac gaggggaacc caggacctga cggtgccccc ggggagcggg gtggccctgg   1380
agagagagga ccacgggga ccccaggccc gcggggacca agaggagacc ctggtgaagc    1440
tggcccgcag ggtgatcagg gaagagaagg gcccgttggt gtccctggag acccgggcga   1500
ggctggccct atcggaccta aaggctaccg aggcgatgag ggtcccccag ggtccgaggg   1560
tgccagagga gccccaggac ctgccggacc ccctggagac ccgggctga tgggagaaag    1620
gggagaagac ggccccgctg gaaatggcac cgagggcttc cccggcttcc ccgggtatcc   1680
cgggaacagg ggcgctcccg ggataaacgg cacgaagggc tacccccggcc tcaaggggga   1740
cgagggagaa gccggggacc ccggagacga taacaacgac attgcacccc gaggagtcaa   1800
aggagcaaag gggtaccggg gtcccgaggg ccccaggga cccccaggac accaaggacc    1860
gcctgggccg gacgaatgcg agattttgga catcatcatg aaaatgtgct cttgctgtga   1920
atgcaagtgc ggccccatcg acctcctgtt cgtgctggac agctcagaga gcattggcct   1980
gcagaacttc gagattgcca aggacttcgt cgtcaaggtc atcgaccggc tgagccggga   2040
cgagctggtc aagttcgagc cagggcagtc gtacgcgggt gtggtgcagt acagccacag   2100
ccagatgcag gagcacgtga gcctgcgcag ccccagcatc cggaacgtgc aggagctcaa   2160
ggaagccatc aagagcctgc agtggatggc gggcggcacc ttcacggggg aggccctgca   2220
gtacacgcgg gaccagctgc tgccgcccag cccgaacaac cgcatcgccc tggtcatcac   2280
tgacgggcgc tcagacactc agagggacac cacaccgctc aacgtgctct gcagccccgg   2340
catccaggtg gtctccgtgg gcatcaaaga cgtgtttgac ttcatcccag gctcagacca   2400
gctcaatgtc atttcttgcc aaggcctggc accatcccag ggccggcccg gcctctcgct   2460
ggtcaaggag aactatgcag agctgctgga ggatgccttc tgaagaatg tcaccgccca   2520
gatctgcata gacaagaagt gtccagatta cacctgcccc atcacgttct cctccccggc   2580
tgacatcacc atcctgctgg acggctccgc cagcgtgggc agccacaact ttgacaccac   2640
caagcgcttc gccaagcgcc tggccgagcg cttcctcaca gcgggcagga cggacccgc    2700
ccacgacgtg cgggtggcgg tggtgcagta cagcggcacg ggcagcagc gcccagagcg    2760
ggcgtcgctg cagttcctgc agaactacac ggccctggcc agtgccgtcg atgccatgga   2820
ctttatcaac gacgccaccg acgtcaacga tgccctgggc tatgtgaccc gcttctaccg   2880
cgaggcctcg tccggcgctg ccaagaagag gctgctgctc ttctcagatg gcaactcgca   2940
gggcgccacg cccgctgcca tcgagaaggc cgtgcaggaa gcccagcggg caggcatcga   3000
```

```
gatcttcgtg gtggtcgtgg gccgccaggt gaatgagccc cacatccgcg tcctggtcac    3060
cggcaagacg gccgagtacg acgtggccta cggcgagagc cacctgttcc gtgtccccag    3120
ctaccaggcc ctgctccgcg gtgtcttcca ccagacagtc tccaggaagg tggcgctggg    3180
ctagcccacc ctgcacgccg gcaccaaacc ctgtcctccc acccctcccc actcatcact    3240
aaacagagcc caagcttgga aagccaggac acaacgctgc tgcctgcttt gtgcagggtc    3300
ctccggggct cagccctgag ttggcatcac ctgcgcaggg ccctctgggg ctcagctctg    3360
agctagtgtc acctgcacag ggccctctga ggctcagccc tgagctggcg tcacctgtgc    3420
agggccctct ggggctcagc cctgagctgg cctcacctgg gttccccacc ccgggctctc    3480
ctgccctgcc ctcctgcccg ccctccctcc tgcctgcgca gctccttccc taggcacctc    3540
tgtgctgcat cccaccagcc tgagcaagac gcctctcggg gcctgtgccg cactagcctc    3600
cctctcctct gtccccatag ctggtttttc ccaccaatcc tcacctaaca gttactttac    3660
aattaaactc aaagcaagct cttcctctca gcttggggca gccattggcc tctgtctcgt    3720
tttgggaaac caaggtcagg aggccgttgc agacataaat ctcggcgact cggccccgtc    3780
tcctgagggt cctgctggtg accggcctgg accttggccc tacagccctg gaggccgctg    3840
ctgaccagca ctgaccccga cctcagagag tactcgcagg ggcgctggct gcactcaaga    3900
ccctcgagat taacggtgct aaccccgtct gctcctccct cccgcagaga ctggggcctg    3960
gactggacat gagagcccct tggtgccaca gagggctgtg tcttactaga aacaacgcaa    4020
acctctcctt cctcagaata gtgatgtgtt cgacgtttta tcaaaggccc cctttctatg    4080
ttcatgttag ttttgctcct tctgtgtttt tttctgaacc atatccatgt tgctgacttt    4140
tccaaataaa ggttttcact cctc                                          4164

<210> SEQ ID NO 18
<211> LENGTH: 3387
<212> TYPE: DNA
<213> ORGANISM: Homo sapiens

<400> SEQUENCE: 18
agggccacag gtgctgccaa gatgctccag ggcacctgct ccgtgctcct gctctgggga     60
atcctggggg ccatccaggc ccagcagcag gaggtcatct cgccggacac taccgagaga    120
aacaacaact gcccagagaa gaccgactgc cccatccacg tgtacttcgt gctggacacc    180
tcggagagcg tcaccatgca gtcccccacg gacatcctgc tcttccacat gaagcagttc    240
gtgccgcagt tcatcagcca gctgcagaac gagttctacc tggaccaggt ggcgctgagc    300
tggcgctacg gcggcctgca cttctctgac caggtggagg tgttcagccc accgggcagc    360
gacccgggcc ccttcatcaa gaacctgcag ggcatcagct cctccgccg cggcaccttc    420 accgactgcg cgctggccaa catgacggag cagatccggc aggaccgcag caagggcacc    480
gtccacttcg ccgtggtcat caccgacggc acgtcaccg gcagccctg cggggggcatc    540 aagctgcagg ccgagcgggc ccgcgaggag ggcatccgc tcttcgccgt ggccccaac    600 cagaacctga agaagcaggg cctgcgggac atcgccagca gccgcacga gctctaccgc    660 aacgactacg ccaccatgct gcccgactcc accgagatca ccaggacac catcaaccgc    720 atcatcaagg tcatgaaaca cgaagcctac ggagagtgct acaaggtgag ctgcctggaa    780
atccctgggc cctctgggcc caagggctac cgtggacaga agggtgccaa gggcaacatg    840
ggtgagccgg gagagcctgg ccagaaggga agacagggag accgggcat cgaaggcccc    900 attggattcc caggacccaa gggcgttcct ggcttcaaag agagaaggg tgaatttgga    960
```

```
gccgacggtc gcaagggggc ccctggcctg gctggcaaga acgggaccga tggacagaag    1020
ggcaagctgg ggcgcatcgg acctcctggc tgcaagggag accctggaaa ccggggcccc    1080
gacggttacc cggggaagc agggagtcca ggggagcgag gagaccaagg cggcaagggg     1140
gaccctggcc gcccaggacg cagagggccc ccgggagaaa tcggggccaa gggaagcaag    1200
gggtatcaag gcaacaatgg agccccagga agtcctggtg tgaaaggagc caagggcggg    1260
cctgggcccc gcggacccaa aggcgagccg gggcgcaggg gagaccccgg caccaagggc    1320
agcccaggca gcgatggccc caaggggag aaggggacc ctggccctga ggcccccgc       1380
ggcctggctg gagaggttgg caacaaagga gccaagggag accgaggctt gcctggaccc    1440
agaggccccc agggagctct tggggagccc ggaaagcagg gatctcgggg agaccccggt    1500
gatgcaggac cccgtggaga ctcaggacag ccaggcccca agggagaccc cggcaggcct    1560
ggattcagct acccaggacc ccgaggagca cccggagaaa aaggcgagcc cggcccacgc    1620
ggccccgagg gaggccgagg cgactttggc ttgaaggag aacctgggag gaaaggagag    1680
aaaggagagc ctgcggatcc tggtccccct ggtgagccag gccctcgggg gccaagagga    1740
gtcccaggac ccgagggtga gcccggcccc cctggagacc ccggtctcac ggagtgtgac    1800
gtcatgacct acgtgaggga gacctgcggg tgctgcgact gtgagaagcg ctgtggcgcc    1860
ctggacgtgg tcttcgtcat cgacagctcc gagagcattg ggtacaccaa cttcacactg    1920
gagaagaact tcgtcatcaa cgtggtcaac aggctgggtg ccatcgctaa ggaccccaag    1980
tccgagacag ggacgcgtgt gggcgtggtg cagtacagcc acgagggcac cttggaggcc    2040
atccagctgg acgacgaaca tatcgactcc ctgtcgagct tcaaggaggc tgtcaagaac    2100
ctcgagtgga ttgcgggcgg cacctggaca ccctcagccc tcaagtttgc ctacgaccgc    2160
ctcatcaagg agagccggcg ccagaagaca cgtgtgtttg cggtggtcat cacggacggg    2220
cgccacgacc ctcgggacga tgacctcaac ttgcgggcgc tgtgcgatcg cgacgtcaca    2280
gtgacggcca tcggcatcgg ggacatgttc cacgagaagc acgagagtga aaacctctac    2340
tccatcgcct gcgacaagcc acagcaggtg cgcaacatga cgctgttctc cgacctggtc    2400
gctgagaagt tcatcgatga catggaggac gtcctctgcc cggaccctca gatcgtgtgc    2460
ccagaccttc cctgccaaac agagctgtcc gtggcacagt gcacgcagcg gcccgtggac    2520
atcgtcttcc tgctggacgg ctccgagcgg ctgggtgagc agaacttcca caaggcccgg    2580
cgcttcgtgg agcaggtggc gcggcggctg acgctggccc ggaggggacga cgaccctctc    2640
aacgcacgcg tggcgctgct gcagtttggt ggccccggcg agcagcaggt ggccttcccg    2700
ctgagccaca acctcactgc catccacgag gcgctggaga ccacacaata cctgaactcc    2760
ttctcgcacg tgggcgcagg cgtggtgcac gccatcaatg ccatcgtgcg cagcccgcgt    2820
ggcgggccc ggaggcacgc agagctgtcc ttcgtgttcc tcacggacgg cgtcacgggc    2880
aacgacagtc tgcacgagtc ggcgcactcc atgcgcaacg agaacgtggt acccaccgtc    2940
ctggccttgg gcagcgacgt ggacatggac gtgctcacca cgctcagcct gggtgaccgc    3000
gccgccgtgt ccacgagaa ggactatgac agcctggcgc aacccggctt cttcgaccgc    3060
ttcatccgct ggatctgcta cgcgccgccg ccgggcccg cagtcgaggg tcgtgagccc    3120
accccgtcca tggtgctaag cgggcccggg tcccacacgg ccagcaccgc tgctcactcg    3180
gacgacgccc tgggcctgca cctctccagc tcctcccacg gggtcccgt agccccggcc    3240
cccgcccagc cccaggtctc cccaggccct ccgcaggctg cccggcctcc ctcccctgc    3300
```

-continued

| | |
|---|---|
| agccatccca aggctcctga cctacctggc ccctgagctc tggagcaagc cctgacccaa | 3360 |
| taaaggcttt gaacccaaaa aaaaaaa | 3387 |

<210> SEQ ID NO 19
<211> LENGTH: 10558
<212> TYPE: DNA
<213> ORGANISM: Homo sapiens

<400> SEQUENCE: 19

| | |
|---|---|
| cagtttggag ctcagtcttc caccaaaggc cgttcagttc tcctgggctc cagcctcctg | 60 |
| caaggactgc aagagttttc ctccgcagct ctgagtctcc acttttttgg tggagaaagg | 120 |
| ctgcaaaaag aaaaagagac gcagtgagtg ggaaaagtat gcatcctatt caaacctaat | 180 |
| tgaatcgagg agcccaggga cacacgcctt caggtttgct caggggttca tatttggtgc | 240 |
| ttagacaaat tcaaaatgag gaaacatcgg cacttgccct tagtggccgt cttttgcctc | 300 |
| tttctctcag gctttcctac aactcatgcc cagcagcagc aagcagatgt caaaaatggt | 360 |
| gcggctgctg atataatatt tctagtggat tcctcttgga ccattggaga ggaacatttc | 420 |
| caacttgttc gagagtttct atatgatgtt gtaaaatcct tagctgtggg agaaaatgat | 480 |
| ttccattttg ctctggtcca gttcaacgga aacccacata ccgagttcct gttaaatacg | 540 |
| tatcgtacta acaagaagt cctttctcat atttccaaca tgtcttatat tgggggaacc | 600 |
| aatcagactg gaaaaggatt agaatacata atgcaaagcc acctcaccaa ggctgctgga | 660 |
| agccgggccg gtgacggagt ccctcaggtt atcgtagtgt taactgatgg acactcgaag | 720 |
| gatggccttg ctctgccctc agcggaactt aagtctgctg atgttaacgt gtttgcaatt | 780 |
| ggagttgagg atgcagatga aggagcgtta aagaaaatag caagtgaacc gctcaatatg | 840 |
| catatgttca acctagagaa ttttacctca cttcatgaca tagtaggaaa cttagtgtcc | 900 |
| tgtgtgcatt catccgtgag tccagaaagg gctggggaca cggaaaccct taaagacatc | 960 |
| acagcacaag actctgctga cattattttc cttattgatg gatcaaacaa caccggaagt | 1020 |
| gtcaatttcg cagtcattct cgacttcctt gtaaatctcc ttgagaaact cccaattgga | 1080 |
| actcagcaga tccgagtggg ggtggtccag tttagcgatg agcccagaac catgttttcc | 1140 |
| ttggacacct actccaccaa ggcccaggtt ctgggtgcag tgaaagccct cgggtttgct | 1200 |
| ggtgggagt tggccaatat cggcctcgcc cttgatttcg tggtggagaa ccacttcacc | 1260 |
| cgggcagggg gcagccgcgt ggaggaaggg gttccccagg tgctggtcct cataagtgcc | 1320 |
| gggccttcta gtgacgagat tcgctacggg gtggtagcac tgaagcaggc tagcgtgttc | 1380 |
| tcattcggcc ttggagccca ggccgcctcc agggcagagc ttcagcacat agctaccgat | 1440 |
| gacaacttgg tgtttactgt cccggaattc cgtagctttg gggacctcca ggagaaatta | 1500 |
| ctgccgtaca ttgttggcgt ggcccaaagg cacattgtct tgaaaccgcc aaccattgtc | 1560 |
| acacaagtca ttgaagtcaa caagagagac atagtcttcc tggtggatgg ctcatctgca | 1620 |
| ctgggactgg ccaacttcaa tgccatccga gacttcattg ctaaagtcat ccagaggctg | 1680 |
| gaaatcggac aggatcttat ccaggtggca gtggcccagt atgcagacac tgtgaggcct | 1740 |
| gaattttatt tcaataccca tccaacaaaa agggaagtca taccgctgt gcggaaaatg | 1800 |
| aagcccctgg acggctcggc cctgtacacg ggctctgctc tagactttgt tcgtaacaac | 1860 |
| ctattcacga gttcagccgg ctaccgggct gccgagggga ttcctaagct tttggtgctg | 1920 |
| atcacaggtg gtaagtccct agatgaaatc agccagcctg cccaggagct gaagagaagc | 1980 |
| agcataatgg cctttgccat tgggaacaag ggtgccgatc aggctgagct ggaagagatc | 2040 |

```
gctttcgact cctccctggt gttcatccca gctgagttcc gagccgcccc attgcaaggc   2100
atgctgcctg gcttgctggc acctctcagg accctctctg gaacccctga agttcactca   2160
aacaaaagag atatcatctt tcttttggat ggatcagcca acgttggaaa aaccaatttc   2220
ccttatgtgc gcgactttgt aatgaaccta gttaacagcc ttgatattgg aaatgacaat   2280
attcgtgttg gttagtgca atttagtgac actcctgtaa cggagttctc tttaaacaca   2340
taccagacca agtcagatat ccttggtcat ctgaggcagc tgcagctcca gggaggttcg   2400
ggcctgaaca caggctcagc cctaagctat gtctatgcca accacttcac ggaagctggc   2460
ggcagcagga tccgtgaaca cgtgccgcag ctcctgcttc tgctcacagc tgggcagtct   2520
gaggactcct atttgcaagc tgccaacgcc ttgacacgcg cgggcatcct gacttttgt    2580
gtgggagcta gccaggcgaa taaggcagag cttgagcaga ttgcttttaa cccaagcctg   2640
gtgtatctca tggatgattt cagctccctg ccagctttgc ctcagcagct gattcagccc   2700
ctaaccacat atgttagtgg aggtgtggag gaagtaccac tcgctcagcc agagagcaag   2760
cgagacattc tgttcctctt tgacggctca gccaatcttg tgggccagtt ccctgttgtc   2820
cgtgactttc tctacaagat tatcgatgag ctcaatgtga agccagaggg gacccgaatt   2880
gcggtggctc agtacagcga tgatgtcaag gtggagtccc gttttgatga gcaccagagt   2940
aagcctgaga tcctgaatct tgtgaagaga atgaagatca agacgggcaa agccctcaac   3000
ctgggctacg cgctggacta tgcacagagg tacatttttg tgaagtctgc tggcagccgg   3060
atcgaggatg gagtgcttca gttcctggtg ctgctggtcg caggaaggtc atctgaccgt   3120
gtggatgggc cagcaagtaa cctgaagcag agtgggggttg tgcctttcat cttccaagcc   3180
aagaacgcag accctgctga gttagagcag atcgtgctgt ctccagcgtt tatcctggct   3240
gcagagtcgc ttcccaagat tggagatctt catccacaga tagtgaatct cttaaaatca   3300
gtgcacaacg gagcaccagc accagtttca ggtgaaaagg acgtggtgtt tctgcttgat   3360
ggctctgagg gcgtcaggag cggcttccct ctgttgaaag agtttgtcca gagagtggtg   3420
gaaagcctgg atgtgggcca ggaccgggtc cgcgtggccg tggtgcagta cagcgaccgg   3480
accaggcccg agttctacct gaattcatac atgaacaagc aggacgtcgt caacgctgtc   3540
cgccagctga ccctgctggg agggccgacc cccaacaccg gggccgccct ggagtttgtc   3600
ctgaggaaca tcctggtcag ctctgcggga agcaggataa cagaaggtgt gccccagctg   3660
ctgatcgtcc tcacggccga caggtctggg gatgatgtgc ggaacccctc cgtggtcgtg   3720
aagagggggtg gggctgtgcc cattggcatt ggcatcggga acgctgacat cacagagatg   3780
cagaccatct ccttcatccc ggactttgcc gtggccattc ccaccttcg ccagctgggg   3840
accgtccaac aggtcatctc tgagagggtg acccagctca cccgcgagga gctgagcagg   3900
ctgcagccgg tgttgcagcc tctaccgagc ccaggtgttg gtggcaagag ggacgtggtc   3960
tttctcatcg atgggtccca aagtgccggg cctgagttcc agtacgttcg caccctcata   4020
gagaggctgg ttgactacct ggacgtgggc tttgacacca cccgggtggc tgtcatccag   4080
ttcagcgatg accccaaggc ggagttcctg ctgaacgccc attccagcaa ggatgaagtg   4140
cagaacgcgg tgcagcggct gaggcccaag ggagggcggc agatcaacgt gggcaatgcc   4200
ctggagtacg tgtccaggaa catcttcaag aggcccctgg ggagccgcat tgaagagggc   4260
gtcccacagt tcctggtcct catctcgtct ggaaagtctg acgatgaggt ggtcgtcccg   4320
gcggtggagc tcaagcagtt tggcgtggcc cctttcacga tcgccaggaa cgcagaccag   4380
```

```
gaggagctgg tgaagatctc gctgagcccc gaatatgtgt tctcggtgag caccttccgg   4440
gagctgccca gcctggagca gaaactgctg acgcccatca cgaccctgac ctcagagcag   4500
atccagaagc tcttagccag cactcgctat ccacctccag cagttgagag tgatgctgca   4560
gacattgtct ttctgatcga cagctctgag ggagttaggc cagatggctt tgcacatatt   4620
cgagattttg ttagcaggat tgttcgaaga ctcaacatcg gccccagtaa agtgagagtt   4680
ggggtcgtgc agttcagcaa tgatgtcttc ccagaattct atctgaaaac ctacagatcc   4740
caggccccgg tgctggacgc catacggcgc ctgaggctca gggggggtc cccactgaac   4800 actggcaagg ctctcgaatt tgtggcaaga aacctctttg ttaagtctgc ggggagtcgc   4860
atagaagacg gggtgcccca cacctggtc ctggtcctgg gtggaaaatc ccaggacgat   4920
gtgtccaggt tcgcccaggt gatccgttcc tcgggcattg tgagtttagg ggtaggagac   4980
cggaacatcg acagaacaga gctgcagacc atcaccaatg ccccagact ggtcttcaca   5040 gtgcgagagt tcagagagct tcccaacata gaagaaagaa tcatgaactc gtttggaccc   5100
tccgcagcca ctcctgcacc tccaggggtg acacccctc ctccttcacg gccagagaag   5160
aagaaagcag acattgtgtt cctgttggat ggttccatca acttcaggag gacagtttc   5220 caggaagtgc ttcgttttgt gtctgaaata gtggacacag tttatgaaga tggcgactcc   5280
atccaagtgg ggcttgtcca gtacaactct gaccccactg acgaattctt cctgaaggac   5340
ttctctacca gaggcagat tattgacgcc atcaacaaag tggtctacaa aggggaaga   5400 cacgccaaca ctaaggtggg ccttgagcac ctgcgggtaa accactttgt gcctgaggca   5460
ggcagccgcc tggaccagcg ggtccctcag attgcctttg tgatcacggg aggaaagtcg   5520
gtggaagatg cacaggatgt gagcctggcc ctcacccaga gggggtcaa agtgtttgct   5580 gttggagtga ggaatatcga ctcggaggag gttggaaaga tagcgtccaa cagcgccaca   5640
gcgttccgcg tgggcaacgt ccaggagctg tccgaactga gcgagcaagt tttggaaact   5700
ttgcatgatg cgatgcatga aacccttgc cctggtgtaa ctgatgctgc caaagcttgt   5760
aatctggatg tgattctggg gtttgatggt tctagagacc agaatgtttt tgtgcccag   5820 aagggcttcg agtccaaggt ggacgccatc ttgaacagaa tcagccagat gcacagggtc   5880
agctgcagcg gtggccgctc gcccaccgtg cgtgtgtcag tggtggccaa cacgccctcg   5940
ggcccggtgg aggcctttga cttttgacgag taccagccag agatgctcga aagttccgg   6000 aacatgcgca gccagcaccc ctacgtcctc acggaggaca ccctgaaggt ctacctgaac   6060
aagttcagac agtcctcgcc ggacagctg aaggtggtca ttcattttac tgatggagca   6120
gacggagatc tggctgattt acacagagca tctgagaacc tccgccaaga aggagtccgt   6180
gccttgatcc tggtgggcct tgaacgagtg gtcaacttgg agcggctaat gcatctggag   6240
tttgggcgag ggtttatgta tgacaggccc ctgaggctta acttgctgga cttggattat   6300
gaactagcgg agcagcttga caacattgcc gagaaagctt gctgtggggt tccctgcaag   6360
tgctctgggc agaggggaga ccgcgggccc atcggcagca tcgggccaaa gggtattcct   6420
ggagaagacg gctaccgagg ctatcctggt gatgagggtg gacccggtga gcgtggtccg   6480
cctggtgtga acggcactca aggtttccag ggctgcccgg ccagagagg agtaaagggc   6540 tctcggggat tccaggagga aaggggcgaa gtaggagaaa ttggactgga tggtctggat   6600
ggtgaagatg gagacaaagg attgcctggt tcttctggag agaaaggaa tcctggaaga   6660 aggggtgata aaggacctcg aggagagaaa ggagaaagag gagatgttgg gattcgaggg   6720
gacccgggta acccaggaca agacagccag gagagaggac ccaaaggaga aaccggtgac   6780
```

```
ctcggcccca tgggtgtccc agggagagat ggagtacctg gaggacctgg agaaactggg    6840
aagaatggtg gctttggccg aaggggaccc cccggagcta agggcaacaa gggcggtcct    6900
ggccagccgg gctttgaggg agagcagggg accagaggtg cacagggccc agctggtcct    6960
gctggtcctc cagggctgat aggagaacaa ggcatttctg gacctagggg aagcggaggt    7020
gcccgtggcg ctcctggaga acgaggcaga accggtccac tgggaagaaa gggtgagccc    7080
ggagagccag gaccaaaagg aggaatcggg aacccgggcc ctcgtgggga gacgggagat    7140
gacgggagag acggagttgg cagtgaagga cgcagaggca aaaaggaga agaggattt      7200 cctggatacc caggaccaaa gggtaaccca ggtgaacctg ggctaaatgg aacaacagga    7260
cccaaaggca tcagaggccg aaggggaaat tcgggacctc cagggatagt tggacagaag    7320
gggagacctg gctacccagg accagctggt ccaaggggca caggggcga ctccatcgat     7380 caatgtgccc tcatccaaag catcaaagat aaatgccctt gctgttacgg gcccctggag    7440
tgccccgtct tcccaacaga actagccttt gctttagaca cctctgaggg agtcaaccaa    7500
gacactttcg gccggatgcg agatgtggtc ttgagtattg tgaatgtcct gaccattgct    7560
gagagcaact gcccgacggg ggcccgggtg gctgtggtca cctacaacaa cgaggtgacc    7620
acggagatcc ggtttgctga ctccaagagg aagtcggtcc tcctggacaa gattaagaac    7680
cttcaggtgg ctctgacatc caaacagcag agtctggaga ctgccatgtc gtttgtggcc    7740
aggaacacat ttaagcgtgt gaggaacgga ttcctaatga ggaaagtggc tgttttcttc    7800
agcaacacac ccacaagagc atccccacag ctcagagagg ctgtgctcaa actctcagat    7860
gcggggatca ccccccttgtt ccttacaagg caggaagacc ggcagctcat caacgctttg    7920
cagatcaata acacagcagt ggggcatgcg cttgtcctgc ctgcagggag agacctcaca    7980
gacttcctgg agaatgtcct cacgtgtcat gtttgcttgg acatctgcaa catcgaccca    8040
tcctgtggat ttggcagttg gaggccttcc ttcaggggaca ggagagcggc agggagtgat   8100
gtggacatcg acatggcttt catcttagac agcgctgaga ccaccaccct gttccagttc    8160
aatgagatga agaagtacat agcgtacctg gtcagcaaac tggacatgag cccagatccc    8220
aaggcctccc agcacttcgc cagagtggca gttgtgcagc acgcgccctc tgagtccgtg    8280
gacaatgcca gcatgccacc tgtgaaggtg gaattctccc tgactgacta tggctccaag    8340
gagaagctgg tggacttcct cagcaggggga atgacacagt tgcagggaac cagggcctta    8400
ggcagtgcca ttgaatacac catagagaat gtctttgaaa gtgccccaaa cccacgggac    8460
ctgaaaattg tggtcctgat gctgacgggc gaggtgccgg agcagcagct ggaggaggcc    8520
cagagagtca tcctgcaggc caaatgcaag ggctacttct tcgtggtcct gggcattggc    8580
aggaaggtga acatcaagga ggtatacacc ttcgccagtg agccaaacga cgtcttcttc    8640
aaattagtgg acaagtccac cgagctcaac gaggagcctt tgatgcgctt cgggaggctg    8700
ttgccgtcct tcgtcagcag tgaaaatgct ttttacttgt ccccagatat caggaaacag    8760
tgtgattggt tccaagggga ccaacccaca aagaaccttg tgaagtttgg tcacaaacaa    8820
gtaaatgttc cgaataacgt tacttcaagt cctacatcca acccagtgac gacaacgaag    8880
ccggtgacta cgacgaagcc ggtgaccacc acaacaaagc tgtaaccac cacaacaaag    8940 cctgtgacta ttataaatca gccatctgtg aagccagccg ctgcaaagcc ggcccctgcg    9000
aaacctgtgg ctgccaagcc tgtgccaca aagacggcca ctgttagacc cccagtggcg    9060
gtgaagccag caacagcagc gaagcctgta gcagcaaagc cagcagctgt aagacccccc    9120
```

```
gctgctgctg caaaaccagt ggcgaccaag cctgaggtcc ctaggccaca ggcagccaaa    9180
ccagctgcca ccaagccagc caccactaag cccgtggtta agatgctccg tgaagtccag    9240
gtgtttgaga taacagagaa cagcgccaaa ctccactggg agaggcctga gcccccggt     9300 ccttattttt atgacctcac cgtcacctca gcccatgatc agtccctggt tctgaagcag    9360
aacctcacgg tcacggaccg cgtcattgga ggcctgctcg ctgggcagac ataccatgtg    9420
gctgtggtct gctacctgag gtctcaggtc agagccacct accacggaag tttcagtaca    9480
aagaaatctc agcccccacc tccacagcca gcaaggtcag cttctagttc aaccatcaat    9540
ctaatggtga gcacagaacc attggctctc actgaaacag atatatgcaa gttgccgaaa    9600
gacgaaggaa cttgcaggga tttcatatta aaatggtact atgatccaaa caccaaaagc    9660
tgtgcaagat tctggtatgg aggttgtggt ggaaacgaaa acaaatttgg atcacagaaa    9720
gaatgtgaaa aggtttgcgc tcctgtgctc gccaaacccg gagtcatcag tgtgatggga    9780
acctaagcgt gggtggccaa catcatatac ctcttgaaga agaaggagtc agccatcgcc    9840
aacttgtctc tgtagaagct ccgggtgtag attcccttgc actgtatcat ttcatgcttt    9900
gatttacact cgaactcggg agggaacatc ctgctgcatg acctatcagt atggtgctaa    9960
tgtgtctgtg gaccctcgct ctctgtctcc agcagttctc tcgaatactt tgaatgttgt    10020
gtaacagtta gccactgctg gtgtttatgt gaacattcct atcaatccaa attccctctg    10080
gagtttcatg ttatgcctgt tgcaggcaaa tgtaaagtct agaaaataat gcaaatgtca    10140
cggctactct atatacttt gcttggttca tttttttcc cttttagtta agcatgactt      10200
tagatgggaa gcctgtgtat cgtggagaaa caagagacca acttttcat tccctgcccc     10260 caatttccca gactagattt caagctaatt ttctttttct gaagcctcta acaaatgatc    10320
tagttcagaa ggaagcaaaa tcccttaatc tatgtgcacc gttgggacca atgccttaat    10380
taaagaattt aaaaaagttg taatagagaa tattttttggc attcctctca atgttgtgtg   10440 ttttttttt ttgtgtgctg gagggagggg atttaatttt aattttaaaa tgtttaggaa     10500
atttatacaa agaaactttt taataaagta tattgaaagt ttaaaaaaaa aaaaaaa       10558
```

TREATMENT OF MUSCULAR DYSTROPHIES AND RELATED DISORDERS

RELATED APPLICATIONS

This application is a national stage filing under 35 U.S.C. 371 of International Application PCT/US02/26021, filed Aug. 15, 2002, which claims the benefit of U.S. Provisional Application No. 60/312,551, filed Aug. 15, 2001, the specification of each of which is incorporated by reference herein. International Application PCT/US02/26021 was published under PCT Article 21(2) in English.

GOVERNMENT GRANTS

This work was made with Government support under Grants HD23924 and MH53571 awarded by the National Institute of Health. Therefore, the U.S. Government has certain rights in this invention.

BACKGROUND OF THE INVENTION

The dystrophin-associated protein complex (DAPC) links the cytoskeleton to the extracellular matrix and is necessary for maintaining the integrity of the muscle cell\plasma membrane. The core DAPC consists of the cytoskeletal scaffolding molecule dystrophin and the dystroglycan and sarcoglycan transmembrane subcomplexes. The DAPC also serves to localize key signaling molecules to the cell surface, at least in part through its associated syntrophins (Brenman, et al. (1996) *Cell*. 84: 757-767; Bredt, et al. (1998), *Proc Natl Acad Sci USA*. 95: 14592). Mutations in either dystrophin or any of the sarcoglycans result in muscular dystrophies characterized by breakdown of the muscle cell membrane, loss of myofibers, and fibrosis (Hoffman, et al. 1987. *Cell*. 51: 919; Straub, and Campbell (1997) *Curr Opin Neurol*. 10: 168). Moreover, mutations in the extracellular matrix protein laminin-α2, which associates with the DAPC on the cell surface, is the basis of a major congenital muscular dystrophy (Helbling-Leclerc, et al. (1995) *Nat Genet*. 11:216).

The α-/β-dystroglycan subcomplex forms a critical structural link in the DAPC. The transmembrane β-dystroglycan and the wholly extracellular α-dystroglycan arise by proteolytic cleavage of a common precursor (Ibraghimov, et al. (1992) *Nature* 355: 696; Bowe, et al. (1994) *Neuron* 12: 1173). The cytoplasmic tail of β-dystroglycan binds dystrophin, while the highly glycosylated, mucin-like α-dystroglycan binds to several ECM elements including agrin, laminin, and perlecan (Ervasti and Campbell, (1993) *J Cell Biol*. 122: 809; Bowe, et al. (1994) *Neuron*. 12: 1173; Gee, et al. (1994) *Cell* 77: 675; Hemler, (1999) *Cell* 97: 543). This binding to matrix proteins appears to be essential for assembly of basal lamina, since mice deficient in dystroglycan fail to form these structures and die very early in development (Henry, M. D. and K. P. Campbell. 1998. *Cell*. 95: 859). β-Dystroglycan can bind the signaling adapter molecule Grb2 and associates indirectly with p125FAK (Yang, et al. (1995) *J. Biol. Chem*. 270: 11711; Cavaldesi, et al. (1999), *J. Neurochem*. 72: 01648). Although the significance of these associations remains unknown, these binding properties suggest that dystroglycan may also serve to localize signaling molecules to the cell surface.

Several lines of evidence suggest that dystroglycan may also function in neuromuscular junction formation, in particular, in postsynaptic differentiation. For purposes of clarity, the components of the neuromuscular junction are summarized here. The major structural features of the neuromuscular junction (NMJ) or nerve-muscle synapse are the pre- and post-synaptic specializations of the motor neuron and muscle, respectively, the intervening synaptic basal lamina, and the specialized Schwann cell cap (Salpeter, et al (1987) *The Vertebrate Neuromuscular Junction*. New York, Alan R. Liss.). The presynaptic apparatus is marked by ordered arrays of synaptic vesicles, a subset of which are poised to fuse with the plasma membrane at the active zones, and release acetylcholine that is recognized by acetylcholine receptors (AChRs) on the muscle, and ultimately results in electrical activation and contraction of the muscle (Heuser, et al (1981) *J. Cell Biol*. 88: 564). Immediately across the 50 nm synaptic cleft from these zones are the crests of the postjunctional folds. These crests bristle with Acetylcholine receptors (AChRs), which can reach densities of >10,000 molecules/$\mu m^2$ (Fertuck, et al (1976) *J. Cell. Biol*. 69: 144). The localized and tightly regulated secretion of acetylcholine into the narrow synaptic cleft, coupled with the high AChR density in the postsynaptic membrane, ensures rapid and reliable synaptic transmission between neuron and muscle. Perturbations of these specializations, such as the decrease in the number of functional AChRs seen in myasthenia gravis, can lead to debilitating and often fatal clinical outcomes (Oosterhuis, et al (1992) *Neurology & Neurosurgery* 5: 638).

The synaptic basal lamina (SBL) is interposed between the pre- and post-synaptic membranes and contains molecules important for the structure, function, and regulation of the neuromuscular junction (Bowe, M. A & Fallon, J. R., (1995) *Ann. Rev. Neurosci*. 18: 443; Sanes, et al. (1999) *Ann. Rev. Neurosci*. 22: 389). It consists of a distinct set of extracellular matrix molecules including specialized laminins, proteoglycans and collagens (Hall, et al (1993) *Neuron* 10: (Suppl.) 99). The SBL also contains molecules essential for the regulation of synaptic structure and function including ACHE, neuregulins, and agrin. The SBL thus serves both as a specialized structure for maintaining the localized differentiation of the synapse as well as a repository for essential regulatory molecules.

The molecular composition of the postsynaptic membrane is known in considerable detail. As noted above, the most abundant membrane protein is the AChR. The cytosolic AChR associated protein rapsyn (formerly known as the 43 kD protein) is present at stoichiometric levels with the receptor and is likely to form a key link between the cytosolic domain of the AChR and the cytoskeleton (Froehner, et al (1995) *Nature* 377: 195; Gautam, et al. (1995) *Nature* 377: 232). The postsynaptic membrane is also enriched in erbB2-4, some or all of which serve as neuregulin receptors (Altiok, et al. (1995) *EMBO J*. 14: 4258; Zhu, et al. (1995) *EMBO J*. 14: 5842). AChR and other molecules essential for nerve-muscle communication. The cytoskeletal elements can be broadly grouped into two subsets. Dystrophin and utrophin are members of the dystrophin-associated protein complex, or DAPC, and are linked to the synaptic basal lamina via the transmembrane heteromer α-/β-dystroglycan. The postsynaptic cytoskeleton is also enriched in several focal adhesion-associated molecules including α-actinin, vinculin, talin, paxillin, and filamin (Sanes, et al (1999) *Ann. Rev. Neurosci*. 22: 389). The latter proteins probably communicate, directly or indirectly, with the extracellular matrix through integrins, some of which are enriched at synapses (Martin, et al. (1996) *Dev. Biol*. 174: 125). Actin is associated with both sets of cytoskeletal molecules (Rybakova et al. (1996) *J. Cell Biol*. 135: 661; Amann, et al. (1998) *J. Biol. Chem*. 273: 28419-23; Schoenwaelder et al. (1999) *Curr. Opin. Cell. Biol*. 11: 274). The functions of these specialized sets of proteins are considered below.

α-Dystroglycan binds the synapse organizing molecule agrin (Bowe, et al. (1994) *Neuron.* 12: 1173; Campanelli, et al. (1994) *Cell.* 77: 663; Gee, et al. (1994) *Cell.* 77: 675; Sugiyama, et al. (1994) *Neuron.* 13: 103; O'Toole, et al. (1996) *Proc Natl Acad Sci USA.* 93: 7369) (reviewed in Fallon and Hall, (1994) *Trends Neurosci.* 17: 469), and β-dystroglycan binds to the AChR-associated protein rapsyn (Cartaud, et al. (1998) *J Biol Chem.* 273: 11321). Further, agrin-induced AChR clustering on the postsynaptic membrane is markedly decreased in muscle cells expressing reduced levels of dystroglycan (Montanaro, et al. (1998) *J Neurosci.* 18: 1250). The precise role of dystroglycan in this process is unknown. Currently available evidence suggests that dystroglycan is not part of the primary agrin receptor, but rather may play a structural role in the organization of postsynaptic specializations (Gesemann, et al. (1995) *Biol.* 128: 625; Glass, et al. (1996) *Cell.* 85: 513; Jacobson, et al. (1998) *J Neurosci.* 18: 6340).

Another molecule that plays an important role in neuromuscular junction formation is the tyrosine kinase receptor MuSK, which becomes phosphorylated in response to agrin. However, agrin does not bind to MuSK and it is unclear how agrin stimulates MuSK. The existence of a co-receptor had been suggested. Activation of MuSK by antibody cross-linking is sufficient to induce the clustering of AChRs on cultured myotubes (Xie et al. (1997) *Nat. Biotechnol.* 15:768 and Hopf and Hoch (1998) *J. Biol. Chem.* 273: 6467) and a constitutively active MuSK can induce postsynaptic differentiation in vivo (Jones et al. (1999) *J. Neurosci.* 19:3376). However, MuSK phosphorylation is necessary but not sufficient for agrin-induced AChR clustering.

The realm of dystroglycan function ranges far beyond muscle. As noted above, mice defective in dystroglycan die long before muscle differentiation. In a surprising development, α-dystroglycan in non-muscle cells has been shown to function as a receptor for Lassa Fever and choriomeningitis fever viruses (Cao, W., et al., 1998, *Science.* 282: 2079), and on Schwann cells as a co-receptor for *Mycobacterium leprae* (Rambukkana, et al. (1998) *Science.* 282: 2076). Dystroglycan is also abundant in brain, but its function there is not understood (Gorecki, et al. (1994) *Hum Mol Genet.* 3: 1589; Smalheiser and Kim (1995) *J Biol Chem.* 270: 15425).

α-Dystroglycan is comprised of three known domains. An amino-terminal domain folds into an autonomous globular configuration (Brancaccio, et al. (1995) *Febs Lett.* 368: 139). The middle third of the protein is serine- and threonine-rich, and is highly glycosylated (Brancaccio, et al. (1997) *Eur J Biochem.* 246: 166). Indeed, the core molecular weight of α-dystroglycan is ~68 kDa, but the native molecule migrates on SDS-PAGE as a polydisperse band whose size ranges from 120-190 kDa, depending upon the species and tissue source (Ervasti and Campbell (1993) *J Cell Biol.* 122: 809; Bowe, et al. (1994) *Neuron.* 12: 1173; Gee, et al. (1994) *Cell.* 77: 675; Matsumura, et al. (1997) *J Biol Chem.* 272: 13904). Glycosylation of α-dystroglycan, probably in this middle third, is essential for its laminin- and agrin-binding properties.

While it is clear that dystroglycan and the DAPC play crucial roles in a variety of processes in muscle as well as in other tissues, the underlying mechanisms remain obscure.

SUMMARY OF THE INVENTION

In certain aspects, the invention provides methods and compositions for stabilizing dystrophin-associated protein complexes (DAPCs) on the surface of a cell. Stabilizing DAPC complexes on cell membranes allows membranes to be less "leaky" and thus, provides a longer life span to cells. In certain aspects, the invention also provides methods for activating a postsynaptic membrane, such as to render the membrane more sensitive to an incoming signal from a neural cell (e.g., at a neuromuscular junction). Activating a postsynaptic membrane may comprise stimulating aggregation of AChR on the cell membrane and/or activating MuSK, such as by phosphorylation. In certain aspects, the invention provides methods for treating a condition associated with a collagen VI abnormality, such as a deficiency or structural disorganization.

In one embodiment, the method comprises contacting the target cell with a biglycan polypeptide comprising an amino acid sequence which is at least about 90% identical to the biglycan sequence of SEQ ID NO: 9 or a portion thereof. In a preferred method, the biglycan polypeptide binds to α-dystroglycan; collagen VI; α-sarcoglycan and/or γ-sarcoglycan. In an even more preferred embodiment, the biglycan polypeptide stimulates phosphorylation of α-sarcoglycan on a cell membrane. The biglycan polypeptide also preferably potentiates agrin-induced AChR aggregation on the surface of the cell; stimulate the phosphorylation of MuSK on the cell; and/or potentiates agrin-induced phosphorylation of MuSK. In certain preferred embodiments, the biglycan polypeptide interacts with and/or stimulates the expression of collagen VI.

The biglycan polypeptide may comprise one or more 24 amino acid repeat motifs in the Leucine Rich Repeat (LRR) of human biglycan having SEQ ID NO: 9. In another embodiment, the biglycan polypeptide comprises a cysteine-rich region, e.g., the C-terminal or the N-terminal Cysteine-rich region. The biglycan polypeptide may include one or more glycosaminoglycan (GAG) chains. In an even more preferred embodiment, the biglycan polypeptide comprises an amino acid sequence which is at least about 90% identical to amino acids 20-368 or 38-368 of SEQ ID NO: 9, even more preferably at least 95% identical or 100% identical to amino acids 20-368 or 38-368 of SEQ ID NO: 9. In another embodiment, the biglycan polypeptide is encoded by a nucleic acid which hybridizes to SEQ ID NO: 8. The biglycan polypeptide can be Torpedo DAG-125, or the human biglycan of SEQ ID NO: 9, or a portion thereof having at least one biological activity of biglycan.

In other embodiments, the biglycan therapeutic is a peptide fragment of the full length protein. Preferably it is a fragment which retains the ability to induce phosphorylation of sarcoglycans and upregulate utrophin activity/expression. For instance, a preferred peptide fragment binds to and activates MuSK. In certain preferred embodiments the peptide fragment has the ability to upregulate collagen VI activity/expression.

In further embodiments, the method comprises contacting the target cell with a collagen VI polypeptide comprising an amino acid sequence which is at least about 90% identical to a collagen α1 (VI) sequence, a collagen α2(VI) sequence or a collagen α3(VI) sequence, exemplified by SEQ ID Nos: 11 and 12, 13 and 14, and 15 and 16, respectively, or a portion thereof. In a preferred method the collagen VI polypeptide is a portion of a mature collagen peptide (e.g. signal sequence is removed). In a preferred method, the collagen VI polypeptide binds to bigycan. In certain embodiments, the method comprises contacting the target cell with a collagen VI therapeutic comprising a collagen VI monomer, the monomer comprising a collagen α1(VI) chain, a collagen α2(VI) chain and a collagen α3(VI) chain in a 1:1:1 ratio. Optionally, the therapeutic comprises multimers of collagen VI monomers.

In other embodiments, the collagen VI therapeutic is a peptide fragment of a full length collagen VI α1(VI) chain α2(VI) chain or α3(VI) chain. Preferably it is a fragment which retains the ability to bind biglycan.

In other embodiments, the subject biglycan or collagen VI therapeutics are peptidomimetics of a portion of a biglycan or collagen VI protein, respectively. Peptidomimetics are compounds based on, or derived from, peptides and proteins. The peptidomimetics of the present invention typically can be obtained by structural modification of a known biglycan or collagen VI peptide sequence using unnatural amino acids, conformational restraints, isosteric replacement, and the like. The subject peptidomimetics constitute the continuum of structural space between peptides and non-peptide synthetic structures; biglycan and collagen VI peptidomimetics may be useful, therefore, in delineating pharmacophores and in helping to translate peptides into nonpeptide compounds with the activity of the parent biglycan or collagen VI peptides.

Moreover, as is apparent from the present disclosure, mimetopes of the subject biglycan and collagen VI peptides can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in *Peptides: Chemistry and Biology*, G. R Marshall ed., ESCOM Publisher: Leiden, Netherlands, 1988, p 123), C-7 mimics (Huffman et al. in *Peptides: Chemistry and Biology*, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), β-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124:141), and methyleneamino-modifed (Roark et al. in *Peptides: Chemistry and Biology*, G. R. Marshall ed., ESCOM Publisher: Leiden, Netherlands, 1988, p 134). Also, see generally, Session III: Analytic and synthetic methods, in *Peptides: Chemistry and Biology*, G. R. Marshall ed., ESCOM Publisher: Leiden, Netherlands, 1988)

In addition to a variety of sidechain replacements which can be carried out to generate the subject biglycan and collagen VI peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

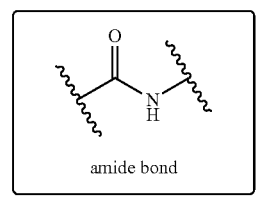

amide bond

Examples of Surrogates

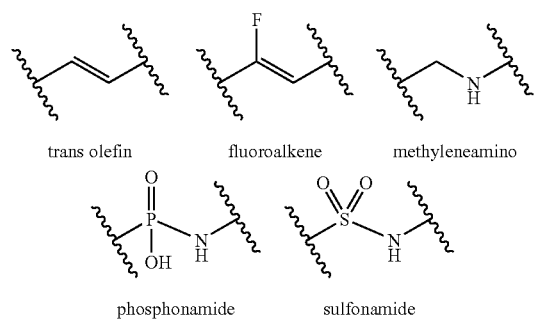

trans olefin     fluoroalkene     methyleneamino phosphonamide     sulfonamide

Additionally, peptidomimietics based on more substantial modifications of the backbone of the biglycan or collagen VI peptide can be used. Peptidomimetics which fall in this category include (i) retro-inverso analogs, and (ii) N-alkyl glycine analogs (so-called peptoids).

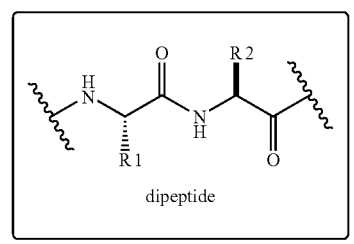

dipeptide

Examples of Analogs

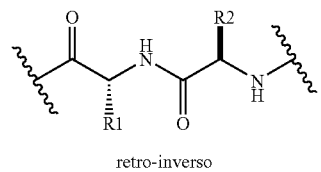

retro-inverso

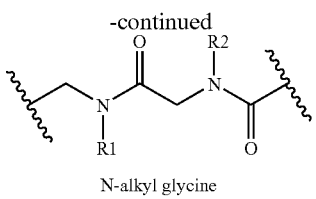

N-alkyl glycine

Furthermore, the methods of combinatorial chemistry are being brought to bear, c.f. Verdine et al. PCT publication WO9948897, on the development of new peptidomimetics. For example, one embodiment of a so-called "peptide morphing" strategy focuses on the random generation of a library of peptide analogs that comprise a wide range of peptide bond substitutes.

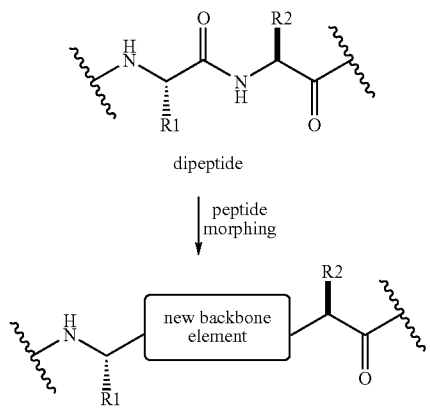

In certain embodiments, the invention also provides a method for treating or preventing a condition associated with an abnormal dystrophin-associated protein complex (DAPC) in cells of a subject, comprising administering to the subject a pharmaceutically efficient amount of a biglycan polypeptide, peptide or peptidomimetic or a biglycan agonist (collectively referred to herein as "biglycan therapeutics") which stabilizes the DAPC. In certain embodiments, the invention provides a method for treating or preventing a condition associated with an abnormal dystrophin-associated protein complex (DAPC) in cells of a subject, comprising administering to the subject a pharmaceutically efficient amount of a collagen VI polypeptide, peptide or peptidomimetic or a biglycan agonist (collectively referred to herein as "collagen VI therapeutics") which stabilizes the DAPC. Optionally, the DAPC is of a type that is deficient in collagen VI function. Examples of diseases that can be treated or prevented include muscular dystrophies, such as Duchenne's Muscular Dystrophy, Becker's Muscular Dystrophy, Congenital Muscular Dystrophy, Ullrich Congenital Muscular Dystrophy, Limbgirdle Muscular Dystrophy, and mytonic dystrophy; cardiomyopathies, Bethlem myopathy and Sorsby's fundus dystrophy. In certain embodiments, the invention relates to a combination therapy comprising administering a collagen VI therapeutic and a biglycan therapeutic, optionally as a single combination therapeutic composition.

In another example, the invention provides a method for treating or preventing a condition characterized by an abnormal neuromuscular junction or synapse in a subject, comprising administering to the subject a pharmaceutically efficient amount of a biglycan therapeutic which binds to, and/or induces phosphorylation of MuSK and/or which induces aggregation of acetylcholine receptors (AChRs), or a collagen VI therapeutic. The condition can be a neuromuscular or neurological disease.

The invention also provides methods for treating, preventing and diagnosing diseases or disorders that are associated with abnormal levels or activity of biglycan; with unstable cytoplasmic membranes, due in particular, to unstable DAPCs; or abnormal synapses or neuromuscular junctions.

In yet another example, the invention provides a diagnostic method for determining whether a subject has or is at risk of developing a condition associated with an abnormal DAPC or abnormal synapse or neuromuscular junction, or other disease associated with an abnormal biglycan level or activity, comprising determining the level or activity of biglycan in a tissue of the subject, wherein the presence of an abnormal level and/or activity of biglycan in the tissue of a subject indicates that the subject has or is at risk of developing a condition associated with an abnormal DAPC or abnormal synapse or neuromuscular junction or other disease associated with an abnormal biglycan level or activity.

In further embodiments, the invention provides screening methods for identifying agents with inhibit or potentiate the activity of biglycan, such as a human biglycan or Torpedo DAG-125, such as agents which potentiate or inhibit biglycan binding to another molecule, such as a member of a DAPC or MuSK. Agents identified in these assays can be used, e.g., in therapeutic methods, as biglycan therapeutics. Screening methods for identifying agents which modulate phosphorylation induced by biglycan are also within the scope of the invention.

In additional embodiments, the invention relates to screening methods for identifying agents with inhibit or potentiate the activity of collagen VI, such as a human collagen VI, such as agents which potentiate or inhibit collagen VI binding to biglycan. Agents identified in these assays can be used, e.g., in therapeutic methods, as collagen VI therapeutics.

Other aspects of the invention are described below or will be apparent to those skilled in the art in light of the present disclosure.

A. Sarcoglycan binding to synaptic membrane fractions from Torpedo electric organ (TEOM). TEOM were separated on SDS-PAGE gels, blotted onto nitrocellulose and probed with either $^{35}$S-methionine-labelled in vitro translated α-dystroglycan or sarcoglycans (α, β, γ, or δ) as indicated and analyzed by autoradiography. α-Dystroglycan as well as α- and γ-sarcoglycan bound to a polydisperse band whose center of migration. was .~125 kD. In previous work a polypeptide with identical mobility and appearance was purified from these fractions and shown to be the proteoglycan biglycan (Bowe et al., 2000). No binding of β- or δ-sarcoglycan to this or any other polypeptide in these fractions was detected. B. Binding of α-dystroglycan and sarcoglycans to purified recombinant biglycan proteoglycan. Biglycan was separated on SDS-PAGE and either stained with silver or blotted onto nitrocellulose ('Overlay') and probed as described in above. α-Dystroglycan and α- and γ-sarcoglycan bind to this recombinant, GAG-containing biglycan proteoglycan while no binding of β- or δ-sarcoglycan is detected. C. The biglycan core polypeptide is sufficient for sarcoglycan binding. Purified recombinant biglycan core polypeptide was separated by SDS-PAGE and either silver stained or blotted and probed as described above. α-Dystroglycan did not bind to this GAG-free biglycan. In contrast, both α- and γ-sarcoglycan bind to the biglycan core polypeptide.

Figure 17A:
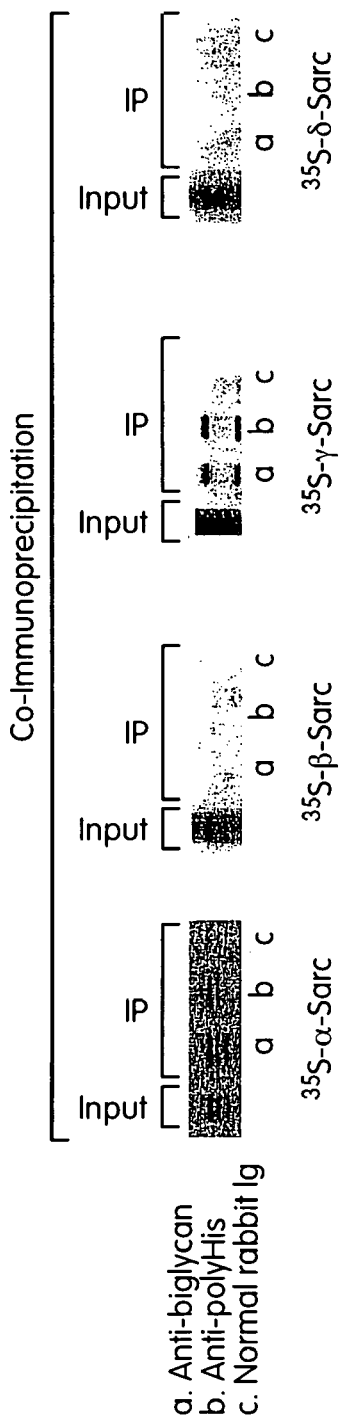
Figure 17B:
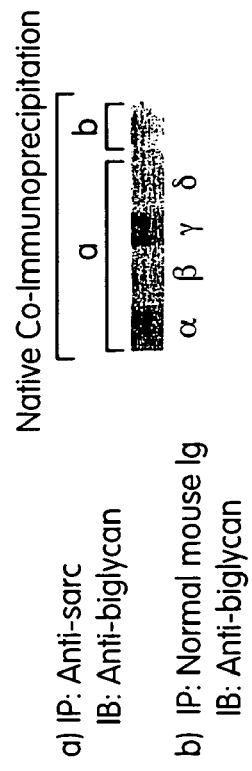

FIG. 17. Solution binding of biglycan and sarcoglycans.

A. Co-immunoprecipitation of purified recombinant biglycan to recombinant sarcoglycan. His-tagged biglycan core polypeptide was incubated with the indicated $^{35}$S-methionine labelled in vitro translated sarcoglycan for 1 hr followed by either anti-biglycan, antipoly-His or normal rabbit Ig. Immune complexes were then precipitated with protein G beads and analyzed by SDS-PAGE and autoradiography. Note that both α- and γ-sarcoglycan co-imnunoprecipitate with biglycan, while β- or δ-sarcoglycan do not. The labelling of the various sarcoglycans is shown by direct autoradiography of SDS-PAGE-separated in vitro translated polypeptides ('Input'). B. Co-immunoprecipitation of biglycan with native sarcoglycans. Purified recombinant biglycan core was incubated with detergent extracts from cultured C2C12 muscle cells. The resulting complexes were then incubated with the indicated anti-sarcoglycan antibodies and western blots of the resulting immunoprecipitates were probed with anti-biglycan antisera. Native α- and γ-sarcoglycan, but not β- or δ-sarcoglycan, co-immunoprecipitate with biglycan. Control experiments showed that each of the anti-sarcoglycan antibodies immunoprecipitated their cognate antigens under these conditions (not shown).

Figure 18A:
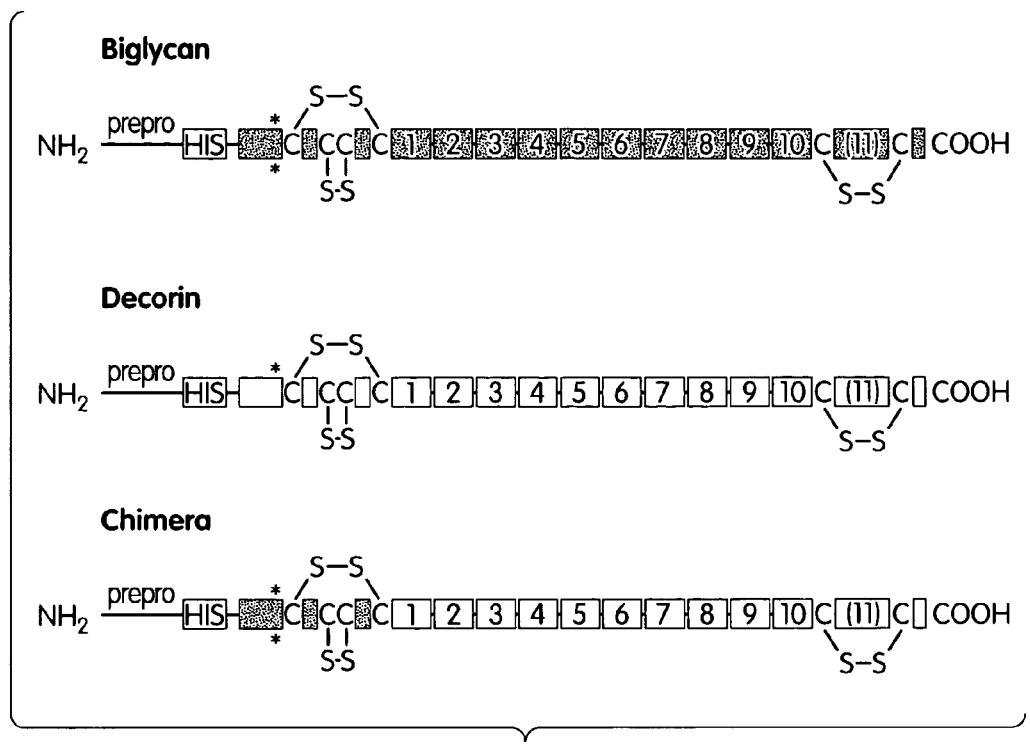
Figure 18B:
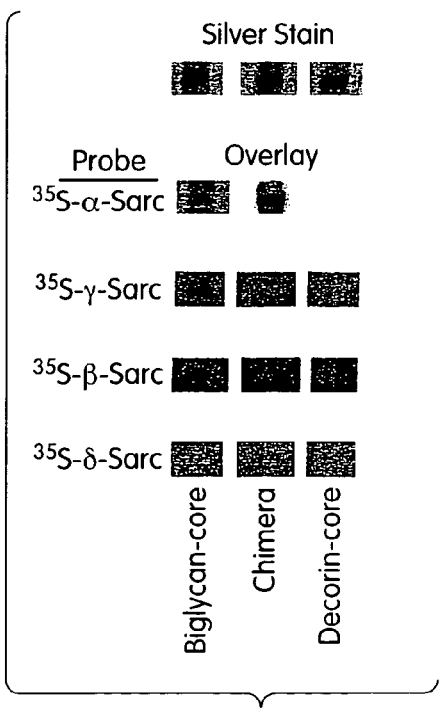

FIG. 18. Distinct binding sites for α- and γ-sarcoglycan on the biglycan core protein A. Predicted domain structure of biglycan, decorin and a biglycan-decorin chimera. The location of the pre-pro peptide ('prepro'), 6-His tag, cysteine-rich amino- and carboyxldomains, LRRS (numbered 1-10; some scheme predicts an 11th) and GAG attachment sites (asterisks) are indicated: Note that these sites are present in the proteins used in this experiment, but they are not substituted with GAGs. B. Binding of sarcoglycans to biglycan, decorin and a chimera One microgram of each of the purified recombinant proteins was separated by SDS-PAGE and either directly stained ('silver') or blotted and probed with $^{35}$S-methionine-labelled, in vitro translated sarcoglycans as indicated. Both α- and γ-sarcoglycan bind to the immobilized biglycan core but not to decorin core. In contrast only α-sarcoglycan binds to the biglycan-decorin chimeric protein. Thus the first 30 amino acids of biglycan is involved in binding to α-sarcoglycan. Neither β-nor δ-sarcoglycan bind to either biglycan, decorin or the chimera These results indicate that the binding sites for α- and γ-sarcoglycan on biglycan are distinct.

Figure 19A:
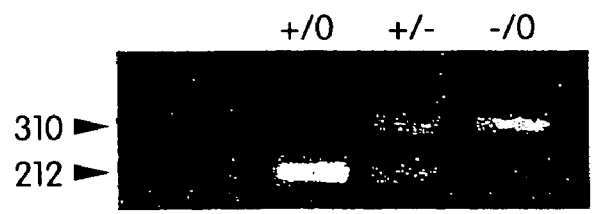
Figure 19B:
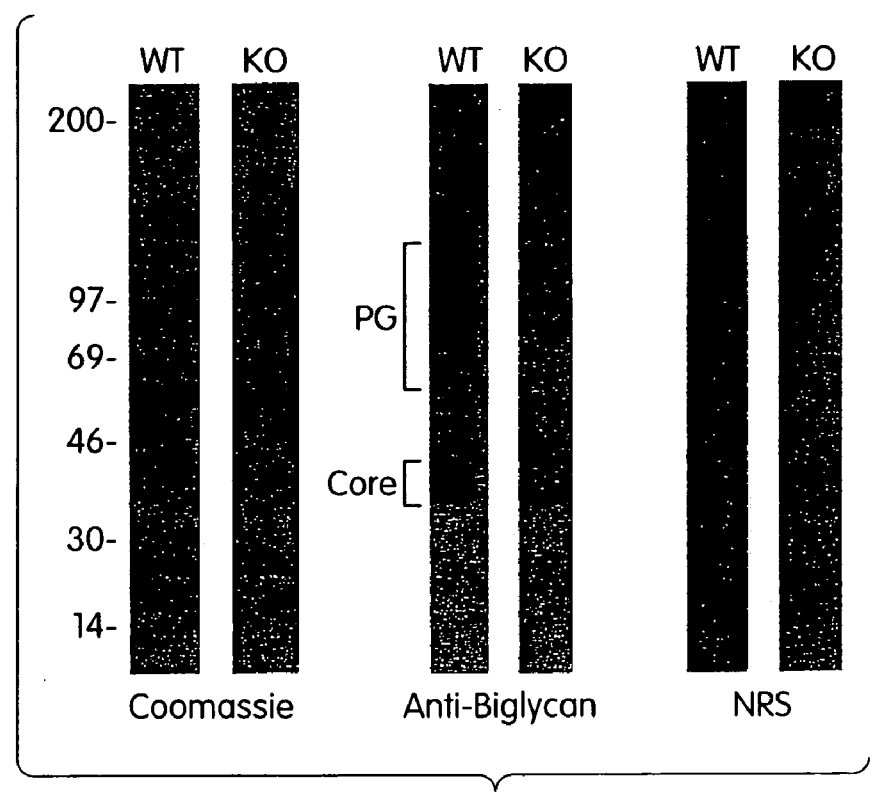

FIG. 19. Two forms of biglycan are expressed in muscle

A. PCR genotyping was performed on genomic DNA using primer pairs specific for mutant and wild type biglycan alleles. Shown are results from a wild type male (+/o), heterozygote female (+/−) and null male (−/o). B. KCl-washed membranes from skeletal muscle of Bgn null and littermate controls were prepared as described in Methods. Each preparation was separated by SDS-PAGE and either stained for total protein (Coomassie) or transferred to nitrocellulose and probed with rabbit anti-biglycan or normal rabbit serum. In wild type muscle the anti-biglycan recognized polypeptides of ~37 kD and ~105 kD which are likely to correspond to the core and proteoglycan form of biglycan, respectively (see Results). Neither polypeptide was detected in membrane fractions from Bgn null mice.

Figure 20A:
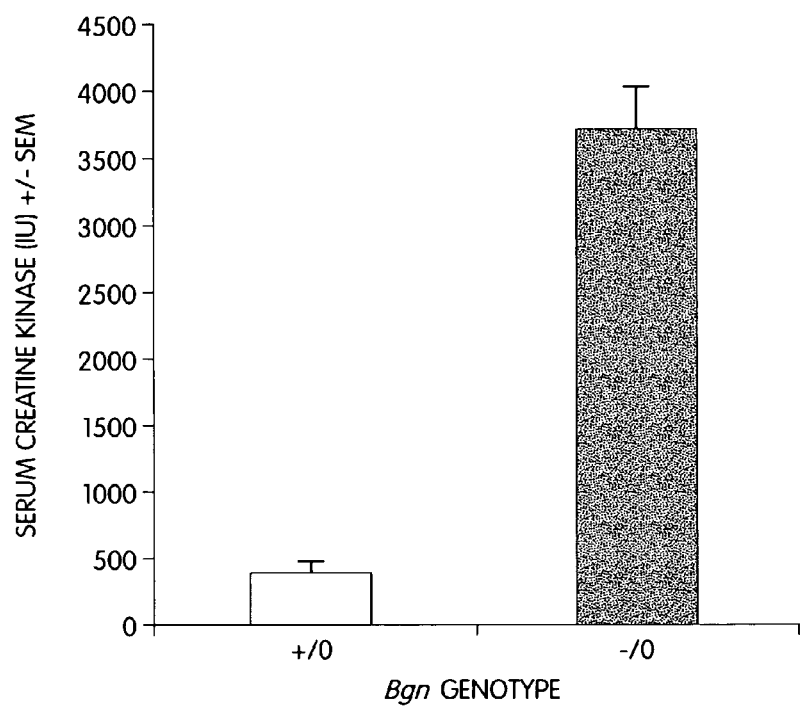
Figure 20B:
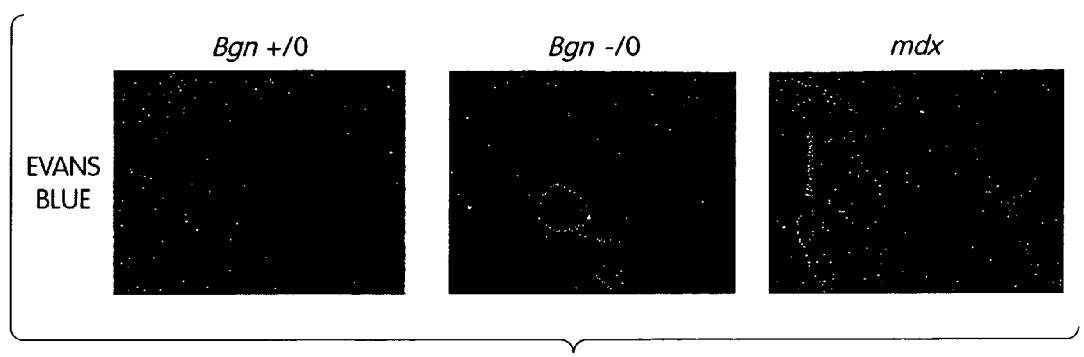

FIG. 20. Loss of muscle membrane integrity in biglycan null mice

A. Serum Creatine Kiriase from Bgn null and wildtype littermate controls was measured in mice from 8-12 weeks old were assayed (Sigma). CK levels from biglycan null mice are ~10 fold greater than wildtype and decorin null mice. B. EBD uptake. Mice were injected intravenously with EBD and then returned to their cage for 6 hr. Dye uptake into muscle was assessed by fluorescence microscopy. In bgn null mice some muscle fibers exhibited complete permeation by dye, while in other cells the uptake was limited to a perimembranous distribution. No uptake was observed in muscle from normal animals, while virtually all fibers in mdx mice showed complete permeation.

Figure 21:
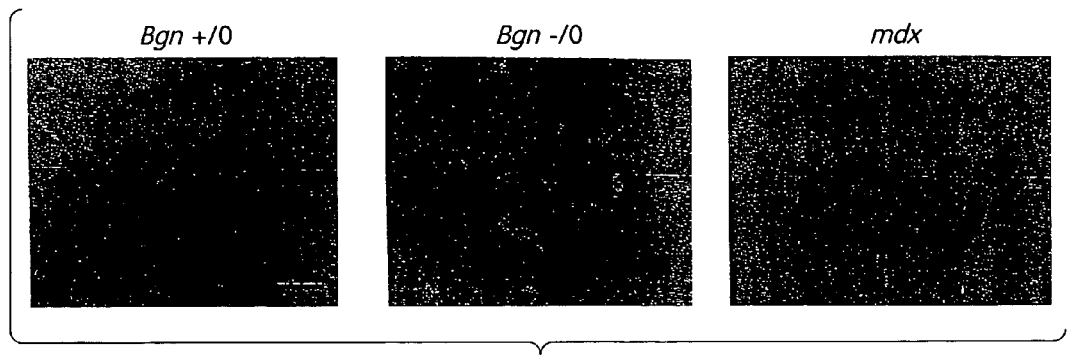

FIG. 21. Histopathology of muscle from biglycan null mice. Haematoxylin and eosin stained fresh-frozen sections of skeletal muscle (quadraceps femoris, 8 um thick) from wildtype and BGN $^{-10}$ mice (AGE). Bgn null mice exhibit groups muscle fibers with centrally nucleated fibers, which are characteristic of muscle fibers that have regenerated in the adult animal. virtually all myofibers show central nuclei in mdx muscle, while such profiles are rarely detected in normal muscle.

Figure 22:
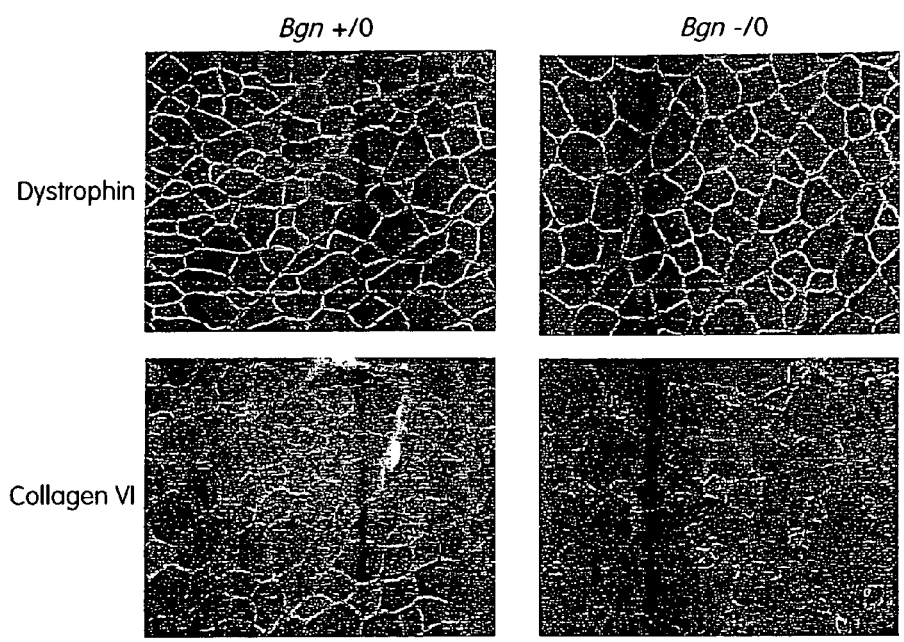

FIG. 22. Reduced collagen VI expression in biglycan null mice. Frozen sections from biglycan null mice and wild type littermate controls were immunolabelled with the indicated antibodies. The expression of dystrophin (and. several other DAPC components, see Table I) is similar in muscles from mice of both genotypes. The level of collagen VI is reduced in biglycan null mice relative to controls. The expression levels of decorin are unaffected in biglycan null mice. All comparisons are from tissue prepared, sectioned and immunostained in the same experiment. Images were acquired under identical conditions for each set.

Figure 23:
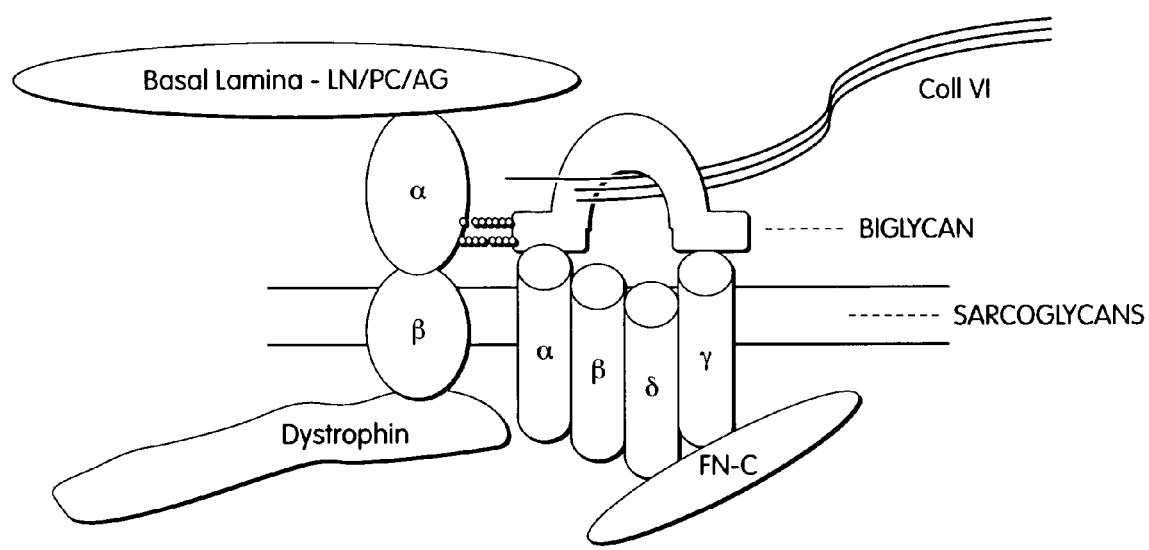

FIG. 23. An exemplary DAPC comprising collagen VI.

DETAILED DESCRIPTION OF THE INVENTION

I. Overview

Certain embodiments of the invention are based in part on the observation that biglycan interacts with, and regulates and/or induces modication of the dystrophin-associated protein complex (DAPC), as well as activates components playing an important role in neuromuscular junction formation. In particular, biglycan is shown to interact with α-dystroglycan, an extracellular component of the DAPC, as well as with α-sarcoglycan and γ-sarcoglycan, which are components of the sarcoglycan complex of the DAPC. Biglycan is also shown to induce phosphorylation of α-sarcoglycan, showing that biglycan does not solely interact with components of the DAPC, but also causes modification of the components. The proteoglycan of the invention has been found to be overexpressed in an animal model of muscular dystrophy that is characterized by the absence of dystrophin. The integrity of the DAPC and its association with the extracellular matrix (ECM) are essential for muscle cell viability. Accordingly, biglycan is believed to stabilize the DAPC complex at the surface of cells, in particular, muscle cells, and can be part of a compensatory mechanism that allows survival of dystrophin negative fibers.

It has also been shown herein that biglycan is involved in neuromuscular junction formation, e.g., induced by agrin. Agrin, which is an extracellular matrix protein present in the synaptic basal lamina, is secreted by the nerve terminal and triggers neuromuscular junction formation by activating the receptor tyrosine kinase MuSK, thereby inducing phosphorylation and clustering of AChR. It had not previously been known how agrin activates the receptor MuSK, since agrin does not bind directly to this receptor. As described below, activation of the receptor MuSK by agrin is actually potentiated by biglycan. This discovery is based at least in part on the finding that biglycan binds directly to the MuSK receptor; biglycan directly induces the tyrosine phosphorylation of MuSK; biglycan potentiates agrin-induced phosphorylation of MuSK; and biglycan potentiates agrin-induced clustering of AChRs. In addition, the appended examples demonstrate that myotubes from biglycan deficient mice show a defective response to agrin, in particular the cells are defective in agrin-induced AChR clustering, which was further shown to be corrected by the addition of biglycan to the culture media of the myotubes. Thus, it is clearly shown that the absence of biglycan in cells results in a deficiency in agrin-induced AChR clustering, which can be corrected by the ectopic addition of biglycan to the cells. The role of biglycan in mediating neuromuscular junction formation, in particular, postynaptic differentiation, is further supported by the fact biglycan binds to α-dystroglycan (shown herein), and that α-and β-dystroglycans interact with components of the postsynaptic membrane. For example, agrin binds to α-dystroglycan (see FIG. 1) and β-dystroglycan binds to the AChR-associated protein rapsyn. In addition, agrin-induced AChR clustering is markedly decreased in muscle cells expressing reduced levels of dystroglycan, further demonstrating the role of dystroglycan in postsynaptic membranes. Thus, it was demonstrated herein that biglycan plays an important role in the formation of neuromuscular junctions both by interacting with the agrin receptor MuSK and by interacting with α-dystroglycan. It is contemplated that biglycan plays both functional and structural roles in the organization of the postsynaptic specializations.

Moreover, as described further below, biglycan also regulates utrophin expression and localization. Agrin can cause an upregulation of utrophin expression and direct it to be localized to specific domains on the cell surface. The signaling receptor for agrin is the receptor tyrosine kinase MuSK. Agrin also induces the tyrosine phosphorylation of α- and γ-sarcoglycan in cultured myotubes. Biglycan can also regulate the tyrosine phosphorylation of α- and γ-sarcoglycan. Moreover, the receptor tyrosine kinase MuSK is required for this biglycan-induced tyrosine phosphorylation of these proteins. These observations indicate that biglycan can act directly to organize the DAPC, including utrophin, on the muscle cell surface.

Furthermore, since DAPCs are also found in brain, agrin has been found in senile plaques in brains of subjects with Alzheimer's disease, and peripheral and central neural deficiencies are present in some patients lacking dystrophin, biglycan is also believed to be involved in formation of synapses.

Thus, the results described herein indicate that biglycan plays an important role in maintaining the integrity of muscle cell plasma membrane, at least in part by interacting with α-dystroglycan and the sarcoglycans in the DAPC; in neuromuscular junction formation, at least in part by mediating agrin-induced AChR clustering and MuSK activation; and also probably in synapse formation. Based at least on these findings, the invention provides compositions and methods for diagnosing, treating and/or preventing diseases or conditions associated with a dysfunctional DAPC, an unstable cellular structure, a defect in neuromuscular junctions or synapses. Such diseases include, in particular, muscular dystrophies, such as Duchenne, Limb-girdle, other myopathies, such as Bethlem myopathy, neuromuscular disorders, and neurological disorders.

Furthermore, in view of the wide tissue distribution of DAPCs and dystroglycans, biglycan is likely to play a role in regulating signaling through the cytoplasmic membrane and/or maintaining the integrity of cytoplasmic membranes of cells other than muscle cells. For example, dystroglycan or other DAPC components are abundant in brain, kidney, and heart. Thus, the invention provides, more generally, compositions, diagnostic and therapeutic methods for diseases or disorders associated with an abnormality of a membrane protein complex with which the protein of the invention interacts, e.g., the DAPC, or MuSK receptor.

Based at least on the fact that dystroglycan is known to be a receptor used by microorganisms for entering cells, e.g., Lassa Fever and choriomeningitis fever viruses, the compositions of the invention, particularly biglycan therapeutics, can be used for treating and/or preventing infections by such microorganisms. Without wanting to be limited to a specific mechanism of action, biglycan therapeutics may hinder or inhibit binding of the microorganism to dystroglycan.

Both human biglycan (described, e.g., in Fischer et al. as "bone small proteoglycan" J. Biol. Chem. 264: 4571 (1996); GenBank Accession No. J04599; SEQ ID NO: 9) and DAG-125 isolated from Torpedo electric organ have been shown to interact with DAPC components. Based on sequence homologies between the two proteins and similar biological activities (further described herein), it is believed that the human biglycan (SEQ ID NO: 9) may be the human ortholog of the Torpedo DAG-125. Alternatively, the human ortholog of the Torpedo DAG-125 may be a protein that is highly related to human biglycan. For purposes of clarity, the term "biglycan" as used herein is intended to include the human biglycan (SEQ ID NO: 9) and Torpedo DAG-125, as well as homologs of these proteoglycans.

In addition, it is shown herein that a biglycan deficiency leads to a decrease in collagen VI in the extracellular matrix, revealing a surprising collagen VI-based mechanism for DAPC association with the extracellular matrix and providing an explanation for the role of collagen VI in muscle. Mutations in the genes encoding this heterotrimeric collagen are the basis for Bethlem myopathy. This myopathy is characterized by dystrophic changes that are most pronounced in infants and children but typically resolve as the affected individual ages. Targeted mutation of the αX(VI) chain results in mice that show elevated EBD uptake and centrally located nuclei. Interestingly, neither these collagen VI mutant mice nor the Bethlem patients show elevated serum creatine kinase levels. The collagen VI-based matrix association is mechanistically and functionally distinct from the well established dystrophin/β-dystroglycan/α-dystroglycan/basal lamina axis (FIG. 24). α-Dystroglycan binds three G-domain containing basal lamina proteins—laminin-2, perlecan and agrin. These interactions generally involve α-dystroglycan glycosylation and involve a different domain than that mediating biglycan interaction. Further, the α-dystroglycan-basal lamina complex persists in the absence of sarcoglycans. Collagen VI is a microfibrillar collagen that is not a basal lamina component. On the other hand, β-dystroglycan, dystrophin and laminin persist in biglycan null mice while collagen VI expression is reduced. Potential cytoskeletal elements of the sarcoglycan-biglycan axis may include filamin-C, which binds to δ- and γ-sarcoglycan. Thus the DAPC has at least two partially independent paths for matrix interaction.

Accordingly, it is disclosed herein that biglycans may be used to treat disorders related to a deficiency in collagen VI, and, furthermore, that collagen VI is a component of certain DAPCs, and may be used to stabilize certain DAPCs. Collagen VI, as it occurs in the healthy human body, is a polymer composed primarily of collagen VI monomers, wherein each monomer is a complex formed from the α1(VI), α2(VI) and α3(VI) polypeptide chains. A deficiency in collagen VI, as the term is used herein, is intended to include any situation where there is less collagen VI than is typical for the relevant tissue or cell type as well as any situation where there is less functionally active or functionally arranged (e.g. assembled into a functional matrix) collagen VI.

II Definitions

For convenience, the meaning of certain terms and phrases employed in the specification, examples, and appended claims are provided below.

"GAGs" refers to glycosaminoglycans, which is used interchangeably herein with "mucopolysaccharides," are long, unbranched polysaccharide chains composed of repeating disaccharide units. One of the two sugars is always an amino sugar (N-acetylglucosamine or N-acetylgalactosamine). Glycosaminoglycans are covalently linked to a serine residue of a core protein, to form a proteoglycan molecule.

The term "glycan" is used interchangeably herein with the term "polysaccharide" and "oligosaccharide."

The term "glycoprotein" refers to a protein which contains one or more carbohydrate groups covalently attached to the polypeptide chain. Typically, a glycoprotein contains from 1% to 60% carbohydrate by weight in the form of numerous, relatively short, branched oligosaccharide chains of variable composition. In contrast to glycoproteins, proteoglycans are much larger (up to millions of daltons), and they contain 90% to 95% carbohydrate by weight in the form of may long, unbranched glycosaminoglycan chains.

The term "proteoglycan of the invention" refers to a proteoglycan molecule having one or more of the characteristics and biological activities of biglycan. Accordingly, a preferred proteoglycan of the invention includes a proteoglycan having one or more of the following characteristics: a molecular weight between 100 and 150 kDa, or an apparent mobility of 125 kDa, as determined on an SDS acrylamide gel; one or more glycosaminoglycan side chain; a molecular weight of the core between 35 and 40 kDa, preferably around 37 kDa; an amino acid sequence selected from SEQ ID NO: 1-6 and 9 or variant thereof; one or more biological activities of biglycan, as listed infra, under the corresponding definition. In one embodiment, the proteoglycan of the invention is a SLRP, e.g., human biglycan. A preferred proteoglycan of the invention is Torpedo DAG-125 or a mammalian, preferably human, ortholog thereof. Another preferred proteoglycan of the invention is biglycan, e.g., human biglycan having SEQ ID NO: 9. The term "proteoglycan of the invention" further includes portions of the wildtype proteoglycan, provided that these portions have at least one biological activity of a biglycan protein. Accordingly, the term "proteoglycan of the invention" includes molecules that consist only of the core (i.e., protein part of the molecule), or of the GAG side chains, portions thereof and/or combinations thereof.

The term "biglycan" refers to proteoglycans having at least one biological activity of human biglycan or Torpedo DAG-125. Preferred biglycans include Torpedo DAG-125 (comprising SEQ ID NO: 1-3), human biglycan (SEQ ID NO: 9), as well as homologs and fragments thereof Preferred homologs are proteoglycans or proteins or peptides having at least about 70% identity, at least about 75% identity, at least about 80% identity, at least about 85% identity, at least about 90% identity, at least about 95% identity, and even more preferably, at least about 98 or 99% identity. Even more preferred homologs are those which have a certain parentage of homology (or identity) with human biglycan or Torpedo DAG-125 and have at least one biological activity of these proteoglycans. The term biglycan is not limited to the full length biglycan, but includes also portions having at least one activity of biglycan.

The term "human biglycan" refers to the proteoglycan described in Fischer et al. J. Biol. Chem. 264: 4571 (1989), having GenBank Accession No. J04599, and the amino acid sequence set forth in SEQ ID NO: 9. A cDNA sequence encoding the human biglycan protein is set forth in SEQ ID NO: 7, and the open reading frame thereof as SEQ ID NO: 8.

The term "biglycan core" refers to a biglycan that does not include GAG chains.

The term "biglycan proteoglycan" or "biglycan PG" refers to a biglycan having at least one GAG chain.

The term "biglycan nucleic acid" refers to a nucleic acid encoding a biglycan proteoglycan, e.g., a nucleic acid encoding a protein having SEQ ID NO: 9.

A "biological activity of biglycan" is intended to refer to one or more of: the ability to maintain the integrity of a plasma membrane; the ability to stabilize DAPCs on plasma membranes; the ability to bind to one or more components of DAPCs; e.g., binding to α-dystroglycan, binding to a sarcoglycan component, such as α-sarcoglycan or γ-sarcoglycan; binding to MuSK; stimulating the formation of neuromuscular junctions, such as by stimulating postsynaptic differentiation; potentiation of AChR aggregation, e.g., agrin-induced AChR aggregation; phosphorylation of DAPC components, e.g., sarcoglycans; stimulation MuSK phosphorylation or potentiating agrin-induced MuSK phosphorylation.

A "biglycan therapeutic" is a compound which can be used for treating or preventing a disease that is associated with an abnormal cytoplasmic membrane, e.g., an unstable membrane; an abnormal DAPC; abnormal neuromuscular junction; abnormal synapse; abnormal AChR aggregation; or abnormal MuSK activation. A biglycan therapeutic can be an agonist or an antagonist of one or more of the biological activities of biglycan. A therapeutic can be any type of compound, including a protein or derivative thereof, e.g., a proteoglycan, a nucleic acid, a glycan, or a small organic or synthetic molecule.

"Collagen VI" is used to describe the collagen VI monomer, which is a complex formed from the α1(VI), α2(VI) and α3(VI) polypeptide chains, as well as multimers comprising more than one collagen VI monomer. For example, collagen VI is frequently found in vivo as part of a network of beaded filaments. A "collagen VI polypeptide" includes any of the complete α1(VI), α2(VI) and α3(VI) polypeptide chains as well as fragments that are recognizably derived from the α1(VI), α2(VI) and α3(VI) polypeptide chains.

A "biological activity of collagen VI" is intended to refer to one or more of: the ability to multimerize with collagen VI monomers and the ability to interact with biglycan.

A "collagen VI therapeutic" is a compound which can be used for treating or preventing a disease that is associated with an abnormal cytoplasmic membrane, e.g., an unstable membrane; an abnormal DAPC; abnormal neuromuscular junction; abnormal synapse; abnormal biglycan deficiency; abnormal AChR aggregation; or abnormal MuSK activation. A collagen VI therapeutic can be an agonist or an antagonist of one or more of the biological activities of collagen VI. A therapeutic can be any type of compound, including a protein or derivative thereof, e.g., a proteoglycan, a nucleic acid, a glycan, or a small organic or synthetic molecule.

The term "abnormal" is used interchangeably herein with "aberrant" and refers to a molecule, or activity with differs from the wild type or normal molecule or activity.

Figure 1:
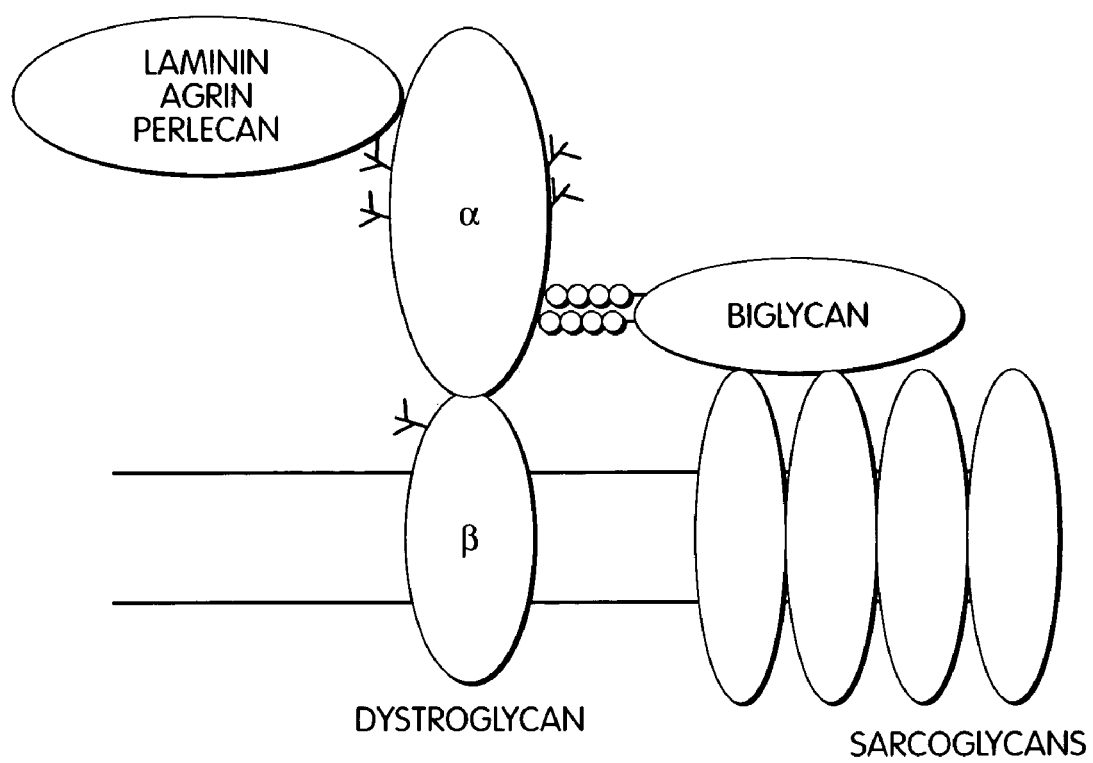
FIG. 1 is a diagram of the interaction between DAG-125 or biglycan with an example of a DAPC.

The term "DAPC" refers to "dystrophin-associated protein complex", a membrane complex of the type set forth in FIG. 1, which comprises dystrophin and one or more of the following: α- and beta-dystroglycans, the sarcoglycan transmembrane complex and collagen VI. A DAPC that is deficient for a component, such as collagen VI, is a DAPC that has less of the component or less of an active form of the component than is typical or healthy.

"Sarcoglycans" exit in different forms including α-, beta-, γ-, delta-, and epsilon-sarcoglycans. Certain sarcoglycans are specific for certain tissues, e.g., alpha and delta-sarcoglycans are skeletal muscle specific.

"Dystrophin-associated proteins" includes proteins or glycoproteins, such as alpha-dystroglycan, dystrobrevin, sarcospan and the syntrophins.

The term "AChR" refers to acetylcholine receptor.

The term "SLRP" refers to small leucine rich repeat proteoglycan.

The term "MASC" refers to muscle cell-associated specificity component.

The term "RATL" refers to rapsyn-associated transmembrane linker.

The term "HSPG" refers to heparan sulfate proteoglycans.

The term "MuSK" used interchangeably herein with "muscle specific kinase," refers to a protein tyrosine kinase, that is expressed in normal and denervated muscle, as well as other tissues including heart, spleen, ovary or retina (See Valenzuela, D., et al., 1995, *Neuron* 15: 573-584). The tyrosine kinase has alternatively been referred to as "Dmk" for "denervated muscle kinase." Thus, the terms MuSK and Dmk may be used interchangeably. The protein appears to be related to the Trk family of tyrosine kinases, and is further described in U.S. Pat. No. 5,814,478.

The term "MuSK activating molecule" as used herein refers to a molecule which is capable of inducing phosphorylation of the MuSK receptor in the context of a differentiated muscle cell. One such activating molecule is agrin as described in the Examples set forth herein.

The term "or" is used herein interchangeably with the term "and/or", unless context clearly indicates otherwise.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of SEQ ID NO: 7 or 8, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (*U.S.A.*) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length human biglycan polynucleotide sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine; and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate the bioactivity of a proteoglycan of the invention.

A "myoblast" is a cell, that by fusion with other myoblasts, gives rise to myotubes that eventually develop into skeletal muscle fibres. The term is sometimes used for all the cells recognisable as immediate precursors of skeletal muscle fibres. Alternatively, the term is reserved for those post-mitotic cells capable of fusion, others being referred to as presumptive myoblasts.

The term "including" is used to mean, and interchangeably with, the phrase "including but not limited to".

"Myofibril" is a long cylindrical organelle of striated muscle, composed of regular arrays of thick and thin filaments, and constituting the contractile apparatus.

A "myotube" is an elongated multinucleate cells (three or more nuclei) that contain some peripherally located myofibrils. They are formed in vivo or in vitro by the fusion of myoblasts and eventually develop into mature muscle fibres that have peripherally located nuclei and most of their cytoplasm filled with myofibrils. In fact, there is no very clear distinction between myotubes and muscle fibers proper.

"Utrophin" (dystrophin associated protein) is an autosomal homologue of dystrophin (of size 395 kD) localised near the neuromuscular junction in adult muscle, though in the absence of dystrophin (i.e. in Duchenne muscular dystrophy) utrophin is also located on the cytoplasmic face of the sarcolemma.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene). Alternatively, a transgene can also be present in an episome. A transgene can include one or more transcriptional regulatory sequences and any other nucleic acid, (e.g. intron), that may be necessary for optimal expression of a selected coding sequence.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Derived from" as that phrase is used herein indicates a peptide or nucleotide sequence selected from within a given sequence. A peptide or nucleotide sequence derived from a named sequence may contain a small number of modifications relative to the parent sequence, in most cases representing deletion, replacement or insertion of less than about 15%, preferably less than about 10%, and in many cases less than about 5%, of amino acid residues or base pairs present in the parent sequence. In the case of DNAs, one DNA molecule is also considered to be derived from another if the two are capable of selectively hybridizing to one another.

The terms "chimeric", "fusion" and "composite" are used to denote a protein, peptide domain or nucleotide sequence or molecule containing at least two component portions which are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences which encode them, are recombinant in the sense that they contain at least two constituent portions which are not otherwise found directly linked (covalently) together in nature.

The term "modulate" refers to inhibiting or stimulating.

The terms "activating a postsynaptic membrane" refers to the stimulation of the transfer of a signal at neuromuscular junction, generally, from a nerve cell to a muscle cell. Activation usually includes the stimulation of aggregation of AChR on the cell membrane at the neuromuscular junction; and/or the phosphorylation of MuSK. Activation results in induction of postsynaptic differentiation.

The term "treating" with regard to a subject, refers to improving at least one symptom of the subject's disease or disorder. Treating can be curing the disease or condition or improving it.

III. Compounds of the Invention

One aspect of the invention provides biglycan therapeutics for use in maintaining the integrity of plasma cell membranes, in particular, biglycan therapeutics which stabilize dystrophin associated protein complexes (DAPC) in these membranes, thereby preventing the disintegration of the membranes. In further aspects, the invention also provides biglycan therapeutics which stimulate neuromuscular junction formation, such as by stimulating postsynaptic membrane differentiation, and more generally compounds which stimulate synapse formation. In certain aspects, the invention provides biglycan therapeutics for use in modulating collagen VI expression or activity, and optionally, biglycan therapeutics may be used to treat or prevent a disorder that involves a collagen VI-deficiency. In certain aspects, the invention provides collagen VI therapeutics, and such therapeutics may be used to stabilize DAPCs.

In a particular embodiment, the biglycan therapeutics bind to one or more components of the DAPC. The compound preferably binds to α-dystroglycan and/or to a sarcoglycan component, such as α-sarcoglycan. In an even more preferred embodiment, the compound of the invention binds both to α-dystroglycan and to a component of the sarcoglycan complex, e.g., selected from the group consisting of α-sarcoglycan, γ-sarcoglycan and δ-sarcoglycan. The component of the sarcoglycan to which the compound of the invention binds is preferably α-sarcoglycan. Generally, the compound of the invention contacts one or more components of the DAPC, e.g., to thereby stabilize the complex and reduce destabilization of the plasma membrane resulting from an abnormal DAPC complex, such as those seen in muscular dystrophies.

In certain embodiments, the biglycan binds to collagen VI or upregulates production or proper organization of collagen VI.

Yet in an even more preferred embodiment, the compound of the invention binds to a region of α-dystroglycan which is different from the region to which agrin, laminin and perlecan bind (see FIG. 1). Binding of the compounds of the invention do not require the presence of glycosyl side chains on α-dystroglycan. More preferably, the compounds of the invention bind to the C-terminal part of α-dystrogylcan, preferably to about amino acids 345 to 891, more preferably to about amino acids 1-750, about amino acids 30-654, about amino acids 345-653, or about amino acids 494-653 of human alpha-dystroglycan. Thus, a preferred compound of the invention binds to a region consisting essentially of the C-terminal 150 amino acids of α-dystroglycan, i.e., amino acids 494-653.

Other biglycan therapeutics of the invention bind to the receptor tyrosine kinase MuSK. Such compounds can bind to MuSK and/or α-dystroglycan and/or a component of the sarcoglycan complex, e.g., α-sarcoglycan. In preferred embodiments, the biglycan therapeutic activates MuSK and induces phosphorylation of α and/or γ-sarcoglycan.

The subject biglycan therapeutics preferably bind specifically to one or more of the above-cited molecules, i.e., they do not significantly or at a detectable level bind to other molecules to produce an undesirable effect in the cell or extracellular space. The compounds preferably bind with a dissociation constant of $10^{-6}$ or less, and even more preferably with a dissociation constant of $10^{-7}$, $10^{-8}$, $10^{-9}$, $10^{-10}$, $10^{-11}$, $10^{-12}$, or $10^{-13}$ M or less. The dissociation constant can be determined according to methods well known in the art.

Binding assays for determining the level of binding of a compound to a component of the DAPC or to MuSK or for identifying members of, e.g., a library of compounds which bind to these molecules are known in the art and are also further described herein. Methods for preparing DAPC components or MuSK for use in such assays are also known. Such components can be isolated from tissue or, when they are proteins, can be prepared recombinantly or synthetically. Their nucleotide and amino acid sequences are publicly available, e.g., from GenBank, or from publications.

Other preferred biglycan therapeutics of the invention have one or more biological activities of biglycan, in addition to, or instead of, being able to bind one or more components of the DAPC and/or MuSK. For example, a biglycan therapeutic of the invention can stimulate neuromuscular junction formation, in particular, postsynatic membrane differentiation, including inducing aggregation of AChRs and/or stimulating or stimulating agrin-induced tyrosine phorphorylation of MusK.

The biglycan therapeutic of the invention can be a protein or derivative thereof, in particular a proteoglycan, a nucleic acid, such as a nucleic acid encoding a proteoglycan of the invention, a glycan, a peptidomimetic or derivative thereof, or a small organic molecule. Generally, the compound can be any type of molecule provided that the compound has the required characteristics, e.g., binding to α-sarcoglycan and/or other DAPC components.

In a preferred embodiment, the biglycan: therapeutic of the invention is a proteoglycan having a molecular weight from about 100 kDa to about 150 kDa, preferably from about 110 kDa to about 140 kDa, and most preferably from about 120 to about 130 kDa, as determined, e.g., by migration on an SDS acrylamide gel. The core of the proteoglycan of the invention has a molecular weight from about 25 to about 45 kDa, preferably from about 30 to about 40 kDa and most preferably around 37 kDa. Fragments or portions of these proteoglycans are also within the scope of the invention. The proteoglycan preferably contains one or more glycosaminoglycan side chains, such as a mucopolysaccharide side chain, e.g., heparan, chondroitin, or dermatan. Preferred side chains consist of chonddroitin sulfate, e.g., 4-sulfate (chondroitin sulfate type A) and 6-sulfate (chondroitin sulfate type C). Any side chain can be used in the invention, provided that the proteoglycan has at least one bioactivity of biglycan.

In an even more preferred embodiment, the proteoglycan biglycan therapeutic of the invention comprises one or more of the following amino acid sequence in its core: IQAIEFEDL (SEQ ID NO: 1); LGLGFNEIR (SEQ ID NO: 2); and TSYHGISLFNNPVNYWDVL (SEQ ID NO: 3), or amino acid sequences related thereto, such as amino acid sequences from the mammalian ortholog of the Torpedo protein from which these amino acid sequences were obtained. The proteoglycan preferably contains all three of these sequences or sequences related thereto. For example, the proteoglycan of the invention can comprise one or more of the following amino acid sequences, which are part of human biglycan: IQAIELEDL (SEQ ID NO: 4); LGLGHNQIR (SEQ ID NO: 5); and AYYNGISLFNNPVPYWEVQ (SEQ ID NO: 6).

Although compositions including, and methods using, Torpedo DAG-125 are within the scope of the invention, preferred compositions and methods are those relating to mammalian, including vertebrate, homologs of Torpedo DAG-125, referred to herein as orthologs of Torpedo DAG-125. Preferred orthologs of Torpedo DAG-125 are human, rodent, murine, canine, feline, ovine, and bovine orthologs. As shown herein, it is highly likely that the mammalian DAG-125 is biglycan, however, it may also be a molecule that is related to biglycan, and, e.g., also to decorin (see below), but is actually a not previously described protein. Thus, the invention also provides compositions comprising the mammalian ortholog of Torpedo DAG-125, such as the human ortholog of Torpedo DAG-125.

A mammalian ortholog of Torpedo DAG-125 can be isolated by screening libraries with probes containing nucleotide sequences encoding one or more of SEQ ID NOs 1-3. Numerous other methods are available for cloning the mammalian ortholog of Torpedo DAG-125. For example, antibodies to Torpedo DAG-125 can be produced and used to screen mammalian expression libraries. The identification of the cloned proteins as mammalian orthologs of Torpedo bAG-125 can be established by performing the same biological assays as those described in the Examples employing Torpedo DAG-125.

Thus, the proteoglycan of the invention can also be a member of the family of small leucine-rich proteoglycans (SLRP), also referred to as "nonaggreagating or small dermatan-sulfate proteoglycans because of their inability to interact with hyaluronan, or because of their type of glycosaminoglycans, respectively. SLRPs are organized into three classes based on their protein and genomic organization. All SLRPs are characterized by a central domain containing leucine rich repeats (LRR) flanked at either side by small, cysteine clusters. The SLRPs are described, e.g., in Iozzo et al. (1998) *Ann. Rev. Biochem.* 67:609, specifically incorporated herein by reference.

Figure 5A:
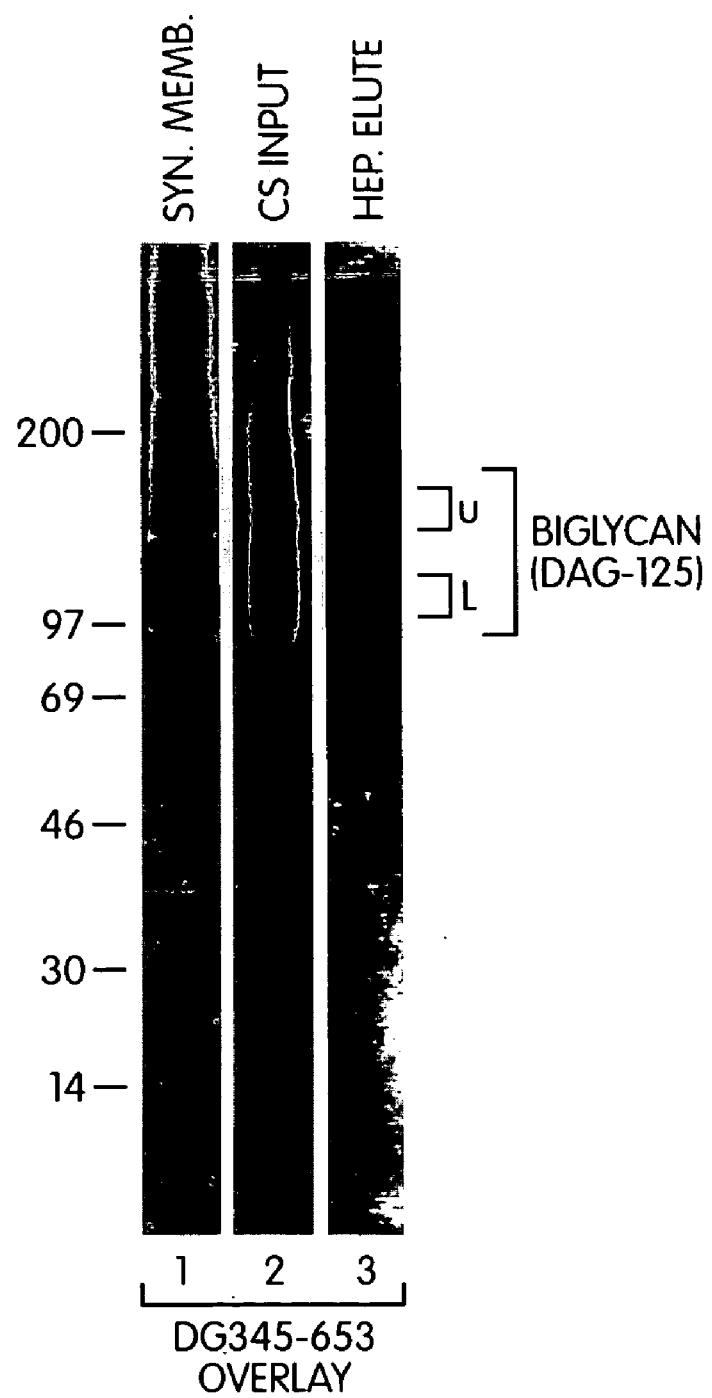
FIG. 5A shows a blot overlay assay in which a filter with synaptic membranes, input or elute from a column was incubated with a portion of alphα-dystroglycan.
Figures 5B, 5C:
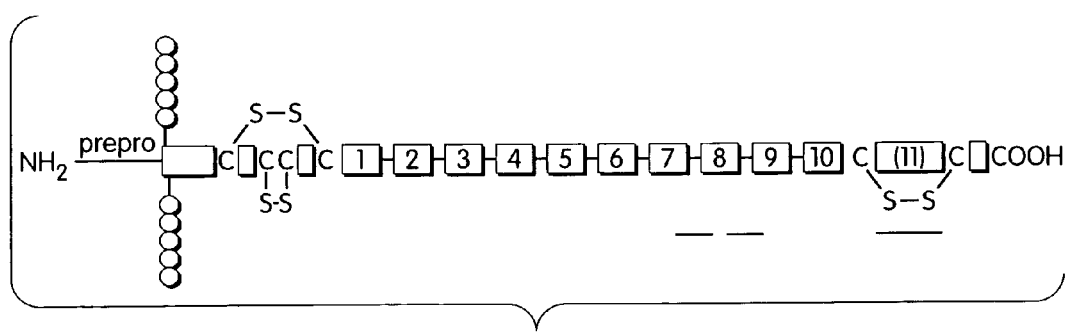
FIG. 5B shows the sequence alignment between the Torpedo DAG-125 sequences (SEQ ID NOs: 1-3) and human biglycan (SEQ ID NOs: 4-6).
FIG. 5C is a diagram of the structure of biglycan: the prepro-region, which is absent in the mature biglycan correponds to amino acids 1-37 of SEQ ID NO: 9; the N-terminal cysteine-rich region corresponds to amino acids 38-80 of SEQ ID NO: 9; the LLR region corresponds to about amino acids 81-314 of SEQ ID NO: 9; and the C-terminal cysteine-rich region corresponds to amino acids 315-368 of SEQ ID NO: 9. Circles represent chondroitin sulfate side chains. "S-S" denotes intrachain disulfide binding.

SLRP protein cores range from 35-45 kD with one or two GAG chains attached at the extreme N-terminus. The general structure of the SLRP protein core consists of a tandem array of 6-10 leucine-rich repeats (LRR) flanked by domains with conserved, disulfide-bonded cysteines (FIG. 5C). Depending upon the extent of glycosylation and number of GAG chains, the native molecular weight ranges from ~100-250 kD. On the basis of their sequence homology, Iozzo, supra, has proposed that SLRPs be grouped into three classes consisting of: 1) biglycan and decorin; 2) fibromodulin, lumican, keratocan, PREPLP, and osteoadherin; and 3) epiphycan and osteoglycin. The most compelling feature of the SLRP protein core are the LRRs. Such repeats (24aa each in the SLRPs) mediate protein-protein interactions in a wide variety of intracellular, transmembrane, and extracellular contexts (Kobe & Deisenhofer, (1994) *Trends Biochem. Sci.* 19: 415-21). The neurotrophin binding site on trkB, for example, is an LRR (Windisch et al., (1995) *Biochemistry* 34: 11256-63). The repeats are thought to have a general structure of an α-helix followed by beta-sheet in an anti-parallel array, although sequence analysis has suggested that this order might be reversed in the SLRPs (Hocking et al., (1998) *Matrix Biol* 17: 1-19). It is likely that the conserved residues of each repeat dictate their secondary structure, while the intervening amino acids determine specificity of ligand binding.

Preferred SLRPs for use in the invention include Class I SLRPs, such as biglycan and decorin. The partial amino acid sequences of DAG-125, the Torpedo proteoglycan which was shown to bind to alphα-dystroglycan (see Examples) shows strong homology to human biglycan (see FIG. 5B): a 78% identity was found in a total of 37 amino acid long sequence. Biglycan from rodent, pig and human are >95% identical. Decorin and biglycan from human are only 55% identical. Such homology is consistent with decorin and biglycan having both shared and unique functions. Thus, although Torpedo DAG-125 has amino acid sequence that more closely resemble that of human biglycan, based on the similarity of structure and function between biglycan and decorin, the latter proteoglycan and derivatives thereof may also be used to practice the invention.

Nucleotide and amino acid sequences of biglycan and decorin genes and proteins from various species are publically available, such as in GenBank. For example, human biglycan can be found under GenBank Accession No. J04599 (human HPGI encoding bone small proteoglycan I (biglycan), described in Fisher et al. (1989) J. Biol. Chem. 264: 4571; SEQ ID Nos: 7-9) and M65154; cow biglycan can be found under GenBank Accession No. L07953; rat biglycan can be found under GenBank Accession No. U17834, mouse biglycan can be found under GenBank Accession No. L20276 and X53928; ovis biglycan can be found under GenBank Accession No. AF034842; human decorin can be found at GenBank Accession No. M14219; rabbit decorin can be found at GenBank Accession No. I47020; chick decorin can be found at GenBank Accession No. P28675; Equus decorin can be found at GenBank Accession No. AF038; bovine decorin can be found at GenBank Accession No. P21793; ovis decorin can be found at GenBank Accession No. AF125041; and rat decorin can be found at GenBank Accession No. Q01129. Sequences of biglycan and decorin and other SLRPs can be found in GenBank.

Decorin and biglycan have one and two glycosaminoglycan (GAG) chains, respectively. Their composition is tissue specific and can be regulated at a number of levels (Hocking et al., (1998) *Matrix Biol* 17: 1-19). For example, the biglycan GAG from skin and cartilage is predominantly dermatan sulfate, while biglycan synthesized in bone is a chondroitin sulfate proteoglycan. Heparan sulfate side chains have not been reported. Both the protein core and the cell type contribute to the distinct glycosylation of these SLRPs.

Other proteoglycans or cores thereof of the invention include fusion proteins. For example, biglycan or a portion thereof can be fused to an immunoglobulin portion. Alternatively, the fusion protein is a combination between two or more portions of proteoglycans of the invention, e.g., a portion of a biglycan molecule fused to a portion of a decorin molecule (see examples).

Portions and fragments of the proteoglycans of the invention are also within the scope of the invention. A portion is typically at least five, 10, 15, or 20 amino acids long. Preferred portions are those which are sufficient for exerting a biological activity, such as interacting with a DAPC component. Portions can comprise or consist of one or more specific domain of a protein. Domains of biglycan and decorin include two cysteine-rich regions (included in the N- and C-terminal 40-50 amino acids of mature biglycan) and leucine-rich repeats (LRRs). The "LRR region" refers to the region of biglycan containing the repeats, and consists essentially of amino acids 81-314. Each individual repeat is referred to herein as an "LRR." LRRs are believed to mediate protein:protein interactions and may thus be sufficient for stabilizing DAPCs and postsynaptic membranes. Based at least on the observation that both decorin and biglycan bind to MuSK and that the LLR region in both of these proteins is very similar, it is believed that the LRRs are involved in mediating the interaction of biglycan (and decorin) with MuSK and may be involved in mediating MuSK phosphorylation.

Another preferred biglycan of the invention consists of a portion of biglycan that is capable of binding to a sarcoglycan. It has been shown that the α-sarcoglycan binding domain of human biglycan is located in the N-terminal domain of the mature biglycan protein, i.e.; amino acids 38-80, and more specifically, amino acids 38-58 of SEQ ID NO: 9. The GAG chains are not necessary for binding to α-sarcoglycan. It has also been shown that the C-terminal cysteine-rich domain mediates interaction with γ-sarcoglycan. Accordingly, preferred biglycans of the invention include portions of biglycan consisting of the N-terminal or the C-terminal cysteine-rich domain, i.e., amino acids 38-80 and 315-368 of SEQ ID NO: 9. Combinations of certain domains of biglycan are also within the scope of the invention.

Thus, preferred fragments consist of at least about 30 amino acids, at least about 40 amino acids, 50, 60, 70, 80, 90, 100, 150, or 200 amino acids. Short portions of the proteoglycans of the invention are termed "mini-proteoglycan of the invention." For example, a biglycan core fragment of about 20, 30 or 40 amino acids is referred to as a "mini-biglycan."

Human biglycan consists of 368 amino acids (SEQ ID NO: 9), of which amino acids 1-19 constitute a signal peptide (GenBank Accession No. NP_001702 and Fisher et al., supra). Thus biglycan without a signal peptide consists of amino acids 20-368 of SEQ ID NO: 9. The mature biglycan protein consists of amino acids 38-368 of SEQ ID NO: 9, since amino acids 1-37, being a pre-propeptide, are cleaved during processing. Amino acids 38-80 correspond to the N-terminal cysteine-rich region. About amino acids 81-314 corresponds to the leucine rich repeat region, containing 10 repeats of about 24 or 23 amino acids. The open reading frame in the cDNA encoding human biglycan corresponds to nucleotides 121-1227 of SEQ ID NO: 7 and is represented as SEQ ID NO: 8. The nucleotide sequence encoding a mature form of biglycan consists in nucleotides 232-1227 of SEQ ID NO: 7.

In addition to agonists, the invention also provides antagonists of biglycan. An antagonist can be, e.g., a portion of the wild type proteoglycan of the invention which inhibits the action of the wild type proteoglycan, such as by competitively inhibiting the binding of the wild type proteoglycan to a target protein such as a component of a DAPC. Thus, an antagonist can be a dominant negative mutant.

The proteoglycan can be a mature form of the proteoglycan core, i.e., deprived of the signal peptide, or the full length proteoglycan with the signal peptide.

Preferred proteoglycans of the invention are encoded by nucleotide sequences which are at least about 70%, preferably at least about 80%, even more preferably at least about 85%, at least about 90%, at least about 95%, at least about 98%, and even more preferably at least about 99% identical to the nucleotide sequence of an SLRP, e.g., biglycan, or ortholog thereof, or portion thereof.

Preferred nucleic acids of the invention include those encoding a polypeptide comprising an amino acid sequence which is at least about 70%, preferably at least about 80%, even; more preferably at least about 85%, at least about 90%, at least about 95%, at least about 98%, and even more preferably at least about 99% identical to the nucleotide sequence of an SLRP, e.g., biglycan (e.g., SEQ ID NO: 7 or 8 encoding human biglycan) or DAG-125 or ortholog thereof, portion thereof. In one embodiment, the nucleic acid encodes a polypeptide containing one or more of SEQ ID NOs: 1-3 or SEQ ID NOs: 4-6 or 9.

Another aspect of the invention provides a nucleic acid which hybridizes under stringent conditions to a nucleic acid encoding biglycan, e.g., having one or more of SEQ ID NOS: 1 to 6 or 9, or complement thereof. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-

6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a nucleic acid of the present invention will bind to one of SEQ ID NOS 1 to 6 or complement thereof or nucleic acid encoding a SLRP under moderately stringent conditions, for example at about 2.0×SSC and about 40° C. In a particularly preferred embodiment, a nucleic acid of the present invention will hybridize to a nucleotide sequence encoding one of SEQ ID NOS: 1 to 6 or 9, such as a nucleic acid having SEQ ID NO: 7 or 8, or a complement thereof under high stringency conditions.

In a further aspect, the invention provides collagen VI therapeutics for use in subject methods, such as for stabilizing dystrophin associated protein complexes (DAPCs). Optionally, the DAPCs to be stabilized are collagen VI-deficient DAPCs.

In a particular embodiment, the collagen VI therapeutics binds to one or more components of the DAPC. The compound preferably binds to biglycan. Generally, the compound of the invention contacts one or more components of the DAPC, e.g., to thereby stabilize the complex and reduce destabilization of the plasma membrane resulting from an abnormal DAPC complex, such as those seen in muscular dystrophies. Methods for assessing the interaction between collagen VI and biglycan are described, for example, in Wiberg et al. (2001) J. Biol. Chem. 276:18947-18952.

The subject collagen VI therapeutics preferably bind specifically to one or more of the above-cited molecules, i.e., they do not significantly or at a detectable level bind to other molecules to produce an undesirable effect in the cell. The compounds preferably bind with a dissociation constant of $10^{-6}$ or less, and even more preferably with a dissociation constant of $10^{-7}$, $10^{-8}$, $10^{-9}$, $10^{-10}$, $10^{-11}$ $10^{-12}$, or $10^{-13}$ M or less. The dissociation constant can be determined according to methods well known in the art.

Other preferred compounds of the invention have one or more biological activities of collagen VI, such as the ability to form collagen VI monomers with endogenous collagen VI subunits or the ability to form collagen VI polymers.

In certain embodiments a collagen VI therapeutic comprises a polypeptide comprising an amino acid sequence which is at least about 90% identical to a collagen α1(VI) sequence, such as shown in SEQ D No: 11 (an example of a human precursor sequence) and SEQ ID No: 12 (an example of a human mature chain). In certain embodiments a collagen VI therapeutic comprises a polypeptide comprising an amino acid sequence which is at least about 90% identical to a collagen α1(VI) sequence, such as shown in SEQ ID No: 11 (an example of a human precursor sequence) and SEQ ID No: 12 (an example of a human mature chain). In certain embodiments a collagen VI therapeutic comprises a polypeptide comprising an amino acid sequence which is at least about 90% identical to a collagen α2(VI) sequence, such as shown in SEQ ID No: 13 (an example of a human precursor sequence) and SEQ ID No: 14 (an example of a human mature chain). In certain embodiments a collagen VI therapeutic comprises a polypeptide comprising an amino acid sequence which is at least about 90% identical to a collagen α3(VI) sequence, such as shown in SEQ ID No: 15 (an example of a human precursor sequence) and SEQ ID No: 16 (an example of a human mature chain). In preferred embodiments, the collagen VI polypeptide is a portion of a mature collagen peptide (e.g. signal sequence is removed). Optionally, the collagen VI polypeptide binds to bigycan. In certain embodiments, a collagen VI therapeutic comprises more than one collagen VI polypeptide. For example, a collagen VI therapeutic may comprise a collagen VI monomer, the monomer comprising a collagen α1(VI) chain, a collagen α2(VI) chain and a collagen α3(VI) chain in a 1:1:1 ratio. Optionally, the therapeutic comprises multimers of collagen VI monomers. Exemplary collagen VI polypeptide and nucleic acid sequences are shown in Tables 1 and 2, respectively.

TABLE 1

Examples of Collagen VI Polypeptides

| Name | Amino Acid Sequence |
|---|---|
| Human α1(VI) precursor chain (gi:13878903) (SEQ ID NO:11) | mraarallpl llqacwtaaq depetprava fqdcpvdlff vldtsesval rlkpygalvd kvksftkrfi dnlrdryyrc drnlvwnaga lhysdeveii qgltrmpggr dalkssvdav kyfgkgtytd caikkgleql lvggshlken kylivvtdgh plegykepcg gledavneak hlgvkvfsva itpdhleprl siiatdhtyr rnftaadwgq srdaeeaisq tidtivdmik nnveqvccsf ecqpargppg lrgdpgfege rgkpglpgek geagdpgrpg dlgpvgyqgm kgekgsrgek gsrgpkgykg ekgkrgidgv dgvkgemgyp glpgckgspg fdgiqgppgp kgdpgafglk gekgepgadg eagrpgargp sgdegpagep gppgekgeag degnpgpdga pgerggpger gprgtpgprg prgdpgeagp qgdqgregpv gvpgdpgeag pigpkgyrgd egppgsegar gapgpagppg dpglmgerge dgpagngteg fpgfpgypgn rgapgingtk gypglkgdeg eagdpgddnn diaprgvkga kgyrgpegpq gppghqgppg pdeceildii mkmcscceck cgpidllfvl dssesiglqn feiakdfvvk vidrlsrdel vkfepgqsya gvvqyshsqm qehvslrsps irnvqelkea ikslqwmagg tftgealqyt rdqllppspn nrialvitdg rsdtqrdttp lnvlcspgiq vvsvgikdvf dfipgsdqln viscqglaps qgrpglslvk enyaelleda flknvtaqic idkkcpdytc pitfsspadi tilldgsasv gshnfdttkr fakrlaerfl tagrtdpahd vrvavvqysg tgqqrperas lqflqnytal asavdamdfi ndatdvndal gyvtrfyrea ssgaakkrll lfsdgnsqga tpaaiekavq eaqragieif vvvvgrgvne phirvlvtgk taeydvpyge shlfrvpsyq allrgvfhqt vsrkvalg |
| Human α1(VI) mature chain | qdepetprava fqdcpvdlff vldtsesval rlkpygalvd kvksftkrfi dnlrdryyrc drnlvwnaga lhysdeveii qgltrmpggr dalkssvdav kyfgkgtytd caikkgleql lvggshlken kylivvtdgh plegykepcg |

TABLE 1-continued

Examples of Collagen VI Polypeptides

| Name | Amino Acid Sequence |
|---|---|
| (SEQ ID NO:12) | gledavneak hlgvkvfsva itpdhleprl siiatdhtyr rnftaadwgq srdaeeaisq tidtivdmik nnveqvccsf ecqpargppg lrgdpgfege rgkpglpgek geagdpgrpg dlgpvgyqgm kgekgsrgek gsrgpkgykg ekgkrgidgv dgvkgemgyp glpgckgspg fdgiqgppgp kgdpgafglk gekgepgadg eagrpgargp sgdegpagep gppgekgeag degnpgpdga pgerggpger gprgtpgprg prgdpgeagp qgdqgregpv gvpgdpgeag pigpkgyrgd egppgsegar gapgpagppg dpglmgerge dgpagngteg fpgfpgypgn rgapgingtk gyplkgdeg eagdpgddnn diaprgvkga kgyrgpegpq gppghqgppg pdeceildii mkmcscceck cgpidllfvl dssesiglqn feiakdfvvk vidrlsrdel vkfepgqsya gvvqyshsqm qehvslrsps irnvqeikea ikslqwmagg tftgealqyt rdqllppspn nrialvitdg rsdtqrdttp lnvlcspgiq vvsvgikdvf dfipgsdqln viscqglaps qgrpgislvk enyaelleda filnvtaqic idkkcpdytc pitfsspadi tilldgsasv gshnfdttkr fakrlaerfl tagrtdpahd vrvavvqysg tgqqrperas lqflqnytal asavdamdfl ndatdvndal gyvtrfyrea ssgaakkrll lfsdgnsqga tpaaiekavq eaqragieif vvvvgrqvne phirvlvtgk taeydvpyge shlfrvpsyq allrgvfhqt vsrkvalg |
| Human α2(VI) precursor chain (gi:13603394) (SEQ ID NO:13) | mlqgtcsvll lwgilgaiqa qqqevispdt ternnncpek tdcpihvyfv ldtsesvtmq sptdiilfhm kqfvpqfisq lqnefyidqv alswrygglh fsdqvevfsp pgsdrasfik nlqgissfrr gtftdcalan mteqirqdrs kgtvhfavvi tdghvtgspc ggiklqaera reegirlfav apnqnikeqg lrdiastphe lyrndyatml pdsteinqdt inriikvmkh eaygecykvs cleipgpsgp kgyrgqkgak gnmgepgepg qkgrqgdpgi egpigfpgpk gvpgfkgekg efgadgrkga pglagkngtd gqkgklgrig ppgckgdpgn rgpdgypgea gspgergdqg gkgdpgrpgr rgppgeigak gskgyqgnng apgspgvkga kggpgprgpk gepgrrgdpg tkgspgsdgp kgekgdpgpe gprglagevg nkgakgdrgl pgprgpqgal gepgkqgsrg dpgdagprgd sgqpgpkgdp grpgfsypgp rgapgekgep gprgpeggrg dfglkgepgr kgekgepadp gppgepgprg prgvpgpege pgppgdpglt ecdvmtyvre tcgccdcekr cgaldvvfvi dssesigytn ftleknfvin vvnrlgaiak dpksetgtrv gvvqyshegt feaiqlddeh idslssfkea vknlewiagg twtpsaikfa ydrlikesrr qktrvfavvi tdgrhdprdd dlnlralcdr dvtvtaigig dmfhekhese nlysiacdkp qqvrnmtifs dlvaekfidd medvlcpdpq ivcpdlpcqt elsvaqctqr pvdivflldg serlgeqnfh karrfveqva rrltlarrdd dplnarvall qfggpgeqqv afplshnlta ihealettqy lnsfshvgag vvhainaivr sprggarrha elsfvfltdg vtgndslhes ahsmrnenvv ptvlalgsdv dmdvlttlsl gdraavfhek dydslaqpgf fdrfirwic |
| Human α2(VI) mature chain (SEQ ID NO:14) | qqqevispdt ternnncpek tdcpihvyfv ldtsesvtmq sptdillfhm kqfvpqfisq lqnefyldqv alswrygglh fsdqvevfsp pgsdrasfik nlqgissfrr gtftdcalan mteqirqdrs kgtvhfavvi tdghvtgspc ggiklqaera reegirlfav apnqnlkeqg lrdiastphe lyrndyatml pdsteinqdt inriikvmkh eaygecykvs cleipgpsgp kgyrgqkgak gnmgepgepg qkgrqgdpgi egpigfpgpk gvpgfkgekg efgadgrkga pglagkngtd gqkgklgrig ppgckgdpgn rgpdgypgea gspgergdqg gkgdpgrpgr rgppgeigak gskgyqgnng apgspgvkga kggpgprgpk gepgrrgdpg tkgspgsdgp kgekgdpgpe gprglagevg nkgakgdrgl pgprgpqgal gepgkqgsrg dpgdagprgd sgqpgpkgdp grpgfsypgp rgapgekgep gprgpeggrg dfglkgepgr kgekgepadp gppgepgprg prgvpgpege pgppgdpglt ecdvmtyvre tcgccdcekr cgaldvvfvi dssesigytn ftleknfvin vvnrlgaiak dpksetgtrv gvvqyshegt feaiqlddeh idslssfkea vknlewiagg twtpsaikfa ydrlikesrr qktrvfavvi tdgrhdprdd dlnlralcdr dvtvtaigig dmfhekhese nlysiacdkp qqvrnmtlfe dlvaekfidd medvlcpdpq ivcpdlpcqt elsvaqctqr pvdivflldg serlgeqnfh karrfveqva rrltlarrdd dplnarvall qfggpgeqqv afplshnlta ihealettqy lnsfshvgag vvhainaivr sprggarrha elsfvfltdg vtgndslhes ahsmrnenvv ptvlalgsdv dmdvlttlsl gdraavfhek dydslaqpgf fdrfirwic |
| Human α3(VI) precursor chain (gi:5921193) (SEQ ID NO:15) | mrkhrhlplv avfclflsgf ptthaqqqqa dvkngaaadi iflvdsswti geehfqlvre flydvvksla vgendfhfal vqfngnphte fllntyrtkq evlshisnms yiggtnqtgk gleyimqshl tkaagsragd gvpqvivvlt dghskdglal psaelksadv nvfaigveda degalkeias eplnmhmfnl enftslhdiv gnlvscvhss vsperagdte tlkditaqds adiiflidga nntgsvnfav ildflvnlle klpigtqqir vgvvqfsdep rtmfsldtys tkaqvlgavk algfaggela niglaldfvv enhftraggs rveegvpqvl vlisagpssd eirygvvalk qasvfsfglg aqaasraelq hiatddnlvf tvpefrsfgd lqekllpyiv gvaqrhivlk pptivtqvie vnkrdivflv dgssalglan fnairdfiak viqrleigqd liqvavaqya dtvrpefyfn thptkrevit avrkmkpldg salytgsald fvrnnlftss agyraaegip kllvlitggk sldeisqpaq elkrssimaf aignkgadqa eleeiafdss lvfipaefra aplqgmlpgl laplrtsgt pevhsnkrdi iflldgsanv |

TABLE 1-continued

Examples of Collagen VI Polypeptides

| Name | Amino Acid Sequence |
|---|---|
| | gktnfpyvrd fvmnlvnsld igndnirvgl vqfsdtpvte fslntyqtks dilghlrqlq lqggsglntg salsyvyanh fteaggsrir ehvpqllllll tagqsedsyl qaanaltrag iltfcvgasg ankaeleqia fnpslvylmd dfsslpalpq qliqplttyv sggveevpla qpeskrdilf lfdgsanlvg qfpvvrdfly kiidelnvkp egtriavaqy sddvkvesrf dehqskpeil nlvkrmkikt gkalnlgyal dyaqryifvk sagsriedgv lqflvllvag rssdrvdgpa snlkqsgvvp fifqaknadp aeleqivlsp afilaaeslp kigdlhpqiv nllksvhnga papvsgekdv vflldgsegv rsgfpllkef vqrvvesldv gqdrvrvavv qysdrtrpef ylnsymnkqd vvnavrqltl lggptpntga alefvlrnil vasagsrite gvpqllivlt adrsgddvrn psvvvkrgga vpigigigna ditemqtisf ipdfavaipt frqlgtvqqv iservtqltr eelsrlqpvl qplpspgvgg krdvvflidg sqsagpefqy vrtlierlvd yldvgfdttr vaviqfsddp kaefllnabs skdevqnavq rlrpkggrqi nvgnaleyvs rnifkrplgs rieegvpqfl vlissgksdd evvvpavelk qfgvapftia rnadqeelvk islspeyvfs vstfrelpsl eqklltpitt ltseqiqkll astrypppav esdaadivfl idsaegvrpd gfahirdfvs rivrrlnigp skvrvgvvqf sndvfpefyl ktyrsqapvl dairrlrlrg gsplntgkal efvarnlfvk sagsriedgv pqhlvlvlgg ksqddvsrfa qvirssgivs lgvgdrnidr telqtitndp rlvftvrefr elpnieerim nsfgpsaatp appgvdtppp srpekkkadi vflldgsinf rrdsfqevlr fvseivdtvy edgdsiqvgl vqynsdptde fflkdfstkr qiidainkvv ykggrhantk vglehlrvnh fvpeagarld qrvpqiafvi tggkavedaq dvslaltqrg vkvfavgvrn idseevgkia snsatafrvg nvqelselse qvletlhdam hetlcpgvtd aakacnldvi lgfdgsrdqn vfvaqkgfes kvdailnris qmhrvscsgg rsptvrvsvv antpsgpvea fdfdeyqpem lekfrnmrsq hpyvltedtl kvylnkfrqs spdsvkvvih ftdgadgdla dlhrasenlr qegvralilv glervvnler lmhlefgrgf mydrplrlnl ldldyelaeq ldniaekacc gvpckcsgqr gdrgpigsig pkgipgedgy rgypgdeggp gergppgvng tqgfqgcpgq rgvkgsrgfp gekgevgeig ldgldgedgd kglpgssgek gnpgrrgdkg prgekgergd vgirgdpgnp gqdsqergpk getgdlpgmg vpgrdgvpgg pgetgknggf grrgppgakg nkggpgqpgf egeqgtrgaq gpagpagppg ligeqgisgp rgsggargap gergrtgplg rkgepgepgp kggignpgpr getgddgrdg vgsegrrgkk gergfpgypg pkgnpgepgl ngttgpkgir grrgnsgppg ivgqkgrpgy pgpagprgnr gdsidqcali qsikdkcpcc ygpiecpvfp telafaldts egvnqdtfgr mrdvvlsivn vltiaesncp tgarvavvty nnevtteirf adskrksvll dkiknlqval tskqqsleta msfvarntfk rvrngflmrk vavffsntpt raspqlreav lklsdagitp lfltrqedrq linalqinnt avghalvlpa grdltdflen vltchvcldi cnidpscgfg swrpsfrdrr aagsdvdidm afildsaett tlfqfnemkk yiaylvrqld mspdpkasqh farvavvqha psesvdnasm ppvkvefslt dygskeklvd flsrgmtqlq gtralgsaie ytienvfesa pnprdlkivv lmltgevpeq qleeaqrvil qakckgyffv vlgigrkvni kevytfasep ndvffklvdk stelneeplm rfgrllpsfv ssenafylap dirkqcdwfq gdqptknlvk fghkqvnvpn nvtssptsnp vttkpvttt kpvttttkpv ttttkpvtii nqpsvkpaaa kpapakpvaa kpvatktatv rppvavkpat aakpvaakpa avrppaaaak pvatkpevpr pqaakpaatk pattkpvvkm lrevqvfeit ensaklhwer peppgpyfyd ltvtsahdqs lvlkqnltvt drviggllag qtyhvavvcy lrsqvratyh gsfstkksqp pppqparsas sstinlmvst eplaltetdi cklpkdegtc rdfilkwyyd pntkscarfw yggcggnenk fgsqkecekv capvlakpgv isvmgt |
| Human α3(VI) mature chain (SEQ ID NO:16) | qqqqa dvkngaaadi iflvdaswti geehfqlvre flydvvksla vgendfhfal vqfngnphte fllntyrtkq evlshisnms yiggtnqtgk gleyimqshl tkaagsragd gvpqvivvlt dghskdglal psaelksadv nvfaigveda degalkeias eplnmhmfnl enftslhdiv gnlvscvhss vsperagdte tlkditaqds adiiflidgs nntgsvnfav ildflvnlle klpigtqqir vgvvqfsdep rtmfsldtys tkaqvlgavk algfaggela niglaldfvv enhftraggs rveegvpqvl vlisagpssd eirygvvalk qasvfsfglg aqaasraelq hiatddnlvf tvpefrsfgd lqekllpyiv gvaqrhivlk pptivtqvie vnkrdivflv dggssalglan fnairdfiak viqrleigqd liqvavaqya dtvrpefyfn thptkrevit avrkmkpldg salytgsald fvrnnlftss agyraaegip kllvlitggk sldeisqpaq elkrssimaf aignkgadqa eleeeiafdss lvfipaefra aplqgmlpgl laplrtlsgt pevhsnkrdi iflldgsanv gktnfpyvrd fvmnlvnsld igndnirvgl vqfsdtpvte fslntyqtks dilghlrqlq lqggsglntg salsyvyanh fteaggsrir ehvpqlllll tagqsedsyl qaanaltrag iltfcvgasq ankaeleqia fnpslvylmd dfsslpalpq qliqplttyv sggveevpla qpeskrdilf lfdgsanlvg qfpvvrdfly kiidelnvkp egtriavaqy sddvkvesrf dehqskpeil nlvkrmkikt gkalnlgyal dyaqryifvk sagsriedgv lqflvllvag rssdrvdgpa snlkqsgvvp fifqaknadp aeleqivlsp afilaaeslp kigdlhpqiv nhlksvhnga papvsgekdv vflldgsegv rsgfpllkef vqrvvesldv gqdrvrvavv qysdrtrpef ylnsymnkqd vvnavrqltl lggptpntga alefvlrnil vssagsrite gvpqllivlt adrsgddvrn psvvvkrgga vpigigigna |

TABLE 1-continued

Examples of Collagen VI Polypeptides

| Name | Amino Acid Sequence |
|---|---|
| | ditemqtisf ipdfavaipt frqlgtvqqv iservtqltr eelsrlqpvl |
| | qplpspgvgg krdvvflidg sqsagpefqy vrtlierlvd yldvgfdttr |
| | vaviqfsddp kaefllnahs skdevqnavq rlrpkggrqi nvgnaleyvs |
| | rnifkrplgs rieegvpqfl vlissgksdd evvvpavelk qfgvapftia |
| | rnadqeelvk islspeyvfs vstfrelpsl eqklltpitt ltseqiqkll |
| | astrypppav esdaadivfl idssegvrpd gfahirdfvs rivrrlnigp |
| | skvrvgvvqf sndvfpefyl ktyrsqapvl dairrlrlrg gsplntgkai |
| | efvarnlfvk sagsriedgv pqhlvlvlgg ksqddvsrfa qvirssgivs |
| | lgvgdrnidr telqtitndp rlvftvrefr elpnieerim nsfgpsaatp |
| | appgvdtppp srpekkkadi vflldgsinf rrdsfqevlr fvseivdtvy |
| | edgdsiqvgl vqynsdptde fflkdfstkr qiidainkvv ykggrhantk |
| | vglehlrvnh fvpeagsrld qrvpqiafvi tggksvedaq dvslaltqrg |
| | vkvfavgvrn idseevgkia snsatafrvg nvqelselse qvletlhdam |
| | hetlcpgvtd aakacnldvi lgfdgsrdqn vfvaqkgfes kvdailnris |
| | qmhrvscsgg rsptvrvsvv antpsgpvea fdfdeyqpem lekfrnmrsq |
| | hpyvltedtl kvylnkfrqs spdsvkvvih ftdgadgdla dlhrasenlr |
| | qegvralilv glervvnler lmhlefgrgf mydrplrlnl ldldyelaeq |
| | ldniaekacc gvpckcsgqr gdrgpigsig pkgipgedgy rgypgdeggp |
| | gergppgvng tqgfqgcpgq rgvkgsrgfp gekgevgeig ldgldgedgd |
| | kglpgasgek gnpgrrgdkg prgekgergd vgirgdpgnp gqdsqergpk |
| | getgdlgpmg vpgrdgvpgg pgetgknggf grrgppgakg nkggpgqpgf |
| | egeqgtrgaq gpagpagppg ligeqgisgp rgsggargap gergrtgplg |
| | rkgepgepgp kggignpgpr getgddgrdg vgsegrrgkk gergfpgypg |
| | pkgnpgepgl ngttgpkgir grrgnsgppg ivgqkgrpgy pgpagprgnr |
| | gdsidqcali qsikdkcpcc ygplecpvfp telafaldts egvnqdtfgr |
| | mrdvvlsivn vltiaesncp tgarvavvty nnevtteirf adskrksvll |
| | dkiknlqval tskqqsleta msfvarntfk rvrngflmrk vavffsntpt |
| | raspqlreav iklsdagitp lfltrqedrq linalqinnt avghalvlpa |
| | grdltdflen vltchvcldi cnidpscgfg swrpsfrdrr aagsdvdidm |
| | afildsaett tlfqfnemkk yiaylvrqld mspdpkasqh farvavvqha |
| | psesvdnasm ppvkvefslt dygskeklvd flsrgmtqlq gtralgsaie |
| | ytienvfesa pnprdlkivv lmltgevpeq qleeaqrvil qakckgyffv |
| | vlgigrkvni kevytfasep ndvffklvdk stelneeplm rfgrllpsfv |
| | ssenafylsp dirkqcdwfq gdqptknlvk fgbkqvnvpn nvtssptsnp |
| | vtttkpvttt kpvttttkpv ttttkpvtii nqpsvkpaaa kpapakpvaa |
| | kpvatktatv rppvavkpat aakpvaakpa avrppaaaak pvatkpevpr |
| | pqaakpaatk pattkpvvkm lrevqvfeit ensaklhwer peppgpyfyd |
| | ltvtsahdqs lvlkqnltvt drviggllag qtyhvavvcy lrsqvratyh |
| | gsfstkksqp pppqparsas sstinlmvst eplaltetdi cklpkdegtc |
| | rdfilkwyyd pntkscarfw yggcggnenk fgsqkecekv capvlakpgv |
| | isvmgt |

TABLE 2

Examples of Nucleic Acids Encoding Collagen VI Polypeptides

| Name | Nucleic Acid Sequences (mRNAs and cDNAs) |
|---|---|
| Human α1(VI) precursor chain (gi:15011912) (SEQ ID NO:17) | cactctggct gggagcagaa ggcagcctcg gtctctgggc ggcggcggcg gccctctctg ccctggccgc gctgtgtggt gaccgcaggc ccgagacatg agggcggccc gtgctctgct gccctgctg ctgcaggcct gctggacagc cgcgcaggat gagccggaga ccccgagggc cgtggccttc caggactgcc ccgtggacct gttctttgtg ctggacacct ctgagagcgt ggccctgagg ctgaagccct acggggccct cgtggacaaa gtcaagtcct tcaccaagcg cttcatcgac aacctgaggg acaggtacta ccgctgtgac cgaaactgg tgtggaacgc aggcgcgctg cactacagtg acgaggtgga gatcatccaa ggcctcacgc gcatgcctg cggccgcgac gcactcaaaa gcagcgtgga cgcggtcaag tactttggga agggcaccta caccgactgc gctatcaaga aggggctgga gcagctcctc gtggggggct cccacctgaa ggagaataag tacctgattg tggtgaccga cgggcacccc ctggagggct acaaggaacc ctgtgggggg ctggaggatg ctgtgaacga ggccaagcac ctgggcgtca aagtcttctc ggtggccatc acacccgacc acctgagcc gcgtctgagc atcatcgcca cggaccacac gtaccggcgc aacttcacgg cggctgactg gggccagagc cgcgacgcag aggaggccat cagccagatc atcgacacca tcgtggacat gatcaaaaat aacgttgagc aagtgtgctg ctccttcgaa tgccagcctg caagaggacc tccgggcctc cggggcgacc ccggctttga gggagaacga ggcaagccgg ggctcccagg agagaaggga gaagccggag atcctggaag accggggac ctcggactg ttgggtacca gggaatgaag ggagaaaaag ggagccgtgg ggagaaggc tccaggggac caaagggcta caagggagag aagggcaagc gtggcatcga cggggtggac ggcgtgaagg gggagatggg gtaccaggc ctgccaggct gcaagggctc gccgggtttt gacggcattc aaggaccccc tggccccaag ggagaccccg gcgcctttgg |

TABLE 2-continued

Examples of Nucleic Acids Encoding Collagen VI Polypeptides

| Name | Nucleic Acid Sequences (mRNAs and cDNAs) |
|---|---|
| | actgaaagga gaaaagggcg agcctggagc tgacggggag gccgggagac |
| | caggagctcg gggaccatct ggagacgagg ggccagccgg agagcctggg |
| | ccccccggag agaaaggaga ggcgggcgac gaggggaacc caggacctga |
| | cggtgccccc ggggagcggg gtggccctgg agagagagga ccacggggga |
| | ccccaggccc gcggggacca agaggagacc ctggtgaagc tggcccgcag |
| | ggtgatcagg gaagagaagg gcccgttggt gtccctggag acccgggcga |
| | ggctggccct atcggaccta aaggctaccg aggcgatgag ggtcccccag |
| | ggtccgaggg tgccagagga gccccaggac ctgccggacc ccctggagac |
| | ccggggctga tgggagaaag gggagaagac ggccccgctg gaaatggcac |
| | cgagggcttc cccggcttcc ccgggtatcc cgggaacagg ggcgctcccg |
| | ggataaacgg cacgaagggc taccccggcc tcaaggggga cgagggagaa |
| | gccggggacc ccggagacga taacaacgac attgcacccc gaggagtcaa |
| | aggagcaaag gggtaccggg gtcccgaggg ccccaggga ccccaggac |
| | accaaggacc gcctggccg gacgaatgcg agatttgga catcatcatg |
| | aaaatgtgct cttgctgtga atgcaagtgc ggcccatcg acctcctgtt |
| | cgtgctggac agctcagaga gcattggcct gcagaacttc gagattgcca |
| | aggacttcgt cgtcaaggtc atcgaccggc tgagccggga cgagctggtc |
| | aagttcgagc cagggcagtc gtacgcgggt gtggtgcagt acagccacag |
| | ccagatgcag gagcacgtga gcctgcgcag ccccagcatc cggaacgtgc |
| | aggagctcaa ggaagccatc aagagcctga gtggatggc gggcggcacc |
| | ttcacggggg aggccctgca gtacacgcgg gaccagctgc tgccgcccag |
| | cccgaacaac cgcatcgccc tggtcatcac tgacgggcgc tcagacactc |
| | agagggacac cacaccgctc aacgtgctct gcagccccgg catccaggtg |
| | gtctccgtgg gcatcaaaga cgtgtttgac ttcatcccag gctcagacca |
| | gctcaatgtc atttcttgcc aaggcctggc accatcccag ggccggcccg |
| | gcctctcgct ggtcaaggag aactatgcag agctgctgga ggatgccttc |
| | ctgaagaatg tcaccgccca gatctgcata gacaagaagt gtccagatta |
| | cacctgcccc atcacgttct cctccccggc tgacatcacc atcctgctgg |
| | acggctccgc cagcgtgggc agccacaact tgacaccac caagcgcttc |
| | gccaagcgcc tggccgagcg cttcctcaca gcgggcagga cggaccccgc |
| | ccacgacgtg cgggtggcgg tggtgcagta cagcggcacg ggccagcagc |
| | gcccagagcg ggcgtcgctg cagttcctgc agaactacac ggccctggcc |
| | agtgccgtcg atgccatgga ctttatcaac gacgccaccg acgtcaacga |
| | tgcctgggc tatgtgaccc gcttctaccg cgaggcctcg tccggcgctg |
| | ccaagaagag gctgctgctc ttctcagatg gcaactcgca gggcgccacg |
| | cccgctgcca tcgagaaggc cgtgcaggaa gcccagcggg caggcatcga |
| | gatcttcgtg gtggtcgtgg gccgccaggt gaatgagccc cacatccgcg |
| | tcctggtcac cggcaagacg gccgagtacg acgtggccta cggcgagagc |
| | cacctgttcc gtgtcccag ctaccaggcc ctgctccgcg gtgtcttcca |
| | ccagacagtc tccaggaagg tggcgctggg ctagcccacc ctgcacgccg |
| | gcaccaaacc ctgtcctccc accctcccc actcatcact aaacagagcc |
| | caagcttgga aagccaggac acaacgctgc tgcctgcttt gtgcagggtc |
| | ctccggggct cagccctgag ttggcatcac ctgcgcaggg ccctctgggg |
| | ctcagctctg agctagtgtc acctgcacag ggccctctga ggctcagccc |
| | tgagctggcg tcacctgtgc agggccctct ggggctcagc cctgagctgg |
| | cctcacctgg gttccccacc ccgggctctc ctgccctgcc ctcctgcccg |
| | cctcctcc tgcctgcgca gctccttccc taggcacctc tgtgctgcat |
| | cccaccagcc tgagcaagac gcctctcggg gcctgtgccg cactagcctc |
| | cctctcctct gtcccatag ctggtttttc ccaccaatcc tcacctaaca |
| | gttactttac aattaaactc aaagcaagct cttctcctca gcttggggca |
| | gccattggcc tctgtctcgt tttgggaaac caaggtcagg aggccgttgc |
| | agacataaat ctcggcgact cggcccgtc tcctgagggt cctgctggtg |
| | accggcctgg accttggccc tacagccctg gaggccgctg ctgaccagca |
| | ctgaccccga cctcagagag tactcgcagg ggcgctggct gcactcaaga |
| | ccctcgagat taacggtgct aaccccgtct gctcctccct cccgcagaga |
| | ctggggcctg gactggacat gagagcccct ggtgccaca gagggctgtg |
| | tcttactaga aacaacgcaa acctctcctt cctcagaata gtgatgtgtt |
| | cgacgtttta tcaaaggccc ctttctatg ttcatgttag ttttgctcct |
| | tctgtgtttt tttctgaacc atatccatgt tgctgacttt tccaaataaa |
| | ggttttcact cctc |
| Human α2(VI) precursor chain (gi:13603393) (SEQ ID NO:18) | agggccacag gtgctgccaa gatgctccag ggcacctgct ccgtgctcct |
| | gctctgggga atcctggggg ccatccaggc ccagcagcag gaggtcatct |
| | cgccggacac taccgagaga acaacaact gcccagagaa gaccgactgc |
| | cccatccacg tgtacttcgt gctggacacc tcggagagcg tcaccatgca |
| | gtccccacg gacatcctgc tcttccacat gaagcagttc gtgccgcagt |
| | tcatcagcca gctgcagaac gagttctacc tggaccaggt ggcgctgagc |
| | tggcgctacg gcggcctgca cttctctgca caggtgagg tgttcagccc |
| | accgggcagc gaccgggcct ccttcatcaa gaacctgcag ggcatcagct |
| | ccttccgccg cggcaccttc accgactgcg cgctggccaa catgacggag |
| | cagatccggc aggaccgcag caagggcacc gtccacttcg ccgtggtcat |
| | caccgacggc cacgtcaccg gcagcccctg cggggcatc aagctgcagg |
| | ccgagcgggc ccgcgaggag ggcatccggc tcttcgccgt gccccccaac |
| | cagaacCtga aggagcaggg cctgcgggac atcgccagca cgccgcacga |
| | gctctaccgc aacgactacg ccaccatgct gcccgactcc accgagatca |

TABLE 2-continued

Examples of Nucleic Acids Encoding Collagen VI Polypeptides

| Name | Nucleic Acid Sequences (mRNAs and cDNAs) |
|---|---|
| | accaggacac catcaaccgc atcatcaagg tcatgaaaca cgaagcctac
ggagagtgct acaaggtgag ctgcctggaa atccctgggc cctctgggcc
caagggctac cgtggacaga agggtgccaa gggcaacatg ggtgagccgg
gagagcctgg ccagaaggga agacagggag acccgggcat cgaaggcccc
attggattcc caggacccaa gggcgttcct ggcttcaaag gagagaaggg
tgaatttgga gccgacggtc gcaagggggc ccctggcctg gctggcaaga
acgggaccga tggacagaag ggcaagctgg ggcgcatcgg acctcctggc
tgcaagggag accctggaaa ccggggcccc gacggttacc cgggggaagc
agggagtcca ggggagcgag gagaccaagg cggcaagggg gaccctggcc
gcccaggacg cagagggccc ccgggagaaa tcggggccaa gggaagcaag
gggtatcaag gcaacaatgg agccccagga agtcctggtg tgaaaggagc
caagggcggg cctgggcccc gcggacccaa aggcgagccg gggcgcaggg
gagaccccgg caccaagggc agcccaggca gcgatgcccc caaggggag
aaggggggacc ctggccctga gggcccccgc ggcctggctg gagaggttgg
caacaaagga gccaagggag accgaggctt gcctggaccc agaggccccc
agggagctct tggggagccc ggaaagcagg gatctcgggg agaccccggt
gatgcaggac cccgtggaga ctcaggacag ccaggcccca agggagaccc
cggcaggcct ggattcagct acccaggacc ccgaggagca cccggagaaa
aaggcgagcc cggcccacgc ggccccgagg gaggccgagg cgactttggc
ttgaaaggag aacctgggag gaaaggagag aaggagagc ctgcggatcc
tggtccccct ggtgagccag gccctcgggg gccaagagga gtcccaggac
ccgagggtga gcccggcccc cctggagacc ccggtctcac ggagtgtgac
gtcatgacct acgtgaggga gacctgcggg tgctgcgact gtgagaagcg
ctgtggcgcc ctggacgtgg tcttcgtcat cgacagctcc gagagcattg
ggtacaccaa cttcacactg gagaagaact tcgtcatcaa cgtggtcaac
aggctgggtg ccatcgctaa ggacccaag tccgagacag ggacgcgtgt
gggcgtggtg cagtacagcc acgagggcac ctttgaggcc atccagctgg
acgacgaaca tatcgactcc ctgtcgagct tcaaggagc tgtcaagaaC
ctcgagtgga ttgcgggcgg cacctggaca ccctcagcc tcaagtttgc
ctacgaccgc ctcatcaagg agagccggcg ccagaagaca cgtgtgtttg
cggtggtcat cacggacggg cgccacgacc ctcgggacga tgacctcaac
ttgcgggcgc tgtgcgatcg cgacgtcaca gtgacggcca tcggcatcgg
ggacatgttc cacgagaagc acgagagtga aaacctctac tccatcgcct
gcgacaagcc acagcaggtg cgcaacatga cgctgttctc cgacctggtc
gctgagaagt tcatcgatga catggaggac gtcctctgcc cggaccctca
gatcgtgtgc ccagaccttc cctgccaaac agagctgtcc gtggcacagt
gcacgcagcg gcccgtggac atcgtcttcc tgctggacgg ctccgagcgg
ctgggtgagc agaacttcca caaggcccgg cgcttcgtgg agcaggtggc
gcggcggctg acgctggccc ggaggacga cgaccctctc aacgcacgcg
tggcgctgct gcagtttggt ggccccggcg agcagcaggt ggccttcccg
ctgagccaca acctcactgc catccacgag gcgctggaga ccacacaata
cctgaactcc ttctcgcacg tgggcgcagg cgtggtgcac gccatcaatg
ccatcgtgcg cagcccgcgt ggcgggggcc ggaggcacgc agagctgtcc
ttcgtgttcc tcacggacgg cgtcacgggc aacgacagtc tgcacgagtc
ggcgcactcc atgcgcaacg agaacgtggt acccaccgtc ctggccttgg
gcagcgacgt ggacatggac gtgctcacca cgctcagcct gggtgaccgc
gccgccgtgt tccacgagaa ggactatgac agcctggcgc aacccggctt
cttcgaccgc ttcatccgct ggatctgcta cgcgccgccg ccgggccccg
cagtcgaggg tcgtgagccc accccgtcca tggtgctaag cgggcccggg
tcccacacgg ccagcaccgc tgctcactcg gacgacgcc tgggcctgca
cctctccagc tcctcccacg gggtccccgt agcccggcc ccgcccagc
cccaggtctc cccaggccct ccgcaggctg cccggcctcc ctccccctgc
agccatccca aggctcctga cctacctggc ccctgagctc tggagcaagc
cctgacccaa taaaggcttt gaacccaaaa aaaaaaa |
| Human α3(VI) precursor chain (gi:3127925) (SEQ ID NO:19) | cagtttggag ctcagtcttc caccaaaggc cgttcagttc tcctgggctc
cagcctcctg caaggactgc aagagttttc ctccgcagct ctgagtctcc
acttttttgg tggagaaagg tgcaaaaag aaaaagagac gcagtgagtg
ggaaaagtat gcatcctatt caaacctaat tgaatcgagg agcccaggga
cacacgcctt caggtttgct caggggttca tatttggtgc ttagacaaat
tcaaaatgag gaaacatcgg cacttgccct tagtggccgt cttttgcctc
tttctctcag gctttcctac aactcatgcc cagcagcagc aagcagatgt
caaaaatggt gcggctgctg atataatatt tctagtggat tcctcttgga
ccattggaga ggaacatttc caacttgttc gagagtttct atatgatgtt
gtaaaatcct tagctgtggg agaaaatgat ttccattttg ctctggtcca
gttcaacgga aacccacata ccgagttcct gttaaatacg tatcgtacta
aacaagaagt cctttctcat atttccaaca tgtcttatat tggggggaacc
aatcagactg gaaaaggatt agaatacata atgcaaagcc acctcaccaa
ggctgctgga agccgggccg gtgacggagt ccctcaggtt atcgtagtgt
taactgatgg acactcgaag gatggccttg ctctgcccctc agcggaactt
aagtctgctg atgttaacgt gtttgcaatt ggagttgagg atgcagatga
aggagcgtta aaagaaatag caagtgaacc gctcaatatg catatgttca
acctagagaa ttttacctca cttcatgaca tagtaggaaa cttagtgtcc
tgtgtgcatt catccgtgag tccagaaagg gctggggaca cggaaaccct
taaagacatc acagcacaag actctgctga cattattttc cttattgatg |

TABLE 2-continued

Examples of Nucleic Acids Encoding Collagen VI Polypeptides

| Name | Nucleic Acid Sequences (mRNAs and cDNAs) |
|---|---|
| | gatcaaacaa caccggaagt gtcaatttcg cagtcattct cgacttcctt |
| | gtaaatctcc ttgagaaact cccaatttgga actcagcaga tccgagtggg |
| | ggtggtccag tttagcgatg agcccagaac catgttttcc ttggacacct |
| | actccaccaa ggcccaggtt ctgggtgcag tgaaagccct cgggtttgct |
| | ggtggggagt tggccaatat cggcctcgcc cttgatttcg tggtggagaa |
| | ccacttcacc cgggcagggg gcagccgcgt ggaggaaggg gttccccagg |
| | tgctggtcCt cataagtgcc gggccttcta gtgacgagat tcgctacggg |
| | gtggtagcac tgaagcaggc tagcgtgttc tcattcggcc ttggagccca |
| | ggccgcctcc agggcagagc ttcagcacat agctaccgat gacaacttgg |
| | tgtttactgt cccggaattc cgtagctttg gggacctcca ggagaaatta |
| | ctgccgtaca ttgttggcgt ggcccaaagg cacattgtct tgaaaccgcc |
| | aaccattgtc acacaagtca ttgaagtcaa caagagagac atagtcttcc |
| | tggtggatgg ctcatctgca ctgggactgg ccaacttcaa tgccatccga |
| | gacttcattg ctaaagtcat ccagaggctg gaaatcggac aggatcttat |
| | ccaggtggca gtggcccagt atgcagacac tgtgaggcct gaattttatt |
| | tcaataccca tccaacaaaa agggaagtca taaccgctgt gcggaaaatg |
| | aagcccctgg acggctcggc cctgtacacg ggctctgctc tagactttgt |
| | tcgtaacaac ctattcacga gttcagccgg ctaccgggct gccgagggga |
| | ttcctaagct tttggtgctg atcacaggtg gtaagtccct agatgaaatc |
| | agccagcctg cccaggagct gaagagaagc agcataatgg cctttgccat |
| | tgggaacaag ggtgccgatc aggctgagct ggaagagatc gcttttcgact |
| | cctccctggt gttcatccca gctgagttcc gagccgcccc attgcaaggc |
| | atgctgcctg gcttgctggc acctctcagg accctctctg gaacccctga |
| | agttcactca aacaaaagag atatcatctt tcttttggat ggatcagcca |
| | acgttggaaa aaccaatttc ccttatgtgc gcgactttgt aatgaaccta |
| | gttaacagcc ttgatattgg aaatgacaat attcgtgttg gtttagtgca |
| | atttagtgac actcctgtaa cggagttctc tttaaacaca taccagacca |
| | agtcagatat ccttggtcat ctgaggcagc tgcagctcca gggaggttcg |
| | ggcctgaaca caggctcagc cctaagctat gtctatgcca accacttcac |
| | ggaagctggc ggcagcagga tccgtgaaca cgtgccgcag ctcctgcttc |
| | tgctcacagc tgggcagtct gaggactcct atttgcaagc tgccaacgcc |
| | ttgacacgcg cgggcatcct gactttttgt gtgggagcta gccaggcgaa |
| | taaggcagag cttgagcaga ttgcttttaa cccaagcctg gtgtatctca |
| | tggatgattt cagctccctg ccagctttgc ctcagcagct gattcagccc |
| | ctaaccacat atgttagtgg aggtgtggag gaagtaccac tcgctcagcc |
| | agagagcaag cgagacattc tgttcctctt tgacggctca gccaatcttg |
| | tgggccagtt ccctgttgtc cgtgactttc tctacaagat tatcgatgag |
| | ctcaatgtga agccagaggg gacccgaatt gcggtggctc agtacagcga |
| | tgatgtcaag gtggagtccc gttttgatga gcaccagagt aagcctgaga |
| | tcctgaatct tgtgaagaga atgaagatca agacgggcaa agccctcaac |
| | ctgggctacg cgctggacta tgcacagagg tacatttttg tgaagtctgc |
| | tggcagccgg atcgaggatg gagtgcttca gttcctggtg ctgctggtcg |
| | caggaaggtc atctgaccgt gtggatgggc cagcaagtaa cctgaagcag |
| | agtgggggttg tgcctttcat cttccaagcc aagaacgcag accctgctga |
| | gttagagcag atcgtgctgt ctccagcgtt tatcctggct gcagagtcgc |
| | ttcccaagat tggagatctt catccacaga tagtaatct cttaaaatca |
| | gtgcacaacg gagcaccagc accagtttca ggtgaaaagg acgtggtgtt |
| | tctgcttgat ggctctgagg gcgtcaggag cggcttccct ctgttgaaag |
| | agtttgtcca gagagtggtg gaaagcctgg atgtgggcca ggaccgggtc |
| | cgcgtggccg tggtgcagta cagcgaccgg accaggcccg agttctacct |
| | gaattcatac atgaacaagc aggacgtcgt caacgctgtc cgccagctga |
| | ccctgctggg agggccgacc cccaacaccg gggccgccct ggagtttgtc |
| | ctgaggaaca tcctggtcag ctctgcggga agcaggataa cagaaggtgt |
| | gccccagctg ctgatcgtcc tcacggccga caggtctggg gatgatgtgc |
| | ggaaccccte cgtggtcgtg aagaggggtg gggctgtgcc cattggcatt |
| | ggcatcggga acgctgacat cacagagatg cagaccatct ccttcatccc |
| | ggactttgcc gtggccattc ccaccttcg ccagctgggg accgtccaac |
| | aggtcatctc tgagagggtg acccagctca cccgcgagga gctgagcagg |
| | ctgcagccgg tgttgcagcc tctaccgagc ccaggtgttg gtggcaagag |
| | ggacgtggtc tttctcatcg atgggtccca aagtgccggg cctgagttcc |
| | agtacgttcg caccctcata gagaggctgt tgactacct ggacgtgggc |
| | tttgacacca cccgggtggc tgtcatccag ttcagcgatg acccccaaggc |
| | ggagttcctg ctgaacgccc attccagcaa ggatgaagtg cagaacgcgg |
| | tgcagcggct gaggcccaag ggagggcggc agatcaacgt gggcaatgcc |
| | ctggagtacg tgtccaggaa catcttcaag aggcccctgg ggagccgcat |
| | tgaagagggc gtcccacagt tcctggtcct catctcgtct ggaaagtctg |
| | acgatgaggt ggtcgtcccg gcggtggagc tcaagcagtt tggcgtggcc |
| | cctttcacga tcgccaggaa cgcagaccag gaggagctgg tgaagatctc |
| | gctgagcccc gaatatgtgt tctcggtgag caccttccgg gagctgccca |
| | gcctggagca gaaactgctg acgcccatca cgacccctgac ctcagagcag |
| | atccagaagc tcttagccag cactcgctat ccacctccag cagttgagag |
| | tgatgctgca gacattgtct ttctgatcga cagctctgag ggagttaggc |
| | cagatggctt tgcacatatt cgagattttg ttagcaggat tgttcgaaga |
| | ctcaacatcg gccccagtaa agtgagagtt ggggtcgtgc agttcagcaa |
| | tgatgtcttc ccagaattct atctgaaaac ctacagatcc caggccccgg |

TABLE 2-continued

Examples of Nucleic Acids Encoding Collagen VI Polypeptides

| Name | Nucleic Acid Sequences (mRNAs and cDNAs) |
|------|------------------------------------------|
| | tgctggacgc catacggcgc ctgaggctca gaggggggtc cccactgaac |
| | actggcaagg ctctcgaatt tgtggcaaga aacctctttg ttaagtctgc |
| | ggggagtcgc atagaagacg gggtgcccca acacctggtc ctggtcctgg |
| | gtggaaaatc ccaggacgat gtgtccaggt tcgcccaggt gatccgttcc |
| | tcgggcattg tgagtttagg ggtaggagac cggaacatcg acagaacaga |
| | gctgcagacc atcaccaatg accccagact ggtcttcaca gtgcgagagt |
| | tcagagagct tcccaacata gaagaaagaa tcatgaactc gtttggaccc |
| | tccgcagcca ctcctgcacc tccaggggtg gacacccctc ctccttcacg |
| | gccagagaag aagaaagcag acattgtgtt cctgttggat ggttccatca |
| | acttcaggag ggacagtttc caggaagtgc ttcgttttgt gtctgaaata |
| | gtggacacag tttatgaaga tggcgactcc atccaagtgg ggcttgtcca |
| | gtacaactct gaccccactg acgaattctt cctgaaggac ttctctacca |
| | agaggcagat tattgacgcc atcaacaaag tggtctacaa aggggggaaga |
| | cacgccaaca ctaaggtggg ccttgagcac ctgcgggtaa accactttgt |
| | gcctgaggca ggcagccgcc tggaccagcg ggtccctcag attgcctttg |
| | tgatcacggg aggaaagtcg gtggaagatg cacaggatgt gagcctggcc |
| | ctcacccaga gggggtcaa agtgtttgct gttggagtga ggaatatcga |
| | ctcggaggag gttggaaaga tagcgtccaa cagcgccaca gcgttccgcg |
| | tgggcaacgt ccaggagctg tccgaactga gcgagcaagt tttggaaact |
| | ttgcatgatg cgatgcatga aacccttttgc cctggtgtaa ctgatgctgc |
| | caaagcttgt aatctggatg tgattctggg gtttgatggt tctagagacc |
| | agaatgtttt tgtgcccag aagggcttcg agtccaaggt ggacgccatc |
| | ttgaacagaa tcagccagat gcacagggtc agctgcagcg gtggccgctc |
| | gcccaccgtg cgtgtgtcag tggtggccaa cacgccctcg ggcccggtgg |
| | aggcctttga ctttgacgag taccagccag agatgctcga gaagttccgg |
| | aacatgcgca gccagcaccc ctacgtcctc acggaggaca ccctgaaggt |
| | ctacctgaac aagttcagac agtcctcgcc ggacagcgtg aaggtggtca |
| | ttcattttac tgatggagca gacggagatc tggctgattt acacagagca |
| | tctgagaacc tccgccaaga aggagtccgt gccttgatcc tggtgggcct |
| | tgaacgagtg gtcaacttgg agcggctaat gcatctggag tttgggcgag |
| | ggtttatgta tgacaggccc ctgaggctta acttgctgga cttggattat |
| | gaactagcgg agcagcttga caacattgcc gagaaagctt gctgtggggt |
| | tccctgcaag tgctctgggc agaggggaga ccgcgggccc atcggcagca |
| | tcgggccaaa gggtattcct ggagaagacg gctaccgagg ctatcctggt |
| | gatgagggtg gacccggtga gcgtggtccg cctggtgtga acggcactca |
| | aggtttccag ggctgcccgg gccagagagg agtaaagggc tctcggggat |
| | tcccaggaga gaagggcgaa gtaggagaaa ttggactgga tggtctggat |
| | ggtgaagatg gagacaaagg attgcctggt tcttctggag agaaagggaa |
| | tcctggaaga agggtgata aaggacctcg aggagagaaa ggagaaagag |
| | gagatgttgg gattcgaggg gacccgggta acccaggaca agacagccag |
| | gagagaggac ccaaaggaga aaccggtgac ctcggcccca tgggtgtccc |
| | agggagagat ggagtacctg gaggacctgg agaaactggg aagaatggtg |
| | gctttggccg aagggggaccc cccggagcta agggcaacaa gggcggtcct |
| | ggccagccgg gctttgaggg agagcagggg accagaggtg cacagggccc |
| | agctggtcct gctggtcctc cagggctgat aggagaacaa ggcatttctg |
| | gacctagggg aagcggaggt gcccgtggcg ctcctggaga gcaggcaga |
| | accggtccac tgggaagaaa gggtgagccc ggagagccag gaccaaaagg |
| | aggaatcggg aacccgggcc ctcgtgggga cagggagat gacgggagag |
| | acggagttgg cagtgaagga cgcagaggca aaaaggaga aagaggattt |
| | cctggatacc caggaccaaa gggtaaccca ggtgaacctg ggctaaatgg |
| | aacaacagga cccaaaggca tcagaggccg aagggggaaat tcgggacctc |
| | cagggatagt tggacagaag gggagacctg gctacccagg accagctggt |
| | ccaaggggca cagggggcga ctccatcgat caatgtgccc tcatccaaag |
| | catcaaagat aaatgccctt gctgttacgg gccctggag tgccccgtct |
| | tcccaacaga actagccttt gctttagaca cctctgaggg agtcaaccaa |
| | gacactttcg gccggatgcg agatgtggtc ttgagtattg tgaatgtcct |
| | gaccattgct gagagcaact gcccgacggg ggcccgggtg gctgtggtca |
| | cctacaacaa cgaggtgacc acggagatcc ggtttgctga ctccaagagg |
| | aagtcggtcc tcctggacaa gattaagaac cttcaggtgg ctctgacatc |
| | caaacagcag agtctggaga ctgccatgtc gtttgtggcc aggaacacat |
| | ttaagcgtgt gaggaacgga ttcctaatga ggaaagtggc tgtttcttc |
| | agcaacacac ccacaagagc atccccacag ctcagagagg ctgtgctcaa |
| | actctcagat gcggggatca cccccttgtt ccttacaagg caggaagacc |
| | ggcagctcat caacgctttg cagatcaata acacagcagt ggggcatgcg |
| | cttgtcctgc ctgcaggag agacctcaca gacttcctgg agaatgtcct |
| | cacgtgtcat gttgcttgg acatctgcaa catcgaccca tcctgtggat |
| | ttggcagttg gaggccttcc ttcaggggaca ggagagcggc aggggagtgat |
| | gtggacatcg acatggcttt catcttagac agcgctgaga ccaccacccct |
| | gttccagttc aatgagatga gaaagtacat agcgtacctg gtcagacaac |
| | tggacatgag cccagatccc aaggcctccc agcacttcgc cagagtggca |
| | gttgtgcagc acgcgccctc tgagtccgtg gacaatgcca gcatgccacc |
| | tgtgaaggtg gaattctccc tgactgacta tggctccaag agaagctggg |
| | tggacttcct cagcagggga atgcacagt tgcagggaac cagggccttca |
| | ggcagtgcca ttgaatacac catagagaat gtctttgaaa gtgccccaaa |
| | cccacgggac ctgaaaattg tggtcctgat gctgacgggc gaggtgccgg |

TABLE 2-continued

Examples of Nucleic Acids Encoding Collagen VI Polypeptides

| Name | Nucleic Acid Sequences (mRNAs and cDNAs) |
|------|------------------------------------------|
| | agcagcagct ggaggaggcc cagagagtca tcctgcaggc caaatgcaag |
| | ggctacttct tcgtggtcct gggcattggc aggaaggtga acatcaagga |
| | ggtatacacc ttcgccagtg agccaaacga cgtcttcttc aaattagtgg |
| | acaagtccac cgagctcaac gaggagcctt tgatgcgctt cgggaggctg |
| | ttgccgtcct tcgtcagcag tgaaaatgct ttttacttgt ccccagatat |
| | caggaaacag tgtgattggt tccaagggga ccaacccaca aagaaccttg |
| | tgaagtttgg tcacaaacaa gtaaatgttc cgaataacgt tacttcaagt |
| | cctacatcca acccagtgac gacaacgaag ccggtgacta cgacgaagcc |
| | ggtgaccacc acaacaaagc ctgtaaccac cacaacaaag cctgtgacta |
| | ttataaatca gccatctgtg aagccagccg ctgcaaagcc ggccctgcg |
| | aaacctgtgg ctgccaagcc tgtggccaca aagacggcca ctgttagacc |
| | cccagtggcg gtgaagccag caacagcagc gaagcctgta gcagcaaagc |
| | cagcagctgt aagaccccc gctgctgctg caaaaccagt ggcgaccaag |
| | cctgaggtcc ctaggccaca ggcagccaaa ccagctgcca ccaagccagc |
| | caccactaag cccgtggtta agatgctccg tgaagtccag gtgtttgaga |
| | taacagagaa cagcgccaaa ctccactggg agaggcctga gccccccggt |
| | ccttatttt atgacctcac cgtcacctca gcccatgatc agtccctggt |
| | tctgaagcag aacctcacgg tcacggaccg cgtcattgga ggcctgctcg |
| | ctgggcagac ataccatgtg gctgtggtct gctacctgag gtctcaggtc |
| | agagccacct accacggaag tttcagtaca aagaaatctc agcccccacc |
| | tccacagcca gcaaggtcag cttctagttc aaccatcaat ctaatggtga |
| | gcacagaacc attggctctc actgaaacag atatatgcaa gttgccgaaa |
| | gacgaaggaa cttgcaggga tttcatatta aaatggtact atgatccaaa |
| | caccaaaagc tgtgcaagat tctggtatgg aggttgtggt ggaaacgaaa |
| | acaaatttgg atcacagaaa gaatgtgaaa aggtttgcgc tcctgtgctc |
| | gccaaacccg gagtcatcag tgtgatggga acctaagcgt gggtggccaa |
| | catcatatac ctcttgaaga agaaggagtc agccatcgcc aacttgtctc |
| | tgtagaagct ccgggtgtag attcccttgc actgtatcat ttcatgcttt |
| | gatttacact cgaactcggg agggaacatc ctgctgcatg acctatcagt |
| | atggtgctaa tgtgtctgtg gaccctcgct ctctgtctcc agcagttctc |
| | tcgaatactt tgaatgttgt gtaacagtta gccactgctg gtgtttatgt |
| | gaacattcct atcaatccaa attccctctg gagtttcatg ttatgcctgt |
| | tgcaggcaaa tgtaaagtct agaaaataat gcaaatgtca cggctactct |
| | atatacttt gcttggttca ttttttttcc cttttagtta agcatgactt |
| | tagatgggaa gcctgtgtat cgtggagaaa caagagacca acttttttcat |
| | tccctgcccc caatttccca gactagattt caagctaatt ttcttttttct |
| | gaagcctcta acaaatgatc tagttcagaa ggaagcaaaa tcccttaatc |
| | tatgtgcacc gttgggacca atgccttaat taaagaattt aaaaaagttg |
| | taatagagaa tattttggc attcctctca atgttgtgtg ttttttttt |
| | ttgtgtgctg gagggagggg atttaatttt aattttaaaa tgtttaggaa |
| | atttatacaa agaaactttt taataaagta tattgaaagt ttaaaaaaaa |
| | aaaaaaaa |

Although compositions including, and methods using, a collagen VI polypeptide from any organism are within the scope of the invention, preferred compositions and methods are those relating to mammalian, including vertebrate, collagen VI polypeptides. Preferred collagen VI polypeptides are human, rodent, murine, canine, feline, ovine, and bovine orthologs, and include naturally occurring variants thereof. Nucleotide and amino acid sequences of collagen VI genes and proteins from various species are publically available, such as in GenBank (see Tables 1 and 2 for examples of Genbank numbers).

In certain embodiments, a collagen VI therapeutic comprises a collagen VI polypeptide fusion protein. For example, a collagen VI polypeptide or a portion thereof can be fused to an immunoglobulin portion, such as an IgG heavy chain or Fc portion.

Portions and fragments of a collagen VI polypeptide, of the invention are also within the scope of the invention. A portion is typically at least five, 10, 15, or 20 amino acids long. Preferred portions are those which are sufficient for exerting a biological activity, such as interacting with a DAPC component (e.g. biglycan) or forming collagen VI monomers or polymers. Portions can comprise or consist of one or more specific domain of a protein. Optionally, fragments of collagen VI polypeptides consist of at least about 30 amino acids, at least about 40 amino acids, 50, 60, 70, 80, 90, 100, 150, or 200 amino acids.

In certain embodiments, collagen VI polypeptides of the invention are encoded by nucleotide sequences which are at least about 70%, preferably at least about 80%, even more preferably at least about 85%, at least about 90%, at least about 95%, at least about 98%, and even more preferably at least about 99% identical to the nucleotide sequence of a naturally-occurring collagen VI coding sequence, such as the human coding sequences shown in SEQ ID Nos: 17-19.

Preferred collagen VI nucleic acids of the invention include those encoding a polypeptide comprising an amino acid sequence which is at least about 70%, preferably at least about 80%, even more preferably at least about 85%, at least about 90%, at least about 95%, at least about 98%, and even more preferably at least about 99% identical to the nucleotide sequence of a human collagen VI coding sequence as shown in SEQ ID Nos: 17-19.

Another aspect of the invention provides a nucleic acid which hybridizes under stringent conditions to a nucleic acid encoding a collagen VI polypeptide, e.g., encoding one or more of SEQ ID NOS: 10-16, or complement thereof. Appropriate stringency conditions which promote DNA hybridization, for example, 6.0× sodium chloride/sodium citrate (SSC)

at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed.

Methods for preparing compounds of the invention are well known in the art. For a compound of the invention which is a protein or a derivative thereof, the compound can be isolated from a tissue or the compound can be recombinantly or synthetically produced. Isolation of protein from a tissue is described in the Examples. The proteins or proteoglycans of the invention isolated from tissue are preferably at least about 70%, preferably at least about 80%, at least about 85%, at least about 90%, at least about 95%, at least about 98% and most preferably, at least about 99% pure. Accordingly, preferred compounds contain less than about 1%, and even more preferably less than about 0.1% of material from which the compound was extracted.

The protein of the invention can also be produced recombinantly, according to methods well known in the art. Typically, a gene encoding the protein is inserted into a plasmid or vector, and the resulting construct is then transfected into appropriate cells, in which the protein is then expressed, and from which the protein is ultimately purified.

Accordingly, the present invention further pertains to methods of producing the subject proteins. For example, a host cell transfected with an expression vector encoding a protein of interest can be cultured under appropriate conditions to allow expression of the protein to occur. The protein may be secreted, by inclusion of a secretion signal sequence, and isolated from a mixture of cells and medium containing the protein. Alternatively, the protein may be retained cytoplasmically and the cells harvested, lysed and the protein isolated. A cell culture includes host cells, media and other byproducts. Suitable media for cell culture are well known in the art. The proteins can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the protein.

Thus, a coding sequence for a protein of the present invention can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures.

Expression vehicles for production of a recombinant protein include plasmids and other vectors. For instance, suitable vectors for the expression of the instant fusion proteins include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al., (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The protein can be produced either in eukaryotic cells, e.g., mammalian cells, yeast cells, insect cell (baculovirus system) or in prokaryotic cells. However, if the protein is a proteoglycan, it is preferable to express it in a cell of the same type as that which normally produces that particular proteoglycan. This assures that the correct types of glucose side chain(s) are attached to the core (i.e., protein) of the proteoglycan. In particular, when biglycan is used in the invention, it is preferable that biglycan contains the appropriate GAG side chains. For example, when biglycan is used in the context of muscle cells, it is preferable to produce biglycan in muscle cells, e.g., C2 muscle cells. The biglycan can also be produced in Torpedo cells, e.g., cells from the electric organ of Torpedo.

Cells that can be used for producing a compound of the invention, e.g., a proteoglycan can further be modified to increase the level and/or activity of an enzyme that catalyzes posttranslational modifications, e.g., glycosylations or sulfonations. For example, a cell can be transformed or cotransfected with an expression construct encoding a sulfotransferase, e.g., a chondroitin sulfotransferase, e.g., a chondroitin-6-sulfotransferase (C6ST; Fukuta et al. (1995) J. Biol. Chem. 270: 18575), or a nervous system involved sulfotransferase (NSIST), described in Nastuk et al. (1998) J. Neuroscience 18: 7167.

Alternatively, a protein core of a proteoglycan can be produced in a prokaryote, which results in a protein without glucose side chains, and the appropriate side chains can be added later, such as by synthetic chemistry. In yet another embodiment, a proteoglycan is produced in one type of eukaryotic cell and the protein can be stripped of its side chains, prior to adding the appropriate side chains. Methods for synthetically adding glycan side chains to a protein are known in the art.

In a preferred embodiment, a recombinant protein of the invention, such as biglycan, a collagen VI polypeptide or decorin, is produced using a vaccinia-based system, as described in Krishnan et al. (1999) J. Biol Chem. 294: 10945 and in Hocking et al. (1996) J. Biol. Chem. 271:19571. Infection of muscle cells with this vector encoding biglycan, a collagen VI polypeptide or decorin for example, results in the production of protein having muscle specific GAG chains. Biophysical studies, such as far UV circular dichroism showed that these recombinant proteins retain their native structure. In an even more preferred embodiment, these recombinant proteins are epitope-tagged, as further described herein, which facilitates co-immunoprecipitation and binding studies.

For example, a proteoglycan of the invention can be produced in a eukaryotic cell using the vaccinia virus/T7 bacteriophage expression system. A recombinant vaccinia virus, vBGN4 encoding the proteoglycan of the invention, e.g., mature biglycan protein, can be expressed as a polyhistidine fusion protein under control of the T7 phage promoter and expressed, e.g., in HT-1080 cells and UMR106 cells, as described in Hocking et al. (1996) J Biol Chem 271: 19571-7.

Immortalized cell lines, e.g., muscle cell lines, such as biglycan negative cell lines, can be obtained as described in Jat et al., PNAS (1991) 88: 5096-100; Noble et al., (1992) Brain Pathology 2: 39-46. In one embodiment, a H-2K$^{b}$/tsA58 transgenic mouse is used. This mouse is a heterozygote harboring a thermolabile immortalizing gene (the tsA58 mutant of SV40 large T antigen) under the control of an interferon-inducible promoter (this mouse is available at Charles River). When cells containing this gene are cultured, they proliferate indefinitely at 33° C. in the presence of interferon. However, when the temperature is raised to 39° C. (at which temperature the tsA58 antigen is non-functional) and interferon is removed, the cells cease dividing.

This method has been used for growing a wide variety of cell types, including astrocytes, osteoclasts, trabecular network, and colon epithelial cells (Chambers et al., (1993) *PNAS* 90: 5578-82; Groves et al., (1993) *Dev. Biol.* 159: 87-104; Whitehead et al., (1993) *PNAS* 90: 587-91; Noble et al., (1995) *Transgenic Res.* 4: 215-25; Tamm et al., (1999) *Invest. Ophtamol Vis. Sci.* 40: 1392-403. This technique is well suited for the production of muscle cell lines. For example, in one study alone 65 separate muscle cell lines were derived from animals ranging in age from neonates to four weeks (Morgan et al., (1994) *Dev. Biol.* 162 486-98). These lines were maintained for upwards of 80 generations. Remarkably, they not only formed myotubes when shifted to non-permissive conditions in culture, but also formed muscle when implanted into host mice. The H-2K$^b$/tsA58 transgenic method was also used by D. Glass and colleagues to produce a MuSK$^{-/-}$ muscle cell line (Sugiyama et al., (1997) *J. Cell Biol.* 139: 181-91).

To produce conditionally immortalized cell lines, mice having a specific mutation, e.g., a deficiency in biglycan or MuSK, can be crossed with heterozygote H-2K$^b$/tsA58 transgenic mice. The crosses are straightforward since only one copy of the gene is required for full activity. Muscle cells from neonatal animals can then be plated out and grown under permissive conditions (33° C. with interferon). Proliferating cells can then be cloned and samples from each line shifted to the non-permissive temperature and tested for their ability to form myotubes. Wild, type; decorin$^{-/-}$; biglycan$^{-/o}$; and decorin$^{-/-}$ biglycan$^{-/o}$ cell lines are examples of cell lines which can be obtained using this technique.

In a further embodiment, the compound of the invention is a glycan or polysaccharide. In fact, in certain applications, it may be that in certain cases, the core of a proteoglycan may not be necessary for the desired activity, such as for stabilizing the DAPC by contacting one or more components thereof. For example, it has been shown herein that the GAG side chains of biglycan are necessary for its interaction with α-dystroglycan, indicating that the interaction is likely to be mediated by the GAG side chains.

The compounds of the invention can also be peptidomimetics or small organic molecules, which can be prepared, e.g., based on the structure of the proteoglycan.

Although the preferred method for treating subjects with a biglycan or collagen VI is by administration of the agent to the subject (based, for example, on the efficiency of the agent when added to cell cultures), the proteoglycans of the invention can also be produced in a subject, by gene therapy techniques. Thus, e.g., a subject can receive an injection in a muscle (e.g., where the subject has a muscle dystrophy) of a vector encoding a protein or proteoglycan of the invention, such that the vector is capable of entering muscle cells and being expressed therein. Alternatively, the vector can be a viral vector, which is provided with the viral capside and the virus infects the cells, e.g., muscle cells and thereby deliver the vector. Methods and vectors for gene therapy are well known in the art. Illustrative methods are set forth below.

The preferred mammalian expression vectors contain both prokaryotic sequences to facilitate the propagation of the vector in bacteria, and one or more eukaryotic transcription units that are expressed in eukaryotic cells. The pcDNAI/ amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant fusion proteins by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the -gal containing pBlueBac III).

In yet other embodiments, the subject expression constructs are derived by insertion of the subject gene into viral vectors including recombinant retroviruses, adenovirus, adeno-associated virus, and herpes simplex virus-1, or recombinant bacterial or eukaryotic plasmids. As described in greater detail below, such embodiments of the subject expression constructs are specifically contemplated for use in various in vivo and ex vivo gene therapy protocols.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a fusion protein of the present invention rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9.14 and other standard laboratory manuals. Examples of suitable retroviruses include pLJ, pZIP, pWE and pEM which are well known to those skilled in the, art. Examples of suitable packaging virus lines for preparing both ecotropic and amphotropic retroviral systems include SYMBOL 121\f "Symbol"Crip, SYMBOL 121\f "Symbol"Cre, SYMBOL 121\f "Symbol"2 and SYMBOL 121\f "Symbol"Am. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) Science 230:1395-1398; Danos and Mulligan, (1988) PNAS USA 85:6460-6464; Wilson et al., (1988) PNAS USA 85:3014-3018; Armentano et al., (1990) PNAS USA 87:6141-6145; Huber et al., (1991) PNAS USA 88:8039-8043; Ferry et al., (1991) PNAS USA 88:8377-8381; Chowdhury et al., (1991) Science 254:1802-1805; van Beusechem et al., (1992) PNAS USA 89:7640-7644; Kay et al., (1992) Human Gene Therapy 3:641-647; Dai et al., (1992) PNAS USA 89:10892-10895; Hwu et al., (1993) J. lmmunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079-9083; Julan et al., (1992) J. Gen Virol 73:3251-3255; and Goud et al., (1983) Virology 163:251-254); or coupling cell surface ligands to the viral env proteins (Neda et al., (1991) J. Biol. Chem. 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al., (1988) BioTechniques 6:616; Rosenfeld et al., (1991) Science 252:431434; and Rosenfeld et al., (1992) Cell 68:143-155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482-6486), hepatocytes (Herz and Gerard, (1993) PNAS USA 90:2812-2816) and muscle cells (Quantin et al., (1992) PNAS USA 89:2581-2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267).

Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109-127). Expression of the inserted chimeric gene can be under control of, for example, the E1A promoter, the major late promoter (MLP) and associated leader sequences, the viral E3 promoter, or exogenously added promoter sequences.

Yet another viral vector system useful for delivery of the subject chimeric genes is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97-129). It is also one of the few viruses that may integrate its DNA into non-dividing cells, and exhibits a high frequency of stable integration (see for example Flotte et al., (1992) Am. J. Respir. Cell. Mol. Biol. 7:349-356; Samulski et al., (1989) J. Virol. 63:3822-3828; and McLaughlin et al., (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251-3260 can be used to introduce DNA into cells. A variety of nucleic acids have been introduced into different cell types using AAV vectors (see for example Hermonat et al., (1984) PNAS USA 81:6466-6470; Tratschin et al., (1985) Mol Cell. Biol. 4:2072-2081; Wondisford et al., (1988) Mol. Endocrinol. 2:32-39; Tratschin et al., (1984) J. Virol. 51:611-619; and Flotte et al., (1993) J. Biol. Chem. 268:3781-3790).

Other viral vector systems that may have application in gene therapy have been derived from herpes virus, vaccinia virus, and several RNA viruses. In particular, herpes virus vectors may provide a unique strategy for persistence of the recombinant gene in cells of the central nervous system and ocular tissue (Pepose et al., (1994) Invest Ophthalmol Vis Sci 35:2662-2666).

In addition to viral transfer methods, such as those illustrated above, non-viral methods can also be employed to cause expression of a protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the gene by the targeted cell. Exemplary gene delivery systems of this type include liposomal derived systems, poly-lysine conjugates, and artificial viral envelopes.

In a representative embodiment, a gene encoding a protein of interest can be entrapped in liposomes bearing positive charges on their surface (e.g., lipofectins) and (optionally) which are tagged with antibodies against cell surface antigens of the target tissue (Mizuno et al., (1992) No Shinkei Geka 20:547-551; PCT publication WO91/06309; Japanese patent application 1047381; and European patent publication EP-A43075). For example, lipofection of muscle, neural or cardiac cells can be carried out using liposomes tagged with monoclonal antibodies against specific tissue-associated antigens (Mizuno et al., (1992) Neurol. Med. Chir. 32:873-876).

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, any of the subject gene constructs can be used to transfect specific cells in vivo using a soluble polynucleotide carrier comprising an antibody conjugated to a polycation, e.g. poly-lysine (see U.S. Pat. No. 5,166,320). It will also be appreciated that effective delivery of the subject nucleic acid constructs via mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al., (1993) Science 260-926; Wagner et al., (1992) PNAS USA 89:7934; and Christiano et al., (1993) PNAS USA 90:2122).

Nucleic acids encoding biglycan or collagen VI proteins can also be administered to a subject as "naked" DNA, as described, e.g., in U.S. Pat. No. 5,679,647 and related patents by Carson et al., in WO 90/11092 and Felgner et al. (1990) Science 247: 1465.

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., (1994) PNAS USA 91: 3054-3057).

A gene encoding a proteoglycan or collagen VI of the invention can be under the control of a constitutive, or inducible promoter. These are well known in the art.

Methods for determining whether a compound has a biological activity of a biglycan protein are described in the Examples. A biological activity of a biglycan protein is intended to refer to one or more of: the ability to maintain the integrity of a plasma membrane; the ability to stabilize DAPCs on plasma membranes; the ability to bind to one or more components of DAPCs; e.g., binding to α-dystroglycan, binding to a sarcoglycan component, such as α-sarcoglycan; phosphorylation of α-sarcoglycan; binding to MuSK; stimulating the formation of neuromuscular junctions, such as by stimulating postsynaptic differentiation; stimulating AChR aggregation; stimulation of MuSK phosphorylation and potentiation of agrin-induced MuSK phosphorylation. Such methods can further be adapted for screening libraries of compounds for identifying compounds having one or more of the above-described activities.

Breakdown of cytoplasmic membranes, e.g., the presence of "leaky membranes" can be determined by assays which measure the release of creatine kinase or the absorption of Evans Blue dye, as described, e.g., in Tinsley et al. (1996) *Nature* 384: 349 and Straub et al. (1997) *J. Cell Biol.* 139: 375).

The compounds of the invention can also be tested in a variety of animal models, in particular the mdx mice, which are dystrophin negative (see Examples).

IV. Methods of Treatment

In certain aspects, the invention provides therapeutic and prophylactic methods of treatment of disorders including muscular, neuromuscular, and neurological disorders. Therapeutic methods are intended to eliminate or at least reduce at least one symptom of a disease or disorder, and preferably cure the disease or disorder. Prophylactic methods include those intended to prevent the appearance of a disease or disorder, i.e., a method which is intended to combat the appearance of the disease or disorder.

As described herein, biglycan was shown to bind to α-dystroglycan and to sarocoglycans, and thereby functions as a link between various components of DAPCs. Furthermore, biglycan levels were found to be high in muscle cells of mice lacking dystrophin (mdx mice, which are a model of muscular dystrophy). Since the absence of dystrophin in muscle cells is known to destabilize the cytoplasmic membrane, the upregulation of biglycan in dystrophin negative muscle cells may be a compensatory mechanism for the absence of dystrophin. Accordingly, the invention provides for methods for preventing and treating diseases or disorders that are associated with plasma membrane instability or organization, in particular, an instability resulting from an abnormal DAPC on the plasma membrane. Since the DAPC is found on the membrane of muscle cells, diseases that can be treated according to the invention include diseases of the muscle, such as muscular dystrophies and muscle atrophy.

In that regard, one promising path for treatment and potentially a cure for muscular dystrophy the activation of an endogenous compensatory mechanism based upon the regulated expression of utrophin. Utrophin is a homolog of dystrophin which shares numerous structural and functional properties with it. However, in both normal and in Duchenne's muscle utrophin is only expressed at a fraction of the muscle membrane: the neuromuscular junction and the myotendinous junction. The bulk of the membrane has no utrophin. However, in animal models it has been shown that forced expression of utrophin in muscle lacking dystrophin leads to restoration of the DAPC in the muscle membrane and to rescue of the dystrophic phenotype. Since the utrophin gene is normal in Duchenne patients, a method to activate its expression in muscle and/or to target it to the muscle membrane could serve to restore the DAPC to the membrane and thus promote the health of the muscle cells.

Several lines of evidence, many of them arising from observations made by the inventors indicate that the small leucine-rich repeat proteoglycan biglycan could be a method for regulating utrophin expression and localization. It has been demonstrated that the protein agrin can cause an upregulation of utrophin expression and direct it to be localized to specific domains on the cell surface. The signaling receptor for agrin is the receptor tyrosine kinase MuSK. It has been observed that agrin can also induce the tyrosine phosphorylation of α- and γ-sarcoglycan in cultured myotubes. It was also observed that biglycan can also regulate the tyrosine phosphorylation of α- and γ-sarcoglycan. Moreover, the receptor tyrosine kinase MuSK is required for this biglycan-induced tyrosine phosphorylation of these proteins. Further, biglycan can bind to MuSK. These observations indicate that biglycan can act directly to organize the DAPC, including utrophin, on the muscle cell surface.

Thus the present invention contemplates the treatment of these disorders with biglycan therapeutics which upregulate utrophin, activate MuSK and/or induce phosphorylation of sarcoglycans.

Furthermore, as disclosed herein, biglycan affects collagen VI production and collagen VI presence in DAPCs, and the invention contemplates treatment of collagen VI-related disorders with a biglycan therapeutic. In addition, in certain aspects the invention provides methods for stabilizing DAPCs, particularly collagen-VI deficient DAPCs, by administering a collagen VI therapeutic.

Merely to illustrate, biglycan polypeptides, peptides or peptidomimetics can be delivered to patients with muscular dystrophy or other conditions where muscle atrophies to upregulate the endogenous utrophin gene expression and/or to promote the localization of utrophin to the muscle membrane. In such embodiments, the biglycan polypeptide may be delivered in the form of a polypeptide in and of itself, or as part of a fusion protein, e.g., fused to a humanized antibody sequence or similar carrier entity. Biglycan polypeptides can be delivered by nucleic acid-based methods including as plasmid DNA, in viral vectors, or other modalities where the nucleic acid sequences encoding biglycan are introduced into patients. The delivery of a biglycan therapeutic can serve to heal the muscle fibers from within by directing the increased expression and regulated localization of utrophin to the muscle cell surface with concomitant restoration of the remainder of the dystrophin-associated protein complex.

However, the present invention also contemplates the use of agents which act upstream of biglycan, e.g., which induce the expression of native biglycan genes. Treatment with such agents as angotensin II, sodium salicylate, forskolin and 8-bromo-cAMP, for example, results in significant increases in expression of biglycan and can be used as part of a treatment protocol for such disorders.

Furthermore, since DAPCs are also found on other cell types, the invention also provides methods for treating diseases associated with any abnormal DAPC. For example, DAPC are present in the brain, and since, in addition, agrin has been found in senile plaques in patients with Alzheimers's disease, neurological diseases can also be treated or prevented according to the methods of the invention. A further indication that neurological disorders can be treated or prevented according to the methods described herein is based on the observation that patients with Muscular dystrophy often also suffer from peripheral and central nervous system disorder. Accordingly, about one third of patients with Duchenne Muscular Dystrophy have a mental affliction, in particular, mental retardation. Thus, dystrophin, and hence, DAPCs, are believed to play a role in the nervous system.

Patients with Duchenne's Muscular Dystrophy also have diaphragm problems, indicating a role for dystrophin, and possibly DAPCs in diaphragms. Thus, therapeutics of the invention would also find an application in disorders associated with diaphragm abnormalities.

It should be noted that diseases that can be treated or prevented include not only those in which biglycan is abnormal, but more generally any disease or condition that is associated with a defect that can be improved or cured by biglycan. In particular, diseases that are characterized by a defect or an abnormality in any component of the DAPC or component associated therewith, thereby resulting, e.g., in an unstable plasma membrane, can be treated or prevented according to the methods of the invention, provided that the proteoglycan of the invention can at least partially cure the defect resulting from the deficient component. In particular, diseases that can be treated according to the method of the invention include any disease associated with an unstable DAPC, which can be rendered more stable by the presence of a proteoglycan of the invention.

Furthermore, since biglycan was shown to bind to, and phosphorylates MuSK, a receptor which is known for mediating agrin-induced stimulation of neuromuscular junction formation, in particular postsynaptic membrane differentiation, to potentiate agrin-induced AChR aggregation, and to correct a defective agrin-induced AChR aggregation in myotubes of biglycan negative mice by its addition to the myotubes, the invention also provides methods for preventing and treating diseases or disorders of neuromuscular junctions, such as neuromuscular disorders. Most interestingly, exogenously added biglycan was shown to be able to correct a defective agrin-induced AChR aggregation in myotubes of biglycan negative mice.

A. Exemplary Diseases and Disorders:

Diseases or disorders that are characterized by a destabilization or improper organization of the plasma membrane of specific cell types include muscular dystrophies (MDs), a group of genetic degenerative myopathies characterized by weakness and muscle atrophy without nervous system involvement. The three main types are pseudohypertrophic (Duchenne, Becker), limb-girdle, and facioscapulohumeral. For example, muscular dystrophies and muscular atrophies are characterized by a breakdown of the muscle cell membrane, i.e., they are characterized by leaky membranes, which are believed to result from a mutation in a component of the DAPC., i.e., dystrophin. Mutations in the sarcoglycans are also known to result in muscular dystrophies and leaky membranes. Accordingly, the invention provides for methods for treating or preventing diseases associated with mutations in dystrophin and/or in sarcoglycans or other component of DAPCs, in particular muscular dystrophies.

Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is wheelchair-bound by age 13 and usually dies by age 20.

Another type of dystrophy that can be treated according to the methods of the invention includes congenital muscular dystrophy (CMD), a very disabling muscle disease of early clinical onset, is the most frequent cause of severe neonatal hypotonia. Its manifestations are noticed at birth or in the first months of life and consist of muscle hypotonia, often associated with delayed motor milestones, severe and early contractures and joint deformities. Serum creatine kinase is raised, up to 30 times the normal values, in the early stage of the disease, and then rapidly decreases. The histological changes in the muscle biopsies consist of large variation in the size of muscle fibers, a few necrotic and regenerating fibers, marked increase in endomysial collagen tissue, and no specific ultrastructural features. The diagnosis of CMD has been based on the clinical picture and the morphological changes in the muscle biopsy, but it cannot be made with certainty, as other muscle disorders may present with similar clinico-pathological features. Within the group of diseases classified as CMD, various forms have been individualized. The two more common forms are the occidental and the Japanese, the latter being associated with severe mental disturbances, and usually referred to as Fukuyama congenital muscular dystrophy (FCMD).

One form of congenital muscular dystrophy (CMD) has recently been characterized as being caused by mutations in the laminin alpha 2-chain gene. Laminin is a protein that associates with DAPCs. Thus, the invention also provides methods for treating diseases that are associated with abnormal molecules which normally associate with DAPCs.

Other muscular dystrophies within the scope of the invention include limb-girdle muscular dystrophy (LGMD), which represents a clinically and genetically heterogeneous class of disorders. These dystrophies are inherited as either autosomal dominant or recessive traits. An autosomal dominant form, LGMD1A, was mapped to 5q31-q33 (Speer, M. C. et al., Am.

J. Hum. Genet. 50:1211, 1992; Yamaoka, L. Y. et al., Neuromusc. Disord.4:471, 1994), while six genes involved in the autosomal recessive forms were mapped to 15q15.1 (LGMD2A)(Beckmann, J. S. et al., C. R. Acad. Sci. Paris 312:141, 1991), 2p16-p13 (LGMD2B)(Bashir, R. et al., Hum. Mol. Genet. 3:455, 1994), 13q12 (LGMD2C)(13en Othmane, K. et al., Nature Genet. 2:315, 1992; Azibi, K. et al., Hum. Mol. Genet. 2:1423, 1993), 17q12-q21.33 (LGMD2D) (Roberds, S. L. et al., Cell 78:625, 1994; McNally, E. M., et. al., Proc. Nat. Acad. Sci. U.S.A. 91:9690, 1994), 4q12 (LG1MD2E)(Lim, L. E., et. al., Nat. Genet. 11:257, 1994; Bonnemann, C. G. et al. Nat. Genet. 11:266, 1995), and most recently to 5q33-q34 (LGMD2F) (Passos-Bueno, M. R., et. al., Hum. Mol. Genet. 5:815, 1996). Patients with LGMD2C, 2D and 2E have a deficiency of components of the sarcoglycan complex resulting from mutations in the genes encoding gamma-, alpha-, and beta-sarcoglycan, respectively. The gene responsible for LGMD2A has been identified as the muscle-specific calpain, whereas the genes responsible for LGMD1A, 2B and 2F are still unknown.

Yet other types of muscular dystrophies that can be treated according to the methods of the invention include Welander distal myopathy (WDM), which is an autosomal dominant myopathy with late-adult onset characterized by slow progression of distal muscle weakness. The disorder is considered a model disease for hereditary distal myopathies. The disease is linked to chromosome 2p13. Another muscular dystrophy is Miyoshi myopathya, which is a distal muscular dystrophy that is caused by mutations in the recently cloned gene dysferlin, gene symbol DYSF (Weiler et al. (1999) *Hum Mol Genet* 8: 871-7). Yet other dystrophies include Hereditary Distal Myopathy, Benign Congenital Hypotonia, Central Core disease, Nemaline Myopathy, and Myotubular (centronuclear) myopathy.

Other diseases that can be treated or prevented according to the methods of the invention include those characterized by tissue atrophy, e.g., muscle atrophy, other than muscle atrophy resulting from muscular dystrophies, provided that the atrophy is stopped or slowed down upon treatment with a therapeutic of the invention. Furthermore, the invention also provides methods for reversing tissue atrophies, e.g., muscle atrophies. This can be achieved, e.g., by providing to the atrophied tissue a therapeutic of the invention, such as DAG-125 or mammalian ortholog thereof, or biglycan.

Muscle atrophies can result from denervation (loss of contact by the muscle with its nerve) due to nerve trauma; degenerative, metabolic or inflammatory neuropathy (e.g., GuillianBarre syndrome), peripheral neuropathy, or damage to nerves caused. by environmental toxins or drugs. In another embodiment, the muscle atrophy results from denervation due to a motor neuronopathy. Such motor neuronopathies include, but are not limited to: adult motor neuron disease, including Amyotrophic Lateral Sclerosis (ALS or Lou Gehrig's disease); infantile and juvenile spinal muscular atrophies, and autoimmune motor neuropathy with multifocal conduction block. In another embodiment, the muscle atrophy results from chronic disuse. Such disuse atrophy may stem from conditions including, but not limited to: paralysis due to stroke, spinal cord injury; skeletal immobilization due to trauma (such as fracture, sprain or dislocation) or prolonged bed rest. In yet another embodiment, the muscle atrophy results from metabolic stress or nutritional insufficiency, including, but not limited to, the cachexia of cancer and other chronic illnesses, fasting or rhabdomyolysis, endocrine disorders such as, but not limited to, disorders of the thyroid gland and diabetes.

Since muscle tissue atrophy and necrosis are often accompanied by fibrosis of the affected tissue, the reversal or the inhibition of atrophy or necrosis can also result in an inhibition or reversal of fibrosis.

In addition, the therapeutics of the invention may be of use in the treatment of acquired (toxic or inflammatory) myopathies. Myopathies which occur as a consequence of an inflammatory disease of muscle, include, but not limited to polymyositis and dermatomyositis. Toxic myopathies may be due to agents, including, but are not limited to adiodarone, chloroquine, clofibrate, colchicine, doxorubicin, ethanol, hydroxychloroquine, organophosphates, perihexiline, and vincristine.

Neuromuscular dystrophies within the scope of the invention include myotonic dystrophy. Myotonic dystrophy (DM; or Steinert's disease) is an autosomal dominant neuromuscular disease which is the most common form of muscular dystrophy affecting adults. The clinical picture in DM is well established but exceptionally variable (Harper, P. S., Myotonic Dystrophy, 2nd ed., W. B. Saunders Co., London, 1989). Although generally considered a disease of muscle, with myotonia, progressive weakness and wasting, DM is characterized by abnormalities in a variety of other systems. DM patients often suffer from cardiac conduction defects, smooth muscle involvement, hypersomnia, cataracts, abnormal glucose response, and, in males, premature balding and testicular atrophy (Harper, P. S., Myotonic Dystrophy, 2nd ed., W. B. Saunders Co., London, 1989). The mildest form, which is occasionally difficult to diagnose, is seen in middle or old age and is characterized by cataracts with little or no muscle involvement. The classical form, showing myotonia and muscle weakness, most frequently has onset in early adult life and in adolescence. The most severe form, which occurs congenitally, is associated with generalized muscular hypoplasia, mental retardation, and high neonatal mortality. This disease and the gene affected is further described in U.S. Pat. No. 5,955,265.

Another neuromuscular disease is spinal muscular atrophy ("SMA"), which is the second most common neuromuscular disease in children after Duchenne muscular dystrophy. SMA refers to a debilitating neuromuscular disorder which primarily affects infants and young children. This disorder is caused by degeneration of the lower motor neurons, also known as the anterior horn cells of the spinal cord. Normal lower motor neurons stimulate muscles to contract. Neuronal degeneration reduces stimulation which causes muscle tissue to atrophy (see, e.g., U.S. Pat. No. 5,882,868).

The above-described muscular dystrophies and myopathies are skeletal muscle disorders. However, the invention also pertains to disorders of smooth muscles, e.g., cardiac myopathies, including hypertrophic cardiomyopathy, dilated cardiomyopathy and restrictive cardiomyopathy. At least certain smooth muscles, e.g., cardiac muscle, are rich in sarcoglycans. Mutations in sarcoglycans can result in sarcolemmal instability at the myocardial level (see, e.g., Melacini (1999) *Muscle Nerve* 22: 473). For example, animal models in which a sarcoglycan is mutated show cardiac creatine kinase elevation. In particular, it has been shown that delta-sarcoglycan (Sgcd) null mice develop cardiomyopathy with focal areas of necrosis as the histological hallmark in cardiac and skeletal muscle. The animals also showed an absence of the sarcoglycan-sarcospan (SG-SSPN) complex in skeletal and cardiac membranes. Loss of vascular smooth muscle SG-SSPN complex was associated with irregularities of the coronary vasculature. Thus, disruption of the SG-SSPN complex in vascular smooth muscle perturbs vascular function, which initiates cardiomyopathy and exacerbates muscular dystrophy (Coral-Vazquez et al. (1999) *Cell* 98: 465).

Similarly to delta-sarcoglycan negative mice, mice lacking γ-sarcoglycan showed pronounced dystrophic muscle changes in early life (Hack et al. (1998) *J Cell Biol* 142: 1279). By 20 wk of age, these mice developed cardiomyopathy and died prematurely. Furthermore, apoptotic myonuclei were abundant in skeletal muscle lacking γ-sarcoglycan, suggesting that programmed cell death contributes to myofiber degeneration. Vital staining with Evans blue dye revealed that muscle lacking γ-sarcoglycan developed membrane disruptions like those seen in dystrophin-deficient muscle. It was also shown that the loss of γ-sarcoglycan produced secondary reduction of beta- and delta-sarcoglycan with partial retention of α- and epsilon-sarcoglycan, indicating that beta-, γ- and delta-sarcoglycan function as a unit. Since the other components of the cytoplasmic membrane complex were functional, the complex could be stabilized by the presence of a therapeutic of the invention.

In addition to animal models, certain cardioimyopathies in humans have been linked to mutations in dystrophin, dystroglycans or sarcoglycans. For example, dystrophin has been identified as the gene responsible for X-linked dilated cardiomyopathy (Towbin J. A. (1998) *Curr Opin Cell Biol* 10: 131, and references therein). In this case, the dystrophin gene contained a 5'-mutation which results in cardiomyopathy without clinically-apparent skeletal myopathy (Bies et al. (1997) *J Mol Cell Cardiol* 29: 3175.

Furthermore, cardiomyopathy was also found in subjects having Duchenne's Muscular Dystrophy (associated with a mutated dystrophin), or other types of muscular dystrophies, such as Limb Girdle Muscular Dystrophy. For example, dilated cardiomyopathy was present in one autosomal dominant case and in three advanced autosomal recessive or sporadic patients, of whom two were found to have alpha sarcoglycan deficiency. Two of these three patients and three other cases showed ECG abnormalities known to be characteristic of the dystrophinopathies. A strong association between the absence of alpha sarcoglycan and the presence of dilated cardiomyopathy was found. In six autosomal dominant cases there were atrioventricular (AV) conduction disturbances, increasing in severity with age and in concomitant presence of muscle weakness. Pacemaker implantation was necessary in certain of these patients (see van der Kooi (1998) *Heart* 79: 73).

Therapeutics of the invention can also be used to treat or prevent cardiomyopathy, e.g., dilated cardiomyopathy, of viral origin, e.g., resulting from an enterovirus infection, e.g., a Coxsackievirus B3. It has been shown that purified Coxsackievirus protease 2A cleaves dystrophin in vitro and during Coxsackievirus infection of cultured myocytes and in infected mouse hearts, leading to impaired dystrophin function (Badorff et al. (1999) *Nat Med* 5: 320. Cleavage of dystrophin results in disruption of the dystrophin-associated glycoproteins α-sarcoglycan and betα-dystroglycan. Thus, cardiomyopathy could be prevented or reversed by administration of a therapeutic of the invention to a subject having been infected with a virus causing cardiomyopathy, e.g., by disruption of dystrophin or a protein associated therewith. Administration of the therapeutic could restabilize or reorganize the cytoplasmic membrane of affected cardiac cells.

Thus, the therapeutics of the invention can also be used to prevent or to treat smooth muscle disorders, such as cardiac myopathies, and to stop atrophy and/or necrosis of cardiac smooth muscle tissue. The treatment can also be used to promote survival of myocytes.

Neurological disorders that can be treated according to the methods of the invention include polymyositis, and neurogenic disorders. Another neurological disease that can be treated is Alzheimers' disease.

Other diseases that can be treated according to the methods of the invention include those in which the proteoglycan of the invention is present at abnormal levels, or has an abnormal activity, relative to that in normal subjects. For example, a disease or disorder could be caused by a lower level of biglycan, resulting in, e.g., unstable cytoplasmic membranes. Alternatively, a disease or disorder could result from an abnormally high level or activity of biglycan, resulting in, e.g., overstimulation of MuSK or over-aggregation of AChRs (see below).

Other diseases that may be treated according to methods disclosed herein are collagen VI-related disorders. For example, Bethlem's myopathy is caused, at least in part, by mutations in collagen VI genes. Collagen VI function is also compromised in Ullrich Congenital Muscular Dystrophy and Sorsby's fundus dystrophy. In certain embodiments, a collagen VI-related disorder may be treated by administering a biglycan therapeutic. In certain embodiments, a collagen VI-related disorder may be treated by administering a therapeutic comprising a polypeptide of a DAPC, such as a utrophin, a sarcoglycan or a portion thereof.

Yet other diseases or disorders that are within the scope of the invention include those that are associated with an abnormal interaction between a proteoglycan of the invention and another molecule (other than those of the DAPC or MuSK), e.g., a complement factor, such as C1q. For example, it has been shown that C1q interacts with biglycan (Hocking et al. (1996) *J. Biol. Chem.* 271: 19571). It is also known that binding of C1q to cell surfaces mediates a number of biological activities including enhancement of phagocytosis and stimulation of superoxide production. Thus, since biglycan binds to C1q, biglycan or another proteoglycan or core thereof, of the invention could be used to inhibit the binding of C1q to its receptor on cell surfaces to inhibit one or more of such biological activities. In addition, compounds of the invention which inhibit the interaction between C1q or other complement component and a cell surface can also be used to inhibit complement mediated necrosis of the cells and tissues containing such cells.

Also within the scope of the invention are methods for preventing or inhibiting infections of cells by microorganisms, e.g., viruses. For example, it has been shown that dystroglycan is a receptor via which certain microorganisms enter eukaryotic cells (*Science* (1998) 282: 2079). Thus, by administrating to a subject a therapeutic of the invention which occupies the site on dystroglycan molecules to which the microorganism binds, entering of the microorganism into the cell can be inhibited. This method can be used, e.g., to prevent or inhibit Lassa Fever virus and lymphocytic choriomeningitis virus (LCMV) infection, as well as infection by other arenaviruses, including Oliveros, and Mobala. Soluble alpha-dystroglycan was shown to block both LCMV and LFV infection (*Science* (1998) 282: 2079).

In addition to cell cultures, e.g., established from patients having, e.g., a muscular dystrophy, various animal models can be used to select the most appropriate therapeutic for treating a disease. In particular, to identify a therapeutic for use in preventing or treating a muscular dystrophy or cardiomyophaty associated with a mutated or absent DAPC component or, mice having mutated versions of these proteins, or having null mutations in the genes encoding these proteins, can be used. For example, mice having a disrupted sarcoglycan, such as delta-sarcoglycan, can be used. Such mice are described, e.g., Coral-Vazquez et al. (1999) *Cell* 98: 465. Alternatively, mice deficient in dystrophin (mdx mice), or in α- or γ-sarcoglycans can be used. Such mice have been described herein and in the literature. Additional mice can be made according to known methods in the art. In an illustrative embodiment to identify therapeutics, different therapeutics are administered to delta-sarcoglycan null mice, and the effect of the therapeutics are evaluated by studying cardiac function. Another animal model that can be used for this purpose is the cardiomyopathic hamster that does not express delta-sarcoglycan due to a genomic deletion. This rat is an animal model for autosomal recessive cardiomyopathy., and is further described in Sakamoto et al. *FEBS Lett* 1999 (1999) 44: 124.

V. Effective Dose and Administration of Therapeutic Compositions

The above-described diseases or disorders can be treated or ameliorated in a subject by administering to the subject a pharmaceutically efficient amount of a bigylcan therapeutic, collagen VI therapeutic or other therapeutic of the invention. Where the therapeutic is to be a biglycan therapeutic, depending on whether the disease is caused by higher levels or activity or by lower levels or activity of biglycan, an agonist or an antagonist biglycan therapeutic is administered to a subject having the disease. Although a person of skill in the art will be able to predict which therapeutic to administer for treating any of the diseases of the invention, tests can be performed to determine the appropriate therapeutic to administer. Such tests can use, e.g., animal models of the disease. Alternatively, in cases where diseases are due to a mutation in, e.g., biglycan or a collagen VI, in vitro tests can be undertaken to determine the effect of the mutation. This will allow the determination of what type of therapeutic should be administered to a subject having this type of mutation.

Another manner of administering a therapeutic of the invention to a subject is by preparing cells expressing and secreting the polypeptide or proteoglycan of interest, inserting the cells into a matrix and administering this matrix to the subject at the desired location. Thus, cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a Host, U.S. Pat. No. 5,314,471 (Baxter International, Inc.); Uludag and Sefton, 1993, J Biomed. Mater. Res. 27(10):1213-24 (HepG2 cells/hydroxyethyl methacrylate-methyl methacrylate membranes); Chang et al, 1993, Hum Gene Ther 4(4):433-40 (mouse Ltk-cells expressing hGH/immunoprotective perm-selective alginate microcapsules; Reddy et al, 1993, J Infect Dis 168(4):1082-3 (alginate); Tai and Sun, 1993, FASEB J 7(11):1061-9 (mouse fibroblasts expressing hGH/alginate-poly-L-lysine-alginate membrane); Ao et al, 1995, Transplanataion Proc. 27(6): 3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(1):37-47 (polymer-encapsulated PC12 cells); Sagen et al, 1993, J Neurosci 13(6):2415-23 (bovine chromaffin cells encapsulated in semipermeable polymer membrane and implanted into rat spinal subarachnoid space); Aebischer et al, 1994, Exp Neurol 126(2):151-8 (polymer-encapsulated rat PC12 cells implanted into monkeys; see also Aebischer, WO 92/19595); Savelkoul et al, 1994, J Immunol Methods 170 (2):185-96 (encapsulated hybridomas producing antibodies; encapsulated transfected cell lines expressing various cytokines); Winn et al, 1994, PNAS USA 91(6):2324-8 (engineered BHK cells expressing human nerve growth factor encapsulated in an immunoisolation polymeric device and transplanted into rats); Emerich et al, 1994, Prog Neuropsychopharmacol Biol Psychiatry 18(5):935-46 (polymer-encapsulated PC12 cells implanted into rats); Kordower et al, 1994, PNAS USA 91(23):10898-902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more proteoglycans of the host species and/or from viral proteins or proteins from species other than the host species.

Alternatively, the therapeutic is a nucleic acid encoding the core of a suitable proteoglycan or a polypeptide disclosed herein. Thus, a subject in need thereof, may receive a dose of viral vector encoding the protein of interest, which may be specifically targeted to a specific tissue, e.g.; a dystrophic tissue. The vector can be administered in naked form, or it can be administered as a viral particle (further described herein). For this purpose, various techniques have been developed for modification of target tissue and cells in vivo. A number of viral vectors have been developed, such as described above, which allow for transfection and, in some cases, integration of the virus into the host. See, for example, Dubensky et al. (1984) Proc. Natl. Acad. Sci. USA 81, 7529-7533; Kaneda et al; (1989) Science 243,375-378; Hiebert et al. (1989) Proc. Natl. Acad. Sci. USA 86, 3594-3598; Hatzoglu et al. (1990) J. Biol. Chem. 265, 17285-17293 and Ferry, et al. (1991) Proc. Natl. Acad. Sci. USA 88, 8377-8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used.

In yet another embodiment, cells are obtained from a subject, modified ex vivo, and introduced into the same or a different subject. Additional methods of administration of the therapeutic compounds are set forth below.

A. Toxicity:

Toxicity and therapeutic efficacy of compounds of the invention can be determined by standard pharmaceutical procedures in cell cultures or experimental animals, e.g., for determining The $Ld_{50}$ (The Dose Lethal To 50% Of The Population) And The $Ed_{50}$ (the dose therapeutically effective in 50% of the population). The dose ratio between toxic and therapeutic effects is the therapeutic index and it can be expressed as the ratio $LD50/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. In particular, where the therapeutic is administered for potentiating AChR aggregation, it is desirable to establish the dose that will result in stimulation, if desired, or inhibition, if desired. Tests can then be continued in medical tests. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

B. Pharmaceutical Compositions:

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art and include, for example, for transmucosal administration bile salts and fusidic acid derivatives in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a gene delivery system for the therapeutic gene encoding a proteoglycan of the invention can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No, 5,328,470) or by stereotactic injection (e.g., Chen et al. (1994) *PNAS* 91: 3054-3057). A gene encoding a proteoglycan of the invention can be delivered in a gene therapy construct by electroporation using techniques described, for example, by Dev et al. ((1994) *Cancer Treat Rev* 20:105-115).

A preferred mode of delivering DNA to muscle cells include using recombinant adeno-associated virus vectors, such as those described in U.S. Pat. No. 5,858,351. Alternatively, genes have been delivered to muscle by direct injection of plasmid DNA, such as described by Wolff et al. (1990) Science 247:1465-1468; Acsadi et al. (1991) Nature 352:815-818; Barr and Leiden (1991) Science 254:1507-1509. However, this mode of administration generally results in sustained but generally low levels of expression. Low but sustained expression levels are expected to be effective for practicing the methods of the invention.

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

VI. Screening Methods

The invention further provides methods for identifying agents, e.g., bigylcan therapeutics or collagen VI therapeutics, which optionally modulate membrane integrity, in particular, by modulating DAPC stability, and agents which modulate neuromuscular junction formation, such as by modulating postsynaptic differentiation. Thus, in certain embodiments, the invention provides methods for identifying agents which modulate the activity of a biglycan or collagen VI, and preferably agents that modulate the interaction (whether direct or indirect) between collagen VI and other DAPC components.

Accordingly, the invention provides screening methods for identifying therapeutics. A therapeutic of the invention can be any type of compound, including a protein, a peptide, a proteoglycan, a polysaccharide, a peptidomimetic, a small molecule, and a nucleic acid. A nucleic acid can be, e.g., a gene, an antisense nucleic acid, a ribozyme, or a triplex molecule.

Preferred agonists include compounds which mimic at least one biological activity of a biglycan or collagen VI or other DAPC component, e.g., the capability to bind to one or more components of a DAPC, such as alpha-dystroglycan, biglycan or collagen VI, or the capability to stimulate MuSK phosphorylation and/or AChR aggregation. Other preferred agonists include compounds which are capable of increasing the production of the proteoglycan of the invention in a cell, e.g., compounds capable of upregulating the expression of the gene encoding the proteoglycan, and compounds which are capable of enhancing an activity of a proteoglycan of the invention, and/or the interaction of a proteoglycan of the invention with another molecule, such as a component of a DAPC or MuSK.

Preferred antagonists include compounds which are dominant negative proteins, which, e.g., are capable of binding to α-sarcoglycan, but not to stabilize DAPCs, such as by competing with the endogenous proteoglycan of the invention. Other preferred antagonists include compounds which decrease or inhibit the production of a proteoglycan of the invention in a cell and compounds which are capable of downregulating expression of a gene encoding a proteoglycan of the invention, and compounds which are capable of donwregulating an activity of a proteoglycan of the invention and/or its interaction with another molecule, such as α-sarcoglycan. In another preferred embodiment, an antagonist is a modified form of an alpha-dystroglycan or other molecule capable of binding to the wildtype proteoglycan of the invention, which is capable of interacting with the proteoglycan of the invention, but which does not have biological activity, e.g., which does not stabilize DAPCs.

The invention also provides screening methods for identifying therapeutics which are capable of binding to a proteoglycan of the invention, e.g., a wild-type proteoglycan of the invention or a mutated form thereof, and thereby modulate the a biological activity of a proteoglycan of the invention, or degrades, or causes the proteoglycan of the invention to be degraded. For example, such a therapeutic can be an antibody or derivative thereof which interacts specifically with a proteoglycan of the invention (either wild-type or mutated).

Thus, the invention provides screening methods for identifying agonist and antagonist compounds, comprising selecting compounds which are capable of interacting with a proteoglycan of the invention or with a molecule interacting with a proteoglycan of the invention, such a component of a DAPC or MuSK, and/or compounds which are capable of modulating the interaction of an a proteoglycan of the invention with another molecule, such as a component of a DAPC or MuSK. In general, a molecule which is capable of interacting with a proteoglycan or collagen VI of the invention is referred to herein as a "candidate therapeutic binding partner" or "CT-binding partner" and can be a component of a DAPC, e.g., a dystroglycan or a sarcoglycan, or MuSK.

The compounds of the invention can be identified using various assays depending on the type of compound and activity of the compound that is desired. Set forth below are at least some assays that can be used for identifying therapeutics of the invention. It is within the skill of the art to design additional assays for identifying therapeutics.

A. Cell-free Assays

Cell-free assays can be used to identify compounds which are capable of interacting with a proteoglycan of the invention or binding partner thereof, to thereby modify the activity of the proteoglycan of the invention or binding partner thereof. Such a compound can, e.g., modify the structure of a proteoglycan of the invention or binding partner thereof and thereby affect its activity. Cell-free assays can also be used to identify compounds which modulate the interaction between a proteoglycan of the invention and a PT-binding partner, such as a component of a DAPC. In a preferred embodiment, cell-free assays for identifying such compounds consist essentially in a reaction mixture containing a proteoglycan of the invention, and a test compound or a library of test compounds with or without a binding partner. A test compound can be, e.g., a derivative of a CT-binding partner, e.g., an biologically inactive target peptide, or a small molecule.

These assays can be performed with a complete proteoglycan molecule of the invention. Alternatively, the screening assays can be performed with potions thereof, such as the core only, one or more LLR domains, the glycosamino glycan chains only, or portions thereof, or combinations of these portions. These can be prepared as set forth supra.

Accordingly, one exemplary screening assay of the present invention includes the steps of contacting a biglycan or collagen VI polypeptide of the invention or functional fragment thereof or a binding partner with a test compound or library of test compounds and detecting the formation of complexes. For detection purposes, the molecule can be labeled with a specific marker and the test compound or library of test compounds labeled with a different marker. Interaction of a test compound with a proteoglycan of the invention or fragment thereof or CT-binding partner can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the proteoglycan of the invention, functional fragment thereof, analog or CT-binding partner is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) a proteoglycan of the invention, (ii) a CT-binding partner (e.g., α-sarcoglycan), and (iii) a test compound; and (b) detecting interaction of the proteoglycan of the invention and the CT-binding protein. The proteoglycan of the invention and CT-binding partner can be produced recombinantly, purified from a source, e.g., plasma, or chemically synthesized, as described herein. A statistically significant change (potentiation or inhibition) in the interaction of the proteoglycan of the invention and CT-binding protein in the presence of the test compound, relative to the interaction in the absence of the test compound, indicates a potential agonist (mimetic or potentiator) or antagonist (inhibitor) of a bioactivity for the test compound. The compounds of this assay can be contacted simultaneously. Alternatively, a proteoglycan of the invention can first be contacted with a test compound for an appropriate amount of time, following which the CT-binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified proteoglycan of the invention or binding partner is added to a composition containing the CT-binding partner or proteoglycan of the invention, and the formation of a complex is quantitated in the absence of the test compound.

Complex formation between a proteoglycan of the invention and a CT-binding partner may be detected by a variety of techniques. Modulation of the formation of complexes can be quantitated using, for example, detectably labeled proteins such as radiolabeled, fluorescently labeled, or enzymatically labeled proteoglycans of the invention or CT-binding partners, by immunoassay, or by chromatographic detection.

Typically, it will be desirable to immobilize either the proteoglycan of the invention or its binding partner to facilitate separation of complexes from uncomplexed forms of one or both of the proteins, as well as to accommodate automation of the assay. Binding of a proteoglycan of the invention to a CT-binding partner, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/ACE-2 (GST/proteoglycan of the invention) fusion proteins can be adsorbed onto glutathione sepharose beads (Sigma Chemical, St. Louis, Mo.) or glutathione derivatized microtitre plates, which are then combined with the PT-binding partner, e.g. an $^{35}$S-labeled CT-binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of proteoglycan of the invention or CT-binding partner found in the bead fraction is quantitated from the gel using standard electrophoretic techniques such as described in the appended examples.

Other techniques for immobilizing proteins on matrices are also available for use in the subject assay. For instance, either the proteoglycan of the invention or its cognate binding partner can be immobilized utilizing conjugation of biotin and streptavidin. For instance, biotinylated proteoglycan molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the proteoglycan of the invention can be derivatized to the wells of the plate, and the proteoglycan of the invention trapped in the wells by antibody conjugation. As above, preparations of a CT-binding protein and a test compound are incubated in the proteoglycan presenting wells of the plate, and the amount of complex trapped in the well can be quantitated. Exemplary methods for detecting such complexes, in addition to those described above for the GST-immobilized complexes, include immunodetection of complexes using antibodies reactive with the CT-binding partner, or which are reactive with protein and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the CT-binding partner. To illustrate, the CT-binding partner can be chemically cross-linked or genetically fused with horseradish peroxidase, and the amount of polypeptide trapped in the complex can: be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the proteoglycan of the invention, can be used. Alternatively, the protein to be detected in the complex can be "epitope tagged" in the form of a fusion protein which includes, in addition to the sequence of the core of the proteoglycan of the invention, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150-21157) which includes a 10-residue sequence from c-myc, as well as the pFLAG system (International Biotechnologies, Inc.) or the pEZZ-protein A system (Pharmacia, N.J.).

Cell-free assays can also be used to identify compounds which interact with a proteoglycan of the invention and modulate an activity of a proteoglycan of the invention. Accordingly, in one embodiment, a proteoglycan of the invention is contacted with a test compound and the catalytic activity of the proteoglycan of the invention is monitored. In one embodiment, the ability of the proteoglycan of the invention to bind to a binding partner is determined. The binding affinity of a proteoglycan of the invention to a binding partner can be determined according to methods known in the art.

B. Cell Based Assays

Cell based assays can be used, in particular, to identify compounds which modulate expression of a gene encoding a proteoglycan of the invention, modulate translation of the mRNA encoding a proteoglycan of the invention, modulate the posttranslational modification of the core protein of the proteoglycan, or which modulate the stability of the mRNA or protein. Accordingly, in one embodiment, a cell which is capable of producing a proteoglycan of the invention, e.g., a muscle cell, is incubated with a test compound and the amount of proteoglycan of the invention produced in the cell medium is measured and compared to that produced from a cell which has not been contacted with the test compound. The specificity of the compound vis a vis the proteoglycan of the invention can be confirmed by various control analysis, e.g., measuring the expression of one or more control genes.

Cell based assays can also rely on a reporter gene system detecting whether two molecules interact or not, e.g., the classic two hybrid system, that can be conducted in yeast or in mammalian cells.

Compounds which can be tested include small molecules, proteins, and nucleic acids. In particular, this assay can be used to determine the efficacity of antisense molecules or ribozymes that bind to RNA encoding the proteoglycan of the invention.

In another embodiment, the effect of a test compound on transcription of a gene encoding a proteoglycan is determined by transfection experiments using a reporter gene operatively linked to at least a portion of the promoter of a gene encoding a proteoglycan of the invention. A promoter region of a gene can be isolated, e.g., from a genomic library according to methods known in the art. Promoters of genes encoding proteoglycans, e.g., biglycan, are publically available, e.g, from GenBank. The reporter gene can be any gene encoding a protein which is readily quantifiable, e.g, the luciferase or CAT gene, well known in the art.

This invention further pertains to novel agents identified by the above-described screening assays and uses thereof for treatments as described herein.

C. Assays for Identifying Compounds which Modulate Phosphorylation

Biglycan was shown to bind and activate MuSK and induce phosphorylation of α-sarcoglycan. Accordingly, compounds which stimulate phosphorylation of such substrates may exercise at least part of the activity of biglycan in stabilizing muscle cell membranes or of potentiating postsynaptic membranes. Thus, also within the scope of the invention are methods for identifying such compounds. In one embodiment, the method comprises contacting a cell, e.g., a muscle cell, with a compound, and monitoring the level of phosphorylation of a DAPC component, such as α-sarcoglycan, or activation of MuSK, wherein a higher level of phosphorylation relative to that in an untreated cell indicates that the compound stimulates phosphorylation. Such assays can also be conducted in vitro using cell extracts or purified proteins. For example, the method may comprise contacting a purified sarcoglycan or MuSK and a cell extract from biglycan-activated cells (i.e., cells contacted with biglycan) or a kinase in the presence of a test compound, and monitoring whether the presence of the test compound prevents or stimulates phosphorylation.

VII. Kits of the Invention

The invention provides kits for diagnostic tests or therapeutic purposes.

Kits for therapeutic or preventive purposes can include a therapeutic and optionally a method for administering the therapeutic or buffer necessary for solubilizing the therapeutic.

The present invention is further illustrated by the following examples which should not be construed as limiting in any way. The contents of all cited references (including literature references, issued patents, published patent applications as cited throughout this application are hereby expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

VIII. EXAMPES

Example 1

Characterization of a Dystroglycan-binding Protein, DAG-125

This Example describes the identification of a dystroglycan-binding protein, termed DAG-125.

In order to identify novel dystroglycan binding partners, a ligand blot overlay assay, was developed as follows. Postsynaptic and non-synaptic membrane fractions from Torpedo electric organ were prepared as previously described (Bowe, et al. (1994) *Neuron.* 12: 1173). All handling of membranes and protein was performed at 4° C.

Membrane proteins were separated by SDS-PAGE (5-15% gradient gel), and transferred to nitrocellulose. To detect dystroglycan binding proteins, the nitrocellulose was rinsed and blocked for 3 hr in Hank's Balanced Salt Solution containing 1 mM $CaCl_2$, 1 mM $MgCl_2$, 1% bovine serum albumin, 1% Nonfat Dry Milk, 1 mM DTT, 10 mM HEPES, pH 7.4, and was then incubated overnight in the same buffer containing $^{35}$S-methionine-labelled dystroglycan fragments produced by in vitro transcription/translation as follows.

DNA fragments encoding $DG_{1-891}$ and $DG_{345-891}$ (human alpha-dystroglycan sequence is described, e.g., in Ibraghimov-BeskrovnayaHum (1993) *Mol Genet* 2: 1651) were cloned in the in vitro expression vector pMGT developed by A. Ahn (Ahn and Kunkel (1995) *J Cell Biol.* 128: 363). Additional in vitro expression plasmids used in this study (including $DGI_{1-750}$, $DG_{776-891}$, and $DG_{345-653}$) were prepared by PCR-based subcloning of these inserts. The PCR primers included restriction sites for religation into the EcoRI site of pMGT. Dystroglycan protein fragments were generated by in vitro transcription/translation using the Promega TNT T7 coupled reticulocyte system as per the manufacturer's instructions. For protein to be used in ligand blot overlay assay, the reaction mixture contained $^{35}$S-methionine (with no unlabeled methionine). After incubation for 2 hr, the reaction mixture was passed over Bio-Spin desalting columns (Bio-Rad, Hercules, Calif.) to remove unincorporated amino acids and salts.

After incubation of the blots with the in vitro translated proteins, the blots were rinsed and dried and bound dystroglycan fragments were visualized by autoradiography. To detect dystroglycan present in the SDS-PAGE sample, an agrin blot overlay assay was performed essentially as described in O'Toole, et al. (1996) *PNAS* 93:7369. Briefly, the nitrocellulose was rinsed and blocked for 3 hr in HEPES-buffered Minimum Essential Medium supplemented with 1% bovine serum albumin and 10% horse serum. It was then incubated for 4 hr in this buffer containing recombinant rat agrin (isoform $A_0B_0$, prepared as described in O'Toole et al., supra), followed by a second layer containing 1 μg/ml anti-agrin antibody $^{125}$I-Mab-131 (Stressgen Laboratories, Victoria, BC). Bound anti-agrin antibody was visualized by autoradiography.

Figure 2:
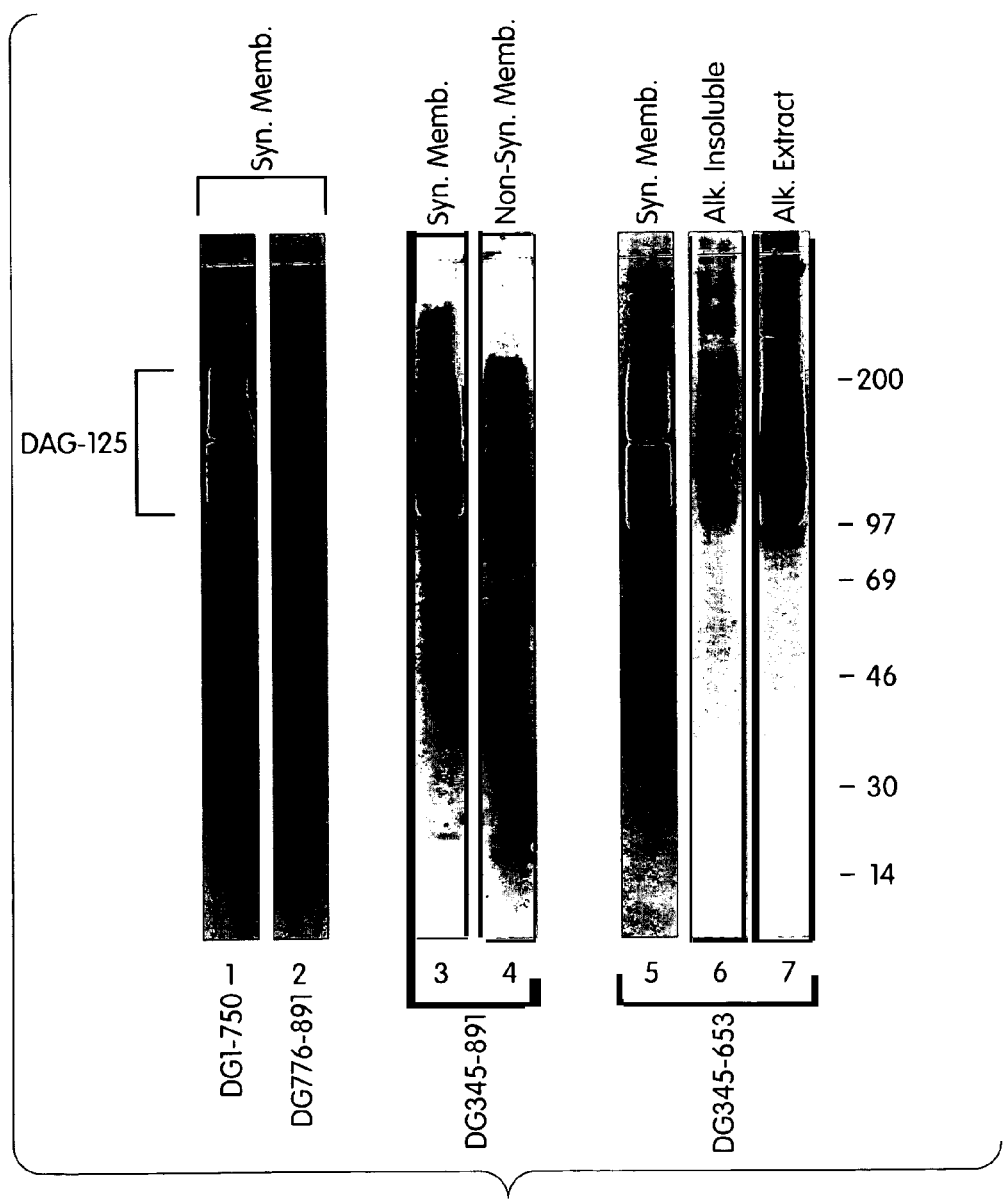
FIG. 2 shows the results of a ligand blot overlay assay, in which filters with various extracts (as indicated) were incubated with portions of α-dystroglycan.

The results are shown in FIG. 2. Lanes 1 and 2 indicate that certain fragments of dystroglycan bound to an about 125 kD, highly glycosylated polypeptide, which was termed DAG-125 (for "Dystroglycan-Associated Glycoprotein, 125 kDa"). As shown in FIG. 2A, the extracellular domain of dystroglycan (lane 1: $DG_{1-750}$) bound to DAG-125, while the intracellular portion of dystroglycan (lane 2: $DG_{776-891}$) did not.

Lanes 3 and 4 of FIG. 2 show that DAG-125 is enriched in synaptic as compared to non-synaptic membranes.

To solubilize DAG-125, synaptic membranes were centrifuged at 100,000×g for 1 hour (hr) and resuspended in ddH$_2$O. The pH was adjusted to 11.0 or 12.0 (as indicated) with NaOH and the membranes stirred for 1 hr. Insoluble material was removed by centrifugation at 100,000×g for 1 hr. The alkaline extract was neutralized with 10 mM Tris HCl and adjusted to pH 7.4. DAG-125 remained soluble under these conditions as determined by resistance to pelleting during a second centrifugation. Lanes 5-7 of FIG. 2 show that DAG-125 is a peripheral membrane protein that can be extracted from the synaptic membrane by alkaline treatment. Synaptic membranes were extracted at pH 12 and the insoluble (lane 6) and soluble fraction (lane 7) were analyzed. Greater than 90% of DAG-125 is solubilized by pH 12.0 treatment. Thus, DAG-125 is likely to be a peripheral membrane protein, since it is removed from the membranes by alkaline-treatment.

Example 2

Association Between α-dystroglycan and DAG-125

This Example demonstrates that DAG-125 associates with in vitro-translated α-dystroglycan, bacterially produced GST-α-dystroglycan fusion protein and native α-dystroglycan in solution.

DAG-125 was solubilized by alkaline-treatment, and neutralized, as described above, and incubated with column matrices and recombinant or native dystroglycan as indicated in FIG. 3. The input material and eluates from the beads were analyzed by ligand blot overlay assay for the presence of DAG-125 ($^{35}$S-DG345-653 as probe) or native α-dystroglycan (agrin overlay, see Example 1).

Figure 3A:
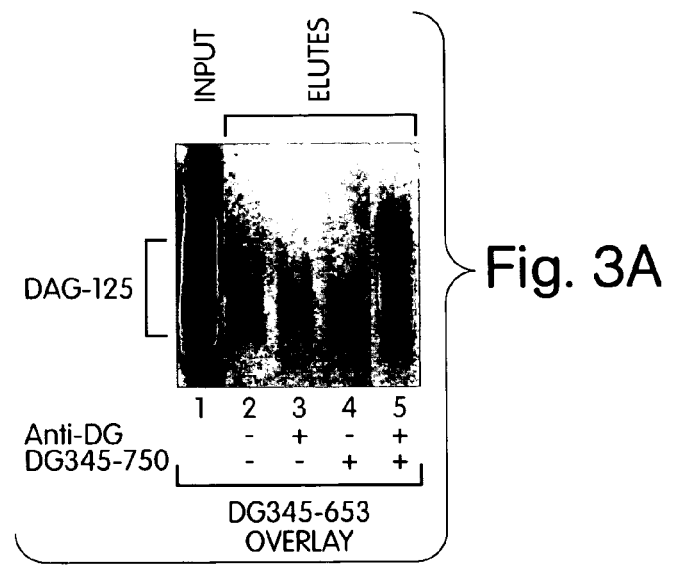
FIG. 3(A-C) shows the results of a blot overlay assays in which filters with input and elutes from columns were incubated with portions of alpha dystroglycan or agrin.

FIG. 3A shows DAG-125 incubated with goat anti-mouse Ig-conjugated agarose beads in the presence or absence of in vitro translated dystroglycan polypeptide ($DG_{345-750}$) and/or anti-dystroglycan monoclonal antibody (NCL-β-DG; Novocastra, Newcastle-on-Tyne, UK). The results indicate that DAG-125 co-precipitated with dystroglycan plus anti-dystroglycan antibody (lane 5), but was not precipitated in the absence of either or both (lanes 2-4). Thus, DAG-125 binds to in vitro translated dystroglycan peptide DG345-750.

Figure 3B:
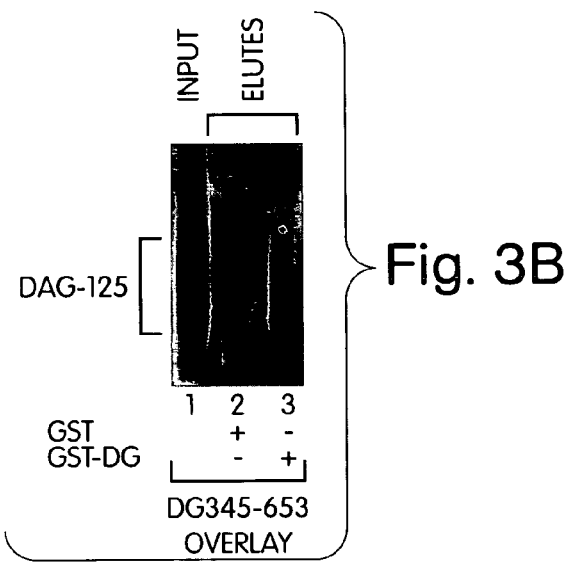

FIG. 3B shows DAG-125 incubated with glutathione-sepharose beads that had been pre-incubated with either bacterially produced GST or a bacterially produced GST-dystroglycan fusion protein (GST-$DG_{345-653}$). A fusion protein of glutathione S-transferase (GST) and amino acids 345-653 of dystroglycan was produced by using PCR-based subcloning to introduce dystroglycan coding sequence into the bacterial protein expression vector pGEX-1 T (Pharmacia, Piscataway, N.J.). The resulting bacterial expression plasmid, pGST-$DG_{345-653}$, was then introduced into the *E. coli* strain BL21 and expressed fusion protein recovered from the cytoplasmic fraction as per manufacturer's instructions. Control protein (GST) was obtained using pGEX-1 T. The results show that DAG-125 was co-precipitated with the dystroglycan fusion protein (lane 3), but not with GST alone (lane 2). Thus, DAG-125 binds to alpha-dystroglycan peptide 345-653 produced in bacteria.

Figure 3C:
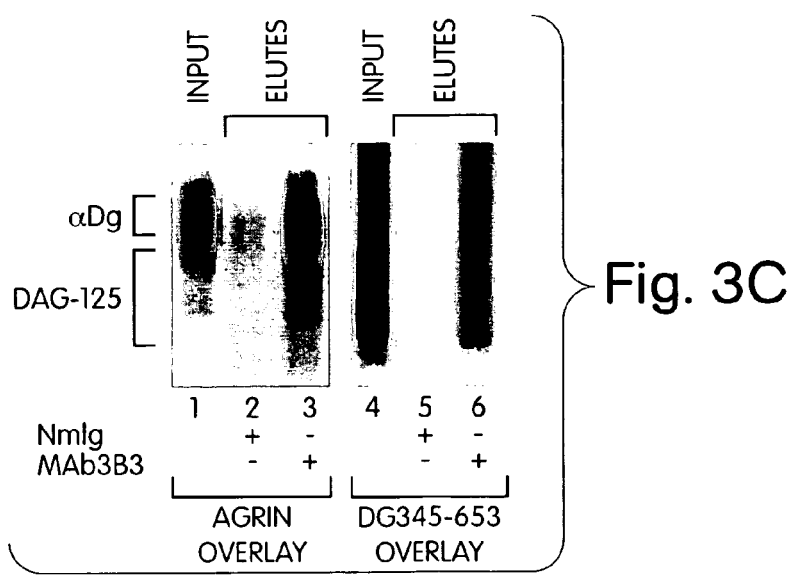

FIG. 3C shows DAG-125 and native α-dystroglycan. Alkaline extracts of Torpedo electric organ membranes contain both DAG-125 and α-dystroglycan. This extract was applied to agarose columns conjugated to either control antibody or to an anti-Torpedo dystroglycan monoclonal antibody (MAb3B3; Bowe, M. A., et al. (1994) *Neuron* 12: 1173). The results show that native α-dystroglycan and DAG-125 were co-precipitated by the anti-Torpedo dystroglycan antibody, Mab3B3, (lanes 3 and 6), but not by control antibody (lanes 2 and 5). Western blots indicate that Mab3B3 does not recognize DAG-125 (see Bowe, M. A., et al., 1994, *Neuron.* 12: 1173-1180).

Thus, FIG. 3 shows that DAG-125 co-precipitates with in vitro-translated alpha-dystroglycan, bacterially produced GST-alpha-dystroglycan protein, and with native alpha-dystroglycan.

Example 3

Localization of the DAG-125 Binding Domain of α-dystroglycan

This Example describes that the DAG-125 binding domain of α-dystroglycan is contained in an approximately 150 amino acid carboxyl-terminal domain of the protein.

Figure 4:
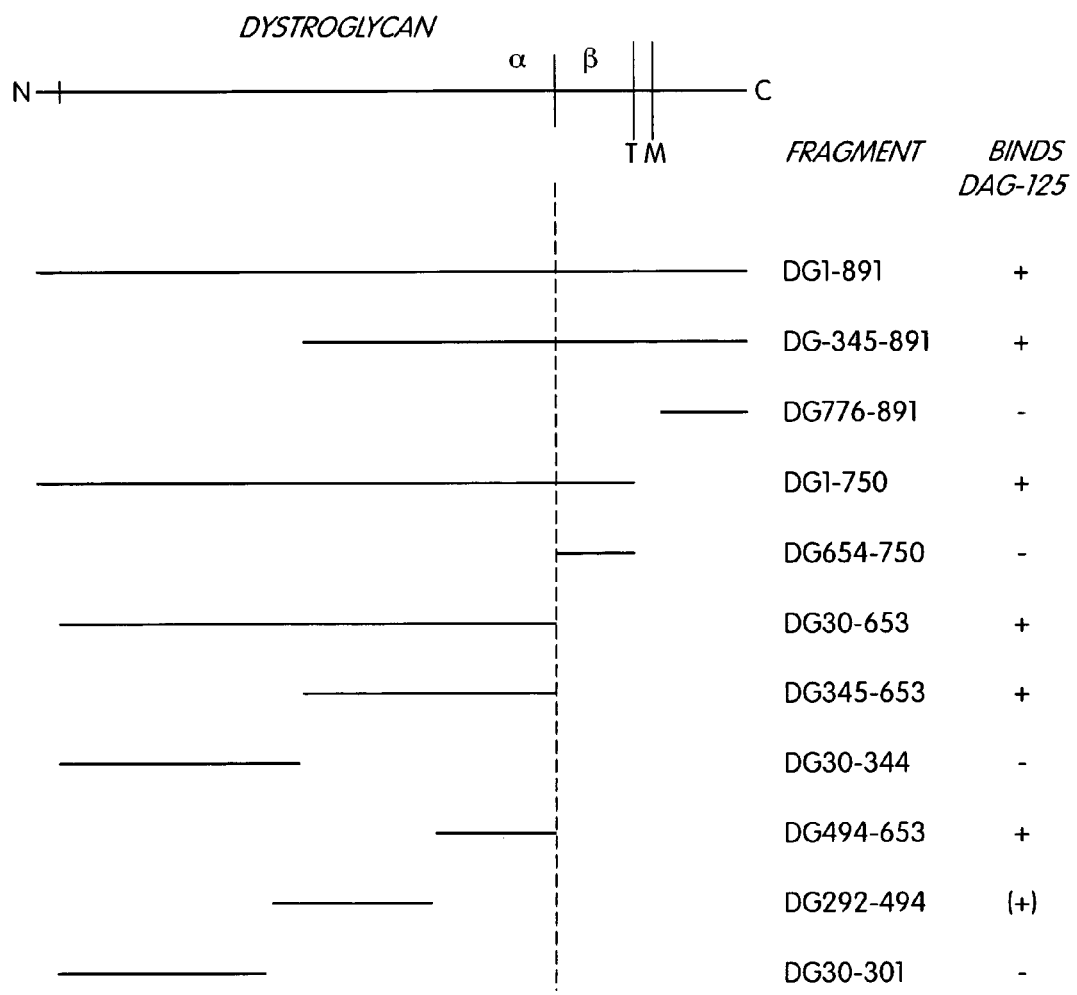
FIG. 4 is a diagram showing portions of dystroglycan used in a blot overlay assays and the presence (+) or absence (−) of binding.

In order to determine the region of α-dystroglycan that interacts with DAG-125, a panel of dystroglycan fragments were prepared by in vitro translation (FIG. 4) and the ability of each to bind DAG-125 was tested using the ligand blot overlay assay. FIG. 4, which show the results, indicates that DAG-125 binds to the carboxyl-terminal one-third of α-dystroglycan. A small contribution from the middle third of α-dystroglycan is also possible. The ectodomain of β-dystroglycan does not appear to contribute to binding of DAG-125. Moreover, these fragments were produced under conditions in which the polypeptides are not glycosylated. Therefore, carbohydrate side chains on dystroglycan are not necessary for its binding to DAG-125.

Thus, the major binding domain is contained in about 150 amino acid region of dystroglycan. The location of this domain and the lack of a carbohydrate requirement indicate that α-dystroglycan's binding site for biglycan is distinct from that mediating association with agrin, laminin, and perlecan.

Example 4

Identification of DAG-125 as Biglycan or a Proteoglycan Related thereto

This Examples demonstrates that DAG-125 is biglycan or a protein related thereto.

It was found that DAG-125 co-purified with postsynaptic membranes, but that, however, it was insoluble in all non-ionic detergents tested including Triton X-100 and n-octyl-β-D-glucopyranoside, both of which efficiently extract α/β-dystroglycan from these membranes (Bowe, et al. (1994) *Neuron.* 12: 1173; Deyst, et al. (1995) *J Biol Chem.* 270: 25956-9). Even without detergent, about 50% of DAG-125 could be extracted at pH 11 and near-complete solubilization was achieved by a short pH 12 treatment (see FIG. 2A). Importantly, DAG-125 remained soluble when returned to neutral pH. Based upon these properties and the findings that DAG-125 binds to both heparin and chondroitin sulfate columns, the following purification protocol was developed.

Postsynaptic-rich membrane fractions were first pre-extracted with 25 mM n-octyl--D-glucopyranoside to remove detergent-soluble proteins. DAG-125 was then solubilized by alkaline extraction (pH 12.0), as described in Example 1. The alkaline extract was diluted in SEN Buffer (20 mM Tris HCl, 100 mM NaCl, 23 µg/ml aprotinin, 0.5 µg/ml leupeptin, 5 mM benzamidine, 0.7 µg/ml pepstatin A, 1 mM phenylmethylsulfonylflouride, 0.02% azide, 0.1% Tween 20, pH 7.6) and recentrifuged to remove any proteins precipitating upon neutralization. The extract remained in SEN Buffer for the remainder of the purification, with only the NaCl concentration changed as indicated. The extract was passed over a MAb3B3 column (Bowe, et al. (1994) *Neuron.* 12: 1173) to remove α-dystroglycan. The MAb3B3 column flow-through was passed over a combined, non-DAG-125-binding lectin-agarose column (peanut agglutinin and ulex europaeus agglutinin I, Vector Labs, Burlingame, Calif.) as a second pre-clear. The flow-through was next applied to a column of chondroitin sulfate-agarose (CS-agarose). The CS-agarose column was prepared by coupling chondroitin sulfate B (Sigma, St. Louis, Mo.; #C-3788) to -aminohexyl-agarose (Sigma) activated with N-ethyl-N'-(3-dimethylaminopropyl)-carbodiimide (Sigma). After incubation with the lectin column flow-through, the CS column was washed extensively and eluted with a 0.1-2.0 M NaCl gradient. DAG-125 eluted in 0.3-0.65 M NaCl. These fractions were pooled, diluted to 0.3 M NaCl, and applied to a heparin-agarose column (Sigma #H-0402). The column was washed and eluted with a 0.3-2 M NaCl gradient. DAG-125 eluted in 0.6-0.85 M NaCl. These fractions were pooled, concentrated by ethanol precipitation (final purity of DAG-125 of about 30%), redissolved in SDS-PAGE sample buffer, separated on a 5-15% gradient gel, and transferred to a PVDF membrane. A portion of the PVDF membrane was analyzed for DAG-125 by blot overlay and the remainder was transiently stained with Ponceau S. Two regions ("U" and "L"; see FIG. 5A) of the DAG-125 band on the Ponceau stained membrane were excised and digested with trypsin. The released peptides were analyzed by HPLC using a C8 column and UV detection. The column profiles were virtually identical, indicating that the polydisperse band is due to the presence of a single, heterogeneously glycosylated protein.

Three peptides from the trypsin digest were collected as fractions from the HPLC analysis and subjected to automated Edman degradation, as described previously (Bowe, et al. (1994) *Neuron.* 12: 1173). The sequences obtained were compared to public databases. The alignment of the Torpedo DAG-125 peptides to the deduced sequence of human biglycan (amino acids 241-249; 258-266; and 330-348) is shown in FIG. 5B. Human biglycan is described in Fisher et al. (1989), infra) and its amino acid sequence is set fort in SEQ ID NO: 9. All DAG-125 peptide fragments were highly homologous to mammalian biglycan, with an overall 76% identity (FIG. 5B). Thus, DAG-125 is a Torpedo orthologue of mammalian biglycan or a close homolog thereof.

Human biglycan, produced in the vaccinia system, as described below, was also shown to bind to α-dystroglycan. The binding was less strong than with Torpedo DAG-125, probably reflecting the fact that the biglycan produced in this system is a mixture of core biglycan and proteoglycan biglycan. However, this further supports that Torpedo orthologue of mammalian biglycan or a close homolog thereof.

The domain structure of human biglycan is shown in FIG. 5C. Biglycan is one of a family of small leucine-rich repeat proteins (Hocking et al. (1998) *Matrix Biol.* 17: 1). It consists of a pre-pro-peptide that is not present in the mature polypeptide. This domain is followed by a short unique sequence with two chondroitin sulfate attachment sites (shown as stacked beads in the Figure). There are two pairs and one pair of disulfide-linked cysteines at the amino and carboxyl-terminal domains, respectively. Finally, the bulk of the protein is comprised of 10 (or 11 depending upon the classification of the region within the carboxyl-terminal cysteine pair) leucine-rich repeats. The position of the three Torpedo peptides relative to the human sequence is indicated by horizontal lines.

Example 5

Chondroitin Sulfate Chains of Biglycan are Necessary for Binding of Biglycan to α-dystroglycan Mammalian biglycan is often substituted with chondroitin sulfate. To determine if Torpedo biglycan is also a chondroitin sulfate proteoglycan and whether glycosylation is important for its binding to α-dystroglycan, DAG-125 was digested with various glycosidases and glycosaminoglycanases and the products were analyzed by α-dystroglycan ligand blot overlay with $^{35}$S-DG345-653.

Enzyme treatments were carried out on alkaline-extracted Torpedo electric organ synaptic membrane proteins at 37° C. overnight. Enzymes, final concentration, supplier and catalog numbers are listed in Table I. All reactions were performed in the protease inhibitors present in SEN Buffer, with the addition of 1 mM EDTA, 10 mM N-ethylmaleimide, and 0.8% mouse serum albumin. Chondroitinases (all forms) were buffered with 100 mM Tris-acetate (pH 8.0). Hyaluronidase and keratanase were buffered with 50 mM sodium acetate (pH 5.0). Heparinases (I, II, and III), chondro-4-sulfatase and chondro-6-sulfatase were buffered with 10 mM NaPO$_4$ (pH 7.4). N-Glycanase, O-glycanase, neuraminidase, α-N-acetyl-galactosaminidase, β-N-acetylglucoasaminidase were buffered with 50 mM Tris HCl (pH 7.3). Control treatments included buffers and protease inhibitors without added enzymes.

Figure 6:
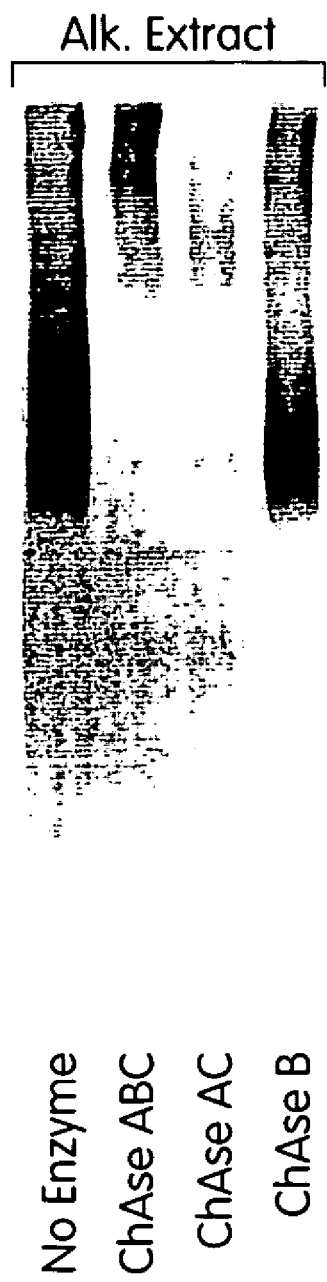
FIG. 6 shows the results of an analysis of Torpedo DAG-125 glycosylation.

The results, are shown in FIG. 6 and in Table I.

Figure 7:
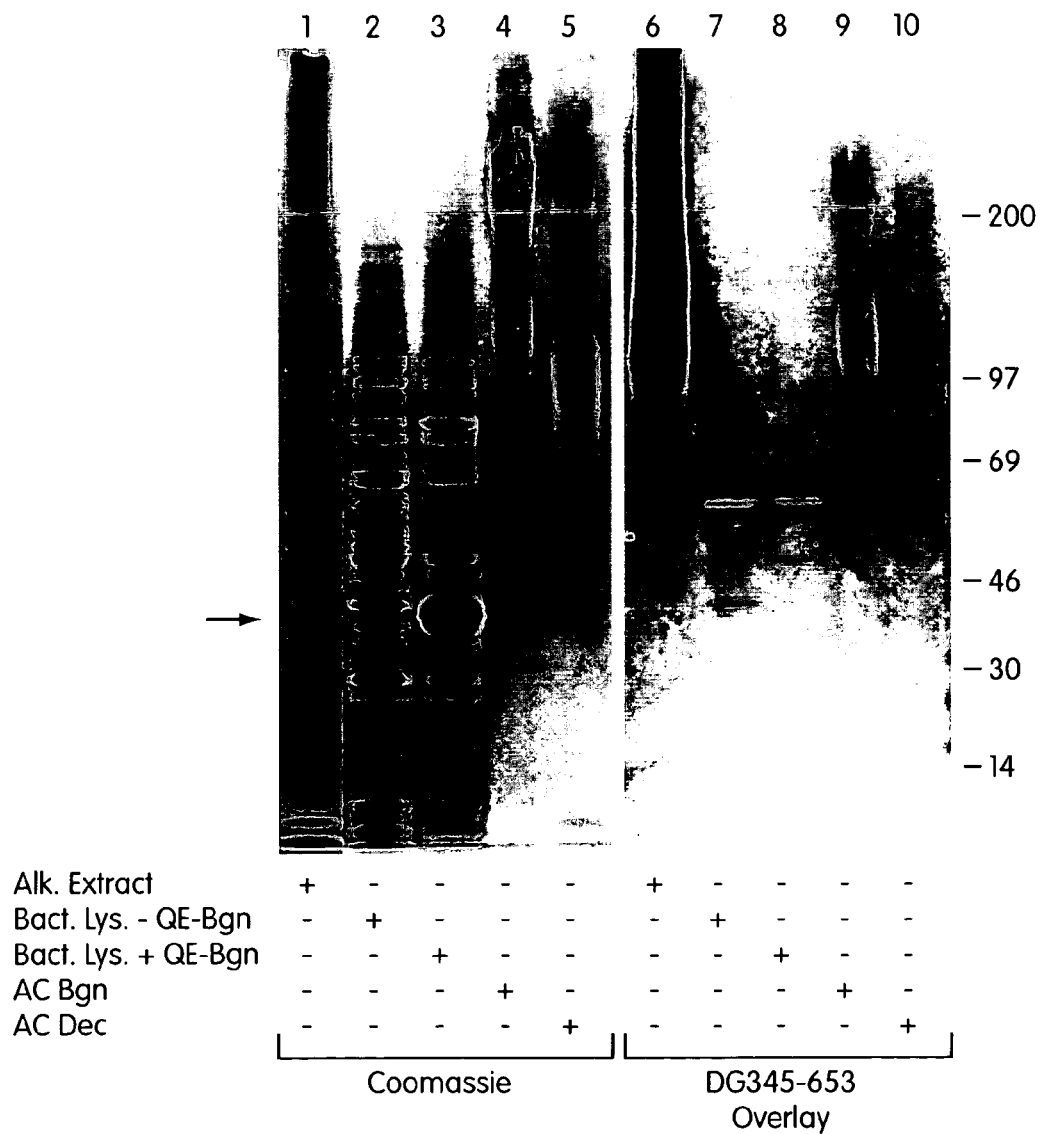
FIG. 7 shows that the binding of dystroglycan to biglycan is dependent upon specific chondroitin sulfate side chains. QE-Bgn is bacterially expressed biglycan core. AC stands for articular cartilage.

Biglycan (or decorin) were analyzed by SDS-PAGE and Coomassie Brilliant Blue staining for protein (lanes 1-5 of FIG. 7) or blot overlay assay for dystroglycan binding (lanes 6-10 of FIG. 7): lanes 1, 6: alkaline extract of Torpedo synaptic membranes (1 μg total protein, of which biglycan is estimated to be <2%); lanes 2, 7: lysate of non-induced bacteria; lanes 3, 8: lysate of induced bacteria expressing recombinant human biglycan (QE-Bgn; prominent band at ~37 kD—arrow); lanes 4, 9: biglycan purified from bovine articular cartilage (4 μg; Sigma); lanes 5, 10: decorin purified from bovine articular cartilage (4 μg; Sigma). The results indicate that biglycan present in electric organ binds dystroglycan much more strongly then biglycan or decorin purified from articular cartilage (compare Coomassie staining to dystroglycan overlay).

The recombinant human biglycan was produced as follows. P16, a cloning plasmid consisting of Bluescript containing a cDNA encoding human biglycan (SEQ ID NO: 9) was provide by Larry Fisher (National Institute of Dental Research, National Institutes of Health) (Fisher et al. (1989),

TABLE I

| Enzyme | Inhibit Binding? | Enzyme (Units/mL) | Conc-Source | Cat. # |
|---|---|---|---|---|
| Chondroitinase ABC | + | 0.5 | Sigma | C-2905 |
| Chondroitinase ABC +5 mM ZnCl$_2$ | − | 0.5 | Sigma | C-2905 |
| Chondroitinase ABC, Protease-free | + | 0.5 | Sigma | C-3667 |
| Chondroitinase ABC, Protease-free | + | 0.5 | Roche | 1080717 |
| Chondroitinase AC | + | 0.5 | Sigma | C-2780 |
| Chondroitinase B | +/− | 25 | Sigma | C-8058 |
| Heparinase I | − | 25 | Sigma | H-2519 |
| Heparinase II | − | 5 | Sigma | H-3812 |
| Heparinase III (Heparitinase) | − | 5 | Sigma | H-8891 |
| Chondro-4-sulfatase | +/− | 0.5 | Sigma | C-2655 |
| Chondro-6-sulfatase | − | 0.5 | Sigma | C-2655 |
| Keratanase | − | 0.02 | Roche | 982954 |
| α-N-acetylgalactosaminidase | − | 2 | Sigma | A-9763 |
| β-N-acetylglucoasaminidase | − | 8 | Sigma | A-2264 |
| N-Glycanase | − | 15 | Genzyme | N-Gly-1 |
| O-Glycanase | − | 0.03 | Genzyme | B2950 |
| Neuraminidase | − | 1 | Genzyme | NSS-1 |

The results indicate that removal of chondroitin sulfate side chains abolished the binding to α-dystroglycan. Chondroitinase B (specific for dermatan sulfate) had a much smaller effect compared to chondroitinases which removed chondroitin sulfate A and C. No other glycosidase or glycosaminoglycanase treatment had a detectable effect on α-dystroglycan binding (see Table I). Several lines of evidence indicate that the effects of chondroitinase digestion are due to chondroitinase activity and not to contaminating proteases: 1) the digestions were performed in a cocktail of protease inhibitors; 2) the same result was seen with four different preparations of chondroitinase, including two which had been affinity purified to remove proteases; and 3) the effect was prevented by addition of 5 mM Zn$^{2+}$, an inhibitor of chondroitinase but not of proteases.

To further investigate the binding properties of biglycan, the binding of α-dystroglycan to biglycan derived from a variety of sources, as well as to decorin, a small leucine-rich proteoglycan that is about 50% identical to biglycan, were investigated.

supra). The sequence encoding the mature secreted peptide (amino acids 1-343) was amplified by PCR and subcloned into the bacterial expression vector pQE9 (Qiagen, Valencia, Calif.). The resulting plasmid, pQE-biglycan, adds the sequence MRGSHHHHHHGS (SEQ ID NO: 10) to the amino terminus. Recombinant protein was produced in E. coli strain M15[pREP4]. Uninduced bacteria provide control protein. Induced or non-induced bacteria were isolated by centrifugation and resuspended in SDS-PAGE sample buffer for analysis by ligand blot overlay. Thus, bacterially-expressed biglycan, which contains no chondroitin sulfate side chains, did not bind α-dystroglycan (FIG. 7), consistent with a requirement for chondroitin sulfate chains. Biglycan purified from articular cartilage bound α-dystroglycan poorly, even at >100-fold higher loading than that used for Torpedo biglycan analysis. These findings indicate that specific chondroitin sulfate chains are required to mediate α-dystroglycan binding to biglycan.

Thus, biglycan from Torpedo synaptic membranes is substituted with chondroitin sulfate chains, which are predominantly chondroitin sulfate A and/or C, and chondroitin sulfate substitution of biglycan is necessary for binding to dystroglycan.

Example 6

Biglycan Binds to Sarcoglycan Components

This Example describes that biglycan core binds to α- and to gamma sarcoglycans and that biglycan proteoglycan also binds to γ-sarcoglycan, and that decorin failed to bind to any of the sarcoglycans (no detectable level of binding was observed).

The binding of biglycan and decorin to the different components of sarcoglycan of the DAPC was investigated by overlay assay using recombinantly produced human sarcoglycans, on biglycan proteoglycan (core and side chains), biglycan core (no side chains), decorin proteoglycan (core and side chains), decorin core (no side chains), a hybrid between biglycan and decorin core (the "hybrid" with side chains), and Torpedo electric organ membrane fraction (TEOM). The hybrid contained the first 30 amino acids of human biglycan (cysteine rich domain) and the remaining portion of the biglycan molecule was swapped with that of decorin. The sarcoglycans were produced by in vitro transcription and translation using a Promega TNT kit, as described in Ahn and Kunkel (1995) *J. Cell Biol.* 128: 363. The biglycan and decorin core polypeptide and proteoglycan were produced recombinantly by vaccinia-virus infection of rat osteosarcoma cells, as described in Hocking et al. (1996) *J. Biol. Chem.* 271:19571. Briefly, the cDNA sequence encoding the mature core protein of human biglycan ligated to a polyhistidine fusion cassette under the control of T7 promoter was inserted into the pBGN4 vector. An encephalomyocarditis virus untranslated region was inserted downstream of the T7 promoter to facilitate cap-independent ribosome binding and thereby increases translation efficiency up to 10-fold. The fusion cassette encodes the canine insulin signal sequence (INS), six consecutive histidine residues (POLYHIS), and the factor Xa recognition site (Xa). A recombinant *vaccina* virus, vBGNA, encoding the T7 regulated BGN4 construct, was generated by a homologus recombination event between wild-type vaccinia virus and thymidine kinase flanking sequences in the plasmid, pBGN4. There are two extra amino acids between the polyhistidine sequence and the Factor Xa site and two extra amino acids between the Factor Xa site and the start of the mature core protein sequence of biglycan. Thus, the vector contains from 5' to 3': EMC UTR-INS-POLYHIS-[Glu-Ser]-Xa-[Leu-Glu]-mature biglycan devoid of the biglycan signal sequence and propeptide sequence). The biglycan that is produced from this system is a mixture containing proteoglycan biglycan and biglycan devoid of glycaosaminoglycan chains ("core biglycan").

The overlay assays were preformed as described above for DAG-125.

Figure 8A:
FIG. 8 A-C show overlay assays blots containing biglycan proteoglycan (BGN-PG), biglycan core (BGN), a biglycan-decorin hybrid (Hybrid), decorin proteoglycan (DEC-PG), decorin (DEC), bacterially produced biglycan (QE-BIG), and Torpedo electric organ membrane fraction (TEOM), which were incubated with $^{35}$S labeled α-sarcoglycan (FIG. 8A), γ-sarcoglycan (FIG. 8B), and delta-sarcoglycan (FIG. 8C).
Figure 8B:
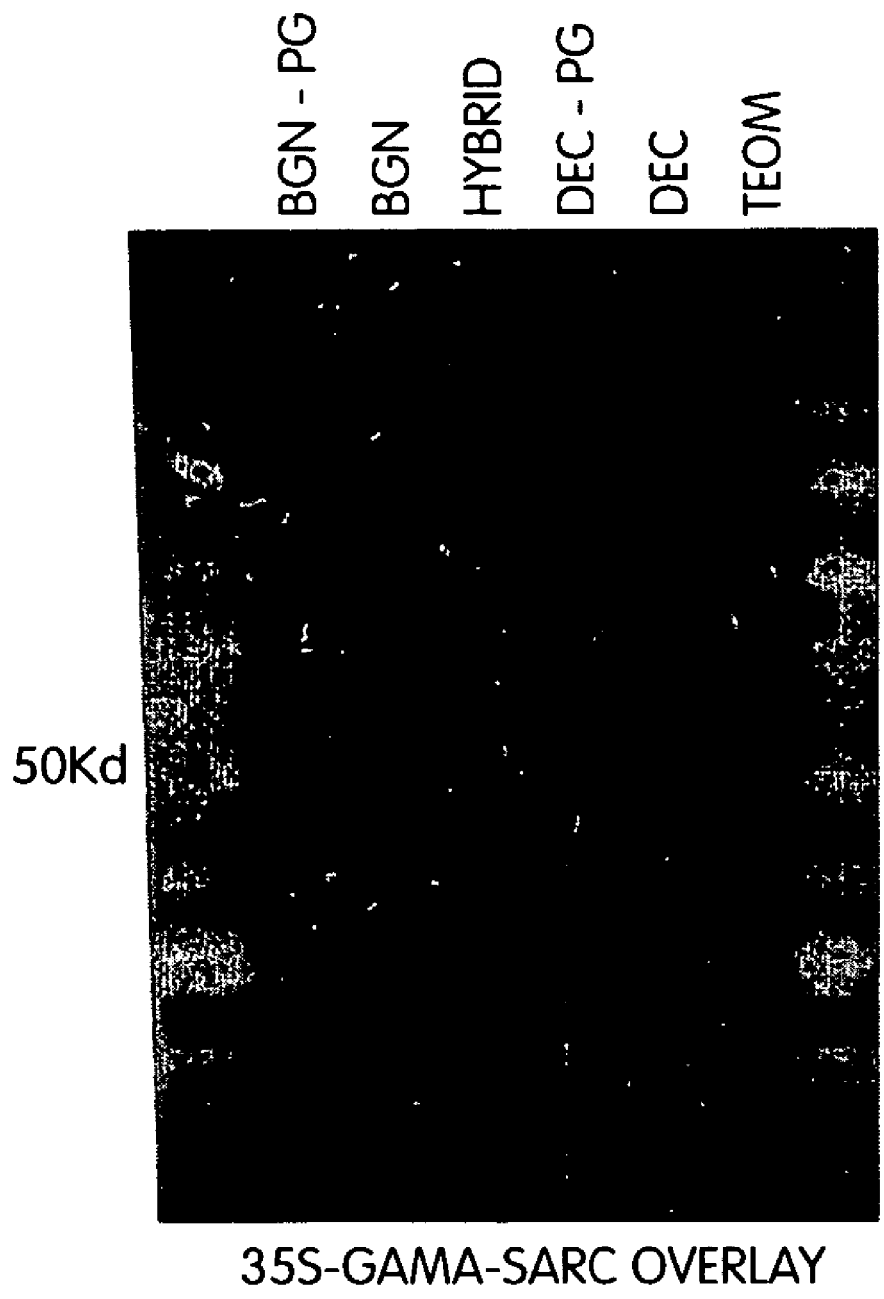
Figure 8C:
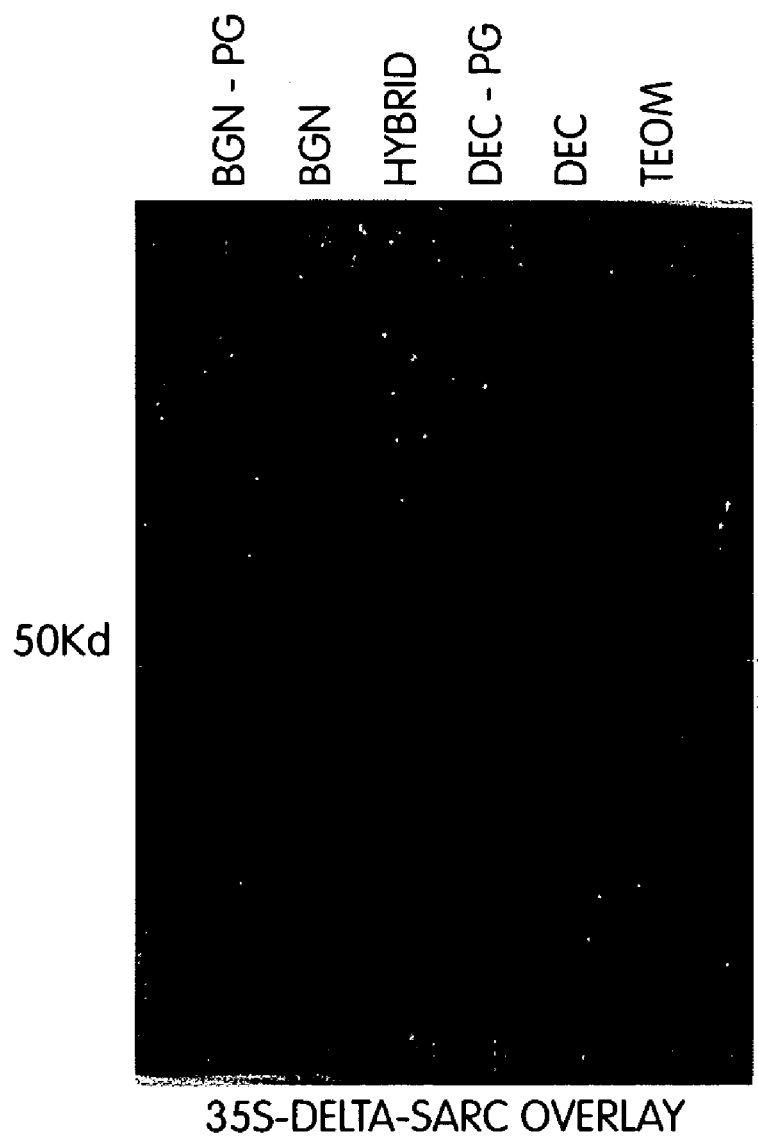

The results, which are shown as FIGS. 8 A-C, indicate the following: α-sarcoglycan binds to biglycan core and to the hybrid; γ-sarcoglycan binds to biglycan core, to biglycan proteoglycan and very weakly to the hybrid; and δ-sarcoglycan binds to biglycan core very weakly.

Thus, biglycan binds to -sarcoglycan via its core peptide. Furthermore, since the hybrid binds to -sarcoglycan, but that decorin does not bind to it, binding of biglycan to α-sarcoglycan occurs through the N-terminal 30 amino acids of biglycan, i.e., the region that includes the cysteine-rich region, but no leucine-rich repeats. In addition, the results indicate that glycosylation of sarcoglycan is not necessary for its binding to biglycan.

Human biglycan was also shown to bind to native α- and γ-sarcoglycan in solution. This was demonstrated by isolating native human α- and γ-sarcoglycan by detergent extraction of cultured mouse myotubes, incubating the extracts with recombinant human core biglycan prepared as described above, and then immumoprecipitating the resulting complexes were then immunoprecipitated with antibodies to α-sarcoglycan (vector laboratories). The immunoprecipitates were then resolved by sds-polyacrylamide gel electrophoresis and western blotted with antibodies to biglycan. The anti-biglycan antibody was raised against a bacterially-produced biglycan fusion protein. The results, which are shown in FIG. 8D, show that native sarcoglycans alpha and gamma bind to biglycan.

Example 7

Biglycan is Expressed at Synaptic and Non-synaptic Regions and is Up-regulated in Dystrophic Muscle Previous reports have shown that biglycan MRNA and protein are expressed in muscle (Bianco, et al. (1990) *J. Histochem Cytochem.* 38: 1549; Bosse,et al. (1993) *J. Histochem. Cytochem.* 41: 13). Since the biglycan that was used in the above-described Examples was obtained from synaptic membranes, it was investigated whether biglycan is also expressed at the neuromuscular junction.

Frozen sections of normal adult mouse muscle were double-labeled with α-bungarotoxin (Bgtx; to localize AChRs) and antibodies to biglycan. Cryostat sections (10 μm) of leg muscle from fresh-frozen wild-type (C57 BL) mice were mounted on slides, fixed, and treated with chondroitinase essentially as described in (Bianco, P., et al., 1990, *J Histochem Cytochem.* 38:1549). Primary antibodies were anti-biglycan (LF-106; generously provided by L. Fisher) diluted in PBS containing 5% BSA, 1% normal goat or horse serum, and 0.1% Triton X-100. Incubation in primary antibodies or non-immune control serum proceeded overnight at 4° C. Except where noted, all subsequent steps were performed at room temperature. Bound antibodies were detected with Cy3-labelled anti-rabbit Ig (Jackson Laboratories, West Grove, Pa.). For double-labelling, sections were first fixed for 5 min in 1% formaldehyde, rinsed and incubated in fluorescein-conjugated α-bungarotoxin (Molecular Probes, Eugene: Oreg.) for 1 hr. The sections were then washed, fixed, treated with chondroitinase and stained for biglycan as described above. Sections were air-dried, mounted in Citifluor (Ted Pella, Redding, Calif.) and examined on a Nikon Eclipse microscope. Images were acquired on a cooled CCD camera using IP Lab Spectrum software and then imported to Adobe Photoshop.

Figure 9:
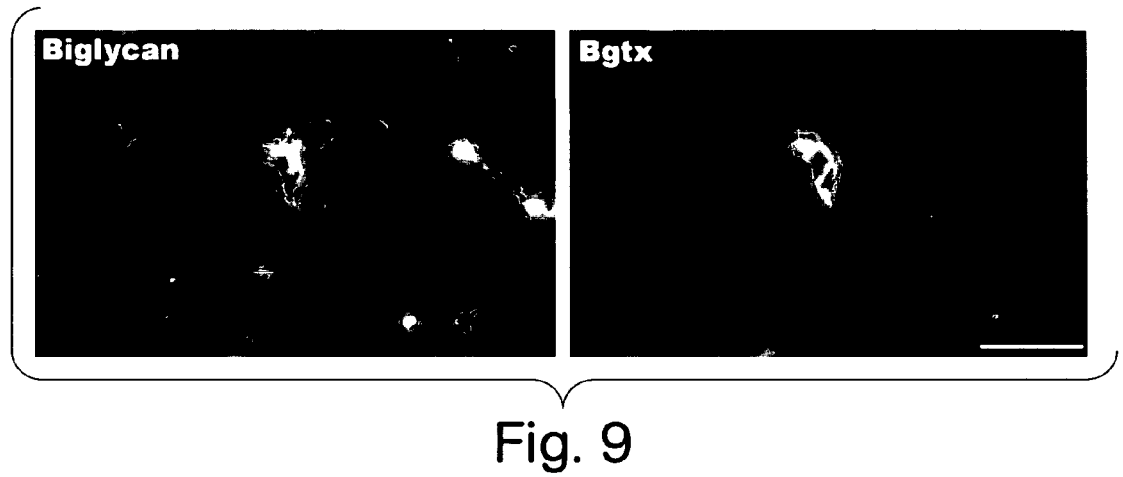
FIG. 9 shows biglycan expression at the neuromuscular junction.

The results, which are shown in FIG. 9, indicate that biglycan imumunoreactivity is distributed over the entire periphery of the myofibers and synapses, and that it is also concentrated at some neuromuscular junctions.

Figure 10:
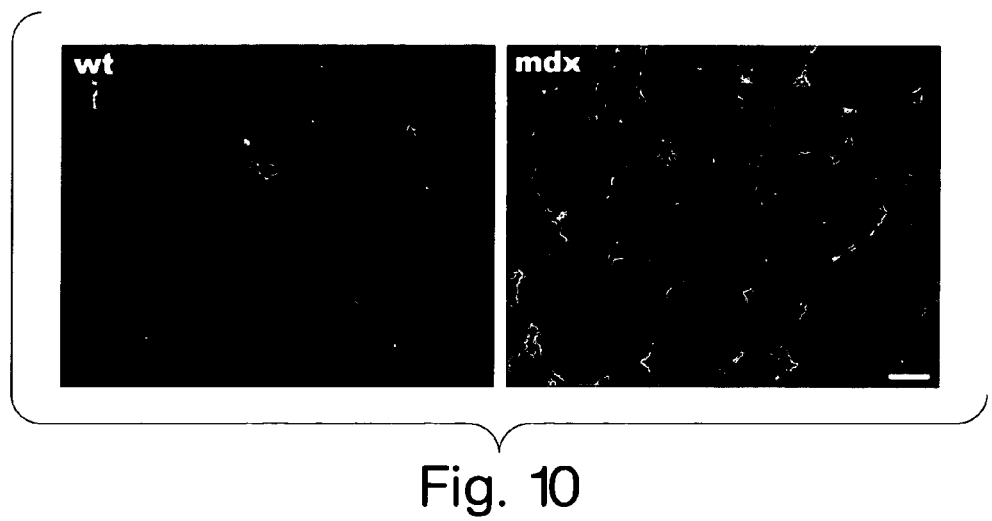
FIG. 10 shows the upregulation of biglycan expression in wild type (wt) and dystrophic (mdx) muscle.

Since biglycan binds to a component of the DAPC, it was investigated whether or not its expression was altered in a mouse model of muscular dystrophy in which dystrophin is absent, i.e., the mdx mouse. Adult mice, which contain almost exclusively regenerated muscle fibers that survive due to utrophin compensation were investigated (Grady, et al. (1997) *Cell* 90: 729). Frozen sections of normal and mdx muscle from 6 wk old mice were mounted on the same slides and immunostained for biglycan as described above. Immunostaining revealed that the level of biglycan expressed in mdr muscle is elevated compared to control animals (FIG. 10). These observations raise the possibility that biglycan could be part of the compensatory mechanism that allows survival of dystrophin negative muscle fibers.

Example 8

Biglycan Binds to the MuSK Ectodomain

This Example demonstrates that biglycan binds to other components of the synaptic membrane, in particular, the MuSK ectodomain.

Figure 11:
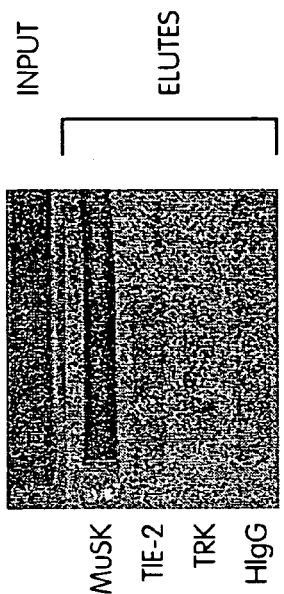
FIG. 11 shows the results of a co-immunoprecipitation of biglycan with recombinant MuSK-Fc.

Torpedo biglycan (DAG-125) was solubilized by alkaline extraction and neutralized, as described in Example 1, and incubated with protein A-agarose beads and with either human IgG (HIgG) or with human Fc fusion proteins containing the ectodomains of recombinant human MuSK (Glass et al. (1996) *Cell*; and Donzuela et al. (1995) *Neuron*), TIE-2, or TRK for co-precipitations. The results, which are shown in FIG. 11, indicate that Torpedo biglycan binds to the MuSK ectodomain, but not to IgG, nor to the two unrelated receptor tyrosine kinase ectodomains TIE-2 and TRK. It was also shown that MuSK solubilized from muscle membranes binds to Torpedo biglycan. Decorin was also shown to bind to MuSK.

Thus, DAG-125 binds to MuSK.

Example 9

Biglycan Preparations Potentiate Agrin-induced AChR Clustering on Myotubes

This Example demonstrates that biglycan potentiates agrin-induced AChR clustering.

Primary chick myotubes were incubated for 20 hours with recombinant biglycan core (no GAG) with or without the addition of 1 unit (about 10 pM) of recombinant rat agrin isoform 12-4-8. Cultures incubated in 1 nM biglycan+agrin increased AChR clustering by an average of 50% over cultures incubated in 1 unit of agrin only. Higher concentrations of biglycan had no effect or possibly inhibited agrin-induced clustering. In another example, exogenous biglycan-enriched preparations (about 30% pure) were also found to potentiate agrin-induced AChR clustering when applied to cultured chick myotubes.

Thus, biglycan potentiaties (50% increase) agrin-induced AChR clustering when present at about $10^{-9}$ M (i.e., about 1.4 nM). At higher concentrations ($10^{-8}$ M, $10^{-7}$ M, i.e., about 140 nM) biglycan inhibits agrin-induced AChR clustering. This was demonstrated on wild-type chick myotubes, which were prepared as described in Nastuk et al., 1991 (*Neuron* 7: 807-818), using either core or proteoglycan human recombinant biglycan, produced by the vaccinia system, described above. Thus, there is a biphasic effect of biglycan on agrin-induced AChR clustering.

Example 10

Biglycan and Decorin Induce Tyrosine Phosphorylation of MuSK

Figure 12:
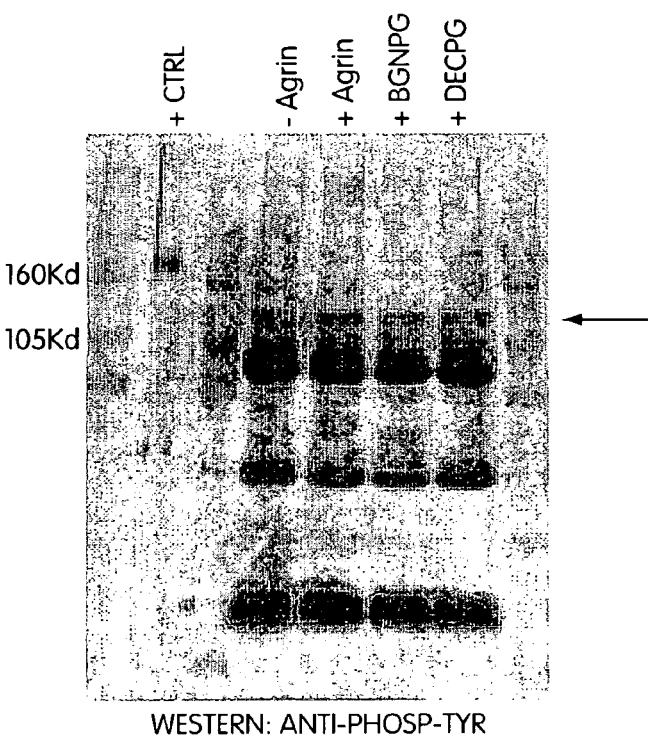
FIG. 12 is a Western blot containing cell extracts of cells incubated with or without agrin and with biglycan proteoglycan (BGNPG) or decoring proteoglycan (DECPG) incubated with anti-phosphotyrosine antibody.

The culture of chick myotubes with agrin resulted, as expected, in the stimulation of phosphorylation of MuSK. It was observed that the stimulation of chick myotubes with human biglycan proteoglycan, decorin-proteoglycan, biglycan core and decorin core (separately) also induce tyrosine phosphorylation of MusK on muscle cells. Phosphorylation was determined by immunoprecipitation and Western blot using an anti-phosphotyrosine antibody. The biglycan and decorin proteoglycan and core were produced by the vaccinia system described above. The results are shown in FIG. 12.

Similarly to agrin-induced AChR clustering, agrin-induced MuSK phosphorylation was also shown to be biphasic: human biglycan core can either potentiate (at 1.4 nM) or inhibit (at 140 nM) agrin-induced MuSK phosphorylation in cultured C2C12 myotubes.

Example 11

Myotubes Cultured from Biglycan$^{-/o}$ Mice Show a Defective Response to Agrin

The role of biglycan in mediating agrin-induced AChR clustering was further proved by using biglycan knockout mice (biglycan$^{-/o}$ male mice).

Figure 13A:
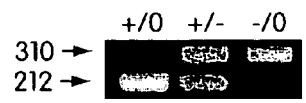
FIG. 13A shows a genotype analysis. PCR genotyping was performed on genomic DNA using primer pairs specific for mutant and wild type biglycan alleles (Xu et al. 1998). PCR products from a wild type (male; +/o), a heterozygote (female; +/−), and a knockout (male; −/o) are shown. Size of PCR products is indicated on left.

Biglycan$^{-/o}$ mice were generated by Marian Young at the NIH. PCR genotyping of the mice was performed on genomic DNA using primer pairs specific for mutant and wild type biglycan alleles (Xu et al. (1998) *Nat. Genet.* 20:78). PCR products from a wild type (male; +/o), a heterozygote (female; +/−), and a knockout (male; −/o) are shown in FIG. 13A.

Figure 13B:
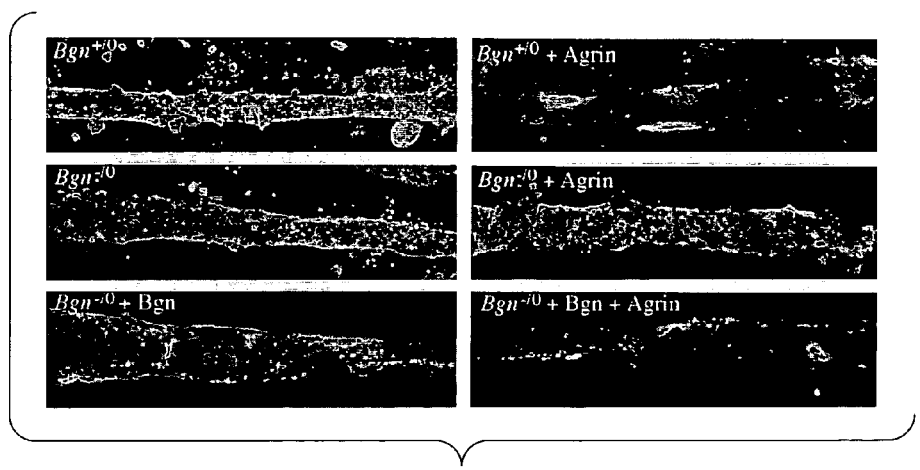
FIG. 13B shows defective agrin-induced AChR clustering in myotubes cultured from biglycan null mice and its rescue by addition of exogneous biglycan. A Bgn female (+/−) was mated to a Bgn male (+/o) and primary cultures were established from each male pup in the resulting litter. The genotype of each pup was determined as shown in FIG. 13A. Myotube cultures derived from each mouse were then treated either with or without recombinant agrin4,8 for 18 hours. Myotubes were then labeled with rhodamine-a-bungarotoxin to visualize AChRs. Wild type myotubes show a robust AChR clustering response to agrin, while myotubes from biglycan−/o mice fail to cluster AChR in response to agrin. Exogenous biglycan (1.4 nM) restores the agrin-induced AChR clustering response.

A Bgn female (+/−) was mated to a Bgn male (+/o) and primary cultures were established from each male pup in the resulting litter. The genotype of each pup was determined as described in the previous paragraph. Myotube cultures derived from each mouse were then treated either with or without recombinant agrin 4,8 for 18 hours. Agrin 4,8 is an alternatively spliced variant, having a four amino acid insert at site Y and an eight amino acid insert at site Z (see, e.g., Iozzo R. I (1998) *Ann. Rev. Biochem.* 67:609, and Firns et al. (1993) Neuron 11:491). Myotubes were then labeled with rhodamine--bungarotoxin to visualize AChRs. As shown in FIG. 13B, the agrin-induced AChR clustering on the biglycan$^{-/o}$ myotubes is greatly reduced compared to those from wild type littermate controls. These results thus provide strong and direct evidence for a role of biglycan in agrin-induced AChR clustering.

Figure 13C:
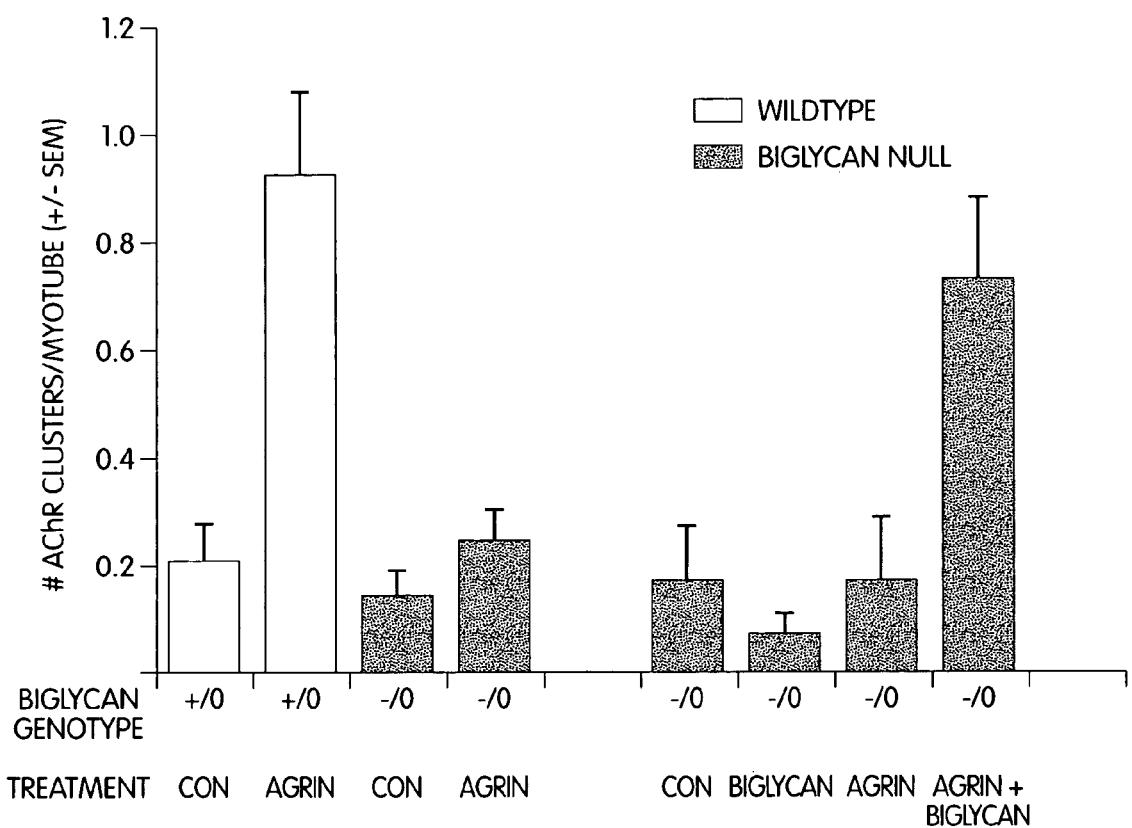
FIG. 13C shows quantification of AChR clustering. AChR clusters and myotubes were counted in a minimum of 10 fields for cultures treated either with (AGRIN) or without (Con) recombinant agrin4,8 in the presence of biglycan (1.4 nM) as indicated. A similar deficit in agrin-induced AChR clustering was observed in two other experiments.
Figure 14:
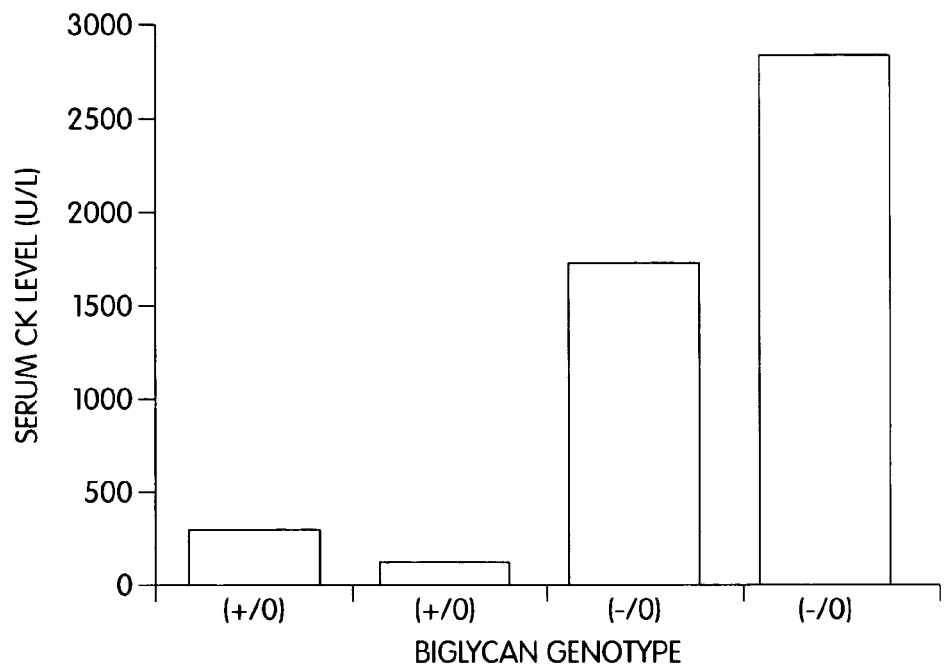
FIG. 14 shows the level of serum creatine kinase in wild type and biglycan knock out mice.

FIG. 13C shows a quantitation of AChR clustering. AChR clusters and myotubes were counted in a minimum of 10 fields for cultures treated either with (AGRIN) or without (Con) recombinant agrin 4,8.

Example 12

Recovery of Response to Agrin in Biglycan$^{-/o}$ Mice by the Addition of Recombinant Biglycan This example shows that the defective response of AChR aggregation in biglycan $^{-/o}$ mice in response to agrin can be rescued by the addition of exogenous recombinant human biglycan core.

This was demonstrated by adding 1.4 nM (0.05 micrograms/ml)of recombinant core human biglycan, produced in the vaccinia system described above, to the cultures of biglycan$^{-/o}$ myotubes described in Example 11. AchR clustering was measured as determined in Example 11.

The results, which are presented in FIG. 13B, indicate that the addition of biglycan core restores the response of biglycan$^{-/o}$ myotubes to agrin.

Thus, this experiment proves the importance of biglycan in agrin-induced AChR clustering. In addition, since this example was performed with core biglycan, i.e., with no proteoglycan side chains, this example demonstrates that the core is particularly important for the agrin-induced postsynaptic differentiation. This further demonstrates that biglycan affects a cell simply by contacting the cell with biglycan.

Example 13

Serum Creatine Kinase is Elevated in Biglycan Knockout Mice

Figure 15:
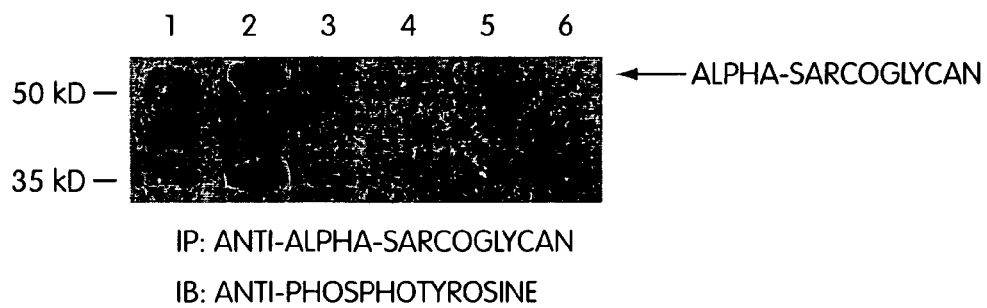
FIG. 15. Exogenous biglycan induces α-sarcoglycan phosphorylation in a MuSK dependent manner. Wild type C2C12 myotubes (lanes 1, 2, and 6) and MuSK null myotubes (lanes 3-5) were treated for thirty minutes as follows: lanes 1, 3, and 6, unstimulated; lanes 2 and 5, stimulated with a mixture of recombinant proteoglycan and core biglycan (produced in osteosarcoma cells; 1 mg/mL); lane 4, stimulated with agrin 12.4.8. The cultures were detergent extracted and α-sarcoglycan was immunoprecipitated, separated by SDS-PAGE, blotted, and probed with anti-phosphotyrosine antibody (lanes 1-5) or MIgG (lane 6). The addition of biglycan induced tyrosine phosphorylation of α-sarcoglycan and p35 in wild type C2C12 cells but not in MuSK knockout cells.
Figure 16A:
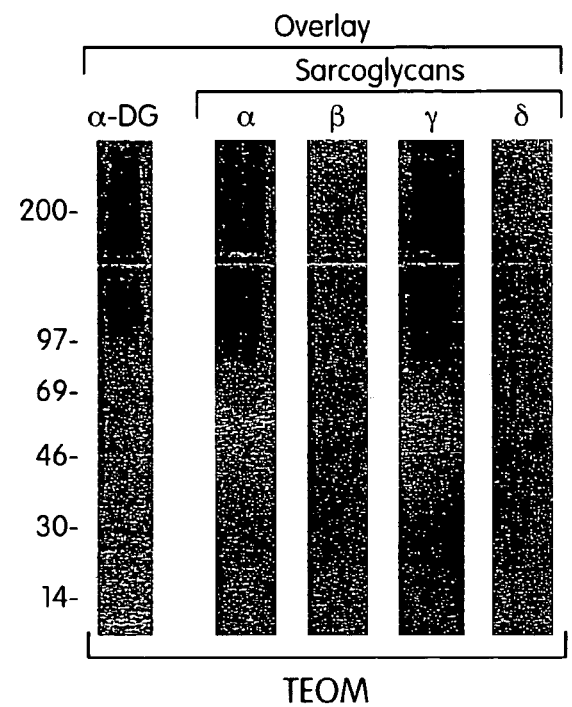
FIG. 16. Biglycan binds to α- and γ-sarcoglycan.
Figure 16B:
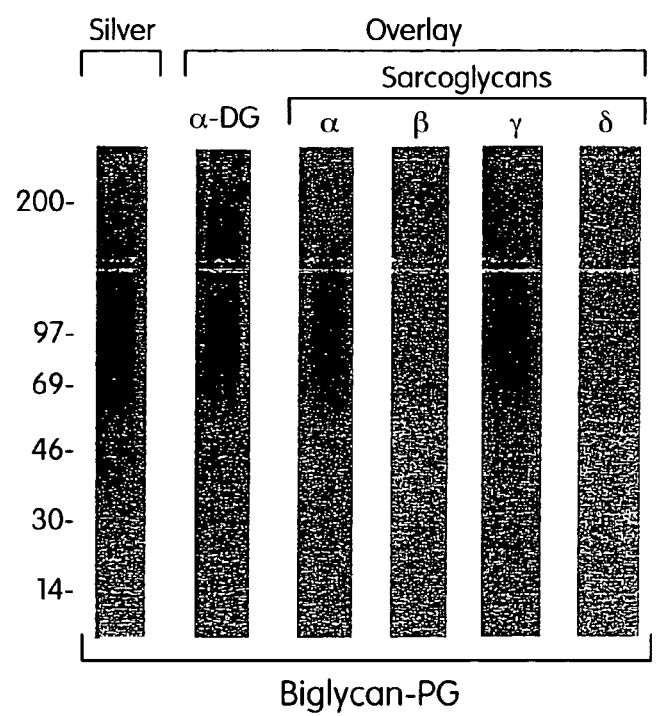
Figure 16C:
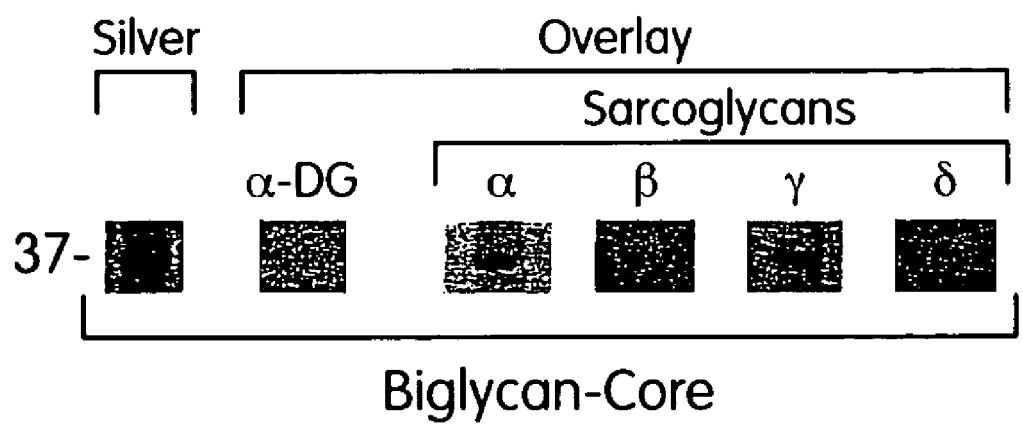

Serum creating kinase (CK) levels from four mice (two male, two female) ages 16 weeks old were assayed. As shown in FIG. 15, CK levels from biglycan knockout mice are about 10 fold greater than wild types. Sera from three other wild type female mice had similar CK levels as these wild type males.

Thus, although biglycan$^{-/o}$ mice do not show gross abnormalities (Xu et al. (1998) Nat. Genet. 20:78), the expression of dystrophin and utrophin are not grossly abnormal, and the synapses also appear grossly normal, they have an abnormally high CK level, relative to wildtype animals. Such elevations are a hallmark of muscle cell damage, such as that seen in muscular dystrophy (Emery (1993) Duchenne Muscular Dystrophy Oxford Monographs on Medical Genetics. Oxford: New York. Oxford Univ. Press). In addition, these mice have leaky membranes, as judged by Evans Blue uptake, and show signs of muscle cell death and regeneration as judged by the presence of myofibers with centrally-located nuclei in the adult. Thus, these results indicate that the muscle cell plasma membrane is likely to be compromised in these animals. These observations, together with the restoration of agrin-induced AChR clustering in myotubes from biglycan$^{-/o}$ mice by the addition of biglycan, strongly suggest that the absence of biglycan or the presence of a defective biglycan results in defective muscle and/or nerve plasma membrane which can be restored by the addition of exogenous biglycan.

The observation that plasma membrane integrity is compromised in biglycan null mice indicated that there may be muscle fiber death and regeneration in these animals. To test this, the histology of muscle from biglycan null mice and littermate controls was examined. As shown in FIG. 22, we observed that approximately 15% of myofibers in biglycan null mice had centrally located nuclei. Such a nuclear disposition is characteristic of regenerating myofibers. A similar percentage of fibers was observed at all ages examined (1, 3 and 6 months). We did not observe any indication of mononuclear cell infiltration, nor was there any evidence of fibrosis. Taken together, these results indicated that biglycan null mice display a distinct, relatively mild muscular dystrophy phenotype.

Immunofluorescence analysis of frozen sections from biglycan null mice showed that the level of dystrophin, α-, β-, γ- and δ-sarcoglycan and β-dystroglycan at the muscle cell is similar in biglycan null mice and littermate controls. However, analysis of collagen VI expression revealed a striking difference. In wild-type littermate controls collagen VI is expressed in the endomysium and the perimysium. In contrast, the levels of collagen VI are reduced in the endomysium of the biglycan null mice. Notably, the expression of decorin, which can also bind this collagen is not affected in the mutant mice. Thus collagen VI expression is selectively reduced in mice lacking biglycan.

Example 14

Biglycan Core Stimulates MuKD Dependent Tyrosine Phosphorylation of α-sarcoglycan and a 35 kD DAPC Component in Myotubes This example demonstrates that biglycan induces tyrosine phosphorylation of DAPC components and has therefore a signaling function.

Human biglycan was prepared using the vaccina system described above Wildtype myotubes or MuSK null myotubes were incubated for 30 minutes in the presence of 1 microgram/ml (27 nM) of a mixture of core and proteoglycan forms of human biglycan. The cultures were detergent extracted and α-sarcoglycan was immunoprecipitated, separated by SDS-PAGE, blotted, and probed with anti-phosphotyrosine antibody or MIgG. The results, which are presented in FIG. 15, show that the tyrosine phosphorylation of α-sarcoglycan is increased in the presence of biglycan in wild type cells, but not in MuSK null myotubes. In addition, it was observed that an unidentified 35 kD DAPC component was also phosphorylated in wild type cells but not in MuSK null myotubes In addition, the results show that biglycan is capable of a signaling function, in the absence of agrin.

Equivalents

Those skilled in the art will recognize, or be able to ascertain using no more than routine experimentation, many equivalents of the specific embodiments of the invention described herein. Such equivalents are intended to be encompassed by the following claims.

The invention claimed is:

1. A method for treating a deficiency in collagen VI expression levels in mammalian muscle, comprising administering to a mammal a biglycan polypeptide in an amount sufficient to increase collagen VI expression levels in the mammalian muscle, wherein the biglycan polypeptide comprises an amino acid sequence which is at least about 95% identical to amino acids 38-368 of SEQ ID NO: 9, or a portion thereof, and which has a biological activity of human biglycan.

2. The method of claim 1, wherein the biglycan polypeptide binds to MuSK.

3. The method of claim 1, wherein the biglycan polypeptide binds to a α-sarcoglycan and/or γ-sarcoglycan.

4. The method of claim 1, wherein the biglycan polypeptide binds to a collagen VI polypeptide.

5. The method of claim 1, wherein the biglycan polypeptide induces phosphorylation of sarcoglycans.

6. The method of claim 1, wherein the biglycan polypeptide upregulates utrophin levels.

7. The method of claim 1, wherein the mammal has a condition selected from the group consisting of Bethlem myopathy, and Ullrich Congenital Muscular Dystrophy.

8. The method of claim 1, wherein the biglycan polypeptide comprises amino acids 38-368 of SEQ ID NO: 9.

9. The method of claim 1, wherein the biglycan polypeptide comprises amino acids 20-368 of SEQ ID NO: 9.

10. The method of claim 1, wherein the biglycan polypeptide comprises at least one repeat motif of 24 amino acids in the Leucine Rich Repeat (LRR) of SEQ ID NO: 9.

11. The method of claim 1, wherein the biglycan polypeptide is encoded by a nucleic acid which hybridizes under conditions of 6.0+sodium chloride/sodium citrate (SSC) at about 45° C. to a complementary strand of SEQ ID NO: 8.

12. The method of claim 1, wherein the biglycan polypeptide comprises the amino acid sequence of SEQ ID NO: 9.

* * * * *

UNITED STATES PATENT AND TRADEMARK OFFICE
CERTIFICATE OF CORRECTION

| | | |
|---|---|---|
| PATENT NO. | : 7,759,314 B2 | Page 1 of 1 |
| APPLICATION NO. | : 10/486678 | |
| DATED | : July 20, 2010 | |
| INVENTOR(S) | : Fallon et al. | |

It is certified that error appears in the above-identified patent and that said Letters Patent is hereby corrected as shown below:

In claim 11, column 152, line 56, please replace "6.0+sodium" with --6.0 × sodium--.

Signed and Sealed this
Twenty-eighth Day of June, 2011

David J. Kappos
*Director of the United States Patent and Trademark Office*

UNITED STATES PATENT AND TRADEMARK OFFICE
CERTIFICATE OF CORRECTION

PATENT NO. : 7,759,314 B2
APPLICATION NO. : 10/486678
DATED : July 20, 2010
INVENTOR(S) : Fallon et al.

Page 1 of 1

It is certified that error appears in the above-identified patent and that said Letters Patent is hereby corrected as shown below:

In the Specification

At column 1, line numbers 16-19, please replace with the following: This ~~work~~ invention was made ~~during~~ with Government support under Grants HD23924 and MH53571 awarded by the National ~~Institute~~ Institutes of Health. ~~Therefore, the~~ The U.S. Government has certain rights in this invention.

Signed and Sealed this
Twenty-fourth Day of December, 2013

Margaret A. Focarino
*Commissioner for Patents of the United States Patent and Trademark Office*